United States Patent
Hultberg et al.

(10) Patent No.: US 9,884,917 B2
(45) Date of Patent: **\*Feb. 6, 2018**

(54) ANTI C-MET ANTIBODIES

(71) Applicant: arGEN-X N.V., Breda (NL)

(72) Inventors: Anna Hultberg, Sint-Martens-Latem (BE); Michael Saunders, Brussels (BE); Johannes De Haard, Oudelande (BE); Els Festjens, Zwevegem (BE); Natalie De Jonge, Aalst (BE); Paolo Michieli, Rivalta di Torino (IT); Cristina Basilico, Pavarolo (IT); Torsten Dreier, Sint-Martens-Latem (BE)

(73) Assignee: ARGEN-X N.V., Breda (NL)

( * ) Notice: Subject to any disclaimer, the term of this patent is extended or adjusted under 35 U.S.C. 154(b) by 0 days.

This patent is subject to a terminal disclaimer.

(21) Appl. No.: 14/098,849

(22) Filed: Dec. 6, 2013

(65) Prior Publication Data

US 2014/0205606 A1 Jul. 24, 2014

Related U.S. Application Data

(62) Division of application No. 13/288,566, filed on Nov. 3, 2011, now Pat. No. 8,637,027.

(60) Provisional application No. 61/409,866, filed on Nov. 3, 2010.

(51) Int. Cl.
  C07K 16/28 (2006.01)
  C07K 16/32 (2006.01)
  A61K 39/395 (2006.01)
  A61K 39/00 (2006.01)

(52) U.S. Cl.
  CPC .......... *C07K 16/32* (2013.01); *C07K 16/2863* (2013.01); *A61K 2039/505* (2013.01); *C07K 2317/14* (2013.01); *C07K 2317/22* (2013.01); *C07K 2317/30* (2013.01); *C07K 2317/33* (2013.01); *C07K 2317/55* (2013.01); *C07K 2317/56* (2013.01); *C07K 2317/565* (2013.01); *C07K 2317/73* (2013.01); *C07K 2317/732* (2013.01); *C07K 2317/74* (2013.01); *C07K 2317/76* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 5,648,273 A | 7/1997 | Bottaro et al. |
| 5,686,292 A | 11/1997 | Schwall et al. |
| 6,099,841 A | 8/2000 | Hillan et al. |
| 6,207,152 B1 | 3/2001 | Schwall et al. |
| 6,214,344 B1 | 4/2001 | Schwall et al. |
| 6,468,529 B1 | 10/2002 | Schwall et al. |
| 7,476,724 B2 | 1/2009 | Dennis et al. |
| 7,498,420 B2 | 3/2009 | Michaud et al. |
| 7,556,804 B2 | 7/2009 | Prat |
| 7,892,550 B2 | 2/2011 | Dennis et al. |
| 7,892,770 B2 | 2/2011 | Cao et al. |
| 8,637,027 B2 | 1/2014 | Hultberg et al. |
| 2007/0098707 A1 | 5/2007 | Kong-Beltran et al. |
| 2009/0068179 A1 | 3/2009 | Nayeri et al. |
| 2009/0175860 A1 | 7/2009 | Stover et al. |
| 2009/0285807 A1 | 11/2009 | Comoglio et al. |
| 2009/0298079 A1 | 12/2009 | Basilico et al. |
| 2010/0016241 A1 | 1/2010 | Kong-Beltran et al. |
| 2010/0040629 A1 | 2/2010 | Michaud et al. |
| 2010/0115639 A1 | 5/2010 | Goetsch |
| 2010/0129369 A1 | 5/2010 | Davies et al. |
| 2010/0146650 A1 | 6/2010 | Goetsch et al. |
| 2010/0285504 A1 | 11/2010 | Cao et al. |
| 2011/0097262 A1 | 4/2011 | Goetsch et al. |
| 2011/0142840 A1 | 6/2011 | Van Der Horst et al. |
| 2011/0239316 A1 | 9/2011 | Goetsch et al. |
| 2011/0280870 A1 | 11/2011 | Schwall et al. |

FOREIGN PATENT DOCUMENTS

| | | |
|---|---|---|
| EP | 567585 B1 | 8/1999 |
| EP | 1692178 A1 | 8/2006 |
| EP | 805203 B1 | 8/2007 |
| EP | 1957102 A2 | 8/2008 |
| EP | 2004693 A2 | 12/2008 |
| EP | 2081592 A1 | 7/2009 |
| EP | 922102 B1 | 4/2010 |
| EP | 1641828 B1 | 4/2010 |
| EP | 1773885 B1 | 4/2010 |
| EP | 2188312 A2 | 5/2010 |
| EP | 2195345 A2 | 6/2010 |
| EP | 1981981 B1 | 6/2011 |
| EP | 2119448 B1 | 6/2011 |
| EP | 2336178 A1 | 6/2011 |
| EP | 2358755 A1 | 8/2011 |
| WO | WO1994006909 A2 | 3/1994 |
| WO | 2005016382 A1 | 2/2005 |
| WO | WO2005016382 A1 | 2/2005 |
| WO | WO2006015371 A2 | 2/2006 |

(Continued)

OTHER PUBLICATIONS

Guisti et al. 'Somatic diversification of S107 from an antiphosphocholine to an anti-DNA autoantibody is due to a single base change in its heavy chain variable region.' Proceedings of the National Academy of Sciences, USA. 1987, vol. 84, pp. 2926.

(Continued)

*Primary Examiner* — Marianne P Allen

(74) *Attorney, Agent, or Firm* — Lathrop Gage LLP; James H. Velema, Esq.

(57) ABSTRACT

The present invention relates to antibodies that specifically bind to the human c-Met receptor protein and that act as strict antagonists of hepatocyte growth factor (HGF)-mediated activation of the c-Met receptor and also inhibit HGF-independent activation of the human c-Met protein.

9 Claims, 23 Drawing Sheets

(56) References Cited

FOREIGN PATENT DOCUMENTS

| WO | WO2007126799 A2 | 11/2007 |
|---|---|---|
| WO | WO2008046724 A1 | 4/2008 |
| WO | WO2009007427 A2 | 1/2009 |
| WO | WO2009142738 A2 | 11/2009 |
| WO | WO2010059654 A1 | 5/2010 |
| WO | 2012059561 A1 | 5/2012 |
| WO | 2012059562 A1 | 11/2012 |

OTHER PUBLICATIONS

Gussow et al. '[5] Humanization of monoclonal antibodies.' Methods in Enzymology. 1991, vol. 203, pp. 99-121.

Lippincott-Schwartz, Jennifer. 'Antibodies as Cell Biological Tools.' Current Protocols in Cell Biology. 2002 Ch. 16, 2 pages 16.0.1-16.0.2

Mariuzza et al. 'The structural basis of antigen-antibody recognition.' Annual Review of Biophysics and Biophysical Chemistry. 1987, vol. 16, No. 1, pp. 139-159.

Rudikoff et al. 'Single amino acid substitution altering antigen-binding specificity.' Proceedings of the National Academy of Sciences. 1982, vol. 79, No. 6, pp. 1979-1983.

Winkler et al. 'Changing the antigen binding specificity by single point mutations of an anti-p24 (HIV-1) antibody.' The Journal of Immunology. 2000, vol. 165, No. 8, pp. 4505-4514.

Basilico C et al. 'A High Affinity Hepatocyte Growth Factor-binding Site in the Immunoglobulin-like Region of Met'. Journal of Biological Chemistry. The American Society of Biological Chemists. Inc. US. 2008 vol. 283 No. 30 pp. 21267-21277.

Christensen J G et al. 'c-Met as a Target for Human Cancer and Characterization of Inhibitors for Therapeutic Intervention'. Cancer Letters 2005 vol. 225 No. 1 pp. 1-26.

Harmsen M M et al. 'Properties, Production, and Applications of Camelid Single-domain Antibody Fragments'. Applied Microbiology and Biotechnology. 2007 vol. 77 No. 1 pp. 13-22.

Toschi, Luca et al. 'Single-agent and Combination Therapeutic Strategies to Inhibit Hepatocyte Growth Factor/MET Signaling in Cancer'. Clinical Cancer Research. The American Association for Cancer Research. 2008 vol. 14 No. 19 pp. 5941-5946.

Van Dor Horst E H et al. 'Discovery of Fully Human Anti-MET Monoclonal Antibodies with Antitumor Activity Against Colon Cancer Tumor Models in vivo'. Neoplasia 2009 vol. 11 No. 4 pp. 355-364.

Shinkawa, T. et al., The absence of fucose but not the presence of galactose or bisecting N-acetylglucosamine of human IgG1 complex-type oligosaccharides shows the critical role of enhancing antibody-dependent cellular cytotoxicity, J Biol Chem. Jan. 31, 2003; 278(5):3466-73.

Figure 15: Alignment of human and llama glama cMet protein sequences

A

Binding of 36C4 mAb to human, llama and chimeric ECD cMet recombinant proteins

B

Binding of 13E6 mAb to human, llama and chimeric ECD cMet recombinant proteins

A

B

*In vivo* U87 MG xenograft experiment testing the effects of 36C4 versus c224G11 administration on tumour growth

A

B

PBS stability of germlined 36C4 variants at various temperatures

A

Thermotolerance of germlined 36C4 clones

B

Thermotolerance of 48A2 germlined clone

A

B

Down regulation of total cMet on MKN-45 cells by mAbs.

Figure 25 hMET - X54559,P08581

Signal peptide

MKAPAVLAPGILVLLFTLVQRSNG

SEMA (1-491)

ECKEALAKSEMNVNMKYQLPNFTAETPIQNVILHEHHIFLGATNYIYVLNEEDLQKVAEY
KTGPVLEHPDCFPCQDCSSKANLSGGVWKDNINMALVVDTYYDDQLISCGSVNRGTCQRH
VFPHNHTADIQSEVHCIFSPQIEEPSQCPDCVVSALGAKVLSSVKDRFINFFVGNTINSS
YFPDHPLHSISVRRLKETKDGFMFLTDQSYIDVLPEFRDSYPIKYVHAFESNNFIYFLTV
QRETLDAQTFHTRIIRFCSINSGLHSYMEMPLECILTEKRKKRSTKKEVFNILQAAYVSK
PGAQLARQIGASLNDDILFGVFAQSKPDSAEPMDRSAMCAFPIKYVNDFFNKIVNKNNVR
CLQHFYGPNHEHCFNRTLLRNSSGCEARRDEYRTEFTTALQRVDLFMGQFSEVLLTSIST
FIKGDLTIANLGTSEGRFMQVVVSRSGPSTPHVNFLLDSHPVSPEVIVEHTLNQNGYTLV
ITGKKITKIPL

PSI (492-543)

NGLGCRHFQSCSQCLSAPPFVQCGWCHDKCVRSEECLSGTWTQQICLPAIYK

IPT-1 (544-632)

VFPNSAPLEGGTRLTICGWDFGFRRNNKFDLKKTRVLLGNESCTLTLSESTMNTLKCTVG
PAMNKHFNMSIIISNGHGTTQYSTFSYVD

IPT-2 (633-717)

PVITSISPKYGPMAGGTLLTLTGNYLNSGNSRHISIGGKTCTLKSVSNSILECYTPAQTI
STEFAVKLKIDLANRETSIFSYRED

IPT-3 (718-814)

PIVYEIHPTKSFISGGSTITGVGKNLNSVSVPRMVINVHEAGRNFTVACQHRSNSEIICC
TTPSLQQLNLQLPLKTKAFFMLDGILSKYFDLIYVHN

IPT-4 (815-909)

PVFKPFEKPVMISMGNENVLEIKGNDIDPEAVKGEVLKVGNKSCENIHLHSEAVLCTVPN
DLLKLNSELNIEWKQAISSTVLGKVIVQPDQNFTG

SEQUENCE LISTING

```
<160> NUMBER OF SEQ ID NOS: 209

<210> SEQ ID NO 1
<211> LENGTH: 5
<212> TYPE: PRT
<213> ORGANISM: Artificial Sequence
<220> FEATURE:
<223> OTHER INFORMATION: CDR Sequence

<400> SEQUENCE: 1

Asp Tyr Ala Met Thr
1               5

<210> SEQ ID NO 2
<211> LENGTH: 17
<212> TYPE: PRT
<213> ORGANISM: Artificial Sequence
<220> FEATURE:
<223> OTHER INFORMATION: CDR Sequence
```

```
<400> SEQUENCE: 2

Thr Ile Ser Trp Asn Asp Ile Asn Thr Tyr Tyr Ala Glu Ser Met Lys
1               5                   10                  15
Asp

<210> SEQ ID NO 3
<211> LENGTH: 14
<212> TYPE: PRT
<213> ORGANISM: Artificial Sequence
<220> FEATURE:
<223> OTHER INFORMATION: CDR Sequence

<400> SEQUENCE: 3

Arg Arg Asp Asn Tyr Tyr Gly Thr Ser Gly Glu Tyr Asp Tyr
1               5                   10

<210> SEQ ID NO 4
<211> LENGTH: 5
<212> TYPE: PRT
<213> ORGANISM: Artificial Sequence
<220> FEATURE:
<223> OTHER INFORMATION: CDR Sequence

<400> SEQUENCE: 4

Asp Tyr Val Met Asn
1               5

<210> SEQ ID NO 5
<211> LENGTH: 17
<212> TYPE: PRT
<213> ORGANISM: Artificial Sequence
<220> FEATURE:
<223> OTHER INFORMATION: CDR Sequence

<400> SEQUENCE: 5

Ala Ile Asn Trp Asn Gly Gly Ser Thr Tyr Tyr Ala Glu Ser Met Lys
1               5                   10                  15
Gly

<210> SEQ ID NO 6
<211> LENGTH: 9
<212> TYPE: PRT
<213> ORGANISM: Artificial Sequence
<220> FEATURE:
<223> OTHER INFORMATION: CDR Sequence

<400> SEQUENCE: 6

Asp Thr Val Val Ser Gly Asn Gly Tyr
1               5

<210> SEQ ID NO 7
<211> LENGTH: 5
<212> TYPE: PRT
<213> ORGANISM: Artificial Sequence
<220> FEATURE:
<223> OTHER INFORMATION: CDR Sequence

<400> SEQUENCE: 7

Asp Tyr Ala Met Ser
1               5
```

```
<210> SEQ ID NO 8
<211> LENGTH: 17
<212> TYPE: PRT
<213> ORGANISM: Artificial Sequence
<220> FEATURE:
<223> OTHER INFORMATION: CDR Sequence

<400> SEQUENCE: 8

Ala Ile Ser Trp Asn Gly Ser Ser Thr Tyr Tyr Ala Glu Ser Met Lys
1               5                   10                  15

Gly

<210> SEQ ID NO 9
<211> LENGTH: 8
<212> TYPE: PRT
<213> ORGANISM: Artificial Sequence
<220> FEATURE:
<223> OTHER INFORMATION: CDR Sequence

<400> SEQUENCE: 9

Asp Leu Ile Gly Ser His Asp Tyr
1               5

<210> SEQ ID NO 10
<211> LENGTH: 7
<212> TYPE: PRT
<213> ORGANISM: Artificial Sequence
<220> FEATURE:
<223> OTHER INFORMATION: CDR Sequence

<400> SEQUENCE: 10

Gly Asn Tyr Tyr Ala Trp Ser
1               5

<210> SEQ ID NO 11
<211> LENGTH: 16
<212> TYPE: PRT
<213> ORGANISM: Artificial Sequence
<220> FEATURE:
<223> OTHER INFORMATION: CDR Sequence

<400> SEQUENCE: 11

Val Ile Ala Tyr Asp Gly Ser Thr Tyr Tyr Ser Pro Ser Leu Lys Ser
1               5                   10                  15

<210> SEQ ID NO 12
<211> LENGTH: 12
<212> TYPE: PRT
<213> ORGANISM: Artificial Sequence
<220> FEATURE:
<223> OTHER INFORMATION: CDR Sequence

<400> SEQUENCE: 12

Gly Pro Gly Trp Tyr Ser Gly Ser Arg Asn Asp Tyr
1               5                   10

<210> SEQ ID NO 13
<211> LENGTH: 5
<212> TYPE: PRT
<213> ORGANISM: Artificial Sequence
<220> FEATURE:
<223> OTHER INFORMATION: CDR Sequence

<400> SEQUENCE: 13

Met Asn Ser Ile Asp
1               5
```

```
<210> SEQ ID NO 14
<211> LENGTH: 17
<212> TYPE: PRT
<213> ORGANISM: Artificial Sequence
<220> FEATURE:
<223> OTHER INFORMATION: CDR Sequence

<400> SEQUENCE: 14

Arg Ile Asp Pro Glu Asp Gly Gly Thr Lys Tyr Ala Gln Lys Phe Gln
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: CDR Sequence

<400> SEQUENCE: 15

Val Asp Asp Tyr Tyr Leu Gly Tyr Asp Tyr
1               5                   10

<210> SEQ ID NO 16
<211> LENGTH: 5
<212> TYPE: PRT
<213> ORGANISM: Artificial Sequence
<220> FEATURE:
<223> OTHER INFORMATION: CDR Sequence

<400> SEQUENCE: 16

Asn Tyr Val Ile Asp
1               5

<210> SEQ ID NO 17
<211> LENGTH: 17
<212> TYPE: PRT
<213> ORGANISM: Artificial Sequence
<220> FEATURE:
<223> OTHER INFORMATION: CDR Sequence

<400> SEQUENCE: 17

Arg Ile Asp Pro Glu Asn Gly Gly Thr Arg Tyr Ala Gln Lys Phe Gln
1               5                   10                  15

Gly

<210> SEQ ID NO 18
<211> LENGTH: 10
<212> TYPE: PRT
<213> ORGANISM: Artificial Sequence
<220> FEATURE:
<223> OTHER INFORMATION: CDR Sequence

<400> SEQUENCE: 18

Leu Glu Asp Tyr Glu Leu Ala Tyr Asp Tyr
1               5                   10

<210> SEQ ID NO 19
<211> LENGTH: 7
<212> TYPE: PRT
<213> ORGANISM: Artificial Sequence
<220> FEATURE:
<223> OTHER INFORMATION: CDR Sequence

<400> SEQUENCE: 19
```

```
Thr Asn Tyr Tyr Tyr Trp Ser
1               5

<210> SEQ ID NO 20
<211> LENGTH: 16
<212> TYPE: PRT
<213> ORGANISM: Artificial Sequence
<220> FEATURE:
<223> OTHER INFORMATION: CDR Sequence

<400> SEQUENCE: 20

Val Ile Ala Tyr Asp Gly Ser Thr Asp Tyr Ser Pro Ser Leu Lys Ser
1               5                   10                  15

<210> SEQ ID NO 21
<211> LENGTH: 17
<212> TYPE: PRT
<213> ORGANISM: Artificial Sequence
<220> FEATURE:
<223> OTHER INFORMATION: CDR Sequence

<400> SEQUENCE: 21

Asp Val Arg Val Ile Ala Thr Gly Trp Ala Thr Ala Asn Ala Leu Asp
1               5                   10                  15

Ala

<210> SEQ ID NO 22
<211> LENGTH: 17
<212> TYPE: PRT
<213> ORGANISM: Artificial Sequence
<220> FEATURE:
<223> OTHER INFORMATION: CDR Sequence

<400> SEQUENCE: 22

Lys Ser Ser Gln Ser Val Leu Trp Arg Ser Asn Gln Lys Asn Tyr Leu
1               5                   10                  15

Ala

<210> SEQ ID NO 23
<211> LENGTH: 7
<212> TYPE: PRT
<213> ORGANISM: Artificial Sequence
<220> FEATURE:
<223> OTHER INFORMATION: CDR Sequence

<400> SEQUENCE: 23

Trp Ala Ser Ile Arg Glu Ser
1               5

<210> SEQ ID NO 24
<211> LENGTH: 9
<212> TYPE: PRT
<213> ORGANISM: Artificial Sequence
<220> FEATURE:
<223> OTHER INFORMATION: CDR Sequence

<400> SEQUENCE: 24

Gln Gln Gly Tyr Ser Phe Pro Tyr Thr
1               5

<210> SEQ ID NO 25
<211> LENGTH: 17
<212> TYPE: PRT
<213> ORGANISM: Artificial Sequence
<220> FEATURE:
<223> OTHER INFORMATION: CDR Sequence
```

```
<400> SEQUENCE: 25

Lys Ser Ser Gln Ser Val Leu Leu Ser Ser Asn Gln Lys Asn Tyr Leu
1               5                   10                  15

Ala

<210> SEQ ID NO 26
<211> LENGTH: 7
<212> TYPE: PRT
<213> ORGANISM: Artificial Sequence
<220> FEATURE:
<223> OTHER INFORMATION: CDR Sequence

<400> SEQUENCE: 26

Trp Ala Ser Thr Arg Glu Ser
1               5

<210> SEQ ID NO 27
<211> LENGTH: 9
<212> TYPE: PRT
<213> ORGANISM: Artificial Sequence
<220> FEATURE:
<223> OTHER INFORMATION: CDR Sequence

<400> SEQUENCE: 27

Gln Gln Gly Val Ser Phe Pro Leu Thr
1               5

<210> SEQ ID NO 28
<211> LENGTH: 14
<212> TYPE: PRT
<213> ORGANISM: Artificial Sequence
<220> FEATURE:
<223> OTHER INFORMATION: CDR Sequence

<400> SEQUENCE: 28

Thr Gly Thr Asn Ser Asp Val Gly Tyr Gly Asn Tyr Val Ser
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDR Sequence

<400> SEQUENCE: 29

Asp Val Asn Arg Arg Ala Ser
1               5

<210> SEQ ID NO 30
<211> LENGTH: 10
<212> TYPE: PRT
<213> ORGANISM: Artificial Sequence
<220> FEATURE:
<223> OTHER INFORMATION: CDR Sequence

<400> SEQUENCE: 30

Ala Ser Tyr Arg Ser Ala Asn Asn Ala Val
1               5                   10

<210> SEQ ID NO 31
<211> LENGTH: 14
<212> TYPE: PRT
<213> ORGANISM: Artificial Sequence
<220> FEATURE:
```

```
<223> OTHER INFORMATION: CDR Sequence

<400> SEQUENCE: 31

Ala Gly Thr Ser Ser Asp Val Gly Tyr Gly Asn Tyr Val Ser
1               5                   10

<210> SEQ ID NO 32
<211> LENGTH: 7
<212> TYPE: PRT
<213> ORGANISM: Artificial Sequence
<220> FEATURE:
<223> OTHER INFORMATION: CDR Sequence

<400> SEQUENCE: 32

Ala Val Ser Tyr Arg Ala Ser
1               5

<210> SEQ ID NO 33
<211> LENGTH: 11
<212> TYPE: PRT
<213> ORGANISM: Artificial Sequence
<220> FEATURE:
<223> OTHER INFORMATION: CDR Sequence

<400> SEQUENCE: 33

Ala Ser Tyr Arg Ser Ser Asn Asn Ala Ala Val
1               5                   10

<210> SEQ ID NO 34
<211> LENGTH: 14
<212> TYPE: PRT
<213> ORGANISM: Artificial Sequence
<220> FEATURE:
<223> OTHER INFORMATION: CDR Sequence

<400> SEQUENCE: 34

Ala Gly Thr Ser Ser Asp Ile Gly Asn Tyr Asn Tyr Val Ser
1               5                   10

<210> SEQ ID NO 35
<211> LENGTH: 7
<212> TYPE: PRT
<213> ORGANISM: Artificial Sequence
<220> FEATURE:
<223> OTHER INFORMATION: CDR Sequence

<400> SEQUENCE: 35

Glu Val Asn Lys Arg Pro Ser
1               5

<210> SEQ ID NO 36
<211> LENGTH: 10
<212> TYPE: PRT
<213> ORGANISM: Artificial Sequence
<220> FEATURE:
<223> OTHER INFORMATION: CDR Sequence

<400> SEQUENCE: 36

Ala Ser Tyr Arg Ser Ser Asn Asn Val Val
1               5                   10

<210> SEQ ID NO 37
<211> LENGTH: 14
<212> TYPE: PRT
<213> ORGANISM: Artificial Sequence
<220> FEATURE:
<223> OTHER INFORMATION: CDR Sequence
```

```
<400> SEQUENCE: 37

Ala Gly Thr Ser Ser Asp Ile Gly Asp Tyr Asn Tyr Val Ser
1               5                   10

<210> SEQ ID NO 38
<211> LENGTH: 7
<212> TYPE: PRT
<213> ORGANISM: Artificial Sequence
<220> FEATURE:
<223> OTHER INFORMATION: CDR Sequence

<400> SEQUENCE: 38

Asp Val Asn Lys Arg Ala Ser
1               5

<210> SEQ ID NO 39
<211> LENGTH: 10
<212> TYPE: PRT
<213> ORGANISM: Artificial Sequence
<220> FEATURE:
<223> OTHER INFORMATION: CDR Sequence

<400> SEQUENCE: 39

Ala Ser Tyr Arg Ser Arg Asn Asp Tyr Ala
1               5                   10

<210> SEQ ID NO 40
<211> LENGTH: 14
<212> TYPE: PRT
<213> ORGANISM: Artificial Sequence
<220> FEATURE:
<223> OTHER INFORMATION: CDR Sequence

<400> SEQUENCE: 40

Ala Gly Thr Ser Ser Asp Val Gly Tyr Gly Asn Tyr Val Ser
1               5                   10

<210> SEQ ID NO 41
<211> LENGTH: 7
<212> TYPE: PRT
<213> ORGANISM: Artificial Sequence
<220> FEATURE:
<223> OTHER INFORMATION: CDR Sequence

<400> SEQUENCE: 41

Ala Val Ser Thr Arg Ala Ser
1               5

<210> SEQ ID NO 42
<211> LENGTH: 10
<212> TYPE: PRT
<213> ORGANISM: Artificial Sequence
<220> FEATURE:
<223> OTHER INFORMATION: CDR Sequence

<400> SEQUENCE: 42

Ala Ser Tyr Arg Ser Ser Asn Asn Tyr Ala
1               5                   10

<210> SEQ ID NO 43
<211> LENGTH: 118
<212> TYPE: PRT
<213> ORGANISM: Mus musculus

<400> SEQUENCE: 43
```

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Ile Phe Thr Ala Tyr
            20                  25                  30

Thr Met His Trp Val Arg Gln Ser Leu Gly Glu Ser Leu Asp Trp Ile
        35                  40                  45

Gly Gly Ile Lys Pro Asn Asn Gly Leu Ala Asn Tyr Asn Gln Lys Phe
    50                  55                  60

Lys Gly Lys Ala Thr Leu Thr Val Asp Lys Ser Ser Thr Ala Tyr
65                  70                  75                  80

Met Asp Leu Arg Ser Leu Thr Ser Glu Asp Ser Ala Val Tyr Tyr Cys
                85                  90                  95

Ala Arg Ser Glu Ile Thr Thr Glu Phe Asp Tyr Trp Gly Gln Gly Thr
            100                 105                 110

Ala Leu Thr Val Ser Ser
            115

<210> SEQ ID NO 44
<211> LENGTH: 111
<212> TYPE: PRT
<213> ORGANISM: Mus musculus

<400> SEQUENCE: 44

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Ser Tyr
            20                  25                  30

Ala Asn Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Ala Asp Asp Val Ala Thr Tyr Tyr Cys Gln Gln Ser Lys
                85                  90                  95

Glu Asp Pro Leu Thr Phe Gly Ser Gly Thr Lys Leu Glu Met Lys
            100                 105                 110

<210> SEQ ID NO 45
<211> LENGTH: 123
<212> TYPE: PRT
<213> ORGANISM: Artificial Sequence
<220> FEATURE:
<223> OTHER INFORMATION: Variable domain

<400> SEQUENCE: 45

Gln Leu Gln Leu Val Glu Ser Gly Gly Gly Met Ala Gln Pro Gly Gly
1               5                   10                  15

Ser Leu Lys Leu Ser Cys Ala Ala Ser Gly Phe Thr Phe Asp Asp Tyr
            20                  25                  30

Ala Met Thr Trp Val Arg Gln Ala Pro Gly Lys Gly Leu Glu Trp Leu
        35                  40                  45

Ser Thr Ile Ser Trp Asn Asp Ile Asn Thr Tyr Tyr Ala Glu Ser Met
    50                  55                  60

Lys Asp Arg Phe Thr Ile Ser Arg Asp Asn Ala Lys Asn Thr Leu Tyr
65                  70                  75                  80

Leu Gln Met Asn Ser Leu Glu Ser Glu Asp Thr Ala Val Tyr Tyr Cys

```
                85                  90                  95
Ala Lys Arg Arg Asp Asn Tyr Tyr Gly Thr Ser Gly Glu Tyr Asp Tyr
            100                 105                 110

Trp Gly Gln Gly Thr Gln Val Thr Val Ser Ser
        115                 120

<210> SEQ ID NO 46
<211> LENGTH: 118
<212> TYPE: PRT
<213> ORGANISM: Artificial Sequence
<220> FEATURE:
<223> OTHER INFORMATION: Variable domain

<400> SEQUENCE: 46

Gln Val Gln Leu Gln Glu Ser Gly Gly Asp Leu Val Gln Pro Gly Gly
1               5                   10                  15

Ser Leu Arg Leu Ser Cys Ala Ala Ser Gly Phe Thr Phe Asp Asp Tyr
            20                  25                  30

Val Met Asn Trp Val Arg Gln Ala Pro Gly Lys Gly Leu Glu Trp Ile
        35                  40                  45

Ser Ala Ile Asn Trp Asn Gly Gly Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Tyr Ser Leu Gln Ser Asp Asp Thr Ala Val Tyr Tyr Cys
                85                  90                  95

Val Lys Asp Thr Val Val Ser Gly Asn Gly Tyr Trp Gly Gln Gly Thr
            100                 105                 110

Gln Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: Variable domain

<400> SEQUENCE: 47

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asp Asp Tyr
            20                  25                  30

Ala Met Ser Trp Val Arg Gln Ala Pro Gly Lys Gly Leu Glu Trp Val
        35                  40                  45

Ser Ala Ile Ser Trp Asn Gly Ser Ser Thr Tyr Tyr Ala Glu Ser Met
    50                  55                  60

Lys Gly Arg Phe Thr Ile Ser Arg Asp Asn Ala Lys Asn Thr Leu Tyr
65                  70                  75                  80

Leu Gln Met Asn Ser Leu Lys Ser Glu Asp Thr Ala Val Tyr Tyr Cys
                85                  90                  95

Ala Lys Asp Leu Ile Gly Ser His Asp Tyr Trp Gly Gln Gly Thr Gln
            100                 105                 110

Val Thr Val Ser Ser
        115

<210> SEQ ID NO 48
<211> LENGTH: 122
```

```
<212> TYPE: PRT
<213> ORGANISM: Artificial Sequence
<220> FEATURE:
<223> OTHER INFORMATION: Variable domain

<400> SEQUENCE: 48

Glu Val Gln Val Gln Glu Ser Gly Pro Gly Leu Val Lys Pro Ser Gln
1               5                   10                  15

Thr Leu Ser Leu Thr Cys Thr Val Ser Gly Gly Ser Met Thr Gly Asn
            20                  25                  30

Tyr Tyr Ala Trp Ser Trp Ile Arg Gln Pro Pro Gly Lys Gly Leu Glu
        35                  40                  45

Trp Met Gly Val Ile Ala Tyr Asp Gly Ser Thr Tyr Tyr Ser Pro Ser
50                  55                  60

Leu Lys Ser Arg Thr Ser Ile Ser Arg Asp Thr Ser Lys Asn Gln Phe
65                  70                  75                  80

Ser Leu Gln Leu Ser Ser Val Ser Pro Glu Asp Thr Ala Val Tyr Tyr
                85                  90                  95

Cys Ala Arg Gly Pro Gly Trp Tyr Ser Gly Ser Arg Asn Asp Tyr Trp
            100                 105                 110

Gly Gln Gly Thr Gln Val Thr Val Ser Ser
        115                 120

<210> SEQ ID NO 49
<211> LENGTH: 119
<212> TYPE: PRT
<213> ORGANISM: Artificial Sequence
<220> FEATURE:
<223> OTHER INFORMATION: Variable domain

<400> SEQUENCE: 49

Glu Val Gln Leu Val Gln Pro Gly Val Glu Leu Arg Asn Pro Gly Ala
1               5                   10                  15

Ser Val Lys Val Ser Cys Lys Ala Ser Gly Tyr Ile Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Asp Gly Gly Thr Lys Tyr Ala Gln Lys Phe
50                  55                  60

Gln Gly Arg Val Thr Phe Thr Ala Asp Thr Ser Thr Ser Thr Ala Tyr
65                  70                  75                  80

Val Glu Leu Asn Ser Leu Arg Ser Glu Asp Thr Ala Val Tyr Tyr Cys
                85                  90                  95

Ala Arg Val Asp Asp Tyr Tyr Leu Gly Tyr Asp Tyr Trp Gly Gln Gly
            100                 105                 110

Thr Gln Val Thr Val Ser Ser
        115

<210> SEQ ID NO 50
<211> LENGTH: 119
<212> TYPE: PRT
<213> ORGANISM: Artificial Sequence
<220> FEATURE:
<223> OTHER INFORMATION: Variable domain

<400> SEQUENCE: 50

Glu Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Asn Tyr
```

-continued

```
                20                  25                  30
Val Ile Asp Trp Val Arg Gln Ala Pro Gly Gln Gly Leu Glu Trp Met
             35                  40                  45
Gly Arg Ile Asp Pro Glu Asn Gly Gly Thr Arg Tyr Ala Gln Lys Phe
         50                  55                  60
Gln Gly Arg Val Thr Phe Thr Ala Asp Thr Ser Thr Ser Thr Ala Tyr
 65                  70                  75                  80
Val Glu Leu Ser Asn Leu Arg Ser Glu Asp Thr Ala Val Tyr Tyr Cys
                 85                  90                  95
Ala Arg Leu Glu Asp Tyr Glu Leu Ala Tyr Asp Tyr Trp Gly Gln Gly
            100                 105                 110
Thr Gln Val Thr Val Ser Ser
            115
```

<210> SEQ ID NO 51
<211> LENGTH: 127
<212> TYPE: PRT
<213> ORGANISM: Artificial Sequence
<220> FEATURE:
<223> OTHER INFORMATION: Variable domain

<400> SEQUENCE: 51

```
Gln Val Gln Leu Val Glu Ser Gly Pro Gly Leu Val Lys Pro Ser Gln
 1               5                  10                  15
Thr Leu Ser Leu Thr Cys Ala Val Ser Gly Gly Ser Ile Thr Thr Asn
             20                  25                  30
Tyr Tyr Tyr Trp Ser Trp Ile Arg Gln Ser Pro Gly Lys Gly Leu Glu
         35                  40                  45
Trp Met Gly Val Ile Ala Tyr Asp Gly Ser Thr Asp Tyr Ser Pro Ser
     50                  55                  60
Leu Lys Ser Arg Thr Ser Ile Ser Arg Asp Thr Ser Lys Asn Gln Phe
 65                  70                  75                  80
Ser Leu Gln Leu Ser Ser Val Thr Pro Glu Asp Thr Ala Val Tyr Tyr
                 85                  90                  95
Cys Ala Arg Asp Val Arg Val Ile Ala Thr Gly Trp Ala Thr Ala Asn
            100                 105                 110
Ala Leu Asp Ala Trp Gly Gln Gly Thr Leu Val Thr Val Ser Ser
        115                 120                 125
```

<210> SEQ ID NO 52
<211> LENGTH: 113
<212> TYPE: PRT
<213> ORGANISM: Artificial Sequence
<220> FEATURE:
<223> OTHER INFORMATION: Variable domain

<400> SEQUENCE: 52

```
Glu Ile Val Met Thr Gln Ser Pro Ser Val Thr Ala Ser Ala Gly
 1               5                  10                  15
Glu Lys Val Thr Ile Asn Cys Lys Ser Ser Gln Ser Val Leu Trp Arg
             20                  25                  30
Ser Asn Gln Lys Asn Tyr Leu Ala Trp Tyr Gln Gln Arg Leu Gly Gln
         35                  40                  45
Ser Pro Arg Leu Leu Ile Ser Trp Ala Ser Ile Arg Glu Ser Gly Val
     50                  55                  60
Pro Asp Arg Phe Ser Gly Ser Gly Ser Thr Thr Asp Phe Thr Leu Thr
 65                  70                  75                  80
```

```
Ile Ser Ser Phe Gln Pro Glu Asp Ala Ala Val Tyr Tyr Cys Gln Gln
                85                  90                  95

Gly Tyr Ser Phe Pro Tyr Thr Phe Gly Ser Gly Thr Arg Leu Glu Ile
            100                 105                 110

Lys

<210> SEQ ID NO 53
<211> LENGTH: 113
<212> TYPE: PRT
<213> ORGANISM: Artificial Sequence
<220> FEATURE:
<223> OTHER INFORMATION: Variable domain

<400> SEQUENCE: 53

Asp Ile Val Met Thr Gln Thr Pro Ser Val Thr Ala Ser Ala Gly
1               5                   10                  15

Glu Lys Val Thr Ile Asn Cys Lys Ser Ser Gln Ser Val Leu Leu Ser
                20                  25                  30

Ser Asn Gln Lys Asn Tyr Leu Ala Trp Tyr Gln Arg Leu Gly Gln
            35                  40                  45

Ser Pro Arg Leu Leu Ile Tyr Trp Ala Ser Thr Arg Glu Ser Gly Val
50                  55                  60

Pro Asp Arg Phe Ser Gly Ser Gly Ser Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Val Ser Phe Pro Leu Thr Phe Gly Gln Gly Thr Lys Val Glu Leu
            100                 105                 110

Lys

<210> SEQ ID NO 54
<211> LENGTH: 110
<212> TYPE: PRT
<213> ORGANISM: Artificial Sequence
<220> FEATURE:
<223> OTHER INFORMATION: Variable domain

<400> SEQUENCE: 54

Gln Ser Ala Leu Thr Gln Pro Pro Ser Val Ser Gly Ser Pro Gly Lys
1               5                   10                  15

Thr Val Thr Ile Ser Cys Thr Gly Thr Asn Ser Asp Val Gly Tyr Gly
                20                  25                  30

Asn Tyr Val Ser Trp Tyr Gln Gln Leu Pro Gly Met Ala Pro Lys Leu
            35                  40                  45

Leu Ile Tyr Asp Val Asn Arg Arg Ala Ser Gly Ile Ala Asp Arg Phe
50                  55                  60

Ser Gly Ser Lys Ser Gly Asn Thr Ala Ser Leu Thr Ile Ser Gly Leu
65                  70                  75                  80

Gln Ser Glu Asp Glu Gly Asp Tyr His Cys Ala Ser Tyr Arg Ser Ala
                85                  90                  95

Asn Asn Ala Val Phe Gly Gly Gly Thr His Leu Phe Val Leu
            100                 105                 110

<210> SEQ ID NO 55
<211> LENGTH: 111
<212> TYPE: PRT
<213> ORGANISM: Artificial Sequence
<220> FEATURE:
<223> OTHER INFORMATION: Variable domain
```

<400> SEQUENCE: 55

Gln Ser Val Leu Thr Gln Pro Pro Ser Val Gly Ser Pro Gly Lys
1               5                   10                  15

Thr Val Thr Ile Ser Cys Ala Gly Thr Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Phe Ala Val Ser Tyr Arg Ala Ser Gly Ile Pro Asp Arg Phe
    50                  55                  60

Ser Gly Ser Lys Ser Gly Asn Thr Ala Phe Leu Thr Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn Ala Ala Val Phe Gly Gly Gly Thr His Leu Thr Val Leu
            100                 105                 110

<210> SEQ ID NO 56
<211> LENGTH: 110
<212> TYPE: PRT
<213> ORGANISM: Artificial Sequence
<220> FEATURE:
<223> OTHER INFORMATION: Variable domain

<400> SEQUENCE: 56

Gln Ser Ala Leu Thr Gln Pro Pro Ser Val Gly Thr Leu Gly Lys
1               5                   10                  15

Thr Val Thr Ile Ser Cys Ala Gly Ser Ser Asp Ile Gly Asn Tyr
            20                  25                  30

Asn Tyr Val Ser Trp Tyr Gln Gln Leu Pro Gly Thr Ala Pro Lys Leu
        35                  40                  45

Leu Ile Tyr Glu Val Asn Lys Arg Pro Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn Val Val Phe Gly Gly Gly Thr Lys Leu Thr Val Leu
            100                 105                 110

<210> SEQ ID NO 57
<211> LENGTH: 110
<212> TYPE: PRT
<213> ORGANISM: Artificial Sequence
<220> FEATURE:
<223> OTHER INFORMATION: Variable domain

<400> SEQUENCE: 57

Gln Ser Val Leu Thr Gln Pro Pro Ser Val Gly Thr Leu Gly Lys
1               5                   10                  15

Thr Val Thr Ile Ser Cys Ala Gly Thr Ser Ser Asp Ile Gly Asp Tyr
            20                  25                  30

Asn Tyr Val Ser Trp Tyr Gln Gln Leu Pro Gly Thr Ala Pro Lys Leu
        35                  40                  45

Leu Ile Tyr Asp Val Asn Lys Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

```
Gln Ser Glu Asp Glu Ala Asp Tyr Tyr Cys Ala Ser Tyr Arg Ser Arg
                85                  90                  95

Asn Asp Tyr Ala Phe Gly Gly Gly Thr Lys Leu Thr Val Leu
            100                 105                 110

<210> SEQ ID NO 58
<211> LENGTH: 110
<212> TYPE: PRT
<213> ORGANISM: Artificial Sequence
<220> FEATURE:
<223> OTHER INFORMATION: Variable domain

<400> SEQUENCE: 58

Gln Ala Val Leu Thr Gln Pro Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Ala Val Ser Thr Arg Ala Ser Gly Ile Pro Asp Arg Phe
    50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn Tyr Ala Phe Gly Ala Gly Thr Lys Leu Thr Val Leu
            100                 105                 110

<210> SEQ ID NO 59
<211> LENGTH: 383
<212> TYPE: DNA
<213> ORGANISM: Artificial Sequence
<220> FEATURE:
<223> OTHER INFORMATION: Polynucleotide encoding variable domain

<400> SEQUENCE: 59
caggtgcagc tcgtggagtc gggcccaggc ctggtgaagc cctcgcagac actctccctc      60
acctgcgctg tctctggtgg ctccatcaca accaactatt actactggag ctggattcgc     120
cagtccccag ggaaggggct ggagtggatg ggagtcatag cttatgatgg cagcactgac     180
tacagcccat ccctcaagag ccgcacttcc atctccaggg acacgtccaa gaaccagttc     240
tccctgcagc tgagctctgt gacccctgag gacacggccg tgtattactg tgccagagat     300
gtaagggtaa tcgctacggg ttgggctact gccaatgctt tggacgcatg gggccagggg     360
accctggtca ctgtctcctc agc                                              383

<210> SEQ ID NO 60
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 60
gaggtccagc tggtgcagcc aggggttgaa ctgagaaacc ctggggcatc agtgaaggtc      60
tcctgcaagg cttctggata cattttcacc atgaactcaa tagactgggt gcgacaggcc     120
cctggacaag gcttgagtg gatgggaaga attgaccctg aagatggtgg cacaaagtat     180
gcacagaagt tccagggcag agtcaccttc actgcagaca cgtccaccag cacagcctac     240
```

```
gtggagctga acagtctgag atctgaggac acggccgtgt attactgtgc gagagtagat    300
gactattacc tagggtatga ctactggggc caggggaccc aggtcaccgt ctcctca       357

<210> SEQ ID NO 61
<211> LENGTH: 358
<212> TYPE: DNA
<213> ORGANISM: Artificial Sequence
<220> FEATURE:
<223> OTHER INFORMATION: Polynucleotide encoding variable domain

<400> SEQUENCE: 61
gaggtccagc tggtgcagcc aggggctgag ctgagaaacc ctggggcatc agtgaaggtc    60
tcctgcaagg cttctggata caccttcacc aactacgtca tagactgggt acgacaggcc   120
cctggacaag gcttgagtg gatgggaaga attgaccctg aaaacggtgg cacgaggtat    180
gcacagaagt tccagggcag agtcaccttc actgcagaca cgtccaccag cacagcctac   240
gtggagttga gcaatctgag atctgaggac acggccgtgt attactgtgc aagactggaa   300
gactacgaat tggcttatga ctactggggc caggggaccc aggtcaccgt ctcttcag     358

<210> SEQ ID NO 62
<211> LENGTH: 351
<212> TYPE: DNA
<213> ORGANISM: Artificial Sequence
<220> FEATURE:
<223> OTHER INFORMATION: Polynucleotide encoding variable domain

<400> SEQUENCE: 62
caggtgcagc tcgtggagtc tgggggaggc ttggtgcagc ctgggggtc tctgagactc     60 tcctgtgcag cctctggatt cacttttgat gattatgcca tgagctgggt ccgacaggct   120
ccagggaagg ggctggagtg ggtctcagct attagctgga atggtagtag cacatactat   180
gcagaatcca tgaagggccg attcaccatc tccagagaca acgccaagaa cacgctgtat   240
ctgcaaatga acagtctgaa atctgaggac acggccgtgt attactgtgc aaaagatcta   300
ataggatccc atgactactg ggccagggg acccaggtca ccgtgtcctc a            351

<210> SEQ ID NO 63
<211> LENGTH: 369
<212> TYPE: DNA
<213> ORGANISM: Artificial Sequence
<220> FEATURE:
<223> OTHER INFORMATION: Polynucleotide encoding variable domain

<400> SEQUENCE: 63
cagttgcagc tggtggagtc tgggggaggc atggcgcagc ctgggggtc tctgaaactc     60 tcctgtgcag cctctggatt cactttcgat gattatgcca tgacctgggt ccgacaggct   120
ccagggaagg ggctggagtg gctctcaact attagctgga atgacattaa cacatactat   180
gcagaatcca tgaaggaccg attcaccatc tccagagaca acgccaagaa cacgctgtat   240
ctgcaaatga acagtctcga atctgaggac acggccgtgt attactgtgc aaaacgtagg   300
gataattact acgggacttc cggggagtat gactactggg gccaggggac ccaggtcacc   360
gtctcctca                                                          369

<210> SEQ ID NO 64
<211> LENGTH: 354
<212> TYPE: DNA
<213> ORGANISM: Artificial Sequence
<220> FEATURE:
```

<223> OTHER INFORMATION: Polynucleotide encoding variable domain

<400> SEQUENCE: 64

| | |
|---|---|
| caggtgcagc tgcaggagtc ggggggagac ttggtgcagc cggggggtc tctgagactc | 60 |
| tcctgtgcag cctctggatt cacttttgat gattatgtca tgaactgggt ccgacaggct | 120 |
| ccagggaagg ggctggagtg gatctcagct attaactgga atggtggtag cacatactat | 180 |
| gcagaatcca tgaagggccg attcaccatc tccagagaca cgccaagaa cacgctgtat | 240 |
| ctgcaaatgt acagtctgca atctgacgac acggccgtgt attactgtgt aaaagatacg | 300 |
| gtagtgtctg gtaatggcta ctggggccag gggacccagg tcaccgtgtc ctca | 354 |

<210> SEQ ID NO 65
<211> LENGTH: 333
<212> TYPE: DNA
<213> ORGANISM: Artificial Sequence
<220> FEATURE:
<223> OTHER INFORMATION: Polynucleotide encoding variable domain

<400> SEQUENCE: 65

| | |
|---|---|
| cagtctgtgt tgacgcagcc tccctccgtg tctgggtctc caggaaagac ggtcaccatc | 60 |
| tcctgtgcag gaaccagcag tgatgttggg tatggaaact atgtctcctg gtaccagcag | 120 |
| ctcccaggca cggccccca actcctgatc tttgcagtca gctatcgagc ctcagggatc | 180 |
| cctgatcgct tctctggctc caagtcaggc aacacggcct ttttgaccat ctctgggctc | 240 |
| cagtccgagg acgaggctga ttattactgt gcctcatata aagcagcaa caatgctgct | 300 |
| gtgttcggcg agggaccca tctgaccgtc ctg | 333 |

<210> SEQ ID NO 66
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 66

| | |
|---|---|
| gaaattgtga tgacgcagtc tcccagctcc gtgactgcgt ctgcaggaga aaggtcacc | 60 |
| atcaattgta agtccagcca gagtgtgtta tggcgctcca accagaaaaa ctacttagct | 120 |
| tggtaccagc agagacttgg acagtctcct aggctgctca tcagctgggc atccatccga | 180 |
| gaatcggggg ttcctgatcg attcagcggc agtgggtcca acagatttt cactcttacc | 240 |
| atcagcagct tccagcctga agacgcggca gtgtattact gccaacaggg ttatagtttt | 300 |
| ccatatacat tcggcagtgg gaccaggctg gaaatcaaa | 339 |

<210> SEQ ID NO 67
<211> LENGTH: 330
<212> TYPE: DNA
<213> ORGANISM: Artificial Sequence
<220> FEATURE:
<223> OTHER INFORMATION: Polynucleotide encoding variable domain

<400> SEQUENCE: 67

| | |
|---|---|
| cagtctgccc tgactcagcc tccctccgtg tccggaactc tgggaaagac ggtcaccatc | 60 |
| tcttgcgctg gaaccagcag tgacattggg aactataact atgtctcctg gtatcaacag | 120 |
| ctcccaggaa cagcccccaa actcctgata tatgaggtca ataaaccgacc ctcagggatc | 180 |
| cctgatcgct tctctggctc caagtcaggc aacacggcct ccctgagcat ctctgggctc | 240 |
| cagtctgagg acgaggctga ttattactgt gcctcatata aagcagcaa caatgttgtg | 300 |

```
ttcggcggag ggaccaagct gaccgtcctc                                    330

<210> SEQ ID NO 68
<211> LENGTH: 330
<212> TYPE: DNA
<213> ORGANISM: Artificial Sequence
<220> FEATURE:
<223> OTHER INFORMATION: Polynucleotide encoding variable domain

<400> SEQUENCE: 68
cagtctgtgt tgacgcagcc tccctccgtg tccggaactc tgggaaagac ggtcaccatc    60
tcctgcgctg gaaccagcag tgacattggg gactataact atgtctcctg gtatcaacag   120
ctcccaggaa cggcccccaa actcctgata tatgacgtca ataaacgagc ctcagggatc   180
cctgatcgct tctctggctc caagtcaggc aacacggcct ccctgagcat ctctgggctc   240
cagtctgagg acgaggctga ttattactgt gcctcatata aagcaggaa cgattatgcc    300 ttcggcggag ggaccaagct gaccgtcctc                                    330

<210> SEQ ID NO 69
<211> LENGTH: 330
<212> TYPE: DNA
<213> ORGANISM: Artificial Sequence
<220> FEATURE:
<223> OTHER INFORMATION: Polynucleotide encoding variable domain

<400> SEQUENCE: 69
caggctgtgc tgactcagcc tccctccgtg tccggaactc tgggaaagac gctcaccatc    60
tcctgcgctg gaaccagcag tgatgttgga tacggaaact atgtctcctg gtaccaacag   120
ctcccaggca cggcccccaa actcctgatc tatgcagtca gcactcgagc ctcagggatc   180
cctgatcgct tctctggctc caagtcaggc aacacggcct ccctgaccat ctctgggctc   240
cagtctgagg acgaggctga ttattactgt gcctcatata aagcagcaa caattatgcg    300 ttcggcgcag ggaccaagct gaccgtcctc                                    330

<210> SEQ ID NO 70
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 70
gatattgtga tgacccagac tcccagctcc gtgactgcgt ctgcaggaga gaaggtcacc    60
atcaattgta gtccagcca gagtgtgtta ttgagctcca accagaaaaa ctacttagct   120
tggtaccagc agagacttgg acagtctcct aggctgctca tctactgggc atccacccga   180
gaatcggggg ttcctgatcg attcagcggc agtgggtcca acagattt cactcttacc    240 atcagcagct ccagcctga agacgcggca gtgtattact gccagcaggg tgtaagtttt    300
ccacttacgt tcggccaggg gaccaaggtg gaactcaaa                         339

<210> SEQ ID NO 71
<211> LENGTH: 5
<212> TYPE: PRT
<213> ORGANISM: Artificial Sequence
<220> FEATURE:
<223> OTHER INFORMATION: CDR Sequence

<400> SEQUENCE: 71
```

Ser Tyr Ala Met Ser
1               5

<210> SEQ ID NO 72
<211> LENGTH: 16
<212> TYPE: PRT
<213> ORGANISM: Artificial Sequence
<220> FEATURE:
<223> OTHER INFORMATION: CDR Sequence

<400> SEQUENCE: 72

Gly Ile Tyr Lys Gly Gly Gly Pro Lys Tyr Ala Asn Ser Val Lys Gly
1               5                   10                  15

<210> SEQ ID NO 73
<211> LENGTH: 12
<212> TYPE: PRT
<213> ORGANISM: Artificial Sequence
<220> FEATURE:
<223> OTHER INFORMATION: CDR Sequence

<400> SEQUENCE: 73

Ser Gly Tyr Gly Ser Ser Leu Gly Asp Phe Gly Ser
1               5                   10

<210> SEQ ID NO 74
<211> LENGTH: 14
<212> TYPE: PRT
<213> ORGANISM: Artificial Sequence
<220> FEATURE:
<223> OTHER INFORMATION: CDR Sequence

<400> SEQUENCE: 74

Thr Gly Ser Ser Ser Asn Ile Gly Gly Gly Tyr Tyr Leu Ser
1               5                   10

<210> SEQ ID NO 75
<211> LENGTH: 7
<212> TYPE: PRT
<213> ORGANISM: Artificial Sequence
<220> FEATURE:
<223> OTHER INFORMATION: CDR Sequence

<400> SEQUENCE: 75

Ser Asn Ile Asn Arg Ala Ser
1               5

<210> SEQ ID NO 76
<211> LENGTH: 11
<212> TYPE: PRT
<213> ORGANISM: Artificial Sequence
<220> FEATURE:
<223> OTHER INFORMATION: CDR Sequence

<400> SEQUENCE: 76

Ser Ser Trp Asp Asp Ser Val Ser Gly Pro Val
1               5                   10

<210> SEQ ID NO 77
<211> LENGTH: 120
<212> TYPE: PRT
<213> ORGANISM: Artificial Sequence
<220> FEATURE:
<223> OTHER INFORMATION: Variable domain

<400> SEQUENCE: 77

Glu Leu Gln Leu Val Glu Ser Gly Gly Ala Leu Val Gln Pro Gly Gly

```
              1               5              10              15
            Ser Leu Arg Leu Ser Cys Val Glu Ser Gly Phe Thr Phe Ser Ser Tyr
                           20                  25                  30

Ala Met Ser Trp Val Arg Gln Ala Pro Gly Lys Gly Leu Glu Trp Val
                           35                  40                  45

Ser Gly Ile Tyr Lys Gly Gly Pro Lys Tyr Ala Asn Ser Val Lys
             50                  55                  60

Gly Arg Phe Thr Ile Ser Arg Asp Asn Ala Lys Asn Thr Leu Tyr Leu
             65                  70                  75                  80

Gln Met Asn Ser Leu Lys Pro Glu Asp Thr Ala Val Tyr Tyr Cys Ala
                           85                  90                  95

Lys Ser Gly Tyr Gly Ser Ser Leu Gly Asp Phe Gly Ser Trp Gly Gln
                          100                 105                 110

Gly Thr Gln Val Thr Val Ser Ser
                          115                 120

<210> SEQ ID NO 78
<211> LENGTH: 111
<212> TYPE: PRT
<213> ORGANISM: Artificial Sequence
<220> FEATURE:
<223> OTHER INFORMATION: Variable domain

<400> SEQUENCE: 78

Gln Ala Gly Leu Thr Gln Leu Ser Ser Met Ser Gly Ser Pro Gly Gln
 1               5                  10                  15

Thr Val Thr Ile Thr Cys Thr Gly Ser Ser Ser Asn Ile Gly Gly Gly
                20                  25                  30

Tyr Tyr Leu Ser Trp Tyr Gln His Leu Pro Gly Thr Ala Pro Lys Leu
                35                  40                  45

Leu Ile Tyr Ser Asn Ile Asn Arg Ala Ser Gly Val Pro Asp Arg Phe
             50                  55                  60

Ser Gly Ser Thr Ser Gly Ile Ser Ala Ser Leu Thr Ile Thr Gly Leu
 65                  70                  75                  80

Gln Ala Glu Asp Glu Ala Asp Tyr Tyr Cys Ser Ser Trp Asp Asp Ser
                85                  90                  95

Val Ser Gly Pro Val Phe Gly Gly Gly Thr Ser Leu Thr Val Leu
               100                 105                 110

<210> SEQ ID NO 79
<211> LENGTH: 360
<212> TYPE: DNA
<213> ORGANISM: Artificial Sequence
<220> FEATURE:
<223> OTHER INFORMATION: Polynucleotide encoding variable domain

<400> SEQUENCE: 79
gagttgcagc tggtggagtc tgggggagcc ttggtgcagc ctgggggtc tctgagactc         60 tcctgtgtag agtctggatt caccttcagt agttatgcca tgagctgggt ccgccaggct       120
ccaggaaagg ggctcgagtg gtctcaggt atttataaag gtggtggtcc aaaatatgca       180
aactccgtga agggccgatt caccatctcc agagacaacg ccaagaacac gctgtatctg       240
caaatgaaca gcctgaaacc tgaggacacg gccgtttatt actgtgcaaa atcggggtac       300
ggtagtagcc ttggggactt tggttcctgg ggccagggga cccaggtcac cgtctcctcg       360

<210> SEQ ID NO 80
<211> LENGTH: 366
```

```
<212> TYPE: DNA
<213> ORGANISM: Artificial Sequence
<220> FEATURE:
<223> OTHER INFORMATION: Polynucleotide encoding variable domain

<400> SEQUENCE: 80
gaggtgcagg tgcaggagtc gggcccaggc ctggtgaagc cctcgcagac gctctccctc      60
acctgcactg tctctggtgg ctccatgaca ggcaactatt atgcttggag ctggatccgc     120
cagcccccag ggaaggggct ggagtggatg ggagtcatag cttatgatgg cagcacttac     180
tacagcccat ccctcaagag ccgcacttct atctccaggg acacgtccaa gaaccagttc     240
tccctgcagt tgagctctgt gagccctgag gacacggccg tgtattactg tgccagaggc     300
ccagggtggt atagtggtag caggaatgac tactggggcc aggggaccca ggtcaccgtc     360
tcctca                                                                 366

<210> SEQ ID NO 81
<211> LENGTH: 336
<212> TYPE: DNA
<213> ORGANISM: Artificial Sequence
<220> FEATURE:
<223> OTHER INFORMATION: Polynucleotide encoding variable domain

<400> SEQUENCE: 81
gcacaggcag ggctgactca gctgtcctcc atgtctggat ccccgggcca gacggtcacc      60
atcacctgca caggaagcag cagcaacatc ggggtggtt attatttgag ctggtaccaa     120
catctgccag gaacggcccc caaactcctg atctacagta acatcaatag gcctcgggg     180 gtcccggacc gcttctctgg ctccacgtcg ggcatctcgg cctccctgac tatcactggg     240
ctccaggctg aggacgaggc tgactattac tgttcatcct gggatgacag cgtcagtggt     300
cctgtgttcg gcggagggac cagtctgacc gtcctc                                336

<210> SEQ ID NO 82
<211> LENGTH: 330
<212> TYPE: DNA
<213> ORGANISM: Artificial Sequence
<220> FEATURE:
<223> OTHER INFORMATION: Polynucleotide encoding variable domain

<400> SEQUENCE: 82
cagtctgccc tgactcagcc tccctccgtg tctgggtctc caggaaagac ggtcaccatc      60
tcctgtacag gaaccaacag tgatgttggg tacggaaact atgtctcctg gtaccagcag     120
ctcccaggaa tggcccccaa actcctgata tatgacgtca atagacgggc ctcagggatc     180
gctgatcgct tctctggctc caagtctggc aacacggcct ccctgaccat ttctgggctc     240
cagtctgagg acgagggtga ttatcattgt gcctcatata gaagtgccaa caatgctgtg     300
ttcggcggag ggacccatct gttcgtcctg                                       330

<210> SEQ ID NO 83
<211> LENGTH: 16
<212> TYPE: PRT
<213> ORGANISM: Artificial Sequence
<220> FEATURE:
<223> OTHER INFORMATION: CDR Sequence

<400> SEQUENCE: 83

Val Ile Ala Tyr Glu Gly Ser Thr Asp Tyr Ser Pro Ser Leu Lys Ser
  1               5                  10                  15
```

<210> SEQ ID NO 84
<211> LENGTH: 16
<212> TYPE: PRT
<213> ORGANISM: Artificial Sequence
<220> FEATURE:
<223> OTHER INFORMATION: CDR Sequence

<400> SEQUENCE: 84

```
Val Ile Ala Tyr Asp Ala Ser Thr Asp Tyr Ser Pro Ser Leu Lys Ser
 1               5                  10                  15
```

<210> SEQ ID NO 85
<211> LENGTH: 17
<212> TYPE: PRT
<213> ORGANISM: Artificial Sequence
<220> FEATURE:
<223> OTHER INFORMATION: CDR Sequence

<400> SEQUENCE: 85

```
Arg Ile Asp Pro Glu Glu Gly Gly Thr Lys Tyr Ala Gln Lys Phe Gln
 1               5                  10                  15

Gly
```

<210> SEQ ID NO 86
<211> LENGTH: 17
<212> TYPE: PRT
<213> ORGANISM: Artificial Sequence
<220> FEATURE:
<223> OTHER INFORMATION: CDR Sequence

<400> SEQUENCE: 86

```
Lys Ser Ser Gln Ser Val Leu Phe Ser Ser Asn Gln Lys Asn Tyr Leu
 1               5                  10                  15

Ala
```

<210> SEQ ID NO 87
<211> LENGTH: 9
<212> TYPE: PRT
<213> ORGANISM: Artificial Sequence
<220> FEATURE:
<223> OTHER INFORMATION: CDR Sequence

<400> SEQUENCE: 87

```
Gln Gln Gly Tyr Ser Phe Pro Tyr Ser
 1               5
```

<210> SEQ ID NO 88
<211> LENGTH: 127
<212> TYPE: PRT
<213> ORGANISM: Artificial Sequence
<220> FEATURE:
<223> OTHER INFORMATION: Variable domain

<400> SEQUENCE: 88

```
Gln Val Gln Leu Val Glu Ser Gly Pro Gly Leu Val Lys Pro Ser Gln
 1               5                  10                  15

Thr Leu Ser Leu Thr Cys Ala Val Ser Gly Gly Ser Ile Thr Thr Asn
                20                  25                  30

Tyr Tyr Tyr Trp Ser Trp Ile Arg Gln Ser Pro Gly Lys Gly Leu Glu
            35                  40                  45

Trp Met Gly Val Ile Ala Tyr Asp Gly Ser Thr Asp Tyr Ser Pro Ser
        50                  55                  60

Leu Lys Ser Arg Thr Ser Ile Ser Arg Asp Thr Ser Lys Asn Gln Phe
65                  70                  75                  80
```

Ser Leu Gln Leu Ser Ser Val Thr Pro Glu Asp Thr Ala Val Tyr Tyr
                85                  90                  95

Cys Ala Arg Asp Val Arg Val Ile Ala Thr Gly Trp Ala Thr Ala Asn
            100                 105                 110

Ala Leu Asp Ala Trp Gly Gln Gly Thr Gln Val Thr Val Ser Ser
        115                 120                 125

<210> SEQ ID NO 89
<211> LENGTH: 113
<212> TYPE: PRT
<213> ORGANISM: Artificial Sequence
<220> FEATURE:
<223> OTHER INFORMATION: Variable domain

<400> SEQUENCE: 89

Asp Ile Val Met Thr Gln Thr Pro Thr Ser Val Thr Ala Ser Ala Gly
1               5                   10                  15

Asp Lys Val Thr Ile Asn Cys Lys Ser Ser Gln Ser Val Leu Phe Ser
            20                  25                  30

Ser Asn Gln Lys Asn Tyr Leu Ala Trp Tyr Gln Gln Arg Leu Gly Gln
        35                  40                  45

Ser Pro Arg Leu Leu Ile Tyr Trp Ala Ser Ile Arg Glu Ser Gly Val
    50                  55                  60

Pro Asp Arg Phe Ser Gly Ser Gly Ser Ala Thr Asp Phe Thr Leu Thr
65                  70                  75                  80

Ile Ser Asn Phe Gln Pro Glu Asp Ala Ala Val Tyr Tyr Cys Gln Gln
                85                  90                  95

Gly Tyr Ser Phe Pro Tyr Ser Phe Gly Ser Gly Thr Arg Leu Glu Ile
            100                 105                 110

Arg

<210> SEQ ID NO 90
<211> LENGTH: 381
<212> TYPE: DNA
<213> ORGANISM: Artificial Sequence
<220> FEATURE:
<223> OTHER INFORMATION: Polynucleotide encoding variable domain

<400> SEQUENCE: 90
caggtgcagc tcgtggagtc gggcccaggc ctggtgaagc cctcgcagac actctccctc      60
acctgcgctg tctctggtgg ctccatcaca accaactatt actactggag ctggattcgc     120
cagtccccag ggaaggggct ggagtggatg ggagtcatag cttatgatgg cagcactgac     180
tacagcccat ccctcaagag ccgcacttcc atctccaggg acacgtccaa gaaccagttc     240
tccctgcagc tgagctctgt gacccctgag gacacggccg tgtattactg tgccagagat     300
gtaagggtaa tcgctacggg ttgggctact gccaatgctt tggacgcatg ggggccagggg   360 acccaggtca ccgtgtcctc a                                               381

<210> SEQ ID NO 91
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 91
gatattgtga tgacccagac tcccacctcc gtgactgcat ctgcaggaga caaggtcacc      60

| | | |
|---|---|---|
| atcaattgta agtccagcca gagtgtgtta ttcagctcca accagaaaaa ctacttagct | | 120 |
| tggtaccagc agagacttgg acagtctcct aggctgctca tctactgggc ttccatccga | | 180 |
| gaatcggggg ttcctgatcg attcagcggc agtgggtccg caacagattt cacgctaacc | | 240 |
| atcagcaact ccagcctga agacgcggca gtatattact gccagcaggg ttatagtttt | | 300 |
| ccatatagtt tcggcagtgg gaccaggctg gaaatcaga | | 339 |

<210> SEQ ID NO 92
<211> LENGTH: 127
<212> TYPE: PRT
<213> ORGANISM: Artificial Sequence
<220> FEATURE:
<223> OTHER INFORMATION: Variable domain

<400> SEQUENCE: 92

Gln Val Gln Leu Val Glu Ser Gly Pro Gly Leu Val Lys Pro Ser Gln
1               5                   10                  15

Thr Leu Ser Leu Thr Cys Thr Val Ser Gly Gly Ser Ile Ser Thr Asn
            20                  25                  30

Tyr Tyr Tyr Trp Ser Trp Ile Arg Gln Ser Pro Gly Lys Gly Leu Glu
        35                  40                  45

Trp Ile Gly Val Ile Ala Tyr Glu Gly Ser Thr Asp Tyr Ser Pro Ser
    50                  55                  60

Leu Lys Ser Arg Val Thr Ile Ser Arg Asp Thr Ser Lys Asn Gln Phe
65                  70                  75                  80

Ser Leu Lys Leu Ser Ser Val Thr Ala Glu Asp Thr Ala Val Tyr Tyr
                85                  90                  95

Cys Ala Arg Asp Val Arg Val Ile Ala Thr Gly Trp Ala Thr Ala Asn
            100                 105                 110

Ala Leu Asp Ala Trp Gly Gln Gly Thr Leu Val Thr Val Ser Ser
        115                 120                 125

<210> SEQ ID NO 93
<211> LENGTH: 111
<212> TYPE: PRT
<213> ORGANISM: Artificial Sequence
<220> FEATURE:
<223> OTHER INFORMATION: Variable domain

<400> SEQUENCE: 93

Gln Ser Ala Leu Thr Gln Pro Pro Ser Val Ser Gly Ser Pro Gly Gln
1               5                   10                  15

Ser Val Thr Ile Ser Cys Ala Gly Thr Ser Ser Asp Val Gly Tyr Gly
            20                  25                  30

Asn Tyr Val Ser Trp Tyr Gln Gln Pro Pro Gly Thr Ala Pro Lys Leu
        35                  40                  45

Leu Ile Phe Ala Val Ser Tyr Arg Ala Ser Gly Val Pro Asp Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ala Ser Tyr Arg Ser Ser
                85                  90                  95

Asn Asn Ala Ala Val Phe Gly Gly Gly Thr Lys Leu Thr Val Leu
            100                 105                 110

<210> SEQ ID NO 94
<211> LENGTH: 127
<212> TYPE: PRT

-continued

<213> ORGANISM: Artificial Sequence
<220> FEATURE:
<223> OTHER INFORMATION: Variable domain

<400> SEQUENCE: 94

Gln Val Gln Leu Gln Glu Ser Gly Pro Gly Leu Val Lys Pro Ser Gln
1               5                   10                  15

Thr Leu Ser Leu Thr Cys Ala Val Ser Gly Gly Ser Ile Ser Thr Asn
            20                  25                  30

Tyr Tyr Tyr Trp Ser Trp Ile Arg Gln His Pro Gly Lys Gly Leu Glu
        35                  40                  45

Trp Ile Gly Val Ile Ala Tyr Glu Gly Ser Thr Asp Tyr Ser Pro Ser
    50                  55                  60

Leu Lys Ser Arg Val Thr Ile Ser Val Asp Thr Ser Lys Asn Gln Phe
65                  70                  75                  80

Ser Leu Gln Leu Ser Ser Val Thr Pro Glu Asp Thr Ala Val Tyr Tyr
                85                  90                  95

Cys Ala Arg Asp Val Arg Val Ile Ala Thr Gly Trp Ala Thr Ala Asn
            100                 105                 110

Ala Leu Asp Ala Trp Gly Gln Gly Thr Leu Val Thr Val Ser Ser
        115                 120                 125

<210> SEQ ID NO 95
<211> LENGTH: 111
<212> TYPE: PRT
<213> ORGANISM: Artificial Sequence
<220> FEATURE:
<223> OTHER INFORMATION: Variable domain

<400> SEQUENCE: 95

Gln Ser Ala Leu Thr Gln Pro Arg Ser Val Ser Gly Ser Pro Gly Gln
1               5                   10                  15

Ser Val Thr Ile Ser Cys Ala Gly Thr Ser Ser Asp Val Gly Tyr Gly
            20                  25                  30

Asn Tyr Val Ser Trp Tyr Gln Gln His Pro Gly Thr Ala Pro Lys Leu
        35                  40                  45

Met Ile Phe Ala Val Ser Tyr Arg Ala Ser Gly Ile Pro Asp Arg Phe
    50                  55                  60

Ser Gly Ser Lys Ser Gly Asn Thr Ala Phe Leu Thr Ile Ser Gly Leu
65                  70                  75                  80

Gln Ala Glu Asp Glu Ala Asp Tyr Tyr Cys Ala Ser Tyr Arg Ser Ser
                85                  90                  95

Asn Asn Ala Ala Val Phe Gly Gly Gly Thr Lys Leu Thr Val Leu
            100                 105                 110

<210> SEQ ID NO 96
<211> LENGTH: 127
<212> TYPE: PRT
<213> ORGANISM: Artificial Sequence
<220> FEATURE:
<223> OTHER INFORMATION: Variable domain

<400> SEQUENCE: 96

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
            20                  25                  30

Tyr Tyr Tyr Trp Ser Trp Ile Arg Gln Ser Pro Gly Lys Gly Leu Glu
        35                  40                  45

```
Trp Ile Gly Val Ile Ala Tyr Glu Gly Ser Thr Asp Tyr Ser Pro Ser
         50                  55                  60

Leu Lys Ser Arg Val Thr Ile Ser Arg Asp Thr Ser Lys Asn Gln Phe
65                  70                  75                  80

Ser Leu Gln Leu Ser Ser Val Thr Ala Glu Asp Thr Ala Val Tyr Tyr
                 85                  90                  95

Cys Ala Arg Asp Val Arg Val Ile Ala Thr Gly Trp Ala Thr Ala Asn
                100                 105                 110

Ala Leu Asp Ala Trp Gly Gln Gly Thr Leu Val Thr Val Ser Ser
            115                 120                 125

<210> SEQ ID NO 97
<211> LENGTH: 111
<212> TYPE: PRT
<213> ORGANISM: Artificial Sequence
<220> FEATURE:
<223> OTHER INFORMATION: Variable domain

<400> SEQUENCE: 97

Gln Ser Val Leu Thr Gln Pro Pro Ser Val Ser Gly Ser Pro Gly Gln
1               5                   10                  15

Thr Val Thr Ile Ser Cys Ala Gly Thr Ser Ser Asp Val Gly Tyr Gly
                20                  25                  30

Asn Tyr Val Ser Trp Tyr Gln Gln Leu Pro Gly Thr Ala Pro Lys Leu
            35                  40                  45

Met Ile Phe Ala Val Ser Tyr Arg Ala Ser Gly Ile Pro Asp Arg Phe
        50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ser Ser
                85                  90                  95

Asn Asn Ala Ala Val Phe Gly Gly Gly Thr Lys Leu Thr Val Leu
            100                 105                 110

<210> SEQ ID NO 98
<211> LENGTH: 127
<212> TYPE: PRT
<213> ORGANISM: Artificial Sequence
<220> FEATURE:
<223> OTHER INFORMATION: Variable domain

<400> SEQUENCE: 98

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Thr Thr Asn
                20                  25                  30

Tyr Tyr Tyr Trp Ser Trp Ile Arg Gln Ser Pro Gly Lys Gly Leu Glu
            35                  40                  45

Trp Ile Gly Val Ile Ala Tyr Asp Ala Ser Thr Asp Tyr Ser Pro Ser
        50                  55                  60

Leu Lys Ser Arg Val Thr Ile Ser Arg Asp Thr Ser Lys Asn Gln Phe
65                  70                  75                  80

Ser Leu Gln Leu Ser Ser Val Thr Ala Glu Asp Thr Ala Val Tyr Tyr
                85                  90                  95

Cys Ala Arg Asp Val Arg Val Ile Ala Thr Gly Trp Ala Thr Ala Asn
                100                 105                 110

Ala Leu Asp Ala Trp Gly Gln Gly Thr Leu Val Thr Val Ser Ser
```

<210> SEQ ID NO 99
<211> LENGTH: 111
<212> TYPE: PRT
<213> ORGANISM: Artificial Sequence
<220> FEATURE:
<223> OTHER INFORMATION: Variable domain

<400> SEQUENCE: 99

Gln Ser Val Leu Thr Gln Pro Pro Ser Val Ser Gly Ser Pro Gly Gln
1               5                   10                  15
Thr Val Thr Ile Ser Cys Ala Gly Thr Ser Ser Asp Val Gly Tyr Gly
            20                  25                  30
Asn Tyr Val Ser Trp Tyr Gln Gln Pro Pro Gly Thr Ala Pro Lys Leu
        35                  40                  45
Met Ile Phe Ala Val Ser Tyr Arg Ala Ser Gly Ile Pro Asp Arg Phe
    50                  55                  60
Ser Gly Ser Lys Ser Gly Asn Thr Ala Phe Leu Thr Ile Ser Gly Leu
65                  70                  75                  80
Gln Ser Glu Asp Glu Ala Asp Tyr Tyr Cys Ala Ser Tyr Arg Ser Ser
                85                  90                  95
Asn Asn Ala Ala Val Phe Gly Gly Gly Thr Lys Leu Thr Val Leu
            100                 105                 110

<210> SEQ ID NO 100
<211> LENGTH: 381
<212> TYPE: DNA
<213> ORGANISM: Artificial Sequence
<220> FEATURE:
<223> OTHER INFORMATION: Polynucleotide encoding variable domain

<400> SEQUENCE: 100
caggtgcagc tcgtggagtc gggcccaggc ctggtgaagc cctcgcagac actctccctc    60
acctgcacag tctctggtgg ctccatcagc accaactatt actactggag ctggattcgc   120
cagtcgccag ggaagggct ggagtggatt ggagtcatag cttatgaagg cagcactgac   180
tacagcccat ccctcaagag ccgcgtgacc atctccaggg acacgtccaa aaaccagttc   240
tccctgaaac tgagctctgt gaccgcggag gacacggccg tgtattactg tgccagagat   300
gtaagggtaa tcgctacggg ttgggctact gccaatgctt ggacgcatg gggccagggg   360
accctggtca ccgtgtcctc a                                             381

<210> SEQ ID NO 101
<211> LENGTH: 333
<212> TYPE: DNA
<213> ORGANISM: Artificial Sequence
<220> FEATURE:
<223> OTHER INFORMATION: Polynucleotide encoding variable domain

<400> SEQUENCE: 101
cagtctgcgt tgacgcagcc tccttccgtg tctgggtctc aggacaaag cgtcaccatc     60
tcctgtgcag gaaccagcag tgatgttggg tatggaaact atgtctcctg gtaccagcag   120
ccgccaggca cggcccccaa actcctgatc tttgcagtca gctatcgagc ctcaggggtt   180
cctgatcgct tctctggctc caagtcaggc aacacggcct ttttgaccat ctctgggctc   240
caggctgagg acgaggctga ttattactgt gcctcatata agcagcaa caatgctgct    300
gtgttcggcg gagggaccaa actgaccgtc cta                                333

<210> SEQ ID NO 102
<211> LENGTH: 381
<212> TYPE: DNA
<213> ORGANISM: Artificial Sequence
<220> FEATURE:
<223> OTHER INFORMATION: Polynucleotide encoding variable domain

<400> SEQUENCE: 102
caggtgcagc tccaggagtc gggcccaggc ctggtgaagc cctcgcagac actctccctc     60
acctgcgcag tctctggtgg ctccatcagc accaactatt actactggag ctggattcgc    120
cagcatccag ggaaggggct ggagtggatt ggagtcatag cttatgaagg cagcactgac    180
tacagcccat ccctcaagag ccgcgtgacc atctccgtgg acacgtccaa gaaccagttc    240
tccctgcaac tgagctctgt gaccccggag gacacggccg tgtattactg tgccagagat    300
gtaagggtaa tcgctacggg ttgggctact gccaatgctt tggacgcatg gggccagggg    360
accctggtca ccgtgtcctc a                                              381

<210> SEQ ID NO 103
<211> LENGTH: 333
<212> TYPE: DNA
<213> ORGANISM: Artificial Sequence
<220> FEATURE:
<223> OTHER INFORMATION: Polynucleotide encoding variable domain

<400> SEQUENCE: 103
cagtctgcgt tgacgcagcc tcgttccgtg tctgggtctc caggacaaag cgtcaccatc     60
tcctgtgcag gaaccagcag tgatgttggg tatggaaact atgtctcctg gtaccagcag    120
catccaggca cggccccccaa actcatgatc tttgcagtca gctatcgagc ctcagggatt    180
cctgatcgct tctctggctc caagtcaggc aacacggcct tttgaccat ctctgggctc    240 caggctgagg acgaggctga ttattactgt gcctcatata aagcagcaa caatgctgct    300 gtgttcggcg gagggaccaa actgaccgtc cta                                 333

<210> SEQ ID NO 104
<211> LENGTH: 381
<212> TYPE: DNA
<213> ORGANISM: Artificial Sequence
<220> FEATURE:
<223> OTHER INFORMATION: Polynucleotide encoding variable domain

<400> SEQUENCE: 104
caggtgcagc tccaggagtc gggcccaggc ctggtgaagc cctcgcagac actctccctc     60
acctgcacag tctctggtgg ctccatcacc accaactatt actactggag ctggattcgc    120
cagtctccag ggaaggggct ggagtggatt ggagtcatag cttatgaagg cagcactgac    180
tacagcccat ccctcaagag ccgcgtgacc atctccaggg acacgtccaa gaaccagttc    240
tccctgcaac tgagctctgt gaccgcggag gacacggccg tgtattactg tgccagagat    300
gtaagggtaa tcgctacggg ttgggctact gccaatgctt tggacgcatg gggccagggg    360
accctggtca ccgtgtcctc a                                              381

<210> SEQ ID NO 105
<211> LENGTH: 333
<212> TYPE: DNA
<213> ORGANISM: Artificial Sequence
<220> FEATURE:
<223> OTHER INFORMATION: Polynucleotide encoding variable domain

<400> SEQUENCE: 105

```
cagtctgtgt tgacgcagcc tccttccgtg tctgggtctc caggacaaac cgtcaccatc      60
tcctgtgcag gaaccagcag tgatgttggg tatggaaact atgtctcctg gtaccagcag     120
ctgccaggca cggccccccaa actcatgatc tttgcagtca gctatcgagc ctcagggatt    180
cctgatcgct tctctggctc caagtcaggc aacacggcct ctttgaccat ctctgggctc     240
cagtctgagg acgaggctga ttattactgt gcctcatata aagcagcaa caatgctgct      300 gtgttcggcg gagggaccaa actgaccgtc cta                                  333
```

<210> SEQ ID NO 106
<211> LENGTH: 381
<212> TYPE: DNA
<213> ORGANISM: Artificial Sequence
<220> FEATURE:
<223> OTHER INFORMATION: Polynucleotide encoding variable domain
<400> SEQUENCE: 106

```
caggtgcagc tccaggagtc gggcccaggc ctggtgaagc cctcgcagac actctccctc      60
acctgcacag tctctggtgg ctccatcacc accaactatt actactggag ctggattcgc     120
cagtcgccag ggaagggggct ggagtggatt ggagtcatag cttatgatgc gagcactgat    180
tacagcccat ccctcaagag ccgcgtgacc atctccaggg acacgtccaa gaaccagttc     240
tccctgcaac tgagctctgt gaccgcggag gacacggccg tgtattactg tgccagagat     300
gtaagggtaa tcgctacggg ttgggctact gccaatgctt tggacgcatg gggccagggg    360
accctggtca ccgtgtcctc a                                               381
```

<210> SEQ ID NO 107
<211> LENGTH: 333
<212> TYPE: DNA
<213> ORGANISM: Artificial Sequence
<220> FEATURE:
<223> OTHER INFORMATION: Polynucleotide encoding variable domain
<400> SEQUENCE: 107

```
cagtctgtgt tgacgcagcc tccttccgtg tctgggtctc caggacaaac cgtcaccatc      60
tcctgtgcag gaaccagcag tgatgttggg tatggaaact atgtctcctg gtaccagcag     120
ccgccaggca cggccccccaa actcatgatc tttgcagtca gctatcgagc ctcagggatt    180
cctgatcgct tctctggctc caagtcaggc aacacggcct ttttgaccat ctctgggctc     240
cagtctgagg acgaggctga ttattactgt gcctcatata aagcagcaa caatgctgct      300 gtgttcggcg gagggaccaa actgaccgtc cta                                  333
```

<210> SEQ ID NO 108
<211> LENGTH: 119
<212> TYPE: PRT
<213> ORGANISM: Artificial Sequence
<220> FEATURE:
<223> OTHER INFORMATION: Variable domain
<400> SEQUENCE: 108

```
Glu Val Gln Leu Val Gln Pro Gly Ala Glu Val Lys Lys Pro Gly Ala
1               5                   10                  15

Ser Val Lys Val Ser Cys Lys Ala Ser Gly Tyr Ile Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
```

```
                    50                  55                  60
Gln Gly Arg Val Thr Met Thr Ala Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Val Asp Asp Tyr Tyr Leu Gly Tyr Asp Tyr Trp Gly Gln Gly
                100                 105                 110

Thr Gln Val Thr Val Ser Ser
            115

<210> SEQ ID NO 109
<211> LENGTH: 113
<212> TYPE: PRT
<213> ORGANISM: Artificial Sequence
<220> FEATURE:
<223> OTHER INFORMATION: Variable domain

<400> SEQUENCE: 109

Asp Ile Val Met Thr Gln Ser Pro Asp Ser Leu Ala Ala Ser Leu Gly
 1               5                  10                  15

Glu Arg Val Thr Ile Asn Cys Lys Ser Ser Gln Ser Val Leu Phe Ser
                20                  25                  30

Ser Asn Gln Lys Asn Tyr Leu Ala Trp Tyr Gln Gln Arg Pro Gly Gln
            35                  40                  45

Ser Pro Lys Leu Leu Ile Tyr Trp Ala Ser Ile Arg Glu Ser Gly Val
        50                  55                  60

Pro Asp Arg Phe Ser Gly Ser Gly Ser Gly Thr Asp Phe Thr Leu Thr
 65                  70                  75                  80

Ile Ser Ser Leu Gln Ala Glu Asp Val Ala Val Tyr Tyr Cys Gln Gln
                 85                  90                  95

Gly Tyr Ser Phe Pro Tyr Ser Phe Gly Ser Gly Thr Arg Leu Glu Ile
                100                 105                 110

Lys

<210> SEQ ID NO 110
<211> LENGTH: 119
<212> TYPE: PRT
<213> ORGANISM: Artificial Sequence
<220> FEATURE:
<223> OTHER INFORMATION: Variable domain

<400> SEQUENCE: 110

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Met Asn
                20                  25                  30

Ser Ile Asp Trp Val Arg Gln Ala Pro Gly Gln Gly Leu Glu Trp Met
            35                  40                  45

Gly Arg Ile Asp Pro Glu Glu Gly Gly Thr Lys Tyr Ala Gln Lys Phe
        50                  55                  60

Gln Gly Arg Val Thr Phe Thr Arg Asp Thr Ser Thr Ser Thr Ala Tyr
 65                  70                  75                  80

Met Glu Leu Ser Ser Leu Arg Ser Asp Asp Thr Ala Val Tyr Tyr Cys
                 85                  90                  95

Ala Arg Val Asp Asp Tyr Tyr Leu Gly Tyr Asp Tyr Trp Gly Gln Gly
                100                 105                 110

Thr Gln Val Thr Val Ser Ser
```

<210> SEQ ID NO 111
<211> LENGTH: 113
<212> TYPE: PRT
<213> ORGANISM: Artificial Sequence
<220> FEATURE:
<223> OTHER INFORMATION: Variable domain

<400> SEQUENCE: 111

```
Asp Ile Val Met Thr Gln Ser Pro Asp Ser Leu Thr Ala Ser Leu Gly
1               5                   10                  15

Glu Arg Val Thr Ile Asn Cys Lys Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Ala Val Tyr Tyr Cys Gln Gln
                85                  90                  95

Gly Tyr Ser Phe Pro Tyr Ser Phe Gly Gln Gly Thr Arg Leu Glu Ile
            100                 105                 110

Arg
```

<210> SEQ ID NO 112
<211> LENGTH: 119
<212> TYPE: PRT
<213> ORGANISM: Artificial Sequence
<220> FEATURE:
<223> OTHER INFORMATION: Variable domain

<400> SEQUENCE: 112

```
Glu Val Gln Leu Val Gln Pro Gly Ala Glu Val Lys Lys Pro Gly Ala
1               5                   10                  15

Ser Val Lys Val Ser Cys Lys Ala Ser Gly Tyr Thr Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
    50                  55                  60

Gln Gly Arg Val Thr Phe Thr Arg Asp Thr Ser Thr Ser Thr Ala Tyr
65                  70                  75                  80

Val Glu Leu Ser Ser Leu Arg Ser Asp Asp Thr Ala Val Tyr Tyr Cys
                85                  90                  95

Ala Arg Val Asp Asp Tyr Tyr Leu Gly Tyr Asp Tyr Trp Gly Gln Gly
            100                 105                 110

Thr Leu Val Thr Val Ser Ser
        115
```

<210> SEQ ID NO 113
<211> LENGTH: 113
<212> TYPE: PRT
<213> ORGANISM: Artificial Sequence
<220> FEATURE:
<223> OTHER INFORMATION: Variable domain

<400> SEQUENCE: 113

```
Asp Ile Val Met Thr Gln Ser Pro Asp Ser Leu Ala Val Ser Glu Gly
1               5                   10                  15

Glu Arg Val Thr Ile Asn Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Ser Pro Arg Leu Leu Ile Tyr Trp Ala Ser Ile Arg Glu Ser Gly Val
    50                  55                  60

Pro Asp Arg Phe Ser Gly Ser Gly Ser Ala Thr Asp Phe Thr Leu Thr
65                  70                  75                  80

Ile Ser Ser Leu Gln Ala Glu Asp Val Ala Val Tyr Tyr Cys Gln Gln
                85                  90                  95

Gly Tyr Ser Phe Pro Tyr Ser Phe Gly Gln Gly Thr Arg Leu Glu Ile
            100                 105                 110

Arg

<210> SEQ ID NO 114
<211> LENGTH: 119
<212> TYPE: PRT
<213> ORGANISM: Artificial Sequence
<220> FEATURE:
<223> OTHER INFORMATION: Variable domain

<400> SEQUENCE: 114

Gln Val Gln Leu Val Gln Pro Gly Val Glu Val Lys Lys Pro Gly Ala
1               5                   10                  15

Ser Val Lys Val Ser Cys Lys Ala Ser Gly Tyr Thr Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Gly Gly Thr Lys Tyr Ala Gln Lys Phe
    50                  55                  60

Gln Gly Arg Val Thr Phe Thr Ala Asp Thr Ser Thr Ser Thr Ala Tyr
65                  70                  75                  80

Met Glu Leu Ser Ser Leu Arg Ser Asp Asp Thr Ala Val Tyr Tyr Cys
                85                  90                  95

Ala Arg Val Asp Asp Tyr Tyr Leu Gly Tyr Asp Tyr Trp Gly Gln Gly
            100                 105                 110

Thr Gln Val Thr Val Ser Ser
        115

<210> SEQ ID NO 115
<211> LENGTH: 113
<212> TYPE: PRT
<213> ORGANISM: Artificial Sequence
<220> FEATURE:
<223> OTHER INFORMATION: Variable domain

<400> SEQUENCE: 115

Asp Ile Val Met Thr Gln Ser Pro Thr Ser Val Ala Val Ser Leu Gly
1               5                   10                  15

Glu Arg Ala Thr Ile Asn Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Pro Pro Arg Leu Leu Ile Tyr Trp Ala Ser Ile Arg Glu Ser Gly Val
    50                  55                  60
```

```
Pro Asp Arg Phe Ser Gly Ser Gly Ser Gly Thr Asp Phe Thr Leu Thr
 65                  70                  75                  80

Ile Ser Ser Leu Gln Pro Glu Asp Val Ala Val Tyr Tyr Cys Gln Gln
                 85                  90                  95

Gly Tyr Ser Phe Pro Tyr Ser Phe Gly Gln Gly Thr Arg Leu Glu Ile
            100                 105                 110

Arg
```

```
<210> SEQ ID NO 116
<211> LENGTH: 119
<212> TYPE: PRT
<213> ORGANISM: Artificial Sequence
<220> FEATURE:
<223> OTHER INFORMATION: Variable domain

<400> SEQUENCE: 116

Gln Val Gln Leu Val Gln Pro Gly Ala Glu Val Lys Lys Pro Gly Ala
 1               5                  10                  15

Ser Val Lys Val Ser Cys Lys Ala Ser Gly Tyr Thr Phe Thr Met Asn
                 20                  25                  30

Ser Ile Asp Trp Val Arg Gln Ala Pro Gly Gln Gly Leu Glu Trp Met
             35                  40                  45

Gly Arg Ile Asp Pro Glu Gly Gly Thr Lys Tyr Ala Gln Lys Phe
 50                  55                  60

Gln Gly Arg Val Thr Phe Thr Ala Asp Thr Ser Ser Thr Ala Tyr
 65                  70                  75                  80

Val Glu Leu Asn Ser Leu Arg Ser Glu Asp Thr Ala Val Tyr Tyr Cys
                 85                  90                  95

Ala Arg Val Asp Asp Tyr Tyr Leu Gly Tyr Asp Tyr Trp Gly Gln Gly
            100                 105                 110

Thr Gln Val Thr Val Ser Ser
            115
```

```
<210> SEQ ID NO 117
<211> LENGTH: 113
<212> TYPE: PRT
<213> ORGANISM: Artificial Sequence
<220> FEATURE:
<223> OTHER INFORMATION: Variable domain

<400> SEQUENCE: 117

Asp Ile Val Met Thr Gln Ser Pro Asp Ser Leu Ala Val Ser Leu Gly
 1               5                  10                  15

Glu Lys Val Thr Ile Asn Cys Lys Ser Ser Gln Ser Val Leu Phe Ser
                 20                  25                  30

Ser Asn Gln Lys Asn Tyr Leu Ala Trp Tyr Gln Gln Arg Pro Gly Gln
             35                  40                  45

Pro Pro Lys Leu Leu Ile Tyr Trp Ala Ser Ile Arg Glu Ser Gly Val
 50                  55                  60

Pro Asp Arg Phe Ser Gly Ser Gly Ser Ala Thr Asp Phe Thr Leu Thr
 65                  70                  75                  80

Ile Ser Ser Leu Gln Pro Glu Asp Val Ala Val Tyr Tyr Cys Gln Gln
                 85                  90                  95

Gly Tyr Ser Phe Pro Tyr Ser Phe Gly Gln Gly Thr Arg Leu Glu Ile
            100                 105                 110

Lys
```

```
<210> SEQ ID NO 118
<211> LENGTH: 119
<212> TYPE: PRT
<213> ORGANISM: Artificial Sequence
<220> FEATURE:
<223> OTHER INFORMATION: Variable domain

<400> SEQUENCE: 118

Gln Val Gln Leu Val Gln Pro Gly Ala Glu Leu Arg Asn Pro Gly Ala
1               5                   10                  15

Ser Val Lys Val Ser Cys Lys Ala Ser Gly Tyr Thr Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
    50                  55                  60

Gln Gly Arg Val Thr Met Thr Arg Asp Thr Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asp Asp Tyr Tyr Leu Gly Tyr Asp Tyr Trp Gly Gln Gly
            100                 105                 110

Thr Gln Val Thr Val Ser Ser
        115

<210> SEQ ID NO 119
<211> LENGTH: 113
<212> TYPE: PRT
<213> ORGANISM: Artificial Sequence
<220> FEATURE:
<223> OTHER INFORMATION: Variable domain

<400> SEQUENCE: 119

Asp Ile Val Met Thr Gln Thr Pro Asp Ser Leu Ala Val Ser Ala Gly
1               5                   10                  15

Glu Arg Val Thr Ile Asn Cys Lys Ser Ser Gln Ser Val Leu Phe Ser
            20                  25                  30

Ser Asn Gln Lys Asn Tyr Leu Ala Trp Tyr Gln Lys Pro Gly Gln
        35                  40                  45

Ser Pro Lys Leu Leu Ile Tyr Trp Ala Ser Ile Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Pro Glu Asp Val Thr Val Tyr Tyr Cys Gln Gln
                85                  90                  95

Gly Tyr Ser Phe Pro Tyr Ser Phe Gly Gln Gly Thr Arg Leu Glu Ile
            100                 105                 110

Lys

<210> SEQ ID NO 120
<211> LENGTH: 119
<212> TYPE: PRT
<213> ORGANISM: Artificial Sequence
<220> FEATURE:
<223> OTHER INFORMATION: Variable domain

<400> SEQUENCE: 120

Gln Val Gln Leu Val Gln Pro Gly Ala Glu Val Lys Lys Pro Gly Ala
1               5                   10                  15
```

Ser Val Lys Val Ser Cys Lys Ala Ser Gly Tyr Ile Phe Thr Met Asn
            20                  25                  30

Ser Ile Asp Trp Val Arg Gln Ala Pro Gly Gln Gly Leu Glu Trp Met
        35                  40                  45

Gly Arg Ile Asp Pro Glu Glu Gly Gly Thr Lys Tyr Ala Gln Lys Phe
    50                  55                  60

Gln Gly Arg Val Thr Met Thr Ala Asp Thr Ser Thr Ser Thr Ala Tyr
65                  70                  75                  80

Met Glu Leu Asn Ser Leu Arg Ser Glu Asp Thr Ala Val Tyr Tyr Cys
                85                  90                  95

Ala Arg Val Asp Asp Tyr Tyr Leu Gly Tyr Asp Tyr Trp Gly Gln Gly
            100                 105                 110

Thr Leu Val Thr Val Ser Ser
        115

<210> SEQ ID NO 121
<211> LENGTH: 113
<212> TYPE: PRT
<213> ORGANISM: Artificial Sequence
<220> FEATURE:
<223> OTHER INFORMATION: Variable domain

<400> SEQUENCE: 121

Asp Ile Val Met Thr Gln Thr Pro Thr Ser Leu Ala Pro Ser Ala Gly
1               5                   10                  15

Glu Arg Ala Thr Ile Asn Cys Lys Ser Ser Gln Ser Val Leu Phe Ser
            20                  25                  30

Ser Asn Gln Lys Asn Tyr Leu Ala Trp Tyr Gln Gln Lys Pro Gly Gln
        35                  40                  45

Pro Pro Lys Leu Leu Ile Tyr Trp Ala Ser Ile Arg Glu Ser Gly Val
    50                  55                  60

Pro Asp Arg Phe Ser Gly Ser Gly Ser Ala Thr Asp Phe Thr Leu Thr
65                  70                  75                  80

Ile Ser Ser Leu Gln Pro Glu Asp Val Ala Val Tyr Tyr Cys Gln Gln
                85                  90                  95

Gly Tyr Ser Phe Pro Tyr Ser Phe Gly Ser Gly Thr Arg Leu Glu Ile
            100                 105                 110

Lys

<210> SEQ ID NO 122
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 122
gaggtccagc tggtgcagcc aggggcggaa gtgaaaaaac tgggcatc agtgaaggtc      60 tcctgcaagg cttctggata catcttcacc atgaactcaa tagactgggt gcgacaggcc    120
cctggacaag gcttgagtg gatgggaaga attgaccctg aagagggtgg cacaaagtat    180
gcacagaagt tccagggcag agtcaccatg actgcagaca cgtccaccag cacagcctac    240
atggagctga gcagtctgag atctgacgac acggccgtgt attactgtgc gagagtagat    300
gactattacc ttgggtatga ctactggggc caggggaccc aggtcaccgt ctcctca       357

<210> SEQ ID NO 123
<211> LENGTH: 339

```
<212> TYPE: DNA
<213> ORGANISM: Artificial Sequence
<220> FEATURE:
<223> OTHER INFORMATION: Polynucleotide encoding variable domain

<400> SEQUENCE: 123
gatattgtga tgacccagag ccccgattcc ttggcagcgt ctttaggaga acgtgtgacc    60
atcaattgta agtccagcca gagtgtgtta ttcagctcca accagaaaaa ctacttagct   120
tggtaccagc agagaccggg acagtctcct aagctgctca tctactgggc ttccatccga   180
gaatcggggg ttcctgatcg attcagcggc agtgggtccg gcacagattt cacgctaacc   240
atcagctctc ttcaggctga agacgtggca gtatattact gccagcaggg ttatagtttt   300
ccatatagtt tcggcagtgg gaccaggctc gagatcaaa                          339

<210> SEQ ID NO 124
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 124
caggtccagc tggtgcagtc tggggcggaa gtgaaaaaac ctggggcatc agtgaaggtc    60
tcctgcaagg cttctggata caccttcacc atgaactcaa tagactgggt gcgagaggcc   120
cctggacaag ggcttgagtg gatgggaaga attgaccctg aagagggtgg cacaaagtat   180
gcacagaagt tccagggcag agtcaccttc actcgagaca cgtccaccag cacagcctac   240
atggagctga gcagtctgag atctgacgac acggccgtgt attactgtgc gagagtagat   300
gactattacc ttgggtatga ctactggggc caggggaccc aggtcaccgt ctcctca      357

<210> SEQ ID NO 125
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 125
gatattgtga tgacccagag ccccgattcc ttgacagcgt ctttaggaga acgtgtgacc    60
atcaattgta agtccagcca gagtgtgtta ttcagctcca accagaaaaa ctacttagct   120
tggtaccagc agaaaccggg acagtctcct aagctgctca tctactgggc ttccatccga   180
gaatcggggg ttcctgatcg attcagcggc agtgggtccg gcacagattt cacgctaacc   240
atcagctctc ttcagcctga agacgtggca gtatattact gccagcaggg ttatagtttt   300
ccatatagtt tcggccaggg caccaggctc gagatcaga                          339

<210> SEQ ID NO 126
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 126
gaggtccagc tggtgcagcc aggggcggaa gtgaaaaaac ctggggcatc agtgaaggtc    60
tcctgcaagg cttctggata caccttcacc atgaactcaa tagactgggt gcgagaggcc   120
cctggacaag ggcttgagtg gatgggaaga attgaccctg aagagggtgg cacaaagtat   180
```

```
gcacagaagt tccagggcag agtcaccttc actcgagaca cgtccaccag cacagcctac    240
gtggagctga gcagtctgag atctgacgac acggccgtgt attactgtgc gagagtagat    300
gactattacc ttgggtatga ctactggggc caggggaccc tggtcaccgt ctcctca       357
```

<210> SEQ ID NO 127
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 127

```
gatattgtga tgacccagag ccccgattcc ttggcagtgt ctgaaggaga acgtgtgacc    60
atcaattgta agtccagcca gagtgtgtta ttcagctcca accagaaaaa ctacttagct    120
tggtaccagc agaaaccggg acagtctcct aggctgctca tctactgggc ttccatccga   180
gaatcggggg ttcctgatcg attcagcggc agtgggtccg ccacagattt cacgctaacc   240
atcagctctc ttcaggctga agacgtggca gtatattact gccagcaggg ttatagtttt    300
ccatatagtt tcggccaggg gaccaggctc gagatcaga                           339
```

<210> SEQ ID NO 128
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 128

```
caggtccagc tggtgcagcc aggggtggaa gtgaaaaaac ctggggcatc agtgaaggtc    60
tcctgcaagg cttctggata caccttcacc atgaactcaa tagactgggt gcgacaggcc    120
cctggacaag gcttgagtg gatgggaaga attgaccctg aagagggtgg cacaaagtat    180
gcacagaagt tccagggcag agtcaccttc actcgcagaca cgtccaccag cacagcctac   240
atggagctga gcagtctgag atctgacgac acggccgtgt attactgtgc gagagtagat    300
gactattacc ttgggtatga ctactggggc caggggaccc aggtcaccgt ctcctca       357
```

<210> SEQ ID NO 129
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 129

```
gatattgtga tgacccagag ccccacctcc gtggcagtgt ctttaggaga acgtgcgacc    60
atcaattgta agtccagcca gagtgtgtta ttcagctcca accagaaaaa ctacttagct    120
tggtaccagc agaaaccggg acagcctcct aggctgctca tctactgggc ttccatccga   180
gaatcggggg ttcctgatcg attcagcggc agtgggtccg gcacagattt cacgctaacc   240
atcagctctc ttcagcctga agacgtggca gtatattact gccagcaggg ttatagtttt    300
ccatatagtt tcggccaggg gaccaggctc gagatcaga                           339
```

<210> SEQ ID NO 130
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 130

| | | |
|---|---|---|
| caggtccagc tggtgcagcc aggggcggaa gtgaaaaaac ctggggcatc agtgaaggtc | 60 |
| tcctgcaagg cttctggata caccttcacc atgaactcaa tagactgggt gcgacaggcc | 120 |
| cctggacaag gcttgagtg gatgggaaga attgaccctg aagagggtgg cacaaagtat | 180 |
| gcacagaagt tccagggcag agtcaccttc actgcagaca cgtccaccag cacagcctac | 240 |
| gtggagctga acagtctgag atctgaggac acggccgtgt attactgtgc gagagtagat | 300 |
| gactattacc ttgggtatga ctactggggc caggggaccc aggtcaccgt ctcctca | 357 |

<210> SEQ ID NO 131
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 131

| | | |
|---|---|---|
| gatattgtga tgacccagag ccccgattcc ttggcagtgt ctttaggaga aaaggtgacc | 60 |
| atcaattgta gtccagcca gagtgtgtta ttcagctcca accagaaaaa ctacttagct | 120 |
| tggtaccagc agagaccggg acagcctcct aagctgctca tctactgggc ttccatccga | 180 |
| gaatcggggg ttcctgatcg attcagcggc agtgggtccg ccacagattt cacgctaacc | 240 |
| atcagctctc ttcagcctga agacgtggca gtatattact gccagcaggg ttatagtttt | 300 |
| ccatatagtt tcggccaggg gaccaggctc gagatcaaa | 339 |

<210> SEQ ID NO 132
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 132

| | | |
|---|---|---|
| gaggtccagc tggtgcagcc aggggcggaa ctgagaaacc ctggggcatc agtgaaggtc | 60 |
| tcctgcaagg cttctggata caccttcacc atgaactcaa tagactgggt gcgacaggcc | 120 |
| cctggacaag gcttgagtg gatgggaaga attgaccctg aagagggtgg cacaaagtat | 180 |
| gcacagaagt tccagggcag agtcaccatg actcgagaca cgtccaccag cacagcctac | 240 |
| atggagctga gcagtctgag atctgaggac acggccgtgt attactgtgc gagagtagat | 300 |
| gactattacc ttgggtatga ctactggggc caggggaccc aggtcaccgt ctcctca | 357 |

<210> SEQ ID NO 133
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 133

| | | |
|---|---|---|
| gatattgtga tgacccagac ccccgattcc ttggcagtgt ctgcaggaga acgtgtgacc | 60 |
| atcaattgta gtccagcca gagtgtgtta ttcagctcca accagaaaaa ctacttagct | 120 |
| tggtaccagc agaaaccggg acagtctcct aagctgctca tctactgggc ttccatccga | 180 |
| gaatcggggg ttcctgatcg attcagcggc agtgggtccg gcacagattt tacgctaacc | 240 |
| atcagctctc ttcagcctga agacgtgaca gtatattact gccagcaggg ttatagtttt | 300 |

```
ccatatagtt tcggccaggg gaccaggctc gagatcaaa                              339
```

<210> SEQ ID NO 134
<211> LENGTH: 357
<212> TYPE: DNA
<213> ORGANISM: Artificial Sequence
<220> FEATURE:
<223> OTHER INFORMATION: Polynucleotide encoding variable domain

<400> SEQUENCE: 134

```
caggtccagc tggtgcagcc aggggcggaa gtgaaaaaac ctggggcatc agtgaaggtc       60
tcctgcaagg cttctggata catcttcacc atgaactcaa tagactgggt gcgacaggcc      120
cctggacaag ggcttgagtg gatgggaaga attgaccctg aagagggtgg cacaaagtat      180
gcacagaagt tccagggcag agtcaccatg actgcagaca cgtccaccag cacagcctac      240
atggagctga acagtctgag atctgaggac acggccgtgt attactgtgc gagagtagat      300
gactattacc ttgggtatga ctactggggc caggggaccc tggtcaccgt ctcctca        357
```

<210> SEQ ID NO 135
<211> LENGTH: 339
<212> TYPE: DNA
<213> ORGANISM: Artificial Sequence
<220> FEATURE:
<223> OTHER INFORMATION: Polynucleotide encoding variable domain

<400> SEQUENCE: 135

```
gatattgtga tgacccagac ccccacctcc ttggcaccgt ctgcaggaga acgtgcgacc       60
atcaattgta gtccagcca gagtgtgtta ttcagctcca accagaaaaa ctacttagct      120
tggtaccagc agaaaccggg acagcctcct aagctgctca tctactgggc ttccatccga      180
gaatcggggg ttcctgatcg attcagcggc agtgggtccg ccacagattt cacgctaacc      240
atcagctctc ttcagcctga agacgtggca gtatattact gccagcaggg ttatagtttt      300
ccatatagtt tcggcagtgg gaccaggctc gagatcaaa                              339
```

<210> SEQ ID NO 136
<211> LENGTH: 111
<212> TYPE: PRT
<213> ORGANISM: Homo sapiens

<400> SEQUENCE: 136

```
Arg Ser Glu Glu Cys Leu Ser Gly Thr Trp Thr Gln Gln Ile Cys Leu
1               5                   10                  15
Pro Ala Ile Tyr Lys Val Phe Pro Asn Ser Ala Pro Leu Glu Gly Gly
            20                  25                  30
Thr Arg Leu Thr Ile Cys Gly Trp Asp Phe Gly Phe Arg Arg Asn Asn
        35                  40                  45
Lys Phe Asp Leu Lys Lys Thr Arg Val Leu Leu Gly Asn Glu Ser Cys
    50                  55                  60
Thr Leu Thr Leu Ser Glu Ser Thr Met Asn Thr Leu Lys Cys Thr Val
65                  70                  75                  80
Gly Pro Ala Met Asn Lys His Phe Asn Met Ser Ile Ile Ile Ser Asn
                85                  90                  95
Gly His Gly Thr Thr Gln Tyr Ser Thr Phe Ser Tyr Val Asp Pro
            100                 105                 110
```

<210> SEQ ID NO 137
<211> LENGTH: 17
<212> TYPE: PRT

```
<213> ORGANISM: Artificial Sequence
<220> FEATURE:
<223> OTHER INFORMATION: CDR Sequence

<400> SEQUENCE: 137

Lys Ser Ser Gln Ser Val Leu Tyr Asn Pro Asn Gln Lys Ser Tyr Leu
1               5                   10                  15

Ala

<210> SEQ ID NO 138
<211> LENGTH: 17
<212> TYPE: PRT
<213> ORGANISM: Artificial Sequence
<220> FEATURE:
<223> OTHER INFORMATION: CDR Sequence

<400> SEQUENCE: 138

Lys Ser Ser Gln Ser Val Leu Tyr Thr Ser Asn His Lys Asn Tyr Leu
1               5                   10                  15

Ala

<210> SEQ ID NO 139
<211> LENGTH: 9
<212> TYPE: PRT
<213> ORGANISM: Artificial Sequence
<220> FEATURE:
<223> OTHER INFORMATION: CDR Sequence

<400> SEQUENCE: 139

Gln Gln Gly Trp Ser Phe Pro Tyr Ser
1               5

<210> SEQ ID NO 140
<211> LENGTH: 17
<212> TYPE: PRT
<213> ORGANISM: Artificial Sequence
<220> FEATURE:
<223> OTHER INFORMATION: CDR Sequence

<400> SEQUENCE: 140

Lys Ser Ser Gln Ser Val Leu Tyr Asn Ser Asn Gln Lys Asn Tyr Leu
1               5                   10                  15

Ala

<210> SEQ ID NO 141
<211> LENGTH: 9
<212> TYPE: PRT
<213> ORGANISM: Artificial Sequence
<220> FEATURE:
<223> OTHER INFORMATION: CDR Sequence

<400> SEQUENCE: 141

Gln Gln Gly Trp Ser Phe Pro Tyr Thr
1               5

<210> SEQ ID NO 142
<211> LENGTH: 17
<212> TYPE: PRT
<213> ORGANISM: Artificial Sequence
<220> FEATURE:
<223> OTHER INFORMATION: CDR Sequence

<400> SEQUENCE: 142

Lys Ser Ser Gln Ser Val Leu Tyr Gly Ser Asn Gln Lys Asn Tyr Leu
1               5                   10                  15
```

Ala

<210> SEQ ID NO 143
<211> LENGTH: 17
<212> TYPE: PRT
<213> ORGANISM: Artificial Sequence
<220> FEATURE:
<223> OTHER INFORMATION: CDR Sequence

<400> SEQUENCE: 143

Lys Ser Ser Gln Ser Val Leu Trp Ser Ser Asn Gln Lys Asn Tyr Leu
1               5                   10                  15
Ala

<210> SEQ ID NO 144
<211> LENGTH: 14
<212> TYPE: PRT
<213> ORGANISM: Artificial Sequence
<220> FEATURE:
<223> OTHER INFORMATION: CDR Sequence

<400> SEQUENCE: 144

Ala Gly Thr Ser Thr Asp Val Gly Tyr Gly Asn Tyr Val Ser
1               5                   10

<210> SEQ ID NO 145
<211> LENGTH: 11
<212> TYPE: PRT
<213> ORGANISM: Artificial Sequence
<220> FEATURE:
<223> OTHER INFORMATION: CDR Sequence

<400> SEQUENCE: 145

Ala Ser Tyr Arg Ser Ser Asn Lys Asn Ala Val
1               5                   10

<210> SEQ ID NO 146
<211> LENGTH: 11
<212> TYPE: PRT
<213> ORGANISM: Artificial Sequence
<220> FEATURE:
<223> OTHER INFORMATION: CDR Sequence

<400> SEQUENCE: 146

Ala Ser Tyr Arg Ile Thr Asn Arg His Ser Val
1               5                   10

<210> SEQ ID NO 147
<211> LENGTH: 11
<212> TYPE: PRT
<213> ORGANISM: Artificial Sequence
<220> FEATURE:
<223> OTHER INFORMATION: CDR Sequence

<400> SEQUENCE: 147

Ala Ser Tyr Arg Arg Ser Thr Asn Val Gly Val
1               5                   10

<210> SEQ ID NO 148
<211> LENGTH: 11
<212> TYPE: PRT
<213> ORGANISM: Artificial Sequence
<220> FEATURE:
<223> OTHER INFORMATION: CDR Sequence

<400> SEQUENCE: 148

```
Ala Ser Tyr Arg Thr Ser Asn Asn Val Ala Val
1               5                   10
```

<210> SEQ ID NO 149
<211> LENGTH: 113
<212> TYPE: PRT
<213> ORGANISM: Artificial Sequence
<220> FEATURE:
<223> OTHER INFORMATION: Variabe domain

<400> SEQUENCE: 149

```
Glu Ile Val Met Thr Gln Ser Pro Ser Val Thr Ala Ser Ala Gly
1               5                   10                  15

Glu Lys Val Thr Ile Asn Cys Lys Ser Ser Gln Ser Val Leu Trp Arg
                20                  25                  30

Ser Asn Gln Lys Asn Tyr Leu Ala Trp Tyr Gln Arg Leu Gly Gln
            35                  40                  45

Ser Pro Arg Leu Leu Ile Ser Trp Ala Ser Ile Arg Glu Ser Gly Val
        50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Tyr Ser Phe Pro Tyr Thr Phe Gly Ser Gly Thr Arg Leu Glu Ile
            100                 105                 110

Lys
```

<210> SEQ ID NO 150
<211> LENGTH: 113
<212> TYPE: PRT
<213> ORGANISM: Artificial Sequence
<220> FEATURE:
<223> OTHER INFORMATION: Variabe domain

<400> SEQUENCE: 150

```
Asp Ile Val Met Thr Gln Thr Pro Ser Ser Val Thr Ala Ala Val Gly
1               5                   10                  15

Glu Lys Val Ala Ile Asn Cys Lys Ser Ser Gln Ser Val Leu Tyr Asn
                20                  25                  30

Pro Asn Gln Lys Ser Tyr Leu Ala Trp Tyr Gln Arg Pro Gly Gln
            35                  40                  45

Ser Pro Arg Leu Leu Ile Tyr Trp Ala Ser Thr Arg Glu Ser Gly Val
        50                  55                  60

Pro Asp Arg Phe Ser Gly Ser Gly Ser Thr Thr Asp Phe Ala Leu Thr
65                  70                  75                  80

Ile Ser Ser Phe Gln Pro Glu Asp Ala Ala Val Tyr Tyr Cys Gln Gln
                85                  90                  95

Gly Tyr Ser Phe Pro Tyr Ser Phe Gly Ser Gly Thr Arg Leu Glu Ile
            100                 105                 110

Arg
```

<210> SEQ ID NO 151
<211> LENGTH: 113
<212> TYPE: PRT
<213> ORGANISM: Artificial Sequence
<220> FEATURE:
<223> OTHER INFORMATION: Variabe domain

<400> SEQUENCE: 151

```
Asp Val Val Met Thr Gln Ser Pro Ser Ser Val Thr Ala Ser Val Gly
1               5                   10                  15

Glu Lys Val Thr Ile Asn Cys Lys Ser Ser Gln Ser Val Leu Tyr Thr
                20                  25                  30

Ser Asn His Lys Asn Tyr Leu Ala Trp Tyr Gln Gln Arg Leu Gly Gln
            35                  40                  45

Ser Pro Arg Leu Leu Ile Tyr Trp Ala Ser Thr Arg Glu Ser Gly Val
        50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Trp Ser Phe Pro Tyr Ser Phe Gly Ser Gly Thr Arg Leu Glu Ile
                100                 105                 110

Lys
```

<210> SEQ ID NO 152
<211> LENGTH: 113
<212> TYPE: PRT
<213> ORGANISM: Artificial Sequence
<220> FEATURE:
<223> OTHER INFORMATION: Variabe domain

<400> SEQUENCE: 152

```
Asp Ile Val Met Thr Gln Thr Pro Ser Ser Val Thr Ala Ser Ala Gly
1               5                   10                  15

Glu Lys Val Thr Ile Asn Cys Lys Ser Ser Gln Ser Val Leu Tyr Asn
                20                  25                  30

Ser Asn Gln Lys Asn Tyr Leu Ala Trp Tyr Gln Gln Arg Leu Gly Gln
            35                  40                  45

Ser Pro Arg Leu Leu Ile Tyr Trp Ala Ser Thr Arg Glu Ser Gly Val
        50                  55                  60

Pro Asp Arg Phe Ser Gly Ser Gly Ser Thr Thr Asp Phe Thr Leu Thr
65                  70                  75                  80

Ile Ser Ser Phe Gln Pro Glu Asp Ala Ala Val Tyr Tyr Cys Gln Gln
                85                  90                  95

Gly Trp Ser Phe Pro Tyr Thr Phe Gly Ser Gly Thr Arg Leu Glu Ile
                100                 105                 110

Lys
```

<210> SEQ ID NO 153
<211> LENGTH: 113
<212> TYPE: PRT
<213> ORGANISM: Artificial Sequence
<220> FEATURE:
<223> OTHER INFORMATION: Variabe domain

<400> SEQUENCE: 153

```
Asp Ile Gln Leu Thr Gln Ser Pro Ser Ser Val Thr Ala Ser Ala Gly
1               5                   10                  15

Glu Lys Val Thr Ile Asn Cys Lys Ser Ser Gln Ser Val Leu Tyr Gly
                20                  25                  30

Ser Asn Gln Lys Asn Tyr Leu Ala Trp Tyr Gln Gln Arg Leu Gly Gln
            35                  40                  45

Ser Pro Arg Leu Leu Ile Tyr Trp Ala Ser Thr Arg Glu Ser Gly Val
        50                  55                  60
```

```
Pro Asp Arg Phe Ser Gly Ser Gly Ser Thr Thr Asp Phe Thr Leu Thr
 65                  70                  75                  80

Ile Ser Ser Phe Gln Pro Glu Asp Ala Ala Val Tyr Tyr Cys Gln Gln
                 85                  90                  95

Gly Trp Ser Phe Pro Tyr Thr Phe Gly Ser Gly Thr Arg Leu Glu Ile
                100                 105                 110

Lys
```

<210> SEQ ID NO 154
<211> LENGTH: 113
<212> TYPE: PRT
<213> ORGANISM: Artificial Sequence
<220> FEATURE:
<223> OTHER INFORMATION: Variabe domain

<400> SEQUENCE: 154

```
Asp Ile Gln Leu Thr Gln Ser Pro Ser Ser Val Thr Val Ser Val Gly
  1               5                  10                  15

Glu Lys Val Thr Ile Asn Cys Lys Ser Ser Gln Ser Val Leu Tyr Asn
                 20                  25                  30

Ser Asn Gln Lys Asn Tyr Leu Ala Trp Tyr Gln Gln Arg Leu Gly Gln
             35                  40                  45

Ser Pro Arg Leu Leu Ile Tyr Trp Ala Ser Thr Arg Glu Ser Gly Val
 50                  55                  60

Pro Asp Arg Phe Ser Gly Ser Gly Ser Thr Thr Asp Phe Thr Leu Thr
 65                  70                  75                  80

Ile Ser Ser Phe Gln Pro Glu Asp Ala Ala Val Tyr Tyr Cys Gln Gln
                 85                  90                  95

Gly Trp Ser Phe Pro Tyr Thr Phe Gly Ser Gly Thr Arg Leu Glu Ile
                100                 105                 110

Lys
```

<210> SEQ ID NO 155
<211> LENGTH: 113
<212> TYPE: PRT
<213> ORGANISM: Artificial Sequence
<220> FEATURE:
<223> OTHER INFORMATION: Variabe domain

<400> SEQUENCE: 155

```
Asp Ile Gln Met Thr Gln Ser Pro Ser Ser Val Thr Ala Ser Ala Gly
  1               5                  10                  15

Glu Lys Val Thr Ile Asn Cys Lys Ser Ser Gln Ser Val Leu Tyr Asn
                 20                  25                  30

Ser Asn Gln Lys Asn Tyr Leu Ala Trp Tyr Gln Gln Arg Leu Gly Gln
             35                  40                  45

Ser Pro Arg Leu Leu Ile Tyr Trp Ala Ser Thr Arg Glu Ser Gly Val
 50                  55                  60

Pro Asp Arg Phe Ser Gly Ser Gly Ser Thr Thr Asp Phe Thr Leu Thr
 65                  70                  75                  80

Ile Ser Ser Phe Gln Pro Glu Asp Ala Ala Val Tyr Tyr Cys Gln Gln
                 85                  90                  95

Gly Trp Ser Phe Pro Tyr Thr Phe Gly Ser Gly Thr Arg Leu Glu Ile
                100                 105                 110

Lys
```

<210> SEQ ID NO 156

```
<211> LENGTH: 113
<212> TYPE: PRT
<213> ORGANISM: Artificial Sequence
<220> FEATURE:
<223> OTHER INFORMATION: Variabe domain

<400> SEQUENCE: 156

Asp Ile Val Met Thr Gln Thr Pro Ala Ser Val Thr Ala Ser Ala Gly
1               5                   10                  15

Glu Lys Val Thr Ile Asn Cys Lys Ser Gln Ser Val Leu Phe Ser
            20                  25                  30

Ser Asn Gln Lys Asn Tyr Leu Ala Trp Tyr Gln Gln Arg Val Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Thr Asp Phe Thr Leu Thr
65                  70                  75                  80

Ile Ser Asn Phe Gln Pro Glu Asp Ala Ala Val Tyr Tyr Cys Gln Gln
                85                  90                  95

Gly Tyr Ser Phe Pro Tyr Ser Phe Gly Ser Gly Thr Arg Leu Glu Ile
            100                 105                 110

Arg

<210> SEQ ID NO 157
<211> LENGTH: 113
<212> TYPE: PRT
<213> ORGANISM: Artificial Sequence
<220> FEATURE:
<223> OTHER INFORMATION: Variabe domain

<400> SEQUENCE: 157

Asp Val Val Met Thr Gln Ser Pro Ser Ser Val Thr Ala Ser Ala Gly
1               5                   10                  15

Glu Lys Val Thr Ile Asn Cys Lys Ser Ser Gln Ser Val Leu Trp Ser
            20                  25                  30

Ser Asn Gln Lys Asn Tyr Leu Ala Trp Tyr Gln Gln Arg Val Gly Gln
        35                  40                  45

Ser Pro Arg Leu Leu Ile Tyr Trp Ala Ser Thr Arg Glu Ser Gly Val
    50                  55                  60

Pro Asp Arg Phe Ser Gly Ser Gly Ser Thr Thr Asp Phe Thr Leu Thr
65                  70                  75                  80

Ile Ser Asn Phe Gln Pro Glu Asp Ala Ala Val Tyr Tyr Cys Gln Gln
                85                  90                  95

Gly Tyr Ser Phe Pro Tyr Ser Phe Gly Ser Gly Thr Arg Leu Glu Ile
            100                 105                 110

Arg

<210> SEQ ID NO 158
<211> LENGTH: 111
<212> TYPE: PRT
<213> ORGANISM: Artificial Sequence
<220> FEATURE:
<223> OTHER INFORMATION: Variabe domain

<400> SEQUENCE: 158

Gln Ser Val Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30
```

```
Asn Tyr Val Ser Trp Tyr Gln Gln Leu Pro Gly Thr Ala Pro Lys Leu
            35                  40                  45

Leu Ile Phe Ala Val Ser Tyr Arg Ala Ser Gly Ile Pro Asp Arg Phe
 50                  55                  60

Ser Gly Ser Lys Ser Gly Asn Thr Ala Phe Leu Thr Ile Ser Gly Leu
 65                  70                  75                  80

Gln Ser Glu Asp Glu Ala Asp Tyr Tyr Cys Ala Ser Tyr Arg Ser Ser
            85                  90                  95

Asn Asn Ala Ala Val Phe Gly Gly Gly Thr His Leu Thr Val Leu
            100                 105                 110

<210> SEQ ID NO 159
<211> LENGTH: 111
<212> TYPE: PRT
<213> ORGANISM: Artificial Sequence
<220> FEATURE:
<223> OTHER INFORMATION: Variabe domain

<400> SEQUENCE: 159

Gln Ser Val Leu Thr Gln Pro Pro Ser Val Ser Gly Thr Leu Gly Lys
 1               5                   10                  15

Thr Leu Thr Ile Ser Cys Ala Gly Thr Ser Thr Asp Val Gly Tyr Gly
            20                  25                  30

Asn Tyr Val Ser Trp Tyr Gln Gln Leu Pro Gly Thr Ala Pro Lys Leu
            35                  40                  45

Leu Ile Phe Ala Val Ser Tyr Arg Ala Ser Gly Ile Pro Asp Arg Phe
 50                  55                  60

Ser Gly Ser Lys Ser Gly Asn Thr Ala Phe Leu Thr Ile Ser Gly Leu
 65                  70                  75                  80

Gln Ser Glu Asp Glu Ala Asp Tyr Tyr Cys Ala Ser Tyr Arg Ser Ser
            85                  90                  95

Asn Asn Ala Ala Val Phe Gly Gly Gly Thr His Leu Thr Val Leu
            100                 105                 110

<210> SEQ ID NO 160
<211> LENGTH: 111
<212> TYPE: PRT
<213> ORGANISM: Artificial Sequence
<220> FEATURE:
<223> OTHER INFORMATION: Variabe domain

<400> SEQUENCE: 160

Gln Ser Ala Leu Thr Gln Pro Pro Ser Val Ser Gly Thr Leu Gly Lys
 1               5                   10                  15

Thr Leu Thr Ile Ser Cys Ala Gly Thr Ser Thr Asp Val Gly Tyr Gly
            20                  25                  30

Asn Tyr Val Ser Trp Tyr Gln Gln Leu Pro Gly Thr Ala Pro Lys Leu
            35                  40                  45

Leu Ile Phe Ala Val Ser Tyr Arg Ala Ser Gly Ile Pro Asp Arg Phe
 50                  55                  60

Ser Gly Ser Lys Ser Gly Asn Thr Ala Phe Leu Thr Ile Ser Gly Leu
 65                  70                  75                  80

Gln Ser Glu Asp Glu Ala Asp Tyr Tyr Cys Ala Ser Tyr Arg Ser Ser
            85                  90                  95

Asn Asn Ala Ala Val Phe Gly Gly Gly Thr His Leu Thr Val Leu
            100                 105                 110
```

-continued

<210> SEQ ID NO 161
<211> LENGTH: 111
<212> TYPE: PRT
<213> ORGANISM: Artificial Sequence
<220> FEATURE:
<223> OTHER INFORMATION: Variabe domain

<400> SEQUENCE: 161

Leu Pro Val Leu Thr Gln Pro Pro Ser Val Ser Gly Thr Leu Gly Lys
1               5                   10                  15

Thr Leu Thr Ile Ser Cys Ala Gly Thr Ser Ser Asp Val Gly Tyr Gly
            20                  25                  30

Asn Tyr Val Ser Trp Tyr Gln Gln Leu Pro Gly Thr Ala Pro Lys Leu
        35                  40                  45

Leu Ile Tyr Ala Val Ser Tyr Arg Ala Ser Gly Ile Pro Asp Arg Phe
    50                  55                  60

Ser Gly Ser Lys Ser Gly Asn Thr Ala Ser Leu Ser Ile Ser Gly Leu
65                  70                  75                  80

Gln Ser Glu Asp Glu Ala Asp Tyr Tyr Cys Ala Ser Tyr Arg Ser Ser
                85                  90                  95

Asn Lys Asn Ala Val Phe Gly Gly Gly Thr His Leu Thr Val Leu
            100                 105                 110

<210> SEQ ID NO 162
<211> LENGTH: 111
<212> TYPE: PRT
<213> ORGANISM: Artificial Sequence
<220> FEATURE:
<223> OTHER INFORMATION: Variabe domain

<400> SEQUENCE: 162

Gln Ser Ala Leu Thr Gln Pro Pro Ser Val Ser Gly Ser Pro Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Lys Leu Pro Gly Thr Ala Pro Lys Leu
        35                  40                  45

Leu Ile Tyr Ala Val Ser Tyr Arg Ala Ser Gly Ile Pro Asp Arg Phe
    50                  55                  60

Ser Gly Ser Arg Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Ile Thr
                85                  90                  95

Asn Arg His Ser Val Phe Gly Gly Gly Thr His Leu Thr Val Leu
            100                 105                 110

<210> SEQ ID NO 163
<211> LENGTH: 111
<212> TYPE: PRT
<213> ORGANISM: Artificial Sequence
<220> FEATURE:
<223> OTHER INFORMATION: Variabe domain

<400> SEQUENCE: 163

Gln Ser Ala Leu Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
            20                  25                  30

Asn Tyr Val Ser Trp Tyr Gln Gln Lys Leu Pro Gly Thr Ala Pro Lys Leu
        35                  40                  45

```
Leu Ile Tyr Ala Val Thr Tyr Arg Ala Ser Gly Ile Pro Asp Arg Phe
     50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr Tyr Cys Ala Ser Tyr Arg Arg Ser
                85                  90                  95

Thr Asn Val Gly Val Phe Gly Gly Gly Thr His Leu Thr Val Leu
            100                 105                 110

<210> SEQ ID NO 164
<211> LENGTH: 111
<212> TYPE: PRT
<213> ORGANISM: Artificial Sequence
<220> FEATURE:
<223> OTHER INFORMATION: Variabe domain

<400> SEQUENCE: 164

Gln Ala Val Leu Thr Gln Pro Pro Ser Val Ser Gly Thr Leu Gly Lys
1               5                   10                  15

Thr Val Thr Ile Ser Cys Ala Gly Thr Ser Ser Asp Val Gly Tyr Gly
                20                  25                  30

Asn Tyr Val Ser Trp Tyr Gln Lys Leu Pro Gly Thr Ala Pro Lys Leu
            35                  40                  45

Leu Ile Tyr Ala Val Ser Tyr Arg Ala Ser Gly Ile Pro Asp Arg Phe
     50                  55                  60

Ser Gly Ser Lys Ser Gly Asn Thr Ala Ser Leu Thr Ile Ser Gly Leu
65                  70                  75                  80

Gln Ser Glu Asp Glu Ala Asp Tyr His Cys Ala Ser Tyr Arg Thr Ser
                85                  90                  95

Asn Asn Val Ala Val Phe Gly Gly Gly Thr Lys Leu Thr Val Leu
            100                 105                 110

<210> SEQ ID NO 165
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 165
gaaattgtga tgacgcagtc tcccagctcc gtgactgcgt ctgcaggaga gaaggtcacc      60
atcaattgta agtccagcca gagtgtgtta tggcgctcca accagaaaaa ctacttagct     120
tggtaccagc agagacttgg acagtctcct aggctgctca tcagctgggc atccatccga     180
gaatcggggg ttcctgatcg attcagcggc agtgggtcca caacagattt cactcttacc     240
atcagcagct tccagcctga agacgcggca gtgtattact gccaacaggg ttatagtttt     300
ccatatacat tcggcagtgg gaccaggctg gaaatcaaa                            339

<210> SEQ ID NO 166
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 166
gatattgtga tgacccagac tcctagctcc gtgactgcgg ctgtaggaga gaaggtcgct      60
atcaactgta agtccagcca gagcgtgtta tataacccca accagaaaag ctacttagct     120
```

```
tggtaccaac agagacctgg acaatctcct aggctgctca tctactgggc atccacccga    180
gaatcggggg ttcctgatcg cttcagcggc agtgggtcca acagatttt cgctcttacc    240 atcagcagct ccagcctga agacgcggca gtgtattact gccagcaggg ttatagtttt    300
ccatatagtt tcggcagtgg gaccaggctg gaaatcaga                          339
```

<210> SEQ ID NO 167
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 167

```
gatgttgtga tgactcagtc tcccagctcc gtgactgcat ctgtaggaga gaaggtcact    60
atcaactgta agtccagcca gagtgtgtta tacacctcca accacaaaaa ctacttagct   120
tggtaccagc agagacttgg acagtctcct aggctgctca tctactgggc atccacccga   180
gaatcggggg ttcctgatcg attcagcggc agtgggtcca acagatttt cactctgacc   240 atcagcagct ccagcctga agacgcggca gtgtattact gccagcaggg atggagtttt   300
ccatatagtt tcggcagtgg gaccaggctg gaaatcaaa                          339
```

<210> SEQ ID NO 168
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 168

```
gatattgtga tgacccagac tcccagctcc gtgactgcgt ctgcaggaga gaaggtcacc    60
atcaattgta agtccagcca gagtgtatta caactcca accagaaaaa ctacttagct    120
tggtaccagc agagacttgg acagtctcct aggctgctca tctactgggc atccacccga   180
gaatcggggg ttcctgatcg attcagcggc agtgggtcca acagatttt cactctgacc   240 atcagcagct ccagcctga agacgcggca gtgtattact gccagcaggg atggagtttt   300
ccatatactt tcggcagtgg gaccaggctg gaaatcaaa                          339
```

<210> SEQ ID NO 169
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 169

```
gatatccagt tgacccagtc tcccagctcc gtgacagcgt ctgcaggaga gaaggtcacc    60
atcaattgta agtccagcca gagtgtgtta tacggctcca accagaaaaa ctacttagct   120
tggtaccagc agagacttgg acagtctcct aggctgctca tctactgggc atccacccga   180
gaatcggggg ttcctgatcg attcagcggc agtgggtcca acagatttt cactctgacc   240 atcagcagct ccagcctga agacgcggca gtgtattact gccagcaggg atggagtttt   300
ccatatactt tcggcagtgg gaccaggctg gaaatcaaa                          339
```

<210> SEQ ID NO 170
<211> LENGTH: 339
<212> TYPE: DNA

<213> ORGANISM: Artificial Sequence
<220> FEATURE:
<223> OTHER INFORMATION: Polynucteotide encoding variable domain

<400> SEQUENCE: 170

```
gacatccagt tgacccagtc tcccagctcc gtgactgtgt ctgtaggaga gaaggtcacc    60
atcaattgta agtccagcca gagtgtatta tacaactcca accagaaaaa ctacttagct   120
tggtaccagc agagacttgg acagtctcct aggctgctca tctactgggc atccacccga   180
gaatcggggg ttcctgatcg attcagcggc agtgggtcca acagatttt cactctgacc    240
atcagcagct ccagcctga agacgcggca gtgtattact gccagcaggg atggagtttt    300
ccatatactt tcggcagtgg gaccaggctg gaaatcaaa                          339
```

<210> SEQ ID NO 171
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 171

```
gacatccaga tgacccagtc tcccagctcc gtgactgcgt ctgcaggaga gaaggtcacc    60
atcaattgta agtccagcca gagtgtatta tacaactcca accagaaaaa ctacttagct   120
tggtaccagc agagacttgg acagtctcct aggctgctca tctactgggc atccacccga   180
gaatcggggg ttcctgatcg attcagcggc agtgggtcca acagatttt cactctgacc    240
atcagcagct ccagcctga agacgcggca gtgtattact gccagcaggg atggagtttt    300
ccatatactt tcggcagtgg gaccaggctg gaaatcaaa                          339
```

<210> SEQ ID NO 172
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 172

```
gatattgtga tgacccagac tcccgcctcc gtgactgcgt ctgcaggaga gaaggtcacc    60
atcaattgta agtccagcca gagtgtgtta ttcagctcca accagaaaaa ctacttagct   120
tggtaccagc agagagttgg acagtctcct aggctgctca tctactgggc atccacccga   180
gaatcggggg ttcctgatcg attcagcggc agtgggtcca acagatttt cactcttacc    240
atcagcaact ccagcctga agacgcggca gtgtattact gccagcaggg ttatagtttt    300
ccatatagtt tcggcagtgg gactaggctg gaaatcaga                          339
```

<210> SEQ ID NO 173
<211> LENGTH: 339
<212> TYPE: DNA
<213> ORGANISM: Artificial Sequence
<220> FEATURE:
<223> OTHER INFORMATION: Polynucteotide encoding variable domain

<400> SEQUENCE: 173

```
gatgttgtga tgactcagtc tcccagctcc gtgactgcgt ctgcaggaga gaaggtcacc    60
atcaattgta agtccagtca gagtgtgtta tggagctcca accagaaaaa ctacttagct   120
tggtaccagc agagagttgg acagtctcct aggctgctca tctactgggc atccacccga   180
gaatcggggg ttcctgatcg attcagcggc agtgggtcca acagatttt cactcttacc    240
```

```
atcagcaact tccagcctga agacgcggca gtgtattact gccagcaggg ttatagtttt    300
ccatatagtt tcggcagtgg gaccaggctg gaaatcaga                          339

<210> SEQ ID NO 174
<211> LENGTH: 333
<212> TYPE: DNA
<213> ORGANISM: Artificial Sequence
<220> FEATURE:
<223> OTHER INFORMATION: Polynucteotide encoding variable domain

<400> SEQUENCE: 174
cagtctgtgt tgacgcagcc tccctccgtg tctgggtctc caggaaagac ggtcaccatc    60
tcctgtgcag gaaccagcag tgatgttggg tatggaaact atgtctcctg gtaccagcag   120
ctcccaggca cggcccccaa actcctgatc tttgcagtca gctatcgagc tcagggatc    180 cctgatcgct tctctggctc caagtcaggc aacacggcct ttttgaccat ctctggctc    240 cagtccgagg acgaggctga ttattactgt gcctcatata aagcagcaa caatgctgct    300 gtgttcggcg gagggaccca tctgaccgtc ctg                                333

<210> SEQ ID NO 175
<211> LENGTH: 336
<212> TYPE: DNA
<213> ORGANISM: Artificial Sequence
<220> FEATURE:
<223> OTHER INFORMATION: Polynucteotide encoding variable domain

<400> SEQUENCE: 175
gcacagtctg tgctgacgca gcctccctcc gtgtccggaa ctctgggcaa gacgctcacc    60
atctcctgcg ctggaaccag cactgatgtt ggatacggaa actatgtctc ctggtaccaa   120
cagctcccag gcacggcccc caaactcctg atctttgcag tcagctatcg agcctcaggg   180
atccctgatc gcttctctgg ctccaagtca ggcaacacgg cctttttgac catctctggg   240
ctccagtccg aggacgaggc tgattattac tgtgcctcat atagaagcag caacaatgct   300
gctgtgttcg gcggagggac ccatctgacc gtcctg                             336

<210> SEQ ID NO 176
<211> LENGTH: 333
<212> TYPE: DNA
<213> ORGANISM: Artificial Sequence
<220> FEATURE:
<223> OTHER INFORMATION: Polynucteotide encoding variable domain

<400> SEQUENCE: 176
cagtctgccc tgactcagcc tccctccgtg tccggaactc tgggcaagac gctcaccatc    60
tcctgcgctg gaaccagcac tgatgttgga tacgaaaact atgtctcctg gtaccaacag   120
ctcccaggca cggcccccaa actcctgatc tttgcagtca gctatcgagc tcagggatc    180 cctgatcgct tctctggctc caagtcaggc aacacggcct ttttgaccat ctctggctc    240 cagtccgagg acgaggctga ttattactgt gcctcatata aagcagcaa caatgctgct    300 gtgttcggcg gagggaccca tctgaccgtc ctg                                333

<210> SEQ ID NO 177
<211> LENGTH: 333
<212> TYPE: DNA
<213> ORGANISM: Artificial Sequence
<220> FEATURE:
<223> OTHER INFORMATION: Polynucteotide encoding variable domain
```

```
<400> SEQUENCE: 177
ctgcctgtgc tgactcagcc tccctccgtg tccggaactc tgggaaagac gctcaccatc      60
tcctgcgctg gaaccagcag tgatgttgga tacggaaact atgtctcctg gtaccaacag     120
ctcccaggca cggcccccaa actcctgatc tatgcagtca gctatcgagc ctcagggatc     180
cctgatcgct tctctggctc caagtcaggc aacacggcct ccctgagcat ctctgggctc     240
cagtctgagg acgaggctga ttattactgt gcctcatata gaagcagcaa caaaaatgct     300
gtgttcggcg gagggaccca tctgaccgtc ctg                                  333

<210> SEQ ID NO 178
<211> LENGTH: 333
<212> TYPE: DNA
<213> ORGANISM: Artificial Sequence
<220> FEATURE:
<223> OTHER INFORMATION: Polynucteotide encoding variable domain

<400> SEQUENCE: 178
cagtctgccc tgactcagcc tccctccgtg tctgggtctc caggaaagac ggtcaccatc      60
tcctgtgcag gaaccagcag tgatgttgga tacggaaact atgtctcctg gtaccaaaag     120
ctcccaggca cagcccccaa actcctgatc tatgcagtca gctatcgagc ctcagggatc     180
cctgatcgct tctctggctc ccggtcaggc aacacggcct ccctgaccat ctctgggctc     240
cagtctgagg acgaggctga ttattactgt gcctcatata gaatcaccaa caggcacagc     300
gtgttcggcg gagggaccca tctgaccgtc ctg                                  333

<210> SEQ ID NO 179
<211> LENGTH: 333
<212> TYPE: DNA
<213> ORGANISM: Artificial Sequence
<220> FEATURE:
<223> OTHER INFORMATION: Polynucteotide encoding variable domain

<400> SEQUENCE: 179
cagtctgccc tgactcagcc tccctccgtg tctggaactc tgggaaagac ggtcaccatc      60
tcctgcgctg gaaccagcag tgatgttggg tatggaaact atgtctcctg gtaccaaaag     120
ctcccaggca cagcccccaa actcctgatc tatgcagtca cctatcgagc ctcagggatc     180
cctgatcgct tctctggctc caagtcgggc aacacggcct ccctgaccat ctctgggctc     240
cagtctgagg acgaggctga ttattactgt gcctcatata gaagaagtac taatgtgggg     300
gtgttcggcg gagggaccca tctgaccgtc ctg                                  333

<210> SEQ ID NO 180
<211> LENGTH: 333
<212> TYPE: DNA
<213> ORGANISM: Artificial Sequence
<220> FEATURE:
<223> OTHER INFORMATION: Polynucteotide encoding variable domain

<400> SEQUENCE: 180
caggctgtgc tgactcagcc tccctccgtg tccggaactc tgggaaagac ggtcaccatc      60
tcctgcgctg gaaccagcag tgatgttgga tacggaaact atgtctcctg gtaccaaaag     120
ctcccaggca cagcccccaa actcctgatc tatgcagtca gctatcgagc ctcagggatc     180
cctgatcgct tctctggctc caagtcaggc aacacggcct ccctgaccat ctctgggctc     240
cagtctgagg acgaggctga ttatcactgt gcctcatata gaaccagcaa caatgtggct     300
gtgttcggcg gagggaccaa gctgaccgtc ctc                                  333
```

<210> SEQ ID NO 181
<211> LENGTH: 102
<212> TYPE: PRT
<213> ORGANISM: Homo sapiens

<400> SEQUENCE: 181

Val Asp Thr Tyr Tyr Asp Asp Gln Leu Ile Ser Cys Gly Ser Val Asn
1               5                   10                  15
Arg Gly Thr Cys Gln Arg His Val Phe Pro His Asn His Thr Ala Asp
            20                  25                  30
Ile Gln Ser Glu Val His Cys Ile Phe Ser Pro Gln Ile Glu Glu Pro
        35                  40                  45
Ser Gln Cys Pro Asp Cys Val Val Ser Ala Leu Gly Ala Lys Val Leu
    50                  55                  60
Ser Ser Val Lys Asp Arg Phe Ile Asn Phe Phe Val Gly Asn Thr Ile
65                  70                  75                  80
Asn Ser Ser Tyr Phe Pro Asp His Pro Leu His Ser Ile Ser Val Arg
                85                  90                  95
Arg Leu Lys Glu Thr Lys
            100

<210> SEQ ID NO 182
<211> LENGTH: 10
<212> TYPE: PRT
<213> ORGANISM: Homo sapiens

<400> SEQUENCE: 182

Glu Pro Lys Ser Cys Asp Lys Thr His Thr
1               5                   10

<210> SEQ ID NO 183
<211> LENGTH: 5
<212> TYPE: PRT
<213> ORGANISM: Homo sapiens

<400> SEQUENCE: 183

Cys Pro Pro Cys Pro
1               5

<210> SEQ ID NO 184
<211> LENGTH: 8
<212> TYPE: PRT
<213> ORGANISM: Homo sapiens

<400> SEQUENCE: 184

Ala Pro Glu Leu Leu Gly Gly Pro
1               5

<210> SEQ ID NO 185
<211> LENGTH: 12
<212> TYPE: PRT
<213> ORGANISM: Homo sapiens

<400> SEQUENCE: 185

Glu Leu Lys Thr Pro Leu Gly Asp Thr Thr His Thr
1               5                   10

<210> SEQ ID NO 186
<211> LENGTH: 5
<212> TYPE: PRT
<213> ORGANISM: Homo sapiens

<400> SEQUENCE: 186

Cys Pro Arg Cys Pro
1               5

<210> SEQ ID NO 187
<211> LENGTH: 15
<212> TYPE: PRT
<213> ORGANISM: Homo sapiens

<400> SEQUENCE: 187

Glu Pro Lys Ser Cys Asp Thr Pro Pro Cys Pro Arg Cys Pro
1               5                   10                  15

<210> SEQ ID NO 188
<211> LENGTH: 7
<212> TYPE: PRT
<213> ORGANISM: Homo sapiens

<400> SEQUENCE: 188

Glu Ser Lys Tyr Gly Pro Pro
1               5

<210> SEQ ID NO 189
<211> LENGTH: 5
<212> TYPE: PRT
<213> ORGANISM: Homo sapiens

<400> SEQUENCE: 189

Cys Pro Ser Cys Pro
1               5

<210> SEQ ID NO 190
<211> LENGTH: 8
<212> TYPE: PRT
<213> ORGANISM: Homo sapiens

<400> SEQUENCE: 190

Ala Pro Glu Phe Leu Gly Gly Pro
1               5

<210> SEQ ID NO 191
<211> LENGTH: 3
<212> TYPE: PRT
<213> ORGANISM: Homo sapiens

<400> SEQUENCE: 191

Glu Arg Lys
1

<210> SEQ ID NO 192
<211> LENGTH: 10
<212> TYPE: PRT
<213> ORGANISM: Homo sapiens

<400> SEQUENCE: 192

Cys Cys Val Glu Cys Pro Pro Cys Pro
1               5                   10

<210> SEQ ID NO 193
<211> LENGTH: 7
<212> TYPE: PRT
<213> ORGANISM: Homo sapiens

<400> SEQUENCE: 193

```
Ala Pro Pro Val Ala Gly Pro
 1               5
```

```
<210> SEQ ID NO 194
<211> LENGTH: 102
<212> TYPE: PRT
<213> ORGANISM: Homo sapiens

<400> SEQUENCE: 194
```

```
Val Asp Thr Tyr Tyr Asp Asp Gln Leu Ile Ser Cys Gly Ser Val Asn
 1               5                  10                  15

Arg Gly Thr Cys Gln Arg His Val Phe Pro His Asn His Thr Ala Asp
            20                  25                  30

Ile Gln Ser Glu Val His Cys Ile Phe Ser Pro Gln Ile Glu Glu Pro
        35                  40                  45

Ser Gln Cys Pro Asp Cys Val Val Ser Ala Leu Gly Ala Lys Val Leu
    50                  55                  60

Ser Ser Val Lys Asp Arg Phe Ile Asn Phe Phe Val Gly Asn Thr Ile
65                  70                  75                  80

Asn Ser Ser Tyr Phe Pro Asp His Pro Leu His Ser Ile Ser Val Arg
                85                  90                  95

Arg Leu Lys Glu Thr Lys
            100
```

```
<210> SEQ ID NO 195
<211> LENGTH: 16
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably T or A
<220> FEATURE:
<221> NAME/KEY: MISC_FEATURE
<222> LOCATION: (2)..(2)
<223> OTHER INFORMATION: X is any amino acid, preferably I
<220> FEATURE:
<221> NAME/KEY: MISC_FEATURE
<222> LOCATION: (3)..(3)
<223> OTHER INFORMATION: X is any amino acid, preferably S or N
<220> FEATURE:
<221> NAME/KEY: MISC_FEATURE
<222> LOCATION: (4)..(4)
<223> OTHER INFORMATION: X is any amino acid, preferably W
<220> FEATURE:
<221> NAME/KEY: MISC_FEATURE
<222> LOCATION: (5)..(5)
<223> OTHER INFORMATION: X is any amino acid, preferably N
<220> FEATURE:
<221> NAME/KEY: MISC_FEATURE
<222> LOCATION: (6)..(6)
<223> OTHER INFORMATION: X is any amino acid, preferably D or G
<220> FEATURE:
<221> NAME/KEY: MISC_FEATURE
<222> LOCATION: (7)..(7)
<223> OTHER INFORMATION: X is any amino acid, preferably I, G or S
<220> FEATURE:
<221> NAME/KEY: MISC_FEATURE
<222> LOCATION: (8)..(8)
<223> OTHER INFORMATION: X8 is any amino acid, preferably N or S

<400> SEQUENCE: 195
```

```
Xaa Xaa Xaa Xaa Xaa Xaa Xaa Xaa Thr Tyr Tyr Ala Glu Ser Met Lys
 1               5                  10                  15
```

```
<210> SEQ ID NO 196
<211> LENGTH: 16
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (9)..(9)
<223> OTHER INFORMATION: X is any amino acid, preferably Y or D

<400> SEQUENCE: 196

Val Ile Ala Tyr Asp Gly Ser Thr Xaa Tyr Ser Pro Ser Leu Lys Ser
1               5                   10                  15

<210> SEQ ID NO 197
<211> LENGTH: 17
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (6)..(6)
<223> OTHER INFORMATION: X is any amino acid, preferably D, N or E

<400> SEQUENCE: 197

Arg Ile Asp Pro Glu Xaa Gly Gly Thr Lys Tyr Ala Gln Lys Phe Gln
1               5                   10                  15

Gly

<210> SEQ ID NO 198
<211> LENGTH: 6
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably D or S
<220> FEATURE:
<221> NAME/KEY: MISC_FEATURE
<222> LOCATION: (4)..(4)
<223> OTHER INFORMATION: X is any amino acid, preferably A or V
<220> FEATURE:
<221> NAME/KEY: MISC_FEATURE
<222> LOCATION: (6)..(6)
<223> OTHER INFORMATION: X is any amino acid, preferably T, N or S

<400> SEQUENCE: 198

Xaa Asp Tyr Xaa Met Xaa
1               5

<210> SEQ ID NO 199
<211> LENGTH: 7
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably G or T
<220> FEATURE:
<221> NAME/KEY: MISC_FEATURE
<222> LOCATION: (5)..(5)
<223> OTHER INFORMATION: X is any amino acid, preferably A or Y

<400> SEQUENCE: 199

Xaa Asn Tyr Tyr Xaa Trp Ser
```

```
1               5

<210> SEQ ID NO 200
<211> LENGTH: 5
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably M or N
<220> FEATURE:
<221> NAME/KEY: MISC_FEATURE
<222> LOCATION: (2)..(2)
<223> OTHER INFORMATION: X is any amino acid, preferably N or Y
<220> FEATURE:
<221> NAME/KEY: MISC_FEATURE
<222> LOCATION: (3)..(3)
<223> OTHER INFORMATION: X is any amino acid, preferably S or V

<400> SEQUENCE: 200

Xaa Xaa Xaa Ile Asp
1               5

<210> SEQ ID NO 201
<211> LENGTH: 9
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (4)..(4)
<223> OTHER INFORMATION: X is any amino acid, preferably Y or W
<220> FEATURE:
<221> NAME/KEY: MISC_FEATURE
<222> LOCATION: (8)..(8)
<223> OTHER INFORMATION: X is any amino acid, preferably Y or L
<220> FEATURE:
<221> NAME/KEY: MISC_FEATURE
<222> LOCATION: (9)..(9)
<223> OTHER INFORMATION: X is any amino acid, preferably T or S

<400> SEQUENCE: 201

Gln Gln Gly Xaa Ser Phe Pro Xaa Xaa
1               5

<210> SEQ ID NO 202
<211> LENGTH: 11
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (5)..(5)
<223> OTHER INFORMATION: X is any amino acid, preferably S, I, R or T
<220> FEATURE:
<221> NAME/KEY: MISC_FEATURE
<222> LOCATION: (6)..(6)
<223> OTHER INFORMATION: X is any amino acid, preferably A, S, T or R
<220> FEATURE:
<221> NAME/KEY: MISC_FEATURE
<222> LOCATION: (7)..(7)
<223> OTHER INFORMATION: X is any amino acid, preferably N or T
<220> FEATURE:
<221> NAME/KEY: MISC_FEATURE
<222> LOCATION: (8)..(8)
<223> OTHER INFORMATION: X is any amino acid, preferably N, D, R or K
<220> FEATURE:
<221> NAME/KEY: MISC_FEATURE
<222> LOCATION: (9)..(9)
<223> OTHER INFORMATION: X is any amino acid, preferably A, V, Y, N or H
```

```
<220> FEATURE:
<221> NAME/KEY: MISC_FEATURE
<222> LOCATION: (10)..(10)
<223> OTHER INFORMATION: X is any amino acid, preferably V, A, S or G

<400> SEQUENCE: 202

Ala Ser Tyr Arg Xaa Xaa Xaa Xaa Xaa Xaa Val
1               5                   10

<210> SEQ ID NO 203
<211> LENGTH: 7
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (4)..(4)
<223> OTHER INFORMATION: X is any amino acid, preferably I or T

<400> SEQUENCE: 203

Trp Ala Ser Xaa Arg Glu Ser
1               5

<210> SEQ ID NO 204
<211> LENGTH: 7
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably D, A or E
<220> FEATURE:
<221> NAME/KEY: MISC_FEATURE
<222> LOCATION: (3)..(3)
<223> OTHER INFORMATION: X is any amino acid, preferably N or S
<220> FEATURE:
<221> NAME/KEY: MISC_FEATURE
<222> LOCATION: (4)..(4)
<223> OTHER INFORMATION: X is any amino acid, preferably R, Y or K
<220> FEATURE:
<221> NAME/KEY: MISC_FEATURE
<222> LOCATION: (6)..(6)
<223> OTHER INFORMATION: X is any amino acid, preferably A, or P

<400> SEQUENCE: 204

Xaa Val Xaa Xaa Arg Xaa Ser
1               5

<210> SEQ ID NO 205
<211> LENGTH: 17
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (8)..(8)
<223> OTHER INFORMATION: X is any amino acid, preferably W, L or F
<220> FEATURE:
<221> NAME/KEY: MISC_FEATURE
<222> LOCATION: (9)..(9)
<223> OTHER INFORMATION: X is any amino acid, preferably R or S
<220> FEATURE:
<221> NAME/KEY: MISC_FEATURE
<222> LOCATION: (10)..(10)
<223> OTHER INFORMATION: X is any amino acid, preferably S or P
<220> FEATURE:
<221> NAME/KEY: MISC_FEATURE
<222> LOCATION: (12)..(12)
<223> OTHER INFORMATION: X is any amino acid, preferably Q or H
```

```
<220> FEATURE:
<221> NAME/KEY: MISC_FEATURE
<222> LOCATION: (14)..(14)
<223> OTHER INFORMATION: X is any amino acid, preferably N or S

<400> SEQUENCE: 205

Lys Ser Ser Gln Ser Val Leu Xaa Xaa Xaa Asn Xaa Lys Xaa Tyr Leu
1               5                   10                  15

Ala

<210> SEQ ID NO 206
<211> LENGTH: 14
<212> TYPE: PRT
<213> ORGANISM: Artificial Sequence
<220> FEATURE:
<223> OTHER INFORMATION: Degenerate CDR Sequence
<220> FEATURE:
<221> NAME/KEY: MISC_FEATURE
<222> LOCATION: (1)..(1)
<223> OTHER INFORMATION: X is any amino acid, preferably A or T
<220> FEATURE:
<221> NAME/KEY: MISC_FEATURE
<222> LOCATION: (3)..(3)
<223> OTHER INFORMATION: X is any amino acid, preferably T or S
<220> FEATURE:
<221> NAME/KEY: MISC_FEATURE
<222> LOCATION: (4)..(4)
<223> OTHER INFORMATION: X is any amino acid, preferably S or N
<220> FEATURE:
<221> NAME/KEY: MISC_FEATURE
<222> LOCATION: (5)..(5)
<223> OTHER INFORMATION: X is any amino acid, preferably S or T
<220> FEATURE:
<221> NAME/KEY: MISC_FEATURE
<222> LOCATION: (6)..(6)
<223> OTHER INFORMATION: X is any amino acid, preferably D or N
<220> FEATURE:
<221> NAME/KEY: MISC_FEATURE
<222> LOCATION: (7)..(7)
<223> OTHER INFORMATION: X is any amino acid, preferably V or I
<220> FEATURE:
<221> NAME/KEY: MISC_FEATURE
<222> LOCATION: (9)..(9)
<223> OTHER INFORMATION: X is any amino acid, preferably Y, G, D or N
<220> FEATURE:
<221> NAME/KEY: MISC_FEATURE
<222> LOCATION: (10)..(10)
<223> OTHER INFORMATION: X is any amino acid, preferably G or Y
<220> FEATURE:
<221> NAME/KEY: MISC_FEATURE
<222> LOCATION: (11)..(11)
<223> OTHER INFORMATION: X is any amino acid, preferably N or Y
<220> FEATURE:
<221> NAME/KEY: MISC_FEATURE
<222> LOCATION: (13)..(13)
<223> OTHER INFORMATION: X is any amino acid, preferably V or L

<400> SEQUENCE: 206

Xaa Gly Xaa Xaa Xaa Xaa Xaa Gly Xaa Xaa Tyr Xaa Ser
1               5                   10

<210> SEQ ID NO 207
<211> LENGTH: 908
<212> TYPE: PRT
<213> ORGANISM: H. sapiens

<400> SEQUENCE: 207

Glu Cys Lys Glu Ala Leu Ala Lys Ser Glu Met Asn Val Asn Met Lys
1               5                   10                  15

Tyr Gln Leu Pro Asn Phe Thr Ala Glu Thr Pro Ile Gln Asn Val Ile
                20                  25                  30
```

```
Leu His Glu His His Ile Phe Leu Gly Ala Thr Asn Tyr Ile Tyr Val
             35                  40                  45

Leu Asn Glu Glu Asp Leu Gln Lys Val Ala Glu Tyr Lys Thr Gly Pro
 50                  55                  60

Val Leu Glu His Pro Asp Cys Phe Pro Cys Gln Asp Cys Ser Ser Lys
 65                  70                  75                  80

Ala Asn Leu Ser Gly Gly Val Trp Lys Asp Asn Ile Asn Met Ala Leu
                 85                  90                  95

Val Val Asp Thr Tyr Tyr Asp Asp Gln Leu Ile Ser Cys Gly Ser Val
            100                 105                 110

Asn Arg Gly Thr Cys Gln Arg His Val Phe Pro His Asn His Thr Ala
        115                 120                 125

Asp Ile Gln Ser Glu Val His Cys Ile Phe Ser Pro Gln Ile Glu Glu
    130                 135                 140

Pro Ser Gln Cys Pro Asp Cys Val Val Ser Ala Leu Gly Ala Lys Val
145                 150                 155                 160

Leu Ser Ser Val Lys Asp Arg Phe Ile Asn Phe Phe Val Gly Asn Thr
                165                 170                 175

Ile Asn Ser Ser Tyr Phe Pro Asp His Pro Leu His Ser Ile Ser Val
            180                 185                 190

Arg Arg Leu Lys Glu Thr Lys Asp Gly Phe Met Phe Leu Thr Asp Gln
        195                 200                 205

Ser Tyr Ile Asp Val Leu Pro Glu Phe Arg Asp Ser Tyr Pro Ile Lys
    210                 215                 220

Tyr Val His Ala Phe Glu Ser Asn Asn Phe Ile Tyr Phe Leu Thr Val
225                 230                 235                 240

Gln Arg Glu Thr Leu Asp Ala Gln Thr Phe His Thr Arg Ile Ile Arg
                245                 250                 255

Phe Cys Ser Ile Asn Ser Gly Leu His Ser Tyr Met Glu Met Pro Leu
            260                 265                 270

Glu Cys Ile Leu Thr Glu Lys Arg Lys Arg Ser Thr Lys Lys Glu
        275                 280                 285

Val Phe Asn Ile Leu Gln Ala Ala Tyr Val Ser Lys Pro Gly Ala Gln
    290                 295                 300

Leu Ala Arg Gln Ile Gly Ala Ser Leu Asn Asp Asp Ile Leu Phe Gly
305                 310                 315                 320

Val Phe Ala Gln Ser Lys Pro Asp Ser Ala Glu Pro Met Asp Arg Ser
                325                 330                 335

Ala Met Cys Ala Phe Pro Ile Lys Tyr Val Asn Asp Phe Phe Asn Lys
            340                 345                 350

Ile Val Asn Lys Asn Asn Val Arg Cys Leu Gln His Phe Tyr Gly Pro
        355                 360                 365

Asn His Glu His Cys Phe Asn Arg Thr Leu Leu Arg Asn Ser Ser Gly
    370                 375                 380

Cys Glu Ala Arg Arg Asp Glu Tyr Arg Thr Glu Phe Thr Thr Ala Leu
385                 390                 395                 400

Gln Arg Val Asp Leu Phe Met Gly Gln Phe Ser Glu Val Leu Leu Thr
                405                 410                 415

Ser Ile Ser Thr Phe Ile Lys Gly Asp Leu Thr Ile Ala Asn Leu Gly
            420                 425                 430

Thr Ser Glu Gly Arg Phe Met Gln Val Val Ser Arg Ser Gly Pro
        435                 440                 445

Ser Thr Pro His Val Asn Phe Leu Leu Asp Ser His Pro Val Ser Pro
```

```
            450                 455                 460
Glu Val Ile Val Glu His Thr Leu Asn Gln Asn Gly Tyr Thr Leu Val
465                 470                 475                 480

Ile Thr Gly Lys Lys Ile Thr Lys Ile Pro Leu Asn Gly Leu Gly Cys
                485                 490                 495

Arg His Phe Gln Ser Cys Ser Gln Cys Leu Ser Ala Pro Pro Phe Val
                500                 505                 510

Gln Cys Gly Trp Cys His Asp Lys Cys Val Arg Ser Glu Glu Cys Leu
            515                 520                 525

Ser Gly Thr Trp Thr Gln Gln Ile Cys Leu Pro Ala Ile Tyr Lys Val
        530                 535                 540

Phe Pro Asn Ser Ala Pro Leu Glu Gly Gly Thr Arg Leu Thr Ile Cys
545                 550                 555                 560

Gly Trp Asp Phe Gly Phe Arg Arg Asn Asn Lys Phe Asp Leu Lys Lys
                565                 570                 575

Thr Arg Val Leu Leu Gly Asn Glu Ser Cys Thr Leu Thr Leu Ser Glu
                580                 585                 590

Ser Thr Met Asn Thr Leu Lys Cys Thr Val Gly Pro Ala Met Asn Lys
            595                 600                 605

His Phe Asn Met Ser Ile Ile Ile Ser Asn Gly His Gly Thr Thr Gln
        610                 615                 620

Tyr Ser Thr Phe Ser Tyr Val Asp Pro Val Ile Thr Ser Ile Ser Pro
625                 630                 635                 640

Lys Tyr Gly Pro Met Ala Gly Gly Thr Leu Leu Thr Leu Thr Gly Asn
                645                 650                 655

Tyr Leu Asn Ser Gly Asn Ser Arg His Ile Ser Ile Gly Gly Lys Thr
                660                 665                 670

Cys Thr Leu Lys Ser Val Ser Asn Ser Ile Leu Glu Cys Tyr Thr Pro
            675                 680                 685

Ala Gln Thr Ile Ser Thr Glu Phe Ala Val Lys Leu Lys Ile Asp Leu
        690                 695                 700

Ala Asn Arg Glu Thr Ser Ile Phe Ser Tyr Arg Glu Asp Pro Ile Val
705                 710                 715                 720

Tyr Glu Ile His Pro Thr Lys Ser Phe Ile Ser Gly Gly Ser Thr Ile
                725                 730                 735

Thr Gly Val Gly Lys Asn Leu Asn Ser Val Ser Val Pro Arg Met Val
                740                 745                 750

Ile Asn Val His Glu Ala Gly Arg Asn Phe Thr Val Ala Cys Gln His
            755                 760                 765

Arg Ser Asn Ser Glu Ile Ile Cys Cys Thr Thr Pro Ser Leu Gln Gln
        770                 775                 780

Leu Asn Leu Gln Leu Pro Leu Lys Thr Lys Ala Phe Phe Met Leu Asp
785                 790                 795                 800

Gly Ile Leu Ser Lys Tyr Phe Asp Leu Ile Tyr Val His Asn Pro Val
                805                 810                 815

Phe Lys Pro Phe Glu Lys Pro Val Met Ile Ser Met Gly Asn Glu Asn
                820                 825                 830

Val Leu Glu Ile Lys Gly Asn Asp Ile Asp Pro Glu Ala Val Lys Gly
            835                 840                 845

Glu Val Leu Lys Val Gly Asn Lys Ser Cys Glu Asn Ile His Leu His
        850                 855                 860

Ser Glu Ala Val Leu Cys Thr Val Pro Asn Asp Leu Leu Lys Leu Asn
865                 870                 875                 880
```

-continued

```
Ser Glu Leu Asn Ile Glu Trp Lys Gln Ala Ile Ser Thr Val Leu
            885                 890                 895

Gly Lys Val Ile Val Gln Pro Asp Gln Asn Phe Thr
            900                 905

<210> SEQ ID NO 208
<211> LENGTH: 909
<212> TYPE: PRT
<213> ORGANISM: Lama glama

<400> SEQUENCE: 208

Glu Cys Lys Glu Ala Leu Val Lys Ser Arg Met Asn Val Asn Met Gln
1               5                   10                  15

Tyr Gln Leu Pro Asn Phe Thr Ala Glu Thr Arg Ile Gln Asn Val Val
            20                  25                  30

Leu His Lys His His Ile Tyr Leu Gly Ala Val Asn Tyr Ile Tyr Val
        35                  40                  45

Leu Asn Asp Lys Asp Leu Gln Lys Val Ala Glu Tyr Lys Thr Gly Pro
    50                  55                  60

Val Leu Glu His Pro His Cys Phe Pro Cys Glu Asp Cys Ser His Lys
65                  70                  75                  80

Ala Asn Leu Ser Asp Gly Val Trp Lys Asp Asn Ile Asn Met Ala Leu
                85                  90                  95

Leu Val Asp Thr Tyr Tyr Asp Asp Gln Leu Ile Ser Cys Gly Ser Val
            100                 105                 110

His Arg Gly Thr Cys Gln Arg His Val Leu Pro Pro Asp Asn Thr Ala
        115                 120                 125

Asp Ile Gln Ser Glu Val Tyr Cys Met Tyr Ser Pro Gln Thr Asp Glu
    130                 135                 140

Glu Pro Gly Gln Cys Pro Asp Cys Val Val Ser Ala Leu Gly Thr Lys
145                 150                 155                 160

Val Leu Leu Ser Glu Lys Asp Arg Phe Ile Asn Phe Phe Val Gly Asn
                165                 170                 175

Thr Ile Asn Ser Ser Tyr Leu Pro Asp His Ser Leu His Ser Ile Ser
            180                 185                 190

Val Arg Arg Leu Lys Glu Thr Gln Asp Gly Phe Lys Phe Leu Thr Asp
        195                 200                 205

Gln Ser Tyr Ile Asp Val Leu Pro Glu Phe Gln Asp Thr Tyr Pro Ile
    210                 215                 220

Lys Tyr Val His Ala Phe Glu Ser Asn His Phe Ile Tyr Phe Leu Thr
225                 230                 235                 240

Val Gln Arg Glu Thr Leu Asp Ala Gln Thr Phe His Thr Arg Ile Ile
                245                 250                 255

Arg Phe Cys Ser Val Asp Ser Gly Leu His Ser Tyr Met Glu Met Pro
            260                 265                 270

Leu Glu Cys Ile Leu Thr Glu Lys Arg Arg Arg Ser Thr Lys Glu
        275                 280                 285

Glu Val Phe Asn Ile Leu Gln Ala Ala Tyr Val Ser Lys Pro Gly Ser
    290                 295                 300

Gln Leu Ala Lys Gln Ile Gly Ala Asn Leu Asn Asp Ile Leu Tyr
305                 310                 315                 320

Gly Val Phe Ala Gln Ser Lys Pro Asp Ser Ala Glu Pro Met Asn Arg
                325                 330                 335

Ser Ala Val Cys Ala Phe Pro Val Lys Tyr Val Asn Glu Phe Phe Asn
```

-continued

```
                340                 345                 350
Lys Ile Val Asn Lys Asn Val Arg Cys Leu Gln His Phe Tyr Gly
                355                 360                 365
Pro Asn His Glu His Cys Phe Asn Arg Thr Leu Leu Arg Asn Ser Ser
        370                 375                 380
Gly Cys Glu Val Arg Asn Asp Glu Tyr Arg Thr Glu Phe Thr Thr Ala
385                 390                 395                 400
Leu Gln Arg Val Asp Leu Phe Thr Gly Gln Phe Asn Gln Val Leu Leu
                405                 410                 415
Thr Ser Ile Ser Thr Phe Ile Lys Gly Asp Leu Thr Ile Ala Asn Leu
                420                 425                 430
Gly Thr Ser Glu Gly Arg Phe Met Gln Val Val Ser Arg Ser Gly
                435                 440                 445
Leu Ser Thr Pro His Val Asn Phe Leu Leu Asp Ser His Pro Val Ser
                450                 455                 460
Pro Glu Ala Ile Val Glu His Pro Leu Asn Gln Asn Gly Tyr Thr Leu
465                 470                 475                 480
Val Val Thr Gly Lys Lys Ile Thr Lys Ile Pro Leu Asn Gly Leu Gly
                485                 490                 495
Cys Glu His Phe Gln Ser Cys Ser Gln Cys Leu Ser Ala Pro Ser Phe
                500                 505                 510
Val Gln Cys Gly Trp Cys His Asp Lys Cys Val Gln Leu Glu Glu Cys
                515                 520                 525
Ser Gly Gly Ile Trp Thr Gln Glu Ile Cys Leu Pro Thr Ile Tyr Lys
                530                 535                 540
Val Leu Pro Thr Ser Ala Pro Leu Glu Gly Gly Thr Thr Leu Thr Ile
545                 550                 555                 560
Cys Gly Trp Asp Phe Gly Phe Arg Arg Asn Asn Lys Ser Asp Leu Lys
                565                 570                 575
Lys Thr Lys Val Phe Leu Gly Asn Glu Ser Cys Thr Leu Thr Leu Ser
                580                 585                 590
Glu Ser Thr Thr Asn Thr Leu Lys Cys Thr Val Gly Pro Ala Met Asn
                595                 600                 605
Glu His Phe Asn Val Ser Ile Ile Ile Ser Asn Asn Arg Gly Thr Ala
        610                 615                 620
Gln Tyr Ser Thr Phe Ser Tyr Val Asp Pro Ile Ile Thr Ser Ile Ser
625                 630                 635                 640
Pro Ser Tyr Gly Pro Lys Thr Gly Gly Thr Leu Leu Thr Leu Thr Gly
                645                 650                 655
Lys His Leu Asn Ser Gly Asn Ser Arg His Ile Ser Ile Gly Gly Lys
                660                 665                 670
Thr Cys Thr Leu Lys Ser Val Ser Asp Ser Ile Leu Glu Cys Tyr Thr
                675                 680                 685
Pro Ala Gln Thr Thr Pro Thr Glu Phe Pro Val Lys Leu Lys Ile Asp
                690                 695                 700
Leu Ala Asn Arg Glu Ile Asn Ser Phe Ser Tyr Arg Glu Asp Pro Val
705                 710                 715                 720
Val Tyr Glu Ile His Pro Thr Lys Ser Phe Ile Ser Gly Gly Ser Thr
                725                 730                 735
Ile Thr Gly Val Gly Lys Tyr Leu Asn Ser Val Ser Val Leu Arg Met
                740                 745                 750
Val Ile Asn Val His Glu Ala Gly Arg Asn Phe Thr Val Ala Cys Gln
                755                 760                 765
```

```
His Arg Ser Asn Ser Glu Ile Ile Cys Cys Thr Thr Pro Ser Leu Gln
        770                 775                 780

Gln Leu Asn Leu Gln Leu Pro Val Lys Thr Lys Ala Phe Phe Met Leu
785                 790                 795                 800

Asp Gly Ile His Ser Lys His Phe Asp Leu Ile Tyr Val His Asn Pro
                805                 810                 815

Val Phe Lys Pro Phe Glu Lys Pro Val Met Ile Ser Ile Gly Asn Glu
            820                 825                 830

Asn Val Leu Glu Ile Lys Gly Asn Asp Ile Asp Pro Glu Ala Val Lys
        835                 840                 845

Gly Glu Val Leu Lys Val Gly Asn Lys Ser Cys Glu Asn Ile His Ser
850                 855                 860

His Ser Glu Ala Val Leu Cys Thr Val Pro Asn Asp Leu Leu Lys Leu
865                 870                 875                 880

Asn Ser Glu Leu Asn Ile Glu Trp Lys Gln Ala Val Ser Ser Thr Val
                885                 890                 895

Leu Gly Lys Val Ile Val Gln Pro Asp Gln Asn Phe Thr
            900                 905
```

<210> SEQ ID NO 209
<211> LENGTH: 933
<212> TYPE: PRT
<213> ORGANISM: H. sapiens

<400> SEQUENCE: 209

```
Met Lys Ala Pro Ala Val Leu Ala Pro Gly Ile Leu Val Leu Leu Phe
1               5                   10                  15

Thr Leu Val Gln Arg Ser Asn Gly Glu Cys Lys Glu Ala Leu Ala Lys
            20                  25                  30

Ser Glu Met Asn Val Asn Met Lys Tyr Gln Leu Pro Asn Phe Thr Ala
        35                  40                  45

Glu Thr Pro Ile Gln Asn Val Ile Leu His Glu His His Ile Phe Leu
    50                  55                  60

Gly Ala Thr Asn Tyr Ile Tyr Val Leu Asn Glu Glu Asp Leu Gln Lys
65                  70                  75                  80

Val Ala Glu Tyr Lys Thr Gly Pro Val Leu Glu His Pro Asp Cys Phe
                85                  90                  95

Pro Cys Gln Asp Cys Ser Ser Lys Ala Asn Leu Ser Gly Gly Val Trp
            100                 105                 110

Lys Asp Asn Ile Asn Met Ala Leu Val Val Asp Thr Tyr Tyr Asp Asp
        115                 120                 125

Gln Leu Ile Ser Cys Gly Ser Val Asn Arg Gly Thr Cys Gln Arg His
    130                 135                 140

Val Phe Pro His Asn His Thr Ala Asp Ile Gln Ser Glu Val His Cys
145                 150                 155                 160

Ile Phe Ser Pro Gln Ile Glu Glu Pro Ser Gln Cys Pro Asp Cys Val
                165                 170                 175

Val Ser Ala Leu Gly Ala Lys Val Leu Ser Ser Val Lys Asp Arg Phe
            180                 185                 190

Ile Asn Phe Phe Val Gly Asn Thr Ile Asn Ser Ser Tyr Phe Pro Asp
        195                 200                 205

His Pro Leu His Ser Ile Ser Val Arg Arg Leu Lys Glu Thr Lys Asp
    210                 215                 220

Gly Phe Met Phe Leu Thr Asp Gln Ser Tyr Ile Asp Val Leu Pro Glu
```

```
            225                 230                 235                 240

Phe Arg Asp Ser Tyr Pro Ile Lys Tyr Val His Ala Phe Glu Ser Asn
                            245                 250                 255

Asn Phe Ile Tyr Phe Leu Thr Val Gln Arg Glu Thr Leu Asp Ala Gln
                    260                 265                 270

Thr Phe His Thr Arg Ile Ile Arg Phe Cys Ser Ile Asn Ser Gly Leu
                275                 280                 285

His Ser Tyr Met Glu Met Pro Leu Glu Cys Ile Leu Thr Glu Lys Arg
            290                 295                 300

Lys Lys Arg Ser Thr Lys Lys Glu Val Phe Asn Ile Leu Gln Ala Ala
        305                 310                 315                 320

Tyr Val Ser Lys Pro Gly Ala Gln Leu Ala Arg Gln Ile Gly Ala Ser
                            325                 330                 335

Leu Asn Asp Asp Ile Leu Phe Gly Val Phe Ala Gln Ser Lys Pro Asp
                    340                 345                 350

Ser Ala Glu Pro Met Asp Arg Ser Ala Met Cys Ala Phe Pro Ile Lys
                355                 360                 365

Tyr Val Asn Asp Phe Phe Asn Lys Ile Val Asn Lys Asn Val Arg
            370                 375                 380

Cys Leu Gln His Phe Tyr Gly Pro Asn His Glu His Cys Phe Asn Arg
        385                 390                 395                 400

Thr Leu Leu Arg Asn Ser Ser Gly Cys Glu Ala Arg Arg Asp Glu Tyr
                            405                 410                 415

Arg Thr Glu Phe Thr Thr Ala Leu Gln Arg Val Asp Leu Phe Met Gly
                    420                 425                 430

Gln Phe Ser Glu Val Leu Leu Thr Ser Ile Ser Thr Phe Ile Lys Gly
                435                 440                 445

Asp Leu Thr Ile Ala Asn Leu Gly Thr Ser Glu Gly Arg Phe Met Gln
            450                 455                 460

Val Val Val Ser Arg Ser Gly Pro Ser Thr Pro His Val Asn Phe Leu
        465                 470                 475                 480

Leu Asp Ser His Pro Val Ser Pro Glu Val Ile Val Glu His Thr Leu
                            485                 490                 495

Asn Gln Asn Gly Tyr Thr Leu Val Ile Thr Gly Lys Lys Ile Thr Lys
                    500                 505                 510

Ile Pro Leu Asn Gly Leu Gly Cys Arg His Phe Gln Ser Cys Ser Gln
                515                 520                 525

Cys Leu Ser Ala Pro Pro Phe Val Gln Cys Gly Trp Cys His Asp Lys
            530                 535                 540

Cys Val Arg Ser Glu Glu Cys Leu Ser Gly Thr Trp Thr Gln Gln Ile
        545                 550                 555                 560

Cys Leu Pro Ala Ile Tyr Lys Val Phe Pro Asn Ser Ala Pro Leu Glu
                            565                 570                 575

Gly Gly Thr Arg Leu Thr Ile Cys Gly Trp Asp Phe Gly Phe Arg Arg
                    580                 585                 590

Asn Asn Lys Phe Asp Leu Lys Lys Thr Arg Val Leu Leu Gly Asn Glu
                595                 600                 605

Ser Cys Thr Leu Thr Leu Ser Glu Ser Thr Met Asn Thr Leu Lys Cys
            610                 615                 620

Thr Val Gly Pro Ala Met Asn Lys His Phe Asn Met Ser Ile Ile Ile
        625                 630                 635                 640

Ser Asn Gly His Gly Thr Thr Gln Tyr Ser Thr Phe Ser Tyr Val Asp
                            645                 650                 655
```

-continued

```
Pro Val Ile Thr Ser Ile Ser Pro Lys Tyr Gly Pro Met Ala Gly Gly
            660             665             670

Thr Leu Leu Thr Leu Thr Gly Asn Tyr Leu Asn Ser Gly Asn Ser Arg
            675             680             685

His Ile Ser Ile Gly Gly Lys Thr Cys Thr Leu Lys Ser Val Ser Asn
    690             695             700

Ser Ile Leu Glu Cys Tyr Thr Pro Ala Gln Thr Ile Ser Thr Glu Phe
705             710             715             720

Ala Val Lys Leu Lys Ile Asp Leu Ala Asn Arg Glu Thr Ser Ile Phe
                725             730             735

Ser Tyr Arg Glu Asp Pro Ile Val Tyr Glu Ile His Pro Thr Lys Ser
            740             745             750

Phe Ile Ser Gly Gly Ser Thr Ile Thr Gly Val Gly Lys Asn Leu Asn
            755             760             765

Ser Val Ser Val Pro Arg Met Val Ile Asn Val His Glu Ala Gly Arg
    770             775             780

Asn Phe Thr Val Ala Cys Gln His Arg Ser Asn Ser Glu Ile Ile Cys
785             790             795             800

Cys Thr Thr Pro Ser Leu Gln Gln Leu Asn Leu Gln Leu Pro Leu Lys
                805             810             815

Thr Lys Ala Phe Phe Met Leu Asp Gly Ile Leu Ser Lys Tyr Phe Asp
            820             825             830

Leu Ile Tyr Val His Asn Pro Val Phe Lys Pro Phe Glu Lys Pro Val
            835             840             845

Met Ile Ser Met Gly Asn Glu Asn Val Leu Glu Ile Lys Gly Asn Asp
    850             855             860

Ile Asp Pro Glu Ala Val Lys Gly Glu Val Leu Lys Val Gly Asn Lys
865             870             875             880

Ser Cys Glu Asn Ile His Leu His Ser Glu Ala Val Leu Cys Thr Val
                885             890             895

Pro Asn Asp Leu Leu Lys Leu Asn Ser Glu Leu Asn Ile Glu Trp Lys
            900             905             910

Gln Ala Ile Ser Ser Thr Val Leu Gly Lys Val Ile Val Gln Pro Asp
    915             920             925

Gln Asn Phe Thr Gly
    930
```

ANTI C-MET ANTIBODIES

RELATED APPLICATIONS

This application is a divisional application of U.S. patent application Ser. No. 13/288,566 filed on Nov. 3, 2011 which claims priority to U.S. Provisional Patent Application No. 61/409,866, filed on Nov. 3, 2010. This application is also related to PCT Patent Application No. PCT/EP2011/069369 filed on Nov. 3, 2011 and PCT Patent Application No. PCT/EP2011/069372. The contents of the aforementioned applications are hereby incorporated by reference in their entirety.

TECHNICAL FIELD

The present invention relates to antibodies that specifically bind to the human c-Met receptor protein and that act as strict antagonists of hepatocyte growth factor (HGF)-mediated activation of the c-Met receptor and/or inhibit HGF-independent activation of the c-Met receptor.

BACKGROUND

The receptor tyrosine kinase, c-Met, and its ligand hepatocyte growth factor (HGF) have become leading candidates for targeted cancer therapies.

c-Met is the cell surface receptor for hepatocyte growth factor (HGF), also known as scatter factor. The c-Met receptor is a disulfide-linked heterodimer consisting of extracellular $\alpha$ and $\beta$ chains. The $\alpha$ chain, heterodimerized to the amino-terminal portion of the $\beta$ chain, forms the major ligand-binding site in the extra cellular domain. HGF binding induces c-Met receptor homodimerization and phosphorylation of two tyrosine residues (Y1234 and Y1235) within the catalytic site, regulating kinase activity.

HGF-mediated activation of c-Met results in a complex genetic programme referred to as "invasive growth", consisting of a series of physiological processes, including proliferation, invasion, and angiogenesis, that occur under normal physiological conditions during embryonic development and pathologically during oncogenesis. Signalling through c-Met promotes proliferation and cell survival through a variety of downstream effectors.

In tumour cells, c-Met activation causes the triggering of a diverse series of signalling cascades resulting in cell growth, proliferation, invasion and protection from apoptosis. The underlying biological mechanisms for tumorigenicity of c-Met are typically achieved in three different ways: (a) with the establishment of HGF/c-Met autocrine loops; (b) via c-Met or HGF over-expression; and (c) in the presence of kinase-activating mutations in the c-Met receptor coding sequence. HGF and c-Met expression has been observed in tumour biopsies of most solid tumours, and c-Met signalling has been documented in a wide range of human malignancies, including bladder, breast, cervical, colorectal, gastric, head and neck, liver, lung, ovarian, pancreatic, prostrate, renal and thyroid cancers.

Activation of c-Met by its ligand, HGF, can occur in either a paracrine or an autocrine manner. Paracrine activation can become pathological in the presence of abnormal HGF production. Autocrine activation occurs when tumour cells aberrantly express both HGF and its receptor. In addition, c-Met activation can occur in an HGF-independent manner, mediated by c-Met homodimerization.

A wide variety of human malignancies exhibit sustained c-Met stimulation, over-expression or mutation, including carcinomas of the breast, liver, lung, ovary, kidney and thyroid. Activating mutations in c-Met have been positively identified in patients with a particular hereditary form of papillary renal cancer, directly implicating c-Met in human tumorigenesis. Aberrant signalling of the c-Met signalling pathway due to disregulation of the c-Met receptor or over-expression of its ligand, HGF, has been associated with an aggressive phenotype. Extensive evidence that c-Met signalling is involved in the progression and spread of several cancers and an enhanced understanding of its role in disease have generated considerable interest in c-Met and HGF as major targets in cancer drug development (Eder et al, Clin Cancer Research; 15(7); 2009).

A variety of c-Met pathway antagonists with potential clinical applications are currently under clinical investigation. Potential c-Met antagonists include monoclonal antibodies which block the interaction of c-Met with its ligand HGF. The most extensively described is the anti-c-Met 5D5 antibody generated by Genentech (WO96/38557). 5D5 behaves as a potent agonist when added alone in various models and as an antagonist when used as a Fab fragment or a one-armed antibody (MetMab).

WO 2009/007427 describes mouse monoclonal antibodies to c-Met and chimeric variants in which the antigen-binding domains of the mouse monoclonal antibody, or a humanised variant thereof, are coupled to the constant region of human IgG1. However, whilst the original mouse monoclonal antibody, 224G11, exhibits antagonist activity without significant intrinsic agonist activity, coupling of the antigen binding domains of 224G11 to human IgG1 generated a chimeric form of 224G11 which exhibited some agonist activity associated with a reduced antagonist efficacy. The agonist activity exhibited by the chimeric form of 224G11 can be reversed by engineering point mutations in the heavy chain hinge domain of the human IgG1. In this engineered variant several human amino residues in the hinge region are replaced by murine residues occurring at equivalent positions in the murine IgG1 sequence. C-Met receptor antagonist activity is restored in the resulting engineered variant, but the overall structural and sequence homology to human antibodies is reduced as a result of the mutations required in the hinge region. In addition, at least one of the hypervariable loops in 224G11 adopts a canonical structure which is not found in the human antibody repertoire.

WO 2007/126799 describes fully human monoclonal antibodies to c-Met. These antibodies behave as antagonists of the interaction with HGF, but no data is presented regarding the intrinsic agonist activity of these antibodies or their ability to inhibit c-Met dimerization.

WO 2010/059654 also describes monoclonal c-Met antibodies. These antibodies are characterised by binding to the $\alpha$-chain of human c-Met and inducing internalisation of cell surface human c-Met.

DESCRIPTION OF THE INVENTION

Provided herein is an isolated antibody, or an antigen binding fragment thereof, that specifically binds to a human c-Met protein, wherein the antibody exhibits at least two or all three of the following properties:
(a) is a strict antagonist of HGF-mediated activation of the human c-Met protein,
(b) inhibits HGF-independent activation of the human c-Met protein, and
(c) does not induce significant down-regulation of cell surface human c-Met protein.

In one embodiment there is provided an isolated antibody, or an antigen binding fragment thereof, that specifically binds to a human c-Met protein, wherein the antibody exhibits the following properties:
(a) is a strict antagonist of HGF-mediated activation of the human c-Met protein,
(b) inhibits HGF-independent activation of the human c-Met protein.

In one embodiment there is provided an isolated antibody, or an antigen binding fragment thereof, that specifically binds to a human c-Met protein, wherein the antibody exhibits the following properties:
(a) is a strict antagonist of HGF-mediated activation of the human c-Met protein, and
(c) does not induce significant down-regulation of cell surface human c-Met protein.

In one embodiment there is provided an isolated antibody, or an antigen binding fragment thereof, that specifically binds to a human c-Met protein, wherein the antibody exhibits the following properties:
(b) inhibits HGF-independent activation of the human c-Met protein, and
(c) does not induce significant down-regulation of cell surface human c-Met protein.

In a further embodiment there is provided an isolated antibody, or an antigen binding fragment thereof, that specifically binds to a human c-Met protein, wherein the antibody exhibits all of the following properties:
(a) is a strict antagonist of HGF-mediated activation of the human c-Met protein,
(b) inhibits HGF-independent activation of the human c-Met protein, and
(c) does not induce significant down-regulation of cell surface human c-Met protein.

In a particular embodiment the antibody or antigen binding fragment may bind to an epitope within the IPT region of the human c-Met protein, in particular an epitope within IPT domains 1-2, 2-3 or 3-4 of the human c-Met protein, or binds to an epitope within the PSI-IPT1 region of the human c-Met protein.

In a further embodiment the antibody or antigen binding fragment may bind to an epitope within the amino acid sequence 523-RSEECLSGTWTQQICLPAIYKVFPNSAP-LEG GTRLTICGWDFGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of said human c-Met protein.

In a further embodiment the antibody or antigen binding fragment may block binding of HGF to the high affinity HGF binding site of the human c-Met protein.

In a further embodiment there is provided an antibody or antigen binding fragment thereof that:
(a) binds to an epitope within the SEMA domain of the human c-Met protein
(b) does not induce down-regulation of cell surface human c-Met protein.

In an exemplary embodiment this antibody or antigen binding fragment thereof binds to an epitope within the peptide 98-VDTYYDDQLISCGSVNRGICQRHVF-PHNHTADIQSEVHCIFSPQIEEPSQCPDCVVSALGAK-VESSV KDRFINFFVGNTINSSYFPDHPLHSISVR-RLKETK-199 (SEQ ID NO: 181) in the SEMA domain of human c-Met.

This antibody or antigen binding fragment may block binding of HGF to the low affinity HGF binding site of human c-Met protein.

In any of the foregoing embodiments the antibody or antigen binding fragment may comprise a hinge region having fully human sequence. The antibody or antigen binding fragment may also have high human homology, as defined herein In one embodiment there is provided an antibody having high human homology which specifically bind to a human c-Met receptor protein and that antagonises HGF-mediated activation of the c-Met receptor.

In an embodiment there is provided an isolated antibody having high human homology which specifically binds to a human c-Met receptor protein, wherein the antibody is a strict antagonist of HGF-mediated activation of the c-Met receptor and comprises a hinge region having fully human sequence, wherein the presence of the human hinge region does not adversely affect the antagonist activity of the antibody.

In a further embodiment there is provided an isolated antibody having high human homology, or an antigen binding fragment thereof, which specifically binds to a human c-Met protein, wherein said antibody or antigen binding fragment blocks the binding of HGF to the high affinity HGF binding site of said human c-Met protein and is a strict antagonist of HGF-mediated activation of the c-Met receptor.

In a further embodiment there is provided an isolated antibody having high human homology, or an antigen binding fragment thereof, that specifically binds to a human c-Met protein, wherein said antibody or antigen binding fragment binds to an epitope within the IPT region or the PSI-IPT1 region of said human c-Met protein and is a strict antagonist of HGF-mediated activation of the c-Met receptor. In one embodiment the antibody, or an antigen binding fragment thereof, binds to an epitope within IPT domains 1-2, 2-3 or 3-4 of the human c-Met protein.

In a further embodiment there is provided an isolated antibody, or an antigen binding fragment thereof, that specifically binds to a human c-Met protein, wherein said antibody or antigen binding fragment binds to an epitope within the peptide 523-RSEECLS GTWTQQICLPAIYK-VFPNSAPLEGGTRLTICGWDEGFRRNNKFDLKKTRV-LLGNESCTLTLSESTM NTLKCTVGPAMNKHFNMSII-ISNGHGTTQYSIFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In another embodiment, the antibody of an antigen binding fragment thereof binds a conformational epitope comprising part of the IPT domains in addition to part of another domain of c-Met, such as the SEMA domain.

In each of the foregoing embodiments, the antibody may be any of, a monoclonal antibody, a fully human monoclonal antibody, or a humanised monoclonal antibody, each of which may exhibit bivalent binding to the human c-Met protein. In a particular embodiment, the antibody having high human homology, or antigen binding fragment thereof, may comprise a heavy chain variable domain (VH) and light chain variable domain (VL), wherein the VH and VL domains, or one or more CDRs thereof, are camelid-derived.

In one embodiment there is provided an isolated antibody, or an antigen binding fragment thereof, that specifically binds to a human c-Met protein and is a strict antagonist of HGF-mediated activation of the c-Met receptor, which antibody or antigen binding fragment comprises a heavy chain variable domain (VH) and a light chain variable domain (VL), wherein the VH and VL domains, or one or more CDRs thereof, are camelid-derived. In a particular embodiment the antibody, or antigen binding fragment thereof, may comprise llama VH and VL domains, or humanised llama VH and VL domains. This antibody, or antigen binding fragment, may also exhibit "high human homology", as defined herein.

In non-limiting embodiments the invention provides the following antibodies, or antigen binding fragments thereof, which are defined by reference to specific structural characteristics, i.e. specified amino acid sequences of either the CDRs (one or more of SEQ ID NOs: 1-21, 71-73 or 83-85 (heavy chain CDRs) or SEQ ID NOs: 22-42, 74-76, 86, 87 or 137-148 (light chain CDRs) or entire variable domains (one or more of SEQ ID NOs: 45-58, 77, 78, 88, 89, 92-121 or 149-164). All of these antibodies specifically bind to the human c-Met protein and are strict antagonists of HGF-mediated activation of the c-Met receptor. In particular embodiments, the antibodies defined by the following structural characteristics may additionally exhibit high human homology, as defined herein. The antibodies may be monoclonal antibodies produced by recombinant means. The CDRs of the following c-Met antibodies may be camelid-derived, i.e. derived from conventional antibodies raised by immunisation of camelids (specifically llama) with c-Met antigen. The invention also provides humanised or human germlined variants, affinity variants and variants containing conservative amino acid substitutions, as defined herein. Specifically provided are chimeric antibodies containing VH and VL domains which are camelid-derived, or humanised or germlined variants thereof, fused to constant domains of human antibodies, in particular human IgG1, IgG2, IgG3 or IgG4. These chimeric antibodies may include a hinge region having fully human sequence, as defined herein.

Exemplary embodiments of the c-Met antibodies are now further described by reference to structural characteristics.

In one embodiment there is provided an isolated antibody or antigen binding fragment thereof, wherein said antibody or antigen binding fragment specifically binds human c-Met protein, said antibody or antigen binding fragment comprising a heavy chain variable domain comprising a variable heavy chain CDR3 comprising a sequence selected from the group consisting of:
SEQ ID NO:21 [DVRVIATGWATANALDA], or sequence variant thereof,
SEQ ID NO:15 [VDDYYLGYDY], or sequence variant thereof,
SEQ ID NO:3 [RRDNYYGTSGEYDY], or sequence variant thereof,
SEQ ID NO:6 [DTVVSGNGY], or sequence variant thereof,
SEQ ID NO:9 [DLIGSHDY], or sequence variant thereof,
SEQ ID NO:12 [GPGWYSGSRNDY], or sequence variant thereof,
SEQ ID NO:18 [LEDYELAYDY], or sequence variant thereof, and
SEQ ID NO:73 [SGYGSSLGDFGS] or sequence variant thereof,
wherein the sequence variant comprises one, two or three amino acid substitutions (e.g., conservative substitutions, humanising substitutions or affinity variants) in the recited sequence.

The heavy chain variable domain of this antibody may further comprise a variable heavy chain CDR2 comprising a sequence selected from the group consisting of (a) SEQ ID NO: 195 [$X_1X_2X_3X_4X_5X_6X_7X_8$TYYAESMK] or sequence variant thereof, wherein
X1 is any amino acid, preferably T or A;
X2 is any amino acid, preferably I,
X3 is any amino acid, preferably S or N;
X4 is any amino acid, preferably W,
X5 is any amino acid, preferably N,
X6 is any amino acid, preferably D or G;
X7 is any amino acid, preferably I, G or S; and
X8 is any amino acid, preferably N or S;
(b) SEQ ID NO: 196 [VIAYDGSTX$_1$YSPSLKS] or sequence variant thereof, wherein
X1 is any amino acid, preferably Y or D; and
(c) SEQ ID NO: 197 [RIDPEX$_1$GGTKYAQKFQG], or sequence variant thereof, wherein,
X1 is any amino acid, preferably D, N or E; and
wherein the sequence variant comprises one, two or three amino acid substitutions (e.g., conservative substitutions, humanising substitutions or affinity variants) in the recited sequence.

The heavy chain variable domain of this antibody may further comprise a variable heavy chain CDR1 comprising a sequence selected from the group consisting of:
(a) SEQ ID NO: 198 [$X_1$DYX$_2$MX$_3$], or sequence variant thereof, wherein
$X_1$ is any amino acid, preferably D or S,
$X_2$ is any amino acid, preferably A or V, and
$X_3$ is any amino acid, preferably T, N or S;
(b) SEQ ID NO: 199 [$X_1$NYYX$_2$WS], or sequence variant thereof, wherein
X1 is any amino acid, preferably G or T, and
X2 is any amino acid, preferably A or Y;
(c) SEQ ID NO: 200 [$X_1X_2X_3$ID], or sequence variant thereof, wherein,
X1 is any amino acid, preferably M or N,
X2 is any amino acid, preferably N or Y, and
X3 is any amino acid, preferably S or V, and
wherein the sequence variant comprises one, two or three amino acid substitutions (e.g., conservative substitutions, humanising substitutions or affinity variants) in the recited sequence.

The antibody or antigen binding fragment may further comprise a light chain variable domain comprising a variable light chain CDR3 comprising an amino acid sequence selected from the group consisting of:
(a) SEQ ID NO: 201 [QQGX$_1$SFPX$_2$X$_3$], or sequence variant thereof, wherein
$X_1$ is any amino acid, preferably Y or W;
$X_2$ is any amino acid, preferably Y or L;
$X_3$ is any amino acid, preferably T or S;
(b) SEQ ID NO: 202 [ASYRX$_1$X$_2$X$_3$X$_4$X$_5$X$_6$V], or sequence variant thereof, wherein
X1 is any amino acid, preferably S, I, R or T;
X2 is any amino acid, preferably A, S, T or R;
X3 is any amino acid, preferably N or T;
X4 is any amino acid, preferably N, D, R or K;
X5 is any amino acid, preferably A, V, Y, N or H;
X6 is any amino acid, preferably V, A, S or G.
wherein the sequence variant comprises one, two or three amino acid substitutions (e.g., conservative substitutions, humanising substitutions or affinity variants) in the recited sequence.

The antibody or antigen binding fragment may further comprise a light chain variable domain CDR2 comprising a sequence selected from the group consisting of:

(a) SEQ ID NO: 203 [WASX$_1$RES], or sequence variant thereof, wherein
   X1 is any amino acid, preferably I or T;
(b) SEQ ID NO: 204 [X$_1$VX$_2$X$_3$RX$_4$S], or sequence variant thereof, wherein
   X1 is any amino acid, preferably D, A or E,
   X2 is any amino acid, preferably N or S,
   X3 is any amino acid, preferably R, Y or K,
   X4 is any amino acid, preferably A, or P,
   wherein the sequence variant comprises one, two or three amino acid substitutions (e.g., conservative substitutions, humanising substitutions or affinity variants) in the recited sequence.

The antibody or antigen binding fragment may further comprise a light chain variable domain CDR1 comprising a sequence selected from the group consisting of:
(a) SEQ ID NO: 205 [KSSQSVLX$_1$X$_2$ X$_3$N X$_4$K X$_5$YLA], or sequence variant thereof, wherein
   X1 is any amino acid, preferably W, L or F;
   X2 is any amino acid, preferably R or S;
   X3 is any amino acid, preferably S or P;
   X4 is any amino acid, preferably Q or H;
   X5 is any amino acid, preferably N or S
(b) SEQ ID NO: 206 [X$_1$GX$_2$X$_3$X$_4$X$_5$X$_6$GX$_7$X$_8$X$_9$YX$_{10}$S], or sequence variant thereof, wherein
   X1 is any amino acid, preferably A or T;
   X2 is any amino acid, preferably T or S;
   X3 is any amino acid, preferably S or N;
   X4 is any amino acid, preferably S or T;
   X5 is any amino acid, preferably D or N;
   X6 is any amino acid, preferably V or I;
   X7 is any amino acid, preferably Y, G, D or N;
   X8 is any amino acid, preferably G or Y;
   X9 is any amino acid, preferably N or Y;
   X10 is any amino acid, preferably V or L
   wherein the sequence variant comprises one, two or three amino acid substitutions (e.g., conservative substitutions, humanising substitutions or affinity variants) in the recited sequence.

The antibody or antigen binding fragment may further comprise a light chain variable domain CDR1 comprising a sequence selected from the group consisting of:
(a) SEQ ID NO: YY5 [KSSQSVLX$_1$X$_2$ X$_3$N X$_4$K X$_5$YLA], or sequence variant thereof, wherein
   X1 is any amino acid, preferably W, L or F;
   X2 is any amino acid, preferably R or S;
   X3 is any amino acid, preferably S or P;
   X4 is any amino acid, preferably Q or H;
   X5 is any amino acid, preferably N or S
(b) SEQ ID NO:YY6 [X$_1$GX$_2$X$_3$X$_4$X$_5$X$_6$GX$_7$X$_8$X$_9$YX$_{10}$S], or sequence variant thereof, wherein
   X1 is any amino acid, preferably A or T;
   X2 is any amino acid, preferably T or S;
   X3 is any amino acid, preferably S or N;
   X4 is any amino acid, preferably S or T;
   X5 is any amino acid, preferably D or N;
   X6 is any amino acid, preferably V or I;
   X7 is any amino acid, preferably Y, G, D or N;
   X8 is any amino acid, preferably G or Y;
   X9 is any amino acid, preferably N or Y;
   X10 is any amino acid, preferably V or L
   wherein the sequence variant comprises one, two or three amino acid substitutions (e.g., conservative substitutions, humanising substitutions or affinity variants) in the recited sequence.

36C4, 20F1 and Variants Thereof

In one embodiment there is provided an isolated antibody or antigen binding fragment thereof which specifically binds human c-Met protein, said antibody or antigen binding fragment comprising a heavy chain variable domain wherein the variable heavy chain CDR3 sequence is SEQ ID NO:12 or SEQ ID NO:21 or sequence variant thereof, wherein the sequence variant comprises one, two or three amino acid substitutions in the recited sequence.

In an embodiment of the antibody or antigen binding fragment thereof
   the variable heavy chain CDR3 sequence is SEQ ID NO:21 or SEQ ID NO:12 or sequence variant thereof;
   the variable heavy chain CDR2 sequence is SEQ ID NO: 196 or sequence variant thereof; and
   the variable heavy chain CDR1 sequence is SEQ ID NO: 199 or sequence variant thereof, and
   wherein the sequence variant comprises one, two or three amino acid substitutions (e.g., conservative substitutions, humanising substitutions or affinity variants) in the recited sequence.

In an embodiment of the antibody or antigen binding fragment thereof
   the variable heavy chain CDR3 sequence is SEQ ID NO:21 or sequence variant thereof;
   the variable heavy chain CDR2 sequence is SEQ ID NO:20 or sequence variant thereof or SEQ ID NO:83 or sequence variant thereof; and
   the variable heavy chain CDR1 sequence is SEQ ID NO:19 or sequence variant thereof, and
   wherein the sequence variant comprises one, two or three amino acid substitutions (e.g., conservative substitutions, humanising substitutions or affinity variants) in the recited sequence.

In an embodiment of the antibody or antigen binding fragment thereof
   the variable heavy chain CDR3 sequence is SEQ ID NO:12 or sequence variant thereof;
   the variable heavy chain CDR2 sequence is SEQ ID NO:11 or sequence variant thereof; and
   the variable heavy chain CDR1 sequence is SEQ ID NO:10 or sequence variant thereof, and
   wherein the sequence variant comprises one, two or three amino acid substitutions (e.g., conservative substitutions, humanising substitutions or affinity variants) in the recited sequence.

In an embodiment of the antibody or antigen binding fragment thereof
   the variable light chain CDR3 sequence is SEQ ID NO: 202 or sequence variant thereof;
   the variable light chain CDR2 sequence is SEQ ID NO: 203 or sequence variant thereof; and
   the variable light chain CDR1 sequence is SEQ ID NO: 206 or sequence variant thereof, and
   wherein the sequence variant comprises one, two or three amino acid substitutions in the recited sequence.

In an embodiment of the antibody or antigen binding fragment thereof
   the variable light chain CDR3 sequence is selected from the group consisting of SEQ ID NO:33 or sequence variant thereof, SEQ ID NO:145 or sequence variant thereof, SEQ ID NO:146 or sequence variant thereof, SEQ ID NO:147 or sequence variant thereof, and SEQ ID NO:148 or sequence variant thereof;
   the variable light chain CDR2 sequence is SEQ ID NO:32 or sequence variant thereof; and the variable light chain CDR1 sequence is SEQ ID NO:31 or sequence variant thereof, or SEQ ID NO:144 or sequence variant thereof, and wherein the sequence variant comprises one, two or three amino acid substitutions (e.g., conservative substitutions, humanising substitutions or affinity variants) in the recited sequence.

In an embodiment of the antibody or antigen binding fragment thereof the variable light chain CDR3 sequence is SEQ ID NO:30 or sequence variant thereof;

the variable light chain CDR2 sequence is SEQ ID NO:29 or sequence variant thereof; and the variable light chain CDR1 sequence is SEQ ID NO:28 or sequence variant thereof, and wherein the sequence variant comprises one, two or three amino acid substitutions (e.g., conservative substitutions, humanising substitutions or affinity variants) in the recited sequence.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:21 or sequence variant thereof;

the variable heavy chain CDR2 sequence is selected from the group consisting of SEQ ID NO:20, SEQ ID NO:83 and SEQ ID NO:84 or sequence variant thereof; and the variable heavy chain CDR1 sequence is SEQ ID NO:19 or sequence variant thereof; and the light chain variable domain includes a combination of CDRs selected from the following:

(i) the variable light chain CDR3 sequence is SEQ ID NO:33 or sequence variant thereof;

the variable light chain CDR2 sequence is SEQ ID NO:32 or sequence variant thereof;

the variable light chain CDR1 sequence is SEQ ID NO:31 or sequence variant thereof, wherein the sequence variant comprises one, two or three amino acid substitutions (e.g., conservative substitutions, humanising substitutions or affinity variants) in the recited sequence; or (ii) the variable light chain CDR3 sequence is SEQ ID NO:145 or sequence variant thereof;

the variable light chain CDR2 sequence is SEQ ID NO:32 or sequence variant thereof;

the variable light chain CDR1 sequence is SEQ ID NO:144 or sequence variant thereof, wherein the sequence variant comprises one, two or three amino acid substitutions (e.g., conservative substitutions, humanising substitutions or affinity variants) in the recited sequence; or (iii) the variable light chain CDR3 sequence is SEQ ID NO:146 or sequence variant thereof;

the variable light chain CDR2 sequence is SEQ ID NO:32 or sequence variant thereof;

the variable light chain CDR1 sequence is SEQ ID NO:31 or sequence variant thereof, wherein the sequence variant comprises one, two or three amino acid substitutions (e.g., conservative substitutions, humanising substitutions or affinity variants) in the recited sequence; or (iv) the variable light chain CDR3 sequence is SEQ ID NO:147 or sequence variant thereof;

the variable light chain CDR2 sequence is SEQ ID NO:32 or sequence variant thereof;

the variable light chain CDR1 sequence is SEQ ID NO:144 or sequence variant thereof, wherein the sequence variant comprises one, two or three amino acid substitutions (e.g., conservative substitutions, humanising substitutions or affinity variants) in the recited sequence; or (v) the variable light chain CDR3 sequence is SEQ ID NO:148 or sequence variant thereof;

the variable light chain CDR2 sequence is SEQ ID NO:32 or sequence variant thereof;

the variable light chain CDR1 sequence is SEQ ID NO:144 or sequence variant thereof, wherein the sequence variant comprises one, two or three amino acid substitutions (e.g., conservative substitutions, humanising substitutions or affinity variants) in the recited sequence.

In exemplary embodiments the antibody, or an antigen binding fragment thereof, binds to an epitope within the peptide 98-VDTYYDDQLISCGSVNRGICQRHVE-PHNHTADIQSEVHCIFSPQIEEPSQCPDCVVSALGAK-VESSV KDRFINFFVGNTINSSYFPDHPLHSISVR-RLKETK-199 (SEQ ID NO: 181) in the SEMA domain of human c-Met.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:12 or sequence variant thereof;

the variable heavy chain CDR2 sequence is SEQ ID NO:11 or sequence variant thereof; and the variable heavy chain CDR1 sequence is SEQ ID NO:10 or sequence variant thereof, the variable light chain CDR3 sequence is SEQ ID NO:30 or sequence variant thereof;

the variable light chain CDR2 sequence is SEQ ID NO:29 or sequence variant thereof; and the variable light chain CDR1 sequence is SEQ ID NO:28 or sequence variant thereof, and wherein the sequence variant comprises one, two or three amino acid substitutions (e.g., conservative substitutions, humanising substitutions or affinity variants) in the recited sequence.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to a sequence selected from the group consisting of: SEQ ID NO:51, 88, 92, 94, 96 and 98.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH amino acid sequence selected from the group consisting of: SEQ ID NO: 51, 88, 92, 94, 96 and 98.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda sequence with at least 80% sequence identity, or at least 85% sequence identity, or at least 90% sequence identity, or at least 95% sequence identity, or at least 97%, 98% or 99% sequence identity, to an amino acid sequence selected from the group consisting of SEQ ID NO:55, 93, 95, 97, 99, 158, 159, 160, 161, 162, 163 and 164.

In a further embodiment there is provided an isolated antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda amino acid sequence selected from the group consisting of SEQ ID NO:55, 93, 95, 97, 99, 158, 159, 160, 161, 162, 163 and 164.

In a further embodiment there is provided an isolated antibody, or an antigen binding fragment thereof, that specifically binds to a human c-Met protein and is preferably a strict antagonist of HGF-mediated activation of the c-Met receptor, the antibody or antigen-binding fragment comprising a heavy chain variable domain and a light chain variable domain, wherein the heavy chain variable domain comprises a VH sequence with at least 85% sequence identity, or at least 90% sequence identity, or at least 95% sequence identity, or at least 97%, 98% or 99% sequence identity to a sequence selected from the group consisting of: SEQ ID NO:51, 88, 92, 94, 96 and 98, and the light chain variable domain comprises a V Lambda sequence with at least 80% sequence identity, or at least 85% sequence identity, or at least 90% sequence identity, or at least 95% sequence identity, or at least 97%, 98% or 99% sequence identity to an amino acid sequence selected from the group consisting of SEQ ID NO:55, 93, 95, 97, 99, 158, 159, 160, 161, 162, 163 and 164.

In exemplary embodiments this antibody binds to an epitope within the peptide 98-VDTYYDDQLISCGSVN-RGICQRHVFPHNHTADIQSEVHCIFSPQIEEPSQCPD-CVVSALGAKVESSV KDRFINFFVGNTINSSYFPDH-PLHSISVRRLKETK-199 (SEQ ID NO: 181) in the SEMA domain of human c-Met.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:51 or SEQ ID NO:88 or a humanised or affinity variant thereof, and a light chain variable domain (VL) comprising the amino acid sequence shown as SEQ ID NO:55, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, the antibody or antigen-binding fragment comprising a heavy chain variable domain and a light chain variable domain, wherein the heavy chain variable domain comprises a VH sequence with at least 85% sequence identity, or at least 90% sequence identity, or at least 95% sequence identity, or at least 97%, 98% or 99% sequence identity the amino acid sequence shown as SEQ ID NO:51 or SEQ ID NO:88, and the light chain variable domain comprises a V Lambda sequence with at least 80% sequence identity, or at least 85% sequence identity, or at least 90% sequence identity, or at least 95% sequence identity, or at least 97%, 98% or 99% sequence identity to the amino acid sequence shown as SEQ ID NO:55, or a humanised, or affinity variant thereof.

This antibody, or antigen-binding region may comprise heavy chain CDRs which are identical to CDR1, CDR2 and CDR3 of SEQ ID NO:51 or to CDR1, CDR2 and CDR3 of SEQ ID NO:88 and light chain CDRs which are identical to CDR1, CDR2 and CDR3 of SEQ ID NO:55, whilst exhibiting amino acid sequence variation within the framework regions.

In exemplary embodiments this antibody or antigen binding fragment binds to an epitope within the peptide 98-VD-TYYDDQLISCGSVNRGICQRHVEPHNHTADIQSEVH-CIFSP
QIEEPSQCPDCVVSALGAKVESS-VKDRFINFFVGNTINSSYFEDHPLHSISVRRLKETK-199 (SEQ ID NO: 181) in the SEMA domain of human c-Met.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody or an antigen binding fragment thereof that specifically binds to a human c-Met protein and is preferably a strict antagonist of HGF-mediated activation of the c-Met receptor, which antibody is a human germlined variant of the antibody 36C4, said germlined variant antibody comprising:—

(a) a heavy chain variable domain (VH) comprising the amino acid sequence shown as SEQ ID NO:92, and a light chain variable domain (VL) comprising the amino acid sequence shown as SEQ ID NO:93; or (b) a heavy chain variable domain (VH) comprising the amino acid sequence shown as SEQ ID NO:94, and a light chain variable domain (VL) comprising the amino acid sequence shown as SEQ ID NO:95; or (c) a heavy chain variable domain (VH) comprising the amino acid sequence shown as SEQ ID NO:96, and a light chain variable domain (VL) comprising the amino acid sequence shown as SEQ ID NO:97; or (d) a heavy chain variable domain (VH) comprising the amino acid sequence shown as SEQ ID NO:98, and a light chain variable domain (VL) comprising the amino acid sequence shown as SEQ ID NO:99; or (e) a heavy chain variable domain (VH) comprising the amino acid sequence shown as SEQ ID NO:88, and a light chain variable domain (VL) comprising an amino acid sequence selected from the group consisting of SEQ ID NO:156, SEQ ID NO:157, SEQ ID NO:158, SEQ ID NO:159, SEQ ID NO:160, SEQ ID NO:161, SEQ ID NO:162, SEQ ID NO:163 and SEQ ID NO:164.

These variant 36C4 antibodies, or antigen-binding regions, are identified as comprising a combination of a VH domain, defined by reference to a specific amino acid sequence, and a VL domain (V Kappa), also defined by reference to a specific amino acid sequence. For each specific VH/VL combination listed, this definition should be taken to include antibodies, or antigen binding regions, formed by combination of a VH domain having at least 85%, at least 90%, at least 95%, at least 97%, or at least 99% sequence identity to the stated VH amino acid sequence and a VL domain having at least 75%, at least 80%, at least 85%, at least 90%, at least 95%, at least 97%, or at least 99% sequence identity to the stated VL amino acid sequence. In each case the VH and VL domains defined by % sequence identity to the stated VH and VL amino acid sequences may retain identical CDR sequences to those present in the stated VH and VL amino acid sequences, whilst exhibiting amino acid sequence variation within the framework regions.

In exemplary embodiments this antibody or antigen binding fragment binds to an epitope within the peptide 98-VDTYYDDQLISCGSVNRGICQRHVEPHNHTADIQSEVH-CIFSP QIEEPSQCPDCVVSALGAKVESS-VKDRFINFFVGNTINSSYFEDHPLHSISVRRLKETK-199 (SEQ ID NO: 181) in the SEMA domain of human c-Met.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, which antibody is an affinity variant of 36C4Q, said affinity variant comprising a heavy chain variable domain (VH) comprising the amino acid sequence shown as SEQ ID NO:88, and a light chain variable domain (VL) comprising an amino acid sequence selected from the group consisting of SEQ ID NO:156, SEQ ID NO:157, SEQ ID NO:158, SEQ ID NO:159, SEQ ID NO:160, SEQ ID NO:161, SEQ ID NO:162, SEQ ID NO:163 and SEQ ID NO:164.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the sequence shown as SEQ ID NO:48.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising the VH amino acid sequence shown as SEQ ID NO:48.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda sequence with at least 80% sequence identity, or at least 85% sequence identity, or at least 90% sequence identity, or at least 95% sequence identity, or at least 97%, 98% or 99% sequence identity, to the sequence shown as SEQ ID NO:54.

In a further embodiment there is provided an isolated antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising the V Lambda amino acid sequence shown as SEQ ID NO:48.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:48, or a humanised or affinity variant thereof, and a light chain variable domain (VL) comprising the amino acid sequence shown as SEQ ID NO:54, or a humanised, or affinity variant thereof.

In one embodiment this antibody may include the CH1 domain, hinge region, CH2 domain and CH3 domain of a human antibody, in particular human IgG1, IgG2, IgG3 or IgG4.

48A2, 38H10, 40B8 and Variants Thereof

In a further embodiment there is provided an isolated antibody or antigen binding fragment thereof which specifically binds human c-Met protein, said antibody or antigen binding fragment comprising a heavy chain variable domain wherein the variable heavy chain CDR3 sequence is SEQ ID NO:15 or SEQ ID NO:18 or sequence variant thereof, wherein the sequence variant comprises one, two or three amino acid substitutions (e.g., conservative substitutions, humanising substitutions or affinity variants) in the recited sequence.

In an embodiment of the antibody or antigen binding fragment thereof
the variable heavy chain CDR3 sequence is SEQ ID NO:15 or SEQ ID NO:18 or sequence variant thereof;
the variable heavy chain CDR2 sequence is SEQ ID NO: 197 or sequence variant thereof; and
the variable heavy chain CDR1 sequence is SEQ ID NO: 200 or sequence variant thereof, and
wherein the sequence variant comprises one, two or three amino acid substitutions (e.g., conservative substitutions, humanising substitutions or affinity variants) in the recited sequence.

In an embodiment of the antibody or antigen binding fragment thereof
the variable heavy chain CDR3 sequence is SEQ ID NO:15 or sequence variant thereof;
the variable heavy chain CDR2 sequence is SEQ ID NO:14 or sequence variant thereof or SEQ ID NO:85 or sequence variant thereof; and
the variable heavy chain CDR1 sequence is SEQ ID NO:13 or sequence variant thereof, and
wherein the sequence variant comprises one, two or three amino acid substitutions (e.g., conservative substitutions, humanising substitutions or affinity variants) in the recited sequence.

In an embodiment of the antibody or antigen binding fragment thereof
the variable heavy chain CDR3 sequence is SEQ ID NO:18 or sequence variant thereof;
the variable heavy chain CDR2 sequence is SEQ ID NO:17 or sequence variant thereof; and
the variable heavy chain CDR1 sequence is SEQ ID NO:16 or sequence variant thereof, and
wherein the sequence variant comprises one, two or three amino acid substitutions (e.g., conservative substitutions, humanising substitutions or affinity variants) in the recited sequence.

In one embodiment the antibody or antigen binding fragment thereof further comprises a light chain variable domain, wherein
the variable light chain CDR3 sequence is SEQ ID NO: 201 or sequence variant thereof;
the variable light chain CDR2 sequence is SEQ ID NO: 203 or sequence variant thereof; and
the variable light chain CDR1 sequence is SEQ ID NO: 205 or sequence variant thereof, and
wherein the sequence variant comprises one, two or three amino acid substitutions (e.g., conservative substitutions, humanising substitutions or affinity variants) in the recited sequence.

In an embodiment of the antibody or antigen binding fragment thereof
the variable light chain CDR3 sequence is selected from the group consisting of SEQ ID NO:87 or sequence variant thereof, SEQ ID NO:139 or sequence variant thereof, and SEQ ID NO:141 or sequence variant thereof;
the variable light chain CDR2 sequence is SEQ ID NO:23 or sequence variant thereof or SEQ ID NO:26 or sequence variant thereof; and
the variable light chain CDR1 sequence is selected from the group consisting of SEQ ID NO:86 or sequence variant thereof, SEQ ID NO:137 or sequence variant thereof, SEQ ID NO:138 or sequence variant thereof, SEQ ID NO:140 or sequence variant thereof, SEQ ID NO:142 or sequence variant thereof, and SEQ ID NO:143 or sequence variant thereof, and
wherein the sequence variant comprises one, two or three amino acid substitutions (e.g., conservative substitutions, humanising substitutions or affinity variants) in the recited sequence.

In an embodiment of the antibody or antigen binding fragment thereof
the variable light chain CDR3 sequence is SEQ ID NO:24 or sequence variant thereof;
the variable light chain CDR2 sequence is SEQ ID NO:23 or sequence variant thereof; and
the variable light chain CDR1 sequence is SEQ ID NO:22 or sequence variant thereof, and
wherein the sequence variant comprises one, two or three amino acid substitutions (e.g., conservative substitutions, humanising substitutions or affinity variants) in the recited sequence.

In an embodiment of the antibody or antigen binding fragment thereof
the variable light chain CDR3 sequence is SEQ ID NO:27 or sequence variant thereof;
the variable light chain CDR2 sequence is SEQ ID NO:26 or sequence variant thereof; and
the variable light chain CDR1 sequence is SEQ ID NO:25 or sequence variant thereof, and
wherein the sequence variant comprises one, two or three amino acid substitutions (e.g., conservative substitutions, humanising substitutions or affinity variants) in the recited sequence.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:
the variable heavy chain CDR3 sequence is SEQ ID NO:15 or sequence variant thereof;
the variable heavy chain CDR2 sequence is SEQ ID NO:14 or sequence variant thereof; and
the variable heavy chain CDR1 sequence is SEQ ID NO:13 or sequence variant thereof,
the variable light chain CDR3 sequence is SEQ ID NO:87 or sequence variant thereof;

the variable light chain CDR2 sequence is SEQ ID NO:23 or sequence variant thereof; and the variable light chain CDR1 sequence is SEQ ID NO:86 or sequence variant thereof, and wherein the sequence variant comprises one, two or three amino acid substitutions (e.g., conservative substitutions, humanising substitutions or affinity variants) in the recited sequence.

In an exemplary embodiment this antibody or antigen binding fragment thereof binds to an epitope within the peptide 523-RSEECLSGTWTQQICLPAIYKVFPNSAP-LEG GTRLTICGWDFGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:15 or sequence variant thereof;

the variable heavy chain CDR2 sequence is SEQ ID NO:14 or sequence variant thereof; and the variable heavy chain CDR1 sequence is SEQ ID NO:13 or sequence variant thereof; and the light chain variable domain includes a combination of CDRs selected from the following:

(i) the variable light chain CDR3 sequence is SEQ ID NO:24 or sequence variant thereof;

the variable light chain CDR2 sequence is SEQ ID NO:23 or sequence variant thereof; and the variable light chain CDR1 sequence is SEQ ID NO:22 or sequence variant thereof, and wherein the sequence variant comprises one, two or three amino acid substitutions (e.g., conservative substitutions, humanising substitutions or affinity variants) in the recited sequence; or (ii) the variable light chain CDR3 sequence is SEQ ID NO:87 or sequence variant thereof;

the variable light chain CDR2 sequence is SEQ ID NO:26 or sequence variant thereof; and the variable light chain CDR1 sequence is SEQ ID NO:137 or sequence variant thereof, and wherein the sequence variant comprises one, two or three amino acid substitutions (e.g., conservative substitutions, humanising substitutions or affinity variants) in the recited sequence; or (iii) the variable light chain CDR3 sequence is SEQ ID NO:139 or sequence variant thereof;

the variable light chain CDR2 sequence is SEQ ID NO:26 or sequence variant thereof; and the variable light chain CDR1 sequence is SEQ ID NO:138 or sequence variant thereof, and wherein the sequence variant comprises one, two or three amino acid substitutions (e.g., conservative substitutions, humanising substitutions or affinity variants) in the recited sequence; or (iv) the variable light chain CDR3 sequence is SEQ ID NO:141 or sequence variant thereof;

the variable light chain CDR2 sequence is SEQ ID NO:26 or sequence variant thereof; and the variable light chain CDR1 sequence is SEQ ID NO:140 or sequence variant thereof, and wherein the sequence variant comprises one, two or three amino acid substitutions (e.g., conservative substitutions, humanising substitutions or affinity variants) in the recited sequence; or (v) the variable light chain CDR3 sequence is SEQ ID NO:141 or sequence variant thereof;

the variable light chain CDR2 sequence is SEQ ID NO:26 or sequence variant thereof; and the variable light chain CDR1 sequence is SEQ ID NO:142 or sequence variant thereof, and wherein the sequence variant comprises one, two or three amino acid substitutions (e.g., conservative substitutions, humanising substitutions or affinity variants) in the recited sequence; or (vi) the variable light chain CDR3 sequence is SEQ ID NO:87 or sequence variant thereof;

the variable light chain CDR2 sequence is SEQ ID NO:26 or sequence variant thereof; and the variable light chain CDR1 sequence is SEQ ID NO:86 or sequence variant thereof, and wherein the sequence variant comprises one, two or three amino acid substitutions (e.g., conservative substitutions, humanising substitutions or affinity variants) in the recited sequence; or (vii) the variable light chain CDR3 sequence is SEQ ID NO:87 or sequence variant thereof;

the variable light chain CDR2 sequence is SEQ ID NO:26 or sequence variant thereof; and the variable light chain CDR1 sequence is SEQ ID NO:143 or sequence variant thereof, and wherein the sequence variant comprises one, two or three amino acid substitutions (e.g., conservative substitutions, humanising substitutions or affinity variants) in the recited sequence.

In an exemplary embodiment this antibody or antigen binding fragment thereof binds to an epitope within the peptide 523-RSEECLSGTWTQQICLPAIYKVFPNSAP-LEG GTRLTICGWDEGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain the variable heavy chain CDR3 sequence is SEQ ID NO:18 or sequence variant thereof;

the variable heavy chain CDR2 sequence is SEQ ID NO:17 or sequence variant thereof; and the variable heavy chain CDR1 sequence is SEQ ID NO:16 or sequence variant thereof, the variable light chain CDR3 sequence is SEQ ID NO:27 or sequence variant thereof;

the variable light chain CDR2 sequence is SEQ ID NO:26 or sequence variant thereof; and the variable light chain CDR1 sequence is SEQ ID NO:25 or sequence variant thereof, and wherein the sequence variant comprises one, two or three amino acid substitutions (e.g., conservative substitutions, humanising substitutions or affinity variants) in the recited sequence.

In an exemplary embodiment this antibody or antigen binding fragment thereof binds to an epitope within the peptide 523-RSEECLSGTWTQQICLPAIYKVFPNSAP-LEG GTRLTICGWDEGFRRNNKFDLKKTRVELG-NESCTLTESESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to an amino acid sequence selected from the group consisting of: SEQ ID NO:49, 108, 110, 112, 114, 116, 118 and 120.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH amino acid sequence selected from the group consisting of: SEQ ID NO: 49, 108, 110, 112, 114, 116, 118 and 120.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Kappa sequence with at least 75% sequence identity, or at least 80% sequence identity, or at least 85% sequence identity, or at least 90% sequence identity, or at least 95% sequence identity, or at least 97%, 98% or 99% sequence identity, to an amino acid sequence selected from the group consisting of SEQ ID NO:52, 89, 109, 111, 113, 115, 117, 119, 121, 149, 150, 151, 152, 153, 154, 155, 156 and 157.

In a further embodiment there is provided an isolated antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a VL amino acid sequence selected from the group consisting of SEQ ID NO:52, 89, 109, 111, 113, 115, 117, 119, 121, 149, 150, 151, 152, 153, 154, 155, 156 and 157.

In a further embodiment there is provided an isolated monoclonal antibody or antigen binding fragment thereof, wherein said antibody or antigen binding fragment specifically binds human c-Met protein, the antibody or antigen-binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity to an amino acid sequence selected from the group consisting of: SEQ ID NO:49, 108, 110, 112, 114, 116, 118 and 120 and the light chain variable domain comprising a V Kappa sequence with at least 75% sequence identity, or at least 80% sequence identity, or at least 85% sequence identity, or at least 90% sequence identity, or at least 95% sequence identity, or at least 97%, 98% or 99% sequence identity to an amino acid sequence selected from the group consisting of SEQ ID NO:52, 89, 109, 111, 113, 115, 117, 119, 121, 149, 150, 151, 152, 153, 154, 155, 156 and 157.

In an exemplary embodiment this antibody or antigen binding fragment thereof binds to an epitope within the peptide 523-RSEECLSGTWTQQICLPAIYKVFPNSAP-LEG GTRLTICGWDEGFRRNNKFDLKKTRVELG-NESCTLTESESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, the antibody or antigen-binding fragment comprising a heavy chain variable domain comprising a VH sequence with at least 85% sequence identity, or at least 90% sequence identity, or at least 95% sequence identity, or at least 97%, 98% or 99% sequence identity to SEQ ID NO:49, and a light chain variable domain (VL) comprising a V Kappa sequence with at least 75% sequence identity, or at least 80% sequence identity, or at least 85% sequence identity, or at least 90% sequence identity, or at least 95% sequence identity, or at least 97%, 98% or 99% sequence identity to the amino acid sequence shown as SEQ ID NO:52 or the amino acid sequence shown as SEQ ID NO:89.

This antibody, or antigen-binding region may comprise heavy chain CDRs which are identical to CDR1, CDR2 and CDR3 of SEQ ID NO:49 and light chain CDRs which are identical to CDR1, CDR2 and CDR3 of SEQ ID NO:89 or CDR1, CDR2 and CDR3 of SEQ ID NO:52, whilst exhibiting amino acid sequence variation within the framework regions.

In an exemplary embodiment this antibody or antigen binding fragment thereof binds to an epitope within the peptide 523-RSEECLSGTWTQQICLPAIYKVFPNSAP-LEG GTRLTICGWDFGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:49, or a humanised or affinity variant thereof, and a light chain variable domain (VL) comprising the amino acid sequence shown as SEQ ID NO:52 or the amino acid sequence shown as SEQ ID NO:89 or a humanised, or affinity variant thereof.

In an exemplary embodiment this antibody or antigen binding fragment thereof binds to an epitope within the peptide 523-RSEECLSGTWTQQICLPAIYKVFPNSAP-LEG GTRLTICGWDFGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof which specifically binds human c-Met protein, said antibody or antigen binding fragment comprising a heavy chain variable domain (VH) comprising the amino acid sequence shown as SEQ ID NO:49, or a humanised or affinity variant thereof, and a light chain variable domain (VL) comprising the amino acid sequence shown as SEQ ID NO:89 or a humanised, or affinity variant thereof.

In an exemplary embodiment this antibody or antigen binding fragment thereof binds to an epitope within the peptide 523-RSEECLSGTWTQQICLPAIYKVFPNSAP-LEG GTRLTICGWDEGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody or an antigen binding fragment thereof that specifically binds to a human c-Met protein and is preferably a strict antagonist of HGF-mediated activation of the c-Met receptor, which antibody is a human germlined variant of the antibody 48A2, said germlined variant antibody comprising:—

(a) a heavy chain variable domain (VH) comprising the amino acid sequence shown as SEQ ID NO:108, and a light chain variable domain (VL) comprising the amino acid sequence shown as SEQ ID NO:109; or (b) a heavy chain variable domain (VH) comprising the amino acid sequence shown as SEQ ID NO:110, and a light chain variable domain (VL) comprising the amino acid sequence shown as SEQ ID NO:111; or (c) a heavy chain variable domain (VH) comprising the amino acid sequence shown as SEQ ID NO:112, and a light chain variable domain (VL) comprising the amino acid sequence shown as SEQ ID NO:113; or (d) a heavy chain variable domain (VH) comprising the amino acid sequence shown as SEQ ID NO:114, and a light chain variable domain (VL) comprising the amino acid sequence shown as SEQ ID NO:115; or (e) a heavy chain variable domain (VH) comprising the amino acid sequence shown as SEQ ID NO:116, and a light chain variable domain (VL) comprising the amino acid sequence shown as SEQ ID NO:117; or (f) a heavy chain variable domain (VH) comprising the amino acid sequence shown as SEQ ID NO:118, and a light chain variable domain (VL) comprising the amino acid sequence shown as SEQ ID NO:119; or (g) a heavy chain variable domain (VH) comprising the amino acid sequence shown as SEQ ID NO:120, and a light chain variable domain (VL) comprising the amino acid sequence shown as SEQ ID NO:121; or (h) a heavy chain variable domain (VH) comprising the amino acid sequence shown as SEQ ID NO:49, and a light chain variable domain (VL) comprising an amino acid sequence selected from the group consisting of SEQ ID NO:149, SEQ ID NO:150, SEQ ID NO:151, SEQ ID NO:152, SEQ ID NO:153, SEQ ID NO:154, SEQ ID NO:155, SEQ ID NO:156 and SEQ ID NO:157.

These variant 48A2 antibodies, or antigen-binding regions, are identified as comprising a combination of a VH domain, defined by reference to a specific amino acid sequence, and a VL domain (V Kappa), also defined by reference to a specific amino acid sequence. For each specific VH/VL combination listed, this definition should be taken to include antibodies, or antigen binding regions, formed by combination of a VH domain having at least 85%, at least 90%, at least 95%, at least 97%, or at least 99% sequence identity to the stated VH amino acid sequence and a VL domain having at least 75%, at least 80%, at least 85%, at least 90%, at least 95%, at least 97%, or at least 99% sequence identity to the stated VL amino acid sequence. In each case the VH and VL domains defined by % sequence identity to the stated VH and VL amino acid sequences may retain identical CDR sequences to those present in the stated VH and VL amino acid sequences, whilst exhibiting amino acid sequence variation within the framework regions.

In an exemplary embodiment this antibody or antigen binding fragment thereof binds to an epitope within the peptide 523-RSEECLSGTWTQQICLPAIYKVFPNSAP-LEG GTRLTICGWDFGFRRNNKFDLKKTRVLLG-NESCTLTLSESTMNTLKCTVGPAM NKHFNMSIIIS-NGHGTTQYSTFSYVDP-633 (SEQ ID NO: 136) in the PSI-IPT1 region of human c-Met protein.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody or an antigen binding fragment thereof that specifically binds to a human c-Met protein and is preferably a strict antagonist of HGF-mediated activation of the c-Met receptor, which antibody is an affinity variant of the reference antibody 48A2, said affinity variant antibody comprising a heavy chain variable domain (VH) comprising the amino acid sequence shown as SEQ ID NO:49, and a light chain variable domain (VL) comprising an amino acid sequence selected from the group consisting of SEQ ID NO:149, SEQ ID NO:150, SEQ ID NO:151, SEQ ID NO:152, SEQ ID NO:153, SEQ ID NO:154, SEQ ID NO:155, SEQ ID NO:156 and SEQ ID NO:157.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:50, or a humanised or affinity variant thereof, and a light chain variable domain (VL) comprising the amino acid sequence shown as SEQ ID NO:53, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

20A11, 13E6, 12G4

In a further embodiment there is provided an isolated antibody, or an antigen binding fragment thereof which specifically binds human c-Met protein, said antibody or antigen binding fragment comprising a heavy chain variable domain wherein the variable heavy chain CDR3 sequence is selected from the group consisting of SEQ ID NO:3, SEQ ID NO:6 or SEQ ID NO:9 or sequence variant thereof, wherein the sequence variant comprises one, two or three amino acid substitutions (e.g., conservative substitutions, humanising substitutions or affinity variants) in the recited sequence.

In one embodiment of the antibody or antigen binding fragment thereof
the variable heavy chain CDR3 sequence is selected from the group consisting of SEQ ID NO:3, SEQ ID NO:6 or SEQ ID NO:9 or sequence variant thereof;
the variable heavy chain CDR2 sequence is SEQ ID NO: 195 or sequence variant thereof; and
the variable heavy chain CDR1 sequence is SEQ ID NO: 198 or sequence variant thereof, and
wherein the sequence variant comprises one, two or three amino acid substitutions (e.g., conservative substitutions, humanising substitutions or affinity variants) in the recited sequence.

In one embodiment of the antibody or antigen binding fragment thereof the variable heavy chain CDR3 sequence is SEQ ID NO:3 or sequence variant thereof;
the variable heavy chain CDR2 sequence is SEQ ID NO:2 or sequence variant thereof; and
the variable heavy chain CDR1 sequence is SEQ ID NO:1 or sequence variant thereof, and
wherein the sequence variant comprises one, two or three amino acid substitutions (e.g., conservative substitutions, humanising substitutions or affinity variants) in the recited sequence.

In one embodiment of the antibody or antigen binding fragment thereof the variable heavy chain CDR3 sequence is SEQ ID NO:6 or sequence variant thereof;
the variable heavy chain CDR2 sequence is SEQ ID NO:5 or sequence variant thereof; and
the variable heavy chain CDR1 sequence is SEQ ID NO:4 or sequence variant thereof, and
wherein the sequence variant comprises one, two or three amino acid substitutions (e.g., conservative substitutions, humanising substitutions or affinity variants) in the recited sequence.

In one embodiment of the antibody or antigen binding fragment thereof the variable heavy chain CDR3 sequence is SEQ ID NO:9 or sequence variant thereof;
the variable heavy chain CDR2 sequence is SEQ ID NO:8 or sequence variant thereof; and
the variable heavy chain CDR1 sequence is SEQ ID NO:7 or sequence variant thereof, and
wherein the sequence variant comprises one, two or three amino acid substitutions (e.g., conservative substitutions, humanising substitutions or affinity variants) in the recited sequence.

In one embodiment the antibody or antigen binding fragment thereof further comprises a light chain variable domain wherein the variable light chain CDR3 sequence is SEQ ID NO: 202 or sequence variant thereof;
the variable light chain CDR2 sequence is SEQ ID NO: 204 or sequence variant thereof; and
the variable light chain CDR1 sequence is SEQ ID NO: 206 or sequence variant thereof, and wherein the sequence variant comprises one, two or three amino acid substitutions (e.g., conservative substitutions, humanising substitutions or affinity variants) in the recited sequence.

In one embodiment of the antibody or antigen binding fragment thereof the variable light chain CDR3 sequence is SEQ ID NO:36 or sequence variant thereof;

the variable light chain CDR2 sequence is SEQ ID NO:35 or sequence variant thereof; and the variable light chain CDR1 sequence is SEQ ID NO:34 or sequence variant thereof, and wherein the sequence variant comprises one, two or three amino acid substitutions (e.g., conservative substitutions, humanising substitutions or affinity variants) in the recited sequence.

In one embodiment of the antibody or antigen binding fragment thereof the variable light chain CDR3 sequence is SEQ ID NO:39 or sequence variant thereof;

the variable light chain CDR2 sequence is SEQ ID NO:38 or sequence variant thereof; and the variable light chain CDR1 sequence is SEQ ID NO:37 or sequence variant thereof, and wherein the sequence variant comprises one, two or three amino acid substitutions (e.g., conservative substitutions, humanising substitutions or affinity variants) in the recited sequence.

In one embodiment of the antibody or antigen binding fragment thereof the variable light chain CDR3 sequence is SEQ ID NO:42 or sequence variant thereof;

the variable light chain CDR2 sequence is SEQ ID NO:41 or sequence variant thereof; and the variable light chain CDR1 sequence is SEQ ID NO:40 or sequence variant thereof, and wherein the sequence variant comprises one, two or three amino acid substitutions (e.g., conservative substitutions, humanising substitutions or affinity variants) in the recited sequence.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:9 or sequence variant thereof;

the variable heavy chain CDR2 sequence is SEQ ID NO:8 or sequence variant thereof; and the variable heavy chain CDR1 sequence is SEQ ID NO:7 or sequence variant thereof, the variable light chain CDR3 sequence is SEQ ID NO:42 or sequence variant thereof;

the variable light chain CDR2 sequence is SEQ ID NO:41 or sequence variant thereof; and the variable light chain CDR1 sequence is SEQ ID NO:40 or sequence variant thereof, and wherein the sequence variant comprises one, two or three amino acid substitutions (e.g., conservative substitutions, humanising substitutions or affinity variants) in the recited sequence.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:6 or sequence variant thereof;

the variable heavy chain CDR2 sequence is SEQ ID NO:5 or sequence variant thereof; and the variable heavy chain CDR1 sequence is SEQ ID NO:4 or sequence variant thereof, the variable light chain CDR3 sequence is SEQ ID NO:39 or sequence variant thereof;

the variable light chain CDR2 sequence is SEQ ID NO:38 or sequence variant thereof; and the variable light chain CDR1 sequence is SEQ ID NO:37 or sequence variant thereof, and wherein the sequence variant comprises one, two or three amino acid substitutions (e.g., conservative substitutions, humanising substitutions or affinity variants) in the recited sequence.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, wherein:

the variable heavy chain CDR3 sequence is SEQ ID NO:3 or sequence variant thereof;

the variable heavy chain CDR2 sequence is SEQ ID NO:2 or sequence variant thereof; and the variable heavy chain CDR1 sequence is SEQ ID NO:1 or sequence variant thereof, the variable light chain CDR3 sequence is SEQ ID NO:36 or sequence variant thereof;

the variable light chain CDR2 sequence is SEQ ID NO:35 or sequence variant thereof; and the variable light chain CDR1 sequence is SEQ ID NO:34 or sequence variant thereof, and wherein the sequence variant comprises one, two or three amino acid substitutions (e.g., conservative substitutions, humanising substitutions or affinity variants) in the recited sequence.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to an amino acid sequence selected from the group consisting of: SEQ ID NO:45, 46 and 47.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH amino acid sequence selected from the group consisting of: SEQ ID NO:45, 46 and 47.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda sequence with at least 80% sequence identity, or at least 85% sequence identity, or at least 90% sequence identity, or at least 95% sequence identity, or at least 97%, 98% or 99% sequence identity, to an amino acid sequence selected from the group consisting of SEQ ID NO: 56, 57 and 58.

In a further embodiment there is provided an isolated antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda amino acid sequence selected from the group consisting of SEQ ID NO:56, 57 and 58.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:45, or a humanised or affinity variant thereof, and a light chain variable domain (VL) comprising the amino acid sequence shown as SEQ ID NO:56, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO: 46, or a humanised or affinity variant thereof, and a light chain variable domain (VL) comprising the amino acid sequence shown as SEQ ID NO:57, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated antibody, or an antigen binding fragment thereof, that specifically binds to a human c-Met protein and is a strict antagonist of HGF-mediated activation of the c-Met receptor, the antibody comprising a heavy chain variable domain (VH) comprising the amino acid sequence shown as SEQ ID NO:47, or a humanised or affinity variant thereof, and a light chain variable domain (VL) comprising the amino acid sequence shown as SEQ ID NO:58, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

34H7

In a further embodiment there is provided an isolated antibody or antigen binding fragment thereof which specifically binds human c-Met protein, said antibody or antigen binding fragment comprising a heavy chain variable domain wherein the variable heavy chain CDR3 sequence is SEQ ID NO:73 or sequence variant thereof, wherein the sequence variant comprises one, two or three amino acid substitutions (e.g., conservative substitutions, humanising substitutions or affinity variants) in the recited sequence.

In one embodiment of the antibody or antigen binding fragment the variable heavy chain CDR3 sequence is SEQ ID NO:73 or sequence variant thereof;

the variable heavy chain CDR2 sequence is SEQ ID NO:72 or sequence variant thereof; and the variable heavy chain CDR1 sequence is SEQ ID NO:71 or sequence variant thereof, and wherein the sequence variant comprises one, two or three amino acid substitutions (e.g., conservative substitutions, humanising substitutions or affinity variants) in the recited sequence.

In one embodiment the antibody or antigen binding fragment further comprises a light chain variable domain wherein the variable light chain CDR3 sequence is SEQ ID NO:76 or sequence variant thereof;

the variable light chain CDR2 sequence is SEQ ID NO:75 or sequence variant thereof; and the variable light chain CDR1 sequence is SEQ ID NO:74 or sequence variant thereof, and wherein the sequence variant comprises one, two or three amino acid substitutions (e.g., conservative substitutions, humanising substitutions or affinity variants) in the recited sequence.

In an exemplary embodiment this antibody, or an antigen binding fragment thereof, comprising all six recited heavy chain and light chain CDRs, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising a VH sequence with at least 85% sequence identity, or at least 90% sequence identity, or at least 95% sequence identity, or at least 97%, 98% or 99% sequence identity, to the amino acid sequence shown as SEQ ID NO:77.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the heavy chain variable domain comprising the VH amino acid sequence shown as SEQ ID NO:77.

In a further embodiment there is provided an isolated monoclonal antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising a V Lambda sequence with at least 80% sequence identity, or at least 85% sequence identity, or at least 90% sequence identity, or at least 95% sequence identity, or at least 97%, 98% or 99% sequence identity, to the amino acid sequence shown as SEQ ID NO:78.

In a further embodiment there is provided an isolated antibody or antigen binding fragment thereof, wherein said antibody or antigen binding fragment specifically binds human c-Met protein, said antibody or antigen binding fragment comprising a heavy chain variable domain and a light chain variable domain, the light chain variable domain comprising the VL amino acid sequence shown as SEQ ID NO:78.

In a further embodiment there is provided an isolated antibody, or an antigen binding fragment thereof, that specifically binds to a human c-Met protein and is preferably a strict antagonist of HGF-mediated activation of the c-Met receptor, the antibody comprising a heavy chain variable domain (VH) comprising the amino acid sequence shown as SEQ ID NO:77, or a humanised or affinity variant thereof, and a light chain variable domain (VL) comprising the amino acid sequence shown as SEQ ID NO:78, or a humanised, or affinity variant thereof.

In an exemplary embodiment this antibody, or an antigen binding fragment thereof, may be a strict antagonist of HGF-mediated activation of the human c-Met protein and may also inhibit HGF-independent activation of the human c-Met protein, and preferably does not induce significant down-regulation of cell surface human c-Met protein.

In one embodiment this antibody may include the CH1 domain, hinge region, CH2 domain and CH3 domain of a human antibody, in particular human IgG1, IgG2, IgG3 or IgG4.

Where particular antibodies, or antigen-binding regions, are identified as comprising a combination of a VH domain, defined by reference to a specific amino acid sequence, and a VL domain (V Kappa), also defined by reference to a specific amino acid sequence, then for each specific VH/VL combination listed (unless otherwise stated) this definition may be taken to include antibodies, or antigen binding regions, formed by combination of a VH domain having at least 85%, at least 90%, at least 95%, at least 97%, or at least 99% sequence identity to the stated VH amino acid sequence and a VL domain having at least 75%, at least 80%, at least 85%, at least 90%, at least 95%, at least 97%, or at least 99% sequence identity to the stated VL amino acid sequence. In each case the VH and VL domains defined by % sequence identity to the stated VH and VL amino acid sequences may retain identical CDR sequences to those present in the stated VH and VL amino acid sequences, whilst exhibiting amino acid sequence variation within the framework regions.

Unless otherwise stated in the present application, % sequence identity between two amino acid sequences may be determined by comparing these two sequences aligned in an optimum manner and in which the amino acid sequence to be compared can comprise additions or deletions with respect to the reference sequence for an optimum alignment between these two sequences. The percentage of identity is calculated by determining the number of identical positions for which the amino acid residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

The c-Met antibodies, or antigen binding fragments thereof, provided herein may each exhibit one or more, or any combination, of the following properties/features:

The antibody or antigen binding fragment may act as an inhibitor of HGF-independent activation of the c-Met receptor.

The antibody or antigen binding fragment may inhibit HGF-independent dimerisation, and more particularly homodimerization and/or heterodimerisation, of human c-Met protein.

The antibody may exhibit one or more effector functions selected from antibody-dependent cell-mediated cytotoxicity (ADCC), complement dependent cytotoxicity (CDC) and antibody-dependent cell-mediated phagocytosis (ADCP) against cells expressing human c-Met protein on the cell surface.

The antibody may exhibit ADCC against c-Met-addicted cancer cells.

The antibody may exhibit enhanced ADCC function in comparison to a reference antibody which is an equivalent antibody comprising a native human Fc domain. In a non-limiting embodiment, the ADCC function may be at least 10× enhanced in comparison to the reference antibody comprising a native human Fc domain. In this context "equivalent" may be taken to mean that the antibody with enhanced ADCC function displays substantially identical antigen-binding specificity and/or shares identical amino acid sequence with the reference antibody, except for any modifications made (relative to native human Fc) for the purposes of enhancing ADCC.

The antibody may contain the hinge region, CH2 domain and CH3 domain of a human IgG, most preferably human IgG1.

The antibody may include modifications in the Fc region, as explained elsewhere herein. In particular, the antibody may be a non-fucosylated IgG.

In further aspects, the invention also provides polynucleotide molecules which encode the above-listed c-Met antibodies and antigen binding fragments thereof, in addition to expression vectors comprising the polynucleotides, host cells containing the vectors and methods of recombinant expression/production of the c-Met antibodies.

In a still further aspect, the invention provides a pharmaceutical composition comprising any one of the c-Met antibodies described above and a pharmaceutically acceptable carrier or excipient.

A still further aspect of the invention concerns methods of medical treatment using the above-listed c-Met antibodies, particularly in the treatment of cancer, including both HGF-dependent cancers and HGF-independent cancers.

Definitions

"Antibody" or "Immunoglobulin"—As used herein, the term "immunoglobulin" includes a polypeptide having a combination of two heavy and two light chains whether or not it possesses any relevant specific immunoreactivity. "Antibodies" refers to such assemblies which have significant known specific immunoreactive activity to an antigen of interest (e.g. human c-Met). The term "c-Met antibodies" is used herein to refer to antibodies which exhibit immunological specificity for human c-Met protein. As explained elsewhere herein, "specificity" for human c-Met does not exclude cross-reaction with species homologues of c-Met. Antibodies and immunoglobulins comprise light and heavy chains, with or without an interchain covalent linkage between them. Basic immunoglobulin structures in vertebrate systems are relatively well understood.

The generic term "immunoglobulin" comprises five distinct classes of antibody that can be distinguished biochemically. All five classes of antibodies are within the scope of the present invention, the following discussion will generally be directed to the IgG class of immunoglobulin molecules. With regard to IgG, immunoglobulins comprise two identical light polypeptide chains of molecular weight approximately 23,000 Daltons, and two identical heavy chains of molecular weight 53,000-70,000. The four chains are joined by disulfide bonds in a "Y" configuration wherein the light chains bracket the heavy chains starting at the mouth of the "Y" and continuing through the variable region.

The light chains of an antibody are classified as either kappa or lambda ($\kappa$, $\lambda$). Each heavy chain class may be bound with either a kappa or lambda light chain. In general, the light and heavy chains are covalently bonded to each other, and the "tail" portions of the two heavy chains are bonded to each other by covalent disulfide linkages or non-covalent linkages when the immunoglobulins are generated either by hybridomas, B cells or genetically engineered host cells. In the heavy chain, the amino acid sequences run from an N-terminus at the forked ends of the Y configuration to the C-terminus at the bottom of each chain. Those skilled in the art will appreciate that heavy chains are classified as gamma, mu, alpha, delta, or epsilon, ($\gamma$, $\mu$, $\alpha$, $\delta$, $\epsilon$) with some subclasses among them (e.g., $\gamma1$-$\gamma4$). It is the nature of this chain that determines the "class" of the antibody as IgG, IgM, IgA IgG, or IgE, respectively. The immunoglobulin subclasses (isotypes) e.g., IgG1, IgG2, IgG3, IgG4, IgA1, etc. are well characterized and are known to confer functional specialization. Modified versions of each of these classes and isotypes are readily discernable to the skilled artisan in view of the instant disclosure and, accordingly, are within the scope of the instant invention.

As indicated above, the variable region of an antibody allows the antibody to selectively recognize and specifically bind epitopes on antigens. That is, the VL domain and VH domain of an antibody combine to form the variable region that defines a three dimensional antigen binding site. This quaternary antibody structure forms the antigen binding site present at the end of each arm of the Y. More specifically, the antigen binding site is defined by three complementary determining regions (CDRs) on each of the VH and VL chains.

"c-Met protein" or "c-Met receptor"—As used herein, the terms "c-Met protein" or "c-Met receptor" or "c-Met" are used interchangeably and refer to the receptor tyrosine kinase that, in its wild-type form, binds Hepatocyte Growth Factor (HGF). The terms "human c-Met protein" or "human c-Met receptor" or "human c-Met" are used interchangeably to refer to human c-Met, including the native human c-Met protein naturally expressed in the human host and/or on the surface of human cultured cell lines, as well as recombinant forms and fragments thereof and also naturally occurring mutant forms, polymorphic variants and functionally active mutant forms. Specific examples of human c-Met include, e.g., the human polypeptide encoded by the nucleotide sequence provided in GenBank Acc No. NM_000245, or the human protein encoded by the polypeptide sequence provided in GenBank Acc. No. NP_000236, or the extracellular domain of thereof. The single chain precursor c-Met protein is post-translationally cleaved to produce the alpha and beta subunits, which are disulfide linked to form the mature receptor. The c-Met antibodies provided herein typically bind both to mature human c-Met protein as expressed on the cell surface, e.g. as expressed on the human gastric cell line MKN-45 and to recombinant human c-Met protein (e.g. recombinant dimeric c-Met obtainable from R&D systems, 358-MT/CF).

"Binding Site"—As used herein, the term "binding site" comprises a region of a polypeptide which is responsible for selectively binding to a target antigen of interest (e.g. human c-Met). Binding domains or binding regions comprise at least one binding site. Exemplary binding domains include an antibody variable domain. The antibody molecules of the invention may comprise a single antigen binding site or multiple (e.g., two, three or four) antigen binding sites.

"Derived From"—As used herein the term "derived from" a designated protein (e.g. a c-Met antibody or antigen-binding fragment thereof) refers to the origin of the polypeptide. In one embodiment, the polypeptide or amino acid sequence which is derived from a particular starting polypeptide is a CDR sequence or sequence related thereto. In one embodiment, the amino acid sequence which is derived from a particular starting polypeptide is not contiguous. For example, in one embodiment, one, two, three, four, five, or six CDRs are derived from a starting antibody. In one embodiment, the polypeptide or amino acid sequence which is derived from a particular starting polypeptide or amino acid sequence has an amino acid sequence that is essentially identical to that of the starting sequence, or a portion thereof wherein the portion consists of at least of at least 3-5 amino acids, 5-10 amino acids, at least 10-20 amino acids, at least 20-30 amino acids, or at least 30-50 amino acids, or which is otherwise identifiable to one of ordinary skill in the art as having its origin in the starting sequence. In one embodiment, the one or more CDR sequences derived from the starting antibody are altered to produce variant CDR sequences, e.g. affinity variants, wherein the variant CDR sequences maintain c-Met binding activity.

"Camelid-Derived"—In certain preferred embodiments, the cMet antibody molecules of the invention comprise framework amino acid sequences and/or CDR amino acid sequences derived from a camelid conventional antibody raised by active immunisation of a camelid with c-Met antigen. However, c-Met antibodies comprising camelid-derived amino acid sequences may be engineered to comprise framework and/or constant region sequences derived from a human amino acid sequence or other non-camelid mammalian species. For example, a human or non-human primate framework region, heavy chain portion, and/or hinge portion may be included in the subject c-Met antibodies. In one embodiment, one or more non-camelid amino acids may be present in the framework region of a "camelid-derived" c-Met antibody, e.g., a camelid framework amino acid sequence may comprise one or more amino acid mutations in which the corresponding human or non-human primate amino acid residue is present. Moreover, camelid-derived VH and VL domains, or humanised variants thereof, may be linked to the constant domains of human antibodies to produce a chimeric molecule, as extensively described elsewhere herein.

"Conservative amino acid substitution"—A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a non-essential amino acid residue in an immunoglobulin polypeptide may be replaced with another amino acid residue from the same side chain family. In another embodiment, a string of amino acids can be replaced with a structurally similar string that differs in order and/or composition of side chain family members.

"Heavy chain portion"—As used herein, the term "heavy chain portion" includes amino acid sequences derived from the constant domains of an immunoglobulin heavy chain. A polypeptide comprising a heavy chain portion comprises at least one of: a CH1 domain, a hinge (e.g., upper, middle, and/or lower hinge region) domain, a CH2 domain, a CH3 domain, or a variant or fragment thereof. In one embodiment, a binding molecule of the invention may comprise the Fc portion of an immunoglobulin heavy chain (e.g., a hinge portion, a CH2 domain, and a CH3 domain). In another embodiment, a binding molecule of the invention lacks at least a portion of a constant domain (e.g., all or part of a CH2 domain). In certain embodiments, at least one, and preferably all, of the constant domains are derived from a human immunoglobulin heavy chain. For example, in one preferred embodiment, the heavy chain portion comprises a fully human hinge domain. In other preferred embodiments, the heavy chain portion comprising a fully human Fc portion (e.g., hinge, CH2 and CH3 domain sequences from a human immunoglobulin). In certain embodiments, the constituent constant domains of the heavy chain portion are from different immunoglobulin molecules. For example, a heavy chain portion of a polypeptide may comprise a CH2 domain derived from an IgG1 molecule and a hinge region derived from an IgG3 or IgG4 molecule. In other embodiments, the constant domains are chimeric domains comprising portions of different immunoglobulin molecules. For example, a hinge may comprise a first portion from an IgG1 molecule and a second portion from an IgG3 or IgG4 molecule. As set forth above, it will be understood by one of ordinary skill in the art that the constant domains of the heavy chain portion may be modified such that they vary in amino acid sequence from the naturally occurring (wild-type) immunoglobulin molecule. That is, the polypeptides of the invention disclosed herein may comprise alterations or modifications to one or more of the heavy chain constant domains (CH1, hinge, CH2 or CH3) and/or to the light chain constant domain (CL). Exemplary modifications include additions, deletions or substitutions of one or more amino acids in one or more domains.

"Chimeric"—A "chimeric" protein comprises a first amino acid sequence linked to a second amino acid sequence with which it is not naturally linked in nature. The amino acid sequences may normally exist in separate proteins that are brought together in the fusion polypeptide or they may normally exist in the same protein but are placed in a new arrangement in the fusion polypeptide. A chimeric protein may be created, for example, by chemical synthesis, or by creating and translating a polynucleotide in which the peptide regions are encoded in the desired relationship. Exemplary chimeric c-Met antibodies include fusion proteins comprising camelid-derived VH and VL domains, or humanised variants thereof, fused to the constant domains of a human antibody, e.g. human IgG1, IgG2, IgG3 or IgG4.

"Variable region" or "variable domain"—The term "variable" refers to the fact that certain portions of the variable domains VH and VL differ extensively in sequence among antibodies and are used in the binding and specificity of each particular antibody for its target antigen. However, the variability is not evenly distributed throughout the variable domains of antibodies. It is concentrated in three segments called "hypervariable loops" in each of the VL domain and the VH domain which form part of the antigen binding site. The first, second and third hypervariable loops of the VLambda light chain domain are referred to herein as L1($\lambda$), L2($\lambda$) and L3($\lambda$) and may be defined as comprising residues 24-33 (L1($\lambda$), consisting of 9, 10 or 11 amino acid residues), 49-53 (L2($\lambda$), consisting of 3 residues) and 90-96 (L3($\lambda$), consisting of 5 residues) in the VL domain (Morea et al., Methods 20:267-279 (2000)). The first, second and third hypervariable loops of the VKappa light chain domain are referred to herein as L1($\kappa$), L2($\kappa$) and L3($\kappa$) and may be defined as comprising residues 25-33 (L1($\kappa$), consisting of 6, 7, 8, 11, 12 or 13 residues), 49-53 (L2($\kappa$), consisting of 3 residues) and 90-97 (L3($\kappa$), consisting of 6 residues) in the VL domain (Morea et al., Methods 20:267-279 (2000)). The first, second and third hypervariable loops of the VH domain are referred to herein as H1, H2 and H3 and may be defined as comprising residues 25-33 (H1, consisting of 7, 8 or 9 residues), 52-56 (H2, consisting of 3 or 4 residues) and 91-105 (H3, highly variable in length) in the VH domain (Morea et al., Methods 20:267-279 (2000)).

Unless otherwise indicated, the terms L1, L2 and L3 respectively refer to the first, second and third hypervariable loops of a VL domain, and encompass hypervariable loops obtained from both Vkappa and Vlambda isotypes. The terms H1, H2 and H3 respectively refer to the first, second and third hypervariable loops of the VH domain, and encompass hypervariable loops obtained from any of the known heavy chain isotypes, including γ, ε, δ, α or μ.

The hypervariable loops L1, L2, L3, H1, H2 and H3 may each comprise part of a "complementarity determining region" or "CDR", as defined below. The terms "hypervariable loop" and "complementarity determining region" are not strictly synonymous, since the hypervariable loops (HVs) are defined on the basis of structure, whereas complementarity determining regions (CDRs) are defined based on sequence variability (Kabat et al., Sequences of Proteins of Immunological Interest, 5th Ed. Public Health Service, National Institutes of Health, Bethesda, Md., 1983) and the limits of the HVs and the CDRs may be different in some VH and VL domains.

The CDRs of the VL and VH domains can typically be defined as comprising the following amino acids: residues 24-34 (CDRL1), 50-56 (CDRL2) and 89-97 (CDRL3) in the light chain variable domain, and residues 31-35 or 31-35b (CDRH1), 50-65 (CDRH2) and 95-102 (CDRH3) in the heavy chain variable domain; (Kabat et al., Sequences of Proteins of Immunological Interest, 5th Ed. Public Health Service, National Institutes of Health, Bethesda, Md. (1991)). Thus, the HVs may be comprised within the corresponding CDRs and references herein to the "hypervariable loops" of VH and VL domains should be interpreted as also encompassing the corresponding CDRs, and vice versa, unless otherwise indicated.

The more highly conserved portions of variable domains are called the framework region (FR), as defined below. The variable domains of native heavy and light chains each comprise four FRs (FR1, FR2, FR3 and FR4, respectively), largely adopting a β-sheet configuration, connected by the three hypervariable loops. The hypervariable loops in each chain are held together in close proximity by the FRs and, with the hypervariable loops from the other chain, contribute to the formation of the antigen-binding site of antibodies. Structural analysis of antibodies revealed the relationship between the sequence and the shape of the binding site formed by the complementarity determining regions (Chothia et al., J. Mol. Biol. 227: 799-817 (1992)); Tramontano et al., J. Mol. Biol, 215:175-182 (1990)). Despite their high sequence variability, five of the six loops adopt just a small repertoire of main-chain conformations, called "canonical structures". These conformations are first of all determined by the length of the loops and secondly by the presence of key residues at certain positions in the loops and in the framework regions that determine the conformation through their packing, hydrogen bonding or the ability to assume unusual main-chain conformations.

"CDR"—As used herein, the term "CDR" or "complementarity determining region" means the non-contiguous antigen combining sites found within the variable region of both heavy and light chain polypeptides. These particular regions have been described by Kabat et al., J. Biol. Chem. 252, 6609-6616 (1977) and Kabat et al., Sequences of protein of immunological interest. (1991), and by Chothia et al., J. Mol. Biol. 196:901-917 (1987) and by MacCallum et al., J. Mol. Biol. 262:732-745 (1996) where the definitions include overlapping or subsets of amino acid residues when compared against each other. The amino acid residues which encompass the CDRs as defined by each of the above cited references are set forth for comparison. Preferably, the term "CDR" is a CDR as defined by Kabat based on sequence comparisons.

TABLE 1

CDR definitions

| | Kabat[1] | Chothia[2] | MacCallum[3] |
|---|---|---|---|
| $V_H$ CDR1 | 31-35 | 26-32 | 30-35 |
| $V_H$ CDR2 | 50-65 | 53-55 | 47-58 |
| $V_H$ CDR3 | 95-102 | 96-101 | 93-101 |
| $V_L$ CDR1 | 24-34 | 26-32 | 30-36 |
| $V_L$ CDR2 | 50-56 | 50-52 | 46-55 |
| $V_L$ CDR3 | 89-97 | 91-96 | 89-96 |

[1]Residue numbering follows the nomenclature of Kabat et al., supra
[2]Residue numbering follows the nomenclature of Chothia et al., supra
[3]Residue numbering follows the nomenclature of MacCallum et al., supra "Framework region"—The term "framework region" or "FR region" as used herein, includes the amino acid residues that are part of the variable region, but are not part of the CDRs (e.g., using the Kabat definition of CDRs). Therefore, a variable region framework is between about 100-120 amino acids in length but includes only those amino acids outside of the CDRs. For the specific example of a heavy chain variable region and for the CDRs as defined by Kabat et al., framework region 1 corresponds to the domain of the variable region encompassing amino acids 1-30; framework region 2 corresponds to the domain of the variable region encompassing amino acids 36-49; framework region 3 corresponds to the domain of the variable region encompassing amino acids 66-94, and framework region 4 corresponds to the domain of the variable region from amino acids 103 to the end of the variable region. The framework regions for the light chain are similarly separated by each of the light claim variable region CDRs. Similarly, using the definition of CDRs by Chothia et al. or McCallum et al. the framework region boundaries are separated by the respective CDR termini as described above. In preferred embodiments the CDRs are as defined by Kabat.

In naturally occurring antibodies, the six CDRs present on each monomeric antibody are short, non-contiguous sequences of amino acids that are specifically positioned to form the antigen binding site as the antibody assumes its three dimensional configuration in an aqueous environment. The remainder of the heavy and light variable domains show less inter-molecular variability in amino acid sequence and are termed the framework regions. The framework regions largely adopt a β-sheet conformation and the CDRs form loops which connect, and in some cases form part of, the β-sheet structure. Thus, these framework regions act to form a scaffold that provides for positioning the six CDRs in correct orientation by inter-chain, non-covalent interactions. The antigen binding site formed by the positioned CDRs defines a surface complementary to the epitope on the immunoreactive antigen. This complementary surface promotes the non-covalent binding of the antibody to the immunoreactive antigen epitope. The position of CDRs can be readily identified by one of ordinary skill in the art.

"Hinge region"—As used herein, the term "hinge region" includes the portion of a heavy chain molecule that joins the CH1 domain to the CH2 domain. This hinge region comprises approximately 25 residues and is flexible, thus allowing the two N-terminal antigen binding regions to move independently. Hinge regions can be subdivided into three distinct domains: upper, middle, and lower hinge domains (Roux et al. J. Immunol. 1998 161:4083). C-Met antibodies comprising a "fully human" hinge region may contain one of the hinge region sequences shown in Table 2 below.

TABLE 2 human hinge sequences

| IgG | Upper hinge | Middle hinge | Lower hinge |
| --- | --- | --- | --- |
| IgG1 | EPKSCDKTHT SEQ ID NO: 182 | CPPCP SEQ ID NO: 183 | APELLGGP SEQ ID NO: 184 |
| IgG3 | ELKTPLGDTTHT SEQ ID NO: 185 | CPRCP (EPKSCDTPPPCPRCP)$_3$ SEQ ID NO: 186 SEQ ID NO: 187 | APELLGGP SEQ ID NO: 184 |
| IgG4 | ESKYGPP SEQ ID NO: 188 | CPSCP SEQ ID NO: 189 | APEFLGGP SEQ ID NO: 190 |
| IgG42 | ERK SEQ ID NO: 191 | CCVECPPPCP SEQ ID NO: 192 | APPVAGP SEQ ID NO: 193 |

"CH2 domain"—As used herein the term "CH2 domain" includes the portion of a heavy chain molecule that extends, e.g., from about residue 244 to residue 360 of an antibody using conventional numbering schemes (residues 244 to 360, Kabat numbering system; and residues 231-340, EU numbering system, Kabat E A et al. Sequences of Proteins of Immunological Interest. Bethesda, US Department of Health and Human Services, NIH. 1991). The CH2 domain is unique in that it is not closely paired with another domain. Rather, two N-linked branched carbohydrate chains are interposed between the two CH2 domains of an intact native IgG molecule. It is also well documented that the CH3 domain extends from the CH2 domain to the C-terminal of the IgG molecule and comprises approximately 108 residues.

"Fragment"—The term "fragment" refers to a part or portion of an antibody or antibody chain comprising fewer amino acid residues than an intact or complete antibody or antibody chain. The term "antigen-binding fragment" refers to a polypeptide fragment of an immunoglobulin or antibody that binds antigen or competes with intact antibody (i.e., with the intact antibody from which they were derived) for antigen binding (i.e., specific binding to human c-Met). As used herein, the term "fragment" of an antibody molecule includes antigen-binding fragments of antibodies, for example, an antibody light chain variable domain (VL), an antibody heavy chain variable domain (VH), a single chain antibody (scFv), a F(ab')2 fragment, a Fab fragment, an Fd fragment, an Fv fragment, a single domain antibody fragment (DAb), a one-armed (monovalent) antibody, or any antigen-binding molecule formed by combination, assembly or conjugation of such antigen binding fragments. Fragments can be obtained, e.g., via chemical or enzymatic treatment of an intact or complete antibody or antibody chain or by recombinant means.

"Valency"—As used herein the term "valency" refers to the number of potential target binding sites in a polypeptide. Each target binding site specifically binds one target molecule or specific site on a target molecule. When a polypeptide comprises more than one target binding site, each target binding site may specifically bind the same or different molecules (e.g., may bind to different ligands or different antigens, or different epitopes on the same antigen). The subject binding molecules preferably have at least one binding site specific for a human c-Met molecule. In particular embodiments the c-Met antibodies provided herein may be at least bivalent.

"Specificity"—The term "specificity" refers to the ability to specifically bind (e.g., immunoreact with) a given target, e.g., c-Met. A polypeptide may be monospecific and contain one or more binding sites which specifically bind a target or a polypeptide may be multispecific and contain two or more binding sites which specifically bind the same or different targets. In one embodiment, an antibody of the invention is specific for more than one target. For example, in one embodiment, a multispecific binding molecule of the invention binds to c-Met and a second molecule expressed on a tumor cell. Exemplary antibodies which comprise antigen binding sites that bind to antigens expressed on tumor cells are known in the art and one or more CDRs from such antibodies can be included in an antibody of the invention.

"Synthetic"—As used herein the term "synthetic" with respect to polypeptides includes polypeptides which comprise an amino acid sequence that is not naturally occurring. For example, non-naturally occurring polypeptides which are modified forms of naturally occurring polypeptides (e.g., comprising a mutation such as an addition, substitution or deletion) or which comprise a first amino acid sequence (which may or may not be naturally occurring) that is linked in a linear sequence of amino acids to a second amino acid sequence (which may or may not be naturally occurring) to which it is not naturally linked in nature.

"Engineered"—As used herein the term "engineered" includes manipulation of nucleic acid or polypeptide molecules by synthetic means (e.g. by recombinant techniques, in vitro peptide synthesis, by enzymatic or chemical coupling of peptides or some combination of these techniques). Preferably, the antibodies of the invention are engineered, including for example, humanized and/or chimeric antibodies, and antibodies which have been engineered to improve one or more properties, such as antigen binding, stability/ half-life or effector function.

"Modified antibody"—As used herein, the term "modified antibody" includes synthetic forms of antibodies which are altered such that they are not naturally occurring, e.g., antibodies that comprise at least two heavy chain portions but not two complete heavy chains (such as, domain deleted antibodies or minibodies); multispecific forms of antibodies (e.g., bispecific, trispecific, etc.) altered to bind to two or more different antigens or to different epitopes on a single antigen); heavy chain molecules joined to scFv molecules and the like. ScFv molecules are known in the art and are described, e.g., in U.S. Pat. No. 5,892,019. In addition, the term "modified antibody" includes multivalent forms of antibodies (e.g., trivalent, tetravalent, etc., antibodies that bind to three or more copies of the same antigen). In another embodiment, a modified antibody of the invention is a fusion protein comprising at least one heavy chain portion lacking a CH2 domain and comprising a binding domain of a polypeptide comprising the binding portion of one member of a receptor ligand pair.

The term "modified antibody" may also be used herein to refer to amino acid sequence variants of a c-Met antibody. It will be understood by one of ordinary skill in the art that a c-Met antibody may be modified to produce a variant c-Met antibody which varies in amino acid sequence in comparison to the c-Met antibody from which it was derived. For example, nucleotide or amino acid substitutions leading to conservative substitutions or changes at "non-essential" amino acid residues may be made (e.g., in CDR and/or framework residues). Amino acid substitutions can include replacement of one or more amino acids with a naturally occurring or non-natural amino acid.

"Humanising substitutions"—As used herein, the term "humanising substitutions" refers to amino acid substitutions in which the amino acid residue present at a particular position in the VH or VL domain antibody c-Met antibody (for example a camelid-derived c-Met antibody) is replaced with an amino acid residue which occurs at an equivalent position in a reference human VH or VL domain. The reference human VH or VL domain may be a VH or VL domain encoded by the human germline, in which case the substituted residues may be referred to as "germlining substitutions". Humanising/germlining substitutions may be made in the framework regions and/or the CDRs of a c-Met antibody, defined herein.

"Affinity variants"—As used herein, the term "affinity variant" refers to "a variant antibody which exhibits one or more changes in amino acid sequence compared to a reference c-Met antibody, wherein the affinity variant exhibits an altered affinity for the human c-Met protein in comparison to the reference antibody. Typically, affinity variants will exhibit an improved affinity for human c-Met, as compared to the reference c-Met antibody. The improvement may be either a lower $K_D$, for human c-Met, or a faster off-rate for human c-Met or an alteration in the pattern of cross-reactivity with non-human c-Met homologues. Affinity variants typically exhibit one or more changes in amino acid sequence in the CDRs, as compared to the reference c-Met antibody. Such substitutions may result in replacement of the original amino acid present at a given position in the CDRs with a different amino acid residue, which may be a naturally occurring amino acid residue or a non-naturally occurring amino acid residue. The amino acid substitutions may be conservative or non-conservative.

"High human homology"—An antibody comprising a heavy chain variable domain (VH) and a light chain variable domain (VL) will be considered as having high human homology if the VH domains and the VL domains, taken together, exhibit at least 90% amino acid sequence identity to the closest matching human germline VH and VL sequences. Antibodies having high human homology may include antibodies comprising VH and VL domains of native non-human antibodies which exhibit sufficiently high % sequence identity human germline sequences, including for example antibodies comprising VH and VL domains of camelid conventional antibodies, as well as engineered, especially humanised, variants of such antibodies and also "fully human" antibodies.

In one embodiment the VH domain of the antibody with high human homology may exhibit an amino acid sequence identity or sequence homology of 80% or greater with one or more human VH domains across the framework regions FR1, FR2, FR3 and FR4. In other embodiments the amino acid sequence identity or sequence homology between the VH domain of the polypeptide of the invention and the closest matching human germline VH domain sequence may be 85% or greater, 90% or greater, 95% or greater, 97% or greater, or up to 99% or even 100%.

In one embodiment the VH domain of the antibody with high human homology may contain one or more (e.g. 1 to 10) amino acid sequence mis-matches across the framework regions FR1, FR2, FR3 and FR4, in comparison to the closest matched human VH sequence.

In another embodiment the VL domain of the antibody with high human homology may exhibit a sequence identity or sequence homology of 80% or greater with one or more human VL domains across the framework regions FR1, FR2, FR3 and FR4. In other embodiments the amino acid sequence identity or sequence homology between the VL domain of the polypeptide of the invention and the closest matching human germline VL domain sequence may be 85% or greater 90% or greater, 95% or greater, 97% or greater, or up to 99% or even 100%.

In one embodiment the VL domain of the antibody with high human homology may contain one or more (e.g. 1 to 10) amino acid sequence mis-matches across the framework regions FR1, FR2, FR3 and FR4, in comparison to the closest matched human VL sequence.

Before analyzing the percentage sequence identity between the antibody with high human homology and human germline VH and VL, the canonical folds may be determined, which allows the identification of the family of human germline segments with the identical combination of canonical folds for H1 and H2 or L1 and L2 (and L3). Subsequently the human germline family member that has the highest degree of sequence homology with the variable region of the antibody of interest is chosen for scoring the sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody of interest is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)).

With the particular human germline V segment known, which uses the same combination of canonical folds for H1 and H2 or L1 and L2 (and L3), the best matching family member in terms of sequence homology can be determined. With bioinformatics tools the percentage sequence identity between the VH and VL domain framework amino acid sequences of the antibody of interest and corresponding sequences encoded by the human germline can be determined, but actually manual alignment of the sequences can be applied as well. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines. To compare the human sequences to the V regions of VH or VL domains in an antibody of interest a sequence alignment algorithm such as available via websites like www.expasy.ch/tools/#align can be used, but also manual alignment with the limited set of sequences can be performed. Human germline light and heavy chain sequences of the families with the same combinations of canonical folds and with the highest degree of homology with the framework regions 1, 2, and 3 of each chain are selected and compared with the variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered "human", despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)). The boundaries of the individual framework regions may be assigned using the IMGT numbering scheme, which is an adaptation of the numbering scheme of Chothia (Lefranc et al., NAR 27: 209-212 (1999); http://imgt.cines.fr).

Antibodies with high human homology may comprise hypervariable loops or CDRs having human or human-like canonical folds, as discussed in detail below. In one embodiment at least one hypervariable loop or CDR in either the VH domain or the VL domain of the antibody with high human homology may be obtained or derived from a VH or VL domain of a non-human antibody, for example a conventional antibody from a species of Camelidae, yet exhibit a predicted or actual canonical fold structure which is substantially identical to a canonical fold structure which occurs in human antibodies.

It is well established in the art that although the primary amino acid sequences of hypervariable loops present in both VH domains and VL domains encoded by the human germline are, by definition, highly variable, all hypervariable loops, except CDR H3 of the VH domain, adopt only a few distinct structural conformations, termed canonical folds (Chothia et al., J. Mol. Biol. 196:901-917 (1987); Tramontano et al. Proteins 6:382-94 (1989)), which depend on both the length of the hypervariable loop and presence of the so-called canonical amino acid residues (Chothia et al., J. Mol. Biol. 196:901-917 (1987)). Actual canonical structures of the hypervariable loops in intact VH or VL domains can be determined by structural analysis (e.g. X-ray crystallography), but it is also possible to predict canonical structure on the basis of key amino acid residues which are characteristic of a particular structure (discussed further below). In essence, the specific pattern of residues that determines each canonical structure forms a "signature" which enables the canonical structure to be recognised in hypervariable loops of a VH or VL domain of unknown structure; canonical structures can therefore be predicted on the basis of primary amino acid sequence alone.

The predicted canonical fold structures for the hypervariable loops of any given VH or VL sequence in an antibody with high human homology can be analysed using algorithms which are publicly available from www.bioinf.org.uk/abs/chothia.html, www.biochem.ucl.ac.uk/~martin/antibodies.html and www.bioc.unizh.ch/antibody/Sequences/Germlines/Vbase_hVk.html. These tools permit query VH or VL sequences to be aligned against human VH or VL domain sequences of known canonical structure, and a prediction of canonical structure made for the hypervariable loops of the query sequence.

In the case of the VH domain, H1 and H2 loops may be scored as having a canonical fold structure "substantially identical" to a canonical fold structure known to occur in human antibodies if at least the first, and preferable both, of the following criteria are fulfilled:
1. An identical length, determined by the number of residues, to the closest matching human canonical structural class.
2. At least 33% identity, preferably at least 50% identity with the key amino acid residues described for the corresponding human H1 and H2 canonical structural classes.
(note for the purposes of the foregoing analysis the H1 and H2 loops are treated separately and each compared against its closest matching human canonical structural class)

The foregoing analysis relies on prediction of the canonical structure of the H1 and H2 loops of the antibody of interest. If the actual structures of the H1 and H2 loops in the antibody of interest are known, for example based on X-ray crystallography, then the H1 and H2 loops in the antibody of interest may also be scored as having a canonical fold structure "substantially identical" to a canonical fold structure known to occur in human antibodies if the length of the loop differs from that of the closest matching human canonical structural class (typically by ±1 or +2 amino acids) but the actual structure of the H1 and H2 loops in the antibody of interest matches the structure of a human canonical fold.

Key amino acid residues found in the human canonical structural classes for the first and second hypervariable loops of human VH domains (H1 and H2) are described by Chothia et al., J. Mol. Biol. 227:799-817 (1992), the contents of which are incorporated herein in their entirety by reference. In particular, Table 3 on page 802 of Chothia et al., which is specifically incorporated herein by reference, lists preferred amino acid residues at key sites for H1 canonical structures found in the human germline, whereas Table 4 on page 803, also specifically incorporated by reference, lists preferred amino acid residues at key sites for CDR H2 canonical structures found in the human germline.

In one embodiment, both H1 and H2 in the VH domain of the antibody with high human homology exhibit a predicted or actual canonical fold structure which is substantially identical to a canonical fold structure which occurs in human antibodies.

Antibodies with high human homology may comprise a VH domain in which the hypervariable loops H1 and H2 form a combination of canonical fold structures which is identical to a combination of canonical structures known to occur in at least one human germline VH domain. It has been observed that only certain combinations of canonical fold structures at H1 and H2 actually occur in VH domains encoded by the human germline. In an embodiment H1 and H2 in the VH domain of the antibody with high human homology may be obtained from a VH domain of a non-human species, e.g. a Camelidae species, yet form a combination of predicted or actual canonical fold structures which is identical to a combination of canonical fold structures known to occur in a human germline or somatically mutated VH domain. In non-limiting embodiments H1 and H2 in the VH domain of the antibody with high human homology may be obtained from a VH domain of a non-human species, e.g. a Camelidae species, and form one of the following canonical fold combinations: 1-1, 1-2, 1-3, 1-6, 1-4, 2-1, 3-1 and 3-5.

An antibody with high human homology may contain a VH domain which exhibits both high sequence identity/sequence homology with human VH, and which contains hypervariable loops exhibiting structural homology with human VH.

It may be advantageous for the canonical folds present at H1 and H2 in the VH domain of the antibody with high human homology, and the combination thereof, to be "correct" for the human VH germline sequence which represents the closest match with the VH domain of the antibody with high human homology in terms of overall primary amino acid sequence identity. By way of example, if the closest sequence match is with a human germline VH3 domain, then it may be advantageous for H1 and H2 to form a combination of canonical folds which also occurs naturally in a human VH3 domain. This may be particularly important in the case of antibodies with high human homology which are derived from non-human species, e.g. antibodies containing VH and VL domains which are derived from camelid conventional antibodies, especially antibodies containing humanised camelid VH and VL domains.

Thus, in one embodiment the VH domain of the c-Met antibody with high human homology may exhibit a sequence identity or sequence homology of 80% or greater, 85% or greater, 90% or greater, 95% or greater, 97% or greater, or up to 99% or even 100% with a human VH domain across the framework regions FR1, FR2, FR3 and FR4, and in addition H1 and H2 in the same antibody are obtained from a non-human VH domain (e.g. derived from a Camelidae species), but form a combination of predicted or actual canonical fold structures which is the same as a canonical fold combination known to occur naturally in the same human VH domain.

In other embodiments, L1 and L2 in the VL domain of the antibody with high human homology are each obtained from a VL domain of a non-human species (e.g. a camelid-derived VL domain), and each exhibits a predicted or actual canonical fold structure which is substantially identical to a canonical fold structure which occurs in human antibodies.

As with the VH domains, the hypervariable loops of VL domains of both VLambda and VKappa types can adopt a limited number of conformations or canonical structures, determined in part by length and also by the presence of key amino acid residues at certain canonical positions.

Within an antibody of interest having high human homology, L1, L2 and L3 loops obtained from a VL domain of a non-human species, e.g. a Camelidae species, may be scored as having a canonical fold structure "substantially identical" to a canonical fold structure known to occur in human antibodies if at least the first, and preferable both, of the following criteria are fulfilled:
1. An identical length, determined by the number of residues, to the closest matching human structural class.
2. At least 33% identity, preferably at least 50% identity with the key amino acid residues described for the corresponding human L1 or L2 canonical structural classes, from either the VLambda or the VKappa repertoire.
(note for the purposes of the foregoing analysis the L1 and L2 loops are treated separately and each compared against its closest matching human canonical structural class)

The foregoing analysis relies on prediction of the canonical structure of the L1, L2 and L3 loops in the VL domain of the antibody of interest. If the actual structure of the L1, L2 and L3 loops is known, for example based on X-ray crystallography, then L1, L2 or L3 loops derived from the antibody of interest may also be scored as having a canonical fold structure "substantially identical" to a canonical fold structure known to occur in human antibodies if the length of the loop differs from that of the closest matching human canonical structural class (typically by ±1 or +2 amino acids) but the actual structure of the Camelidae loops matches a human canonical fold.

Key amino acid residues found in the human canonical structural classes for the CDRs of human VLambda and VKappa domains are described by Morea et al. Methods, 20: 267-279 (2000) and Martin et al., J. Mol. Biol., 263:800-815 (1996). The structural repertoire of the human VKappa domain is also described by Tomlinson et al. EMBO J. 14:4628-4638 (1995), and that of the VLambda domain by Williams et al. J. Mol. Biol., 264:220-232 (1996). The contents of all these documents are to be incorporated herein by reference.

L1 and L2 in the VL domain of an antibody with high human homology may form a combination of predicted or actual canonical fold structures which is identical to a combination of canonical fold structures known to occur in a human germline VL domain. In non-limiting embodiments L1 and L2 in the VLambda domain of an antibody with high human homology (e.g. an antibody containing a camelid-derived VL domain or a humanised variant thereof) may form one of the following canonical fold combinations: 11-7, 13-7(A,B,C), 14-7(A,B), 12-11, 14-11 and 12-12 (as defined in Williams et al. J. Mol. Biol. 264:220-32 (1996) and as shown on http://www.bioc.uzh.ch/antibody/Sequences/Germlines/VBase_hVL.html). In non-limiting embodiments L1 and L2 in the Vkappa domain may form one of the following canonical fold combinations: 2-1, 3-1, 4-1 and 6-1 (as defined in Tomlinson et al. EMBO J. 14:4628-38 (1995) and as shown on http://www.bioc.uzh.ch/antibody/Sequences/Germlines/VBase_hVK.html).

In a further embodiment, all three of L1, L2 and L3 in the VL domain of an antibody with high human homology may exhibit a substantially human structure. It is preferred that the VL domain of the antibody with high human homology exhibits both high sequence identity/sequence homology with human VL, and also that the hypervariable loops in the VL domain exhibit structural homology with human VL.

In one embodiment, the VL domain of the c-Met antibody with high human homology may exhibit a sequence identity of 80% or greater, 85% or greater, 90% or greater, 95% or greater, 97% or greater, or up to 99% or even 100% with a human VL domain across the framework regions FR1, FR2, FR3 and FR4, and in addition hypervariable loop L1 and hypervariable loop L2 may form a combination of predicted or actual canonical fold structures which is the same as a canonical fold combination known to occur naturally in the same human VL domain.

It is, of course, envisaged that VH domains exhibiting high sequence identity/sequence homology with human VH, and also structural homology with hypervariable loops of human VH will be combined with VL domains exhibiting high sequence identity/sequence homology with human VL, and also structural homology with hypervariable loops of human VL to provide antibodies with high human homology containing VH/VL pairings (e.g camelid-derived VH/V1 pairings) with maximal sequence and structural homology to human-encoded VH/VL pairings.

"Strict antagonist"—As defined herein, a "strict antagonist" of HGF-mediated activation of the c-Met receptor has the following properties: (1) it is an antagonist of HGF-mediated activation of the c-Met receptor, and (2) it does not exhibit significant intrinsic agonist activity.

As used herein, the term "antagonist of HGF-mediated activation of the c-Met receptor" refers to a molecule, such as a c-Met antibody, which is capable of inhibiting HGF-dependent c-Met activation/signalling in an appropriate assay system. Effective antagonist antibodies may be capable of inhibiting at least 50%, or at least 60%, or at least 70%, or at least 75%, or at least 80% of HGF maximal effect in at least one assay system capable of detecting HGF-dependent c-Met activation or signalling, including for example an assay of HGF-dependent c-Met phosphorylation, or an assay of HGF-induced tumour cell proliferation, cell survival assays, etc. A c-Met antibody provided herein may also be recognised as a potent antagonist of HGF-mediated activation of the c-Met receptor if the antagonist activity obtained is at least as potent as that obtained with reference antibody c224G11 (as described in WO 2009/007427), which reference antibody is a murine-human chimeric antibody of the IgG1 isotype comprising a heavy chain variable domain having the amino acid sequence shown as SEQ ID NO:43 and the light chain variable domain having the amino acid sequence shown as SEQ ID NO:44 and a human constant region which is not hinge-modified, i.e. which comprises the wild-type hinge region of human IgG1.

As used herein, the term "intrinsic agonist activity" of a c-Met antibody refers to the ability of the antibody to activate the c-Met receptor in the absence of the ligand HGF. Intrinsic agonist activity can be tested in a suitable assay system, for example an assay of c-Met phosphorylation in the presence and absence of HGF. In one embodiment, an antibody exhibits "significant intrinsic agonist activity" if the agonist effect produced in the absence of HGF is greater than 20%, or greater than 16% of the maximal HGF effect in the same assay system. Conversely, a c-Met antibody is considered not to exhibit significant intrinsic agonist activity if the agonist effect produced in the absence of HGF is less than 20%, or less than 16%, or less than 10%, or less than 5% of the maximal HGF effect in the same assay system. By way of example, the antagonist activity and intrinsic agonist activity of a c-Met antibody may be evaluated by performing a cell scatter assay, in the presence and absence of HGF. "Strict antagonist" antibodies, i.e. lacking significant intrinsic agonist activity, will typically produce no detectable scattering effect in the absence of HGF, but exhibit strong inhibition of HGF-induced scattering in the same assay system. Intrinsic agonist activity may also be evaluated using the phosphorylation assay described in Example 9 of the present application. The c-Met antibody preferably exhibits less than 20% of the maximal HGF effect in this assay system.

The c-Met antibodies provided herein are also considered not to exhibit significant intrinsic agonist activity if the agonist effect produced in the absence of HGF is equal to or lower than that obtained with reference antibody c224G11 (as described in WO 2009/007427), which reference antibody is a murine-human chimeric antibody of the IgG1 isotype comprising a heavy chain variable domain having the amino acid sequence shown as SEQ ID NO:43 and the light chain variable domain having the amino acid sequence shown as SEQ ID NO:44 and a human constant region which is not hinge-modified, i.e. which comprises the wild-type hinge region of human IgG1.

As summarised above, the invention relates to isolated antibodies (which may be monoclonal antibodies) having high human homology that specifically bind to a human c-Met receptor protein, wherein the antibodies are strict antagonists of HGF-mediated activation of the c-Met receptor. The properties and characteristics of the c-Met antibodies, and antibody fragments, according to the invention will now be described in further detail.

c-Met Binding and Affinity

Isolated antibodies having high human homology that specifically bind to a human c-Met receptor protein will typically exhibit a binding affinity ($K_D$) for human c-Met, and more particularly the extracellular domain of human c-Met, of about 10 nM or less, or 1 nM or less, or 0.1 nM or less, or 10 pM or less, and may exhibit a dissociation off-rate for human c-Met binding of $10^{-3}s^{-1}$ or less, or $10^{-4}s^{-1}$ or less. Binding affinity ($K_D$) and dissociation rate ($k_{off}$) can be measured using standard techniques well known to persons skilled in the art, such as for example surface plasmon resonance (BIAcore), as described in the accompanying examples.

The c-Met antibodies described herein exhibit immunological specificity for binding to human c-Met, and more specifically the extracellular domain of human c-Met, but cross-reactivity with non-human homologues of c-Met is not excluded. The binding affinity exhibited with non-human primate homologues of c-Met (e.g. rhesus macaque c-Met) is typically 1-10, e.g. 5-10, fold lower than the binding affinity for human c-Met.

Antagonist/Agonist Properties

As described elsewhere, the c-Met antibodies provided herein are "strict antagonists" of HGF-mediated activation of the human c-Met receptor, according to the definition given above. The antibodies exhibit potent antagonism of HGF-mediated c-Met activation with minimal agonist activity. This balance between high antagonist activity and minimal intrinsic agonist activity is critical for therapeutic utility of the c-Met antibodies, since it has been demonstrated previously (WO 2010/069765) that the loss of in vitro antagonist activity which accompanies the gain in agonist activity in the chimeric form of the murine monoclonal antibody 224G11 can result in significant loss of in vivo antagonist activity.

Many in vitro and in vivo assays suitable for testing antagonism of HGF-mediated c-Met activation and/or agonist activity of c-Met antibodies have been described in the art and would be readily available to persons of skill in the art (see for example WO 2010/059654, WO 2009/07427, WO 2010/069765, Pacchicina et al., JBC, manuscript M110.134031, September 2010, the technical teachings of which relating to such assays are to be incorporated herein by reference). Suitable assays include, for example, scatter assay, wound healing assay, proliferation assay, c-Met phosphorylation assay, branching morphogenesis assay and assays based on growth inhibition/apoptosis.

Inhibition of HGF-Independent c-Met Activation

The c-Met antibodies provided herein may have the capability to inhibit HGF-independent activation of the c-Met receptor. In vitro assays suitable for testing HGF-independent activation of the c-Met receptor are described in the accompanying example.

In particular embodiments, the c-Met antibodies may inhibit HGF-independent c-Met receptor activation, and more specifically may inhibit HGF-independent phosphorylation of c-Met, in the human gastric carcinoma cell line MKN-45. In particular embodiments, the c-Met antibody may exhibit at least 40%, or at least 50%, or at least 60%, or at least 70% or at least 80% inhibition of HGF-independent c-Met receptor activation. More specifically the c-Met antibody may exhibit at least 40%, or at least 50%, or at least 60%, or at least 70% or at least 80% inhibition of HGF-independent autophosphorylation c-Met, as measured by phosphorylation assay, e.g. the phosphorylation assay described herein performed in the human gastric cell line MKN-45.

The c-Met antibody should preferably exhibit at least the same potency as reference antibody c224G11 and should preferably exhibit more potent inhibition of HGF-independent activation (autophosphorylation) of c-Met than the reference antibody c224G11, particularly when measured by phosphorylation assay in MKN-45 cells. Certain of the c-Met antibodies provided herein, in particular those comprising the antigen-binding domains of 36C4, 48A2 and germlined variants thereof, are shown to be more potent inhibitors of HGF-independent autophosphorylation of c-Met than the reference antibody c224G11, whilst still exhibiting comparable (or better) antagonism of HGF-dependent c-Met activation than the reference antibody c224G11 and lower levels of intrinsic agonist activity than the reference antibody c224G11. As noted elsewhere herein, reference antibody c224G11 (as described in WO 2009/007427) is a murine-human chimeric antibody of the IgG1 isotype comprising a heavy chain variable domain having the amino acid sequence shown as SEQ ID NO:181 and the light chain variable domain having the amino acid sequence shown as SEQ ID NO:182 and a human constant region which is not hinge-modified, i.e. which comprises the wild-type hinge region of human IgG1.

The c-Met antibodies provided herein also exhibit substantially more potent inhibition of HGF-independent autophosphorylation of c-Met than the reference antibody 5D5, which does not display any inhibition in this assay system.

Inhibition of c-Met Dimerization

The c-Met antibodies provided herein preferably exhibit the capability to inhibit dimerization of c-Met receptors, and more particularly the ability to inhibit homodimerization and or heterodimerization of membrane-bound c-Met receptors present on the cell surface of tumor cells. The ability to inhibit c-Met dimerization is relevant to therapeutic utility of c-Met antibodies, since antibodies which inhibit c-Met dimerization may be useful in the treatment of HGF-independent c-Met-associated cancers, in addition to HGF-dependent activated c-Met cancers. Heterodimerization of c-Met is discussed in Trusolino et al., Nature Reviews, Molecular Cell Biology., 2010, 11: 834-848.

Assays suitable for testing the ability of c-Met antibodies to inhibit c-Met dimerization have been described in the art and would be readily available to persons of skill in the art (see for example WO 2009/07427 and WO 2010/069765, the technical teachings of which relating to such assays are to be incorporated herein by reference)

In particular embodiments, the c-Met antibodies may exhibit inhibition of c-Met dimerization in a "Met-addicted" cell line, such as for example EBC-1 cells. In particular, the c-Met antibodies may exhibit at least 20%, or at least 25%, or at least 30%, or at least 35%, or at least 40%, or at least 45%, or at least 50% inhibition of c-Met (homo)dimerization in a c-Met—addicted cell line, such as EBC-1 cells. The phenotype of "Met-addiction" occurs in cell lines which exhibit stable chromosomal amplification of the MET oncogene, as described in Smolen et al, PNAS, vol. 103, pp 2316-2321, 2006.

Down-Regulation of Cell-Surface c-Met Protein Expression

The c-Met antibodies provided herein preferably do not induce significant down-regulation of cell surface human c-Met protein. The ability of a given c-Met antibody to induce down-regulation of cell surface human c-Met protein may be assessed using flow cytometry in a c-Met expressing cell line, such as for example MKN-45. In one embodiment, the c-Met antibodies provided herein are considered not to induce significant down-regulation of cell surface human c-Met protein if they induce less than 20%, or less than 15%, or less than 10% or less than 5% down-regulation of c-Met protein in this assay system. The c-Met antibodies provided herein are also considered not to induce significant down-regulation of cell surface human c-Met protein if they induce equal to or lower down-regulation of c-Met protein than the reference antibody c224G11 described herein.

c-Met antibodies which do not induce significant down-regulation of cell surface c-Met protein may be particularly suitable for therapeutic applications which benefit from antibody effector function, i.e. ADCC, CDC, ADCP, and in particular enhanced effector function. The c-Met antibodies which do not induce significant down-regulation of cell surface c-Met protein are not internalised, and hence may remain bound to cell surface c-Met for significantly longer than c-Met antibodies which are internalised. A reduced rate of internalisation (or lack of significant internalisation) is a distinct advantage in c-Met antibodies which exhibit effector function via at least one of ADCC, CDC or ADCP. Hence, the c-Met antibodies described herein which exhibit effector function (or enhanced effector function) and which do not induce significant down-regulation of cell surface c-Met protein may be particularly advantageous for certain therapeutic applications, e.g. cancer treatments which benefit from antibody effector function.

c-Met Epitopes

The c-Met antibodies described herein bind to epitopes within the extracellular domain of human c-Met and block binding of HGF to the extracellular domain of c-Met, to varying degrees.

The ability of the c-Met antibodies provided herein to block binding of HGF to c-Met may be measured by means of a competition assay. Typically, c-Met antibodies block binding of HGF to c-Met with an $IC_{50}$ of 0.5 nM or less.

The term "epitope" refers to a specific arrangement of amino acids located on a peptide or protein to which an antibody or antibody fragment binds. Epitopes often consist of a chemically active surface grouping of molecules such as amino acids or sugar side chains, and have specific three dimensional structural characteristics as well as specific charge characteristics. Epitopes can be linear, i.e., involving binding to a single sequence of amino acids, or conformational, i.e., involving binding to two or more sequences of amino acids in various regions of the antigen that may not necessarily be contiguous.

The c-Met antibodies provided herein may bind to different (overlapping or non-overlapping) epitopes within the extracellular domain of the human c-Met protein.

Certain of the c-Met antibodies may bind to epitopes within the SEMA domain of human c-Met. The SEMA domain is contained within amino acid residues 1-491 of the mature human c-Met protein (lacking signal sequence, as shown in FIG. 25) and has been recognised in the art as containing a binding site for the c-Met ligand HGF.

In one particular embodiment, the c-Met antibody provided herein may bind to an epitope within the peptide 98-VDTYYDDQLISCGSVNRGTCQRHVFPHNHTA DIQSEVHCIFSPQIEEPSQCPDCVVSALGAKVLSS-VKDRFINFFVGNTINSSYFPDHP LHSISVRRLKETK-199 of human c-Met (SEQ ID NO: 181). In particular, the antibody denoted 36C4, and the germlined variants and affinity variants thereof, all bind to an epitope within this peptide region of the SEMA domain. This region of the SEMA domain is significant since it is known to contain a binding site for the c-Met ligand HGF. Particularly advantageous are c-Met antibodies, e.g. antibodies comprising the antigen-binding regions of 36C4 or one of the germlined or affinity variants thereof, which bind to this peptide epitope within the SEMA domain of human c-Met and which do not induce significant down-regulation of cell surface c-Met protein. Such antibodies may further exhibit one or more effector functions selected from ADCC, CDC and ADCP, or enhanced effector function(s).

Other c-Met antibodies provided herein may bind to epitopes within the IPT region of human c-Met. The IPT region is known to include amino acid residues 544-909 of the mature human c-Met protein lacking the signal peptide. The IPT region itself is sub-divided into IPT domains 1, 2, 3 and 4, as shown in FIG. 25. By means of epitope mapping, it has been determined that several of the c-Met antibodies described herein may bind to epitopes within IPT domains 1-2 of human c-Met (IPT-1 comprises amino acid residues 544-632 of mature human c-Met; IPT-2 comprises amino acid 633-717 of mature human c-Met), whereas others may bind to epitopes within IPT domains 2-3 of human c-Met (IPT-2 comprises amino acid residues 633-717 of mature human c-Met; IPT-3 comprises amino acid residues 718-814 of mature human c-Met), and others may bind to epitopes within IPT domains 3-4 of c-Met (IPT-3 comprises amino acid residues 718-814 of mature human c-Met; IPT-4 comprises amino acid residues 815-909 of mature human c-Met).

IPT domains 3-4 have been identified as containing a high affinity binding site for the ligand HGF (see for example EP 2119448 incorporated herein by reference) but to date no antibodies capable of binding to IPT domains 3-4 and antagonising HGF-mediated activation of c-Met have been described. Potent, strictly antagonistic c-Met antibodies binding to the IPT domains, and particularly IPT domains 1-2, 2-3 and 3-4, or to the PSI-IPT region of human c-Met are now provided herein. Crucially, these antibodies can exhibit high human homology, as defined herein, and can be provided in recombinant form containing a fully human hinge region and Fc domain, particularly of the human IgG1 isotype, without significant loss of antagonist activity or gain of agonist activity. Yet other c-Met antibodies provided herein may bind to conformational epitopes with part or all of the recognition site within the IPT region of human c-Met.

A specific therapeutic utility may be achieved by targeting c-Met antibodies to the IPT domains, as defined above, or to junctions between IPT domains or to conformational epitopes with all or part of the recognition site within the IPT region of human c-Met.

Other c-Met antibodies provided herein may bind to an epitope within the region of human c-Met spanning the junction between the PSI domain and IPT domain 1 (PSI-IPT1). The PSI domain of human c-Met spans amino acid residues 492-543 of the mature human c-Met protein (lacking the signal peptide), whereas IPT domain 1 spans residues 544-632 of mature human c-Met. In one particular embodiment, the c-Met antibody may bind to an epitope within the amino acid sequence 523-EECLSGTWTQQICLPAIYKVF-PNSAPLEGGTRLTICGWDFGFRRNNKFDLKKTRVLL GNESCILTLSESTMNTLKCTVGPAMNKHFNMSIIIS-NGHGTTQYSTFSYVDP-633 (SEQ ID NO: 136) in the PSI-IPT1 region of the human c-Met protein. In particular, the c-Met antibody denoted herein 48A2, and the germlined variants and affinity variants of 48A2 described herein, have been demonstrated to bind a conformational epitope within this PSI-IPT1 peptide of human c-Met. Binding of a c-Met antibody to an epitope within the PSI-IPT1 region, and more specifically binding to the epitope bound by antibody 48A2 and its variants, may produce an effect both by blocking binding of the c-Met ligand HGF to a binding site within the IPT region and by preventing the conformational change which normally accompanies binding of HGF to c-Met.

Camelid-Derived c-Met Antibodies

The antibodies of the invention may comprise at least one hypervariable loop or complementarity determining region obtained from a VH domain or a VL domain of a species in the family Camelidae, such as VH and/or VL domains, or CDRs thereof, obtained by active immunisation of outbred camelids, e.g. llamas, with a human c-Met antigen.

By "hypervariable loop or complementarity determining region obtained from a VH domain or a VL domain of a species in the family Camelidae" is meant that that hypervariable loop (HV) or CDR has an amino acid sequence which is identical, or substantially identical, to the amino acid sequence of a hypervariable loop or CDR which is encoded by a Camelidae immunoglobulin gene. In this context "immunoglobulin gene" includes germline genes, immunoglobulin genes which have undergone rearrangement, and also somatically mutated genes. Thus, the amino acid sequence of the HV or CDR obtained from a VH or VL domain of a Camelidae species may be identical to the amino acid sequence of a HV or CDR present in a mature Camelidae conventional antibody. The term "obtained from" in this context implies a structural relationship, in the sense that the HVs or CDRs of the c-Met antibody embody an amino acid sequence (or minor variants thereof) which was originally encoded by a Camelidae immunoglobulin gene. However, this does not necessarily imply a particular relationship in terms of the production process used to prepare the c-Met antibody.

Camelid-derived c-Met antibodies may be derived from any camelid species, including inter alia, llama, dromedary, alpaca, vicuna, guanaco or camel.

c-Met antibodies comprising camelid-derived VH and VL domains, or CDRs thereof, are typically recombinantly expressed polypeptides, and may be chimeric polypeptides. The term "chimeric polypeptide" refers to an artificial (non-naturally occurring) polypeptide which is created by juxtaposition of two or more peptide fragments which do not otherwise occur contiguously. Included within this definition are "species" chimeric polypeptides created by juxtaposition of peptide fragments encoded by two or more species, e.g. camelid and human.

Camelid-derived CDRs may comprise one of the CDR sequences shown as SEQ ID NOs: 1-21, 71-73 or 83-85 (heavy chain CDRs) or one of the CDR sequences shown as SEQ ID NOs: 22-42, 74-76, 86, 87 or 137-148 (light chain CDRs).

In one embodiment the entire VH domain and/or the entire VL domain may be obtained from a species in the family Camelidae. In specific embodiments, the camelid-derived VH domain may comprise the amino acid sequence shown as SEQ ID NO: 45, 46, 47, 48, 49, 50, 51, 77 or 88 whereas the camelid-derived VL domain may comprise the amino acid sequence show as SEQ ID NO: 52, 53, 54, 55, 56, 57, 58, 78, 89 or 149-164. The camelid-derived VH domain and/or the camelid-derived VL domain may then be subject to protein engineering, in which one or more amino acid substitutions, insertions or deletions are introduced into the camelid amino acid sequence. These engineered changes preferably include amino acid substitutions relative to the camelid sequence. Such changes include "humanisation" or "germlining" wherein one or more amino acid residues in a camelid-encoded VH or VL domain are replaced with equivalent residues from a homologous human-encoded VH or VL domain.

Isolated camelid VH and VL domains obtained by active immunisation of a camelid (e.g. llama) with a human c-Met antigen can be used as a basis for engineering antigen binding polypeptides according to the invention. Starting from intact camelid VH and VL domains, it is possible to engineer one or more amino acid substitutions, insertions or deletions which depart from the starting camelid sequence. In certain embodiments, such substitutions, insertions or deletions may be present in the framework regions of the VH domain and/or the VL domain. The purpose of such changes in primary amino acid sequence may be to reduce presumably unfavourable properties (e.g. immunogenicity in a human host (so-called humanization), sites of potential product heterogeneity and or instability (glycosylation, deamidation, isomerisation, etc.) or to enhance some other favourable property of the molecule (e.g. solubility, stability, bioavailability, etc.). In other embodiments, changes in primary amino acid sequence can be engineered in one or more of the hypervariable loops (or CDRs) of a Camelidae VH and/or VL domain obtained by active immunisation. Such changes may be introduced in order to enhance antigen binding affinity and/or specificity, or to reduce presumably unfavourable properties, e.g. immunogenicity in a human host (so-called humanization), sites of potential product heterogeneity and or instability, glycosylation, deamidation, isomerisation, etc., or to enhance some other favourable property of the molecule, e.g. solubility, stability, bioavailability, etc.

Thus, in one embodiment, the invention provides a variant c-Met antibody which contains at least one amino acid substitution in at least one framework or CDR region of either the VH domain or the VL domain in comparison to a camelid-derived VH or VL domain, examples of which include but are not limited to the camelid VH domains comprising the amino acid sequences shown as SEQ ID NO: 45, 46, 47, 48, 49, 50, 51, 77 or 88, and the camelid VL domains comprising the amino acid sequences show as SEQ ID NO: 52, 53, 54, 55, 56, 57, 58, 78, 89 or 149-164.

In other embodiments, there are provided "chimeric" antibody molecules comprising camelid-derived VH and VL domains (or engineered variants thereof) and one or more constant domains from a non-camelid antibody, for example human-encoded constant domains (or engineered variants thereof). In such embodiments it is preferred that both the VH domain and the VL domain are obtained from the same species of camelid, for example both VH and VL may be from *Lama glama* or both VH and VL may be from *Lama pacos* (prior to introduction of engineered amino acid sequence variation). In such embodiments both the VH and the VL domain may be derived from a single animal, particularly a single animal which has been actively immunised with a human c-Met antigen.

As an alternative to engineering changes in the primary amino acid sequence of Camelidae VH and/or VL domains, individual camelid-derived hypervariable loops or CDRs, or combinations thereof, can be isolated from camelid VH/VL domains and transferred to an alternative (i.e. non-Camelidae) framework, e.g. a human VH/VL framework, by CDR grafting. In particular, non-limiting, embodiments the camelid-derived CDRs may be selected from CDRs having the amino acid sequences shown as SEQ ID NOs: 1-21, 71-73 or 83-85 (heavy chain CDRs) or CDRs having the amino acid sequences shown as SEQ ID NOs: 22-42, 74-76, 86, 87 or 137-148 (light chain CDRs).

c-Met antibodies comprising camelid-derived VH and VL domains, or CDRs thereof, can take various different embodiments in which both a VH domain and a VL domain are present. The term "antibody" herein is used in the broadest sense and encompasses, but is not limited to, monoclonal antibodies (including full length monoclonal antibodies), polyclonal antibodies, multispecific antibodies (e.g., bispecific antibodies), so long as they exhibit the appropriate immunological specificity for a human c-Met protein. The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes) on the antigen, each monoclonal antibody is directed against a single determinant or epitope on the antigen.

"Antibody fragments" comprise a portion of a full length antibody, generally the antigen binding or variable domain thereof. Examples of antibody fragments include Fab, Fab', F(ab')2, bi-specific Fab' s, and Fv fragments, diabodies, linear antibodies, single-chain antibody molecules, a single chain variable fragment (scFv), domain antibodies and multispecific antibodies formed from antibody fragments (see Holliger and Hudson, Nature Biotechnol. 23:1126-36 (2005), the contents of which are incorporated herein by reference).

In non-limiting embodiments, c-Met antibodies comprising camelid-derived VH and VL domains, or CDRs thereof, may comprise CH1 domains and/or CL domains, the amino acid sequence of which is fully or substantially human. Where the antigen binding polypeptide of the invention is an antibody intended for human therapeutic use, it is typical for the entire constant region of the antibody, or at least a part thereof, to have fully or substantially human amino acid sequence. Therefore, one or more or any combination of the CH1 domain, hinge region, CH2 domain, CH3 domain and CL domain (and CH4 domain if present) may be fully or substantially human with respect to it's amino acid sequence.

Advantageously, the CH1 domain, hinge region, CH2 domain, CH3 domain and CL domain (and CH4 domain if present) may all have fully or substantially human amino acid sequence. In the context of the constant region of a humanised or chimeric antibody, or an antibody fragment, the term "substantially human" refers to an amino acid sequence identity of at least 90%, or at least 95%, or at least 97%, or at least 99% with a human constant region. The term "human amino acid sequence" in this context refers to an amino acid sequence which is encoded by a human immunoglobulin gene, which includes germline, rearranged and somatically mutated genes. The invention also contemplates polypeptides comprising constant domains of "human" sequence which have been altered, by one or more amino acid additions, deletions or substitutions with respect to the human sequence, excepting those embodiments where the presence of a "fully human" hinge region is expressly required.

The presence of a "fully human" hinge region in the c-Met antibodies of the invention may be beneficial both to minimise immunogenicity and to optimise stability of the antibody.

As discussed elsewhere herein, it is contemplated that one or more amino acid substitutions, insertions or deletions may be made within the constant region of the heavy and/or the light chain, particularly within the Fc region Amino acid substitutions may result in replacement of the substituted amino acid with a different naturally occurring amino acid, or with a non-natural or modified amino acid. Other structural modifications are also permitted, such as for example changes in glycosylation pattern (e.g. by addition or deletion of N- or O-linked glycosylation sites). Depending on the intended use of the antibody, it may be desirable to modify the antibody of the invention with respect to its binding properties to Fc receptors, for example to modulate effector function. For example cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., J. Exp. Med. 176:1191-1195 (1992) and Shopes, B. J. Immunol. 148:2918-2922 (1992). Alternatively, a c-Met antibody can be engineered which has dual Fc regions and may thereby have enhanced complement lysis and ADCC capabilities. See Stevenson et al., Anti-Cancer Drug Design 3:219-230 (1989). The invention also contemplates immunoconjugates comprising an antibody as described herein conjugated to a cytotoxic agent such as a chemotherapeutic agent, toxin (e.g., an enzymatically active toxin of bacterial, fungal, plant or animal origin, or fragments thereof), or a radioactive isotope (i.e., a radioconjugate). Fc regions may also be engineered for half-life extension, as described by Chan and Carter, Nature Reviews: Immunology, Vol. 10, pp 301-316, 2010, incorporated herein by reference.

Variant c-Met antibodies in which the Fc region is modified by protein engineering, as described herein, may also exhibit an improvement in efficacy (e.g. in cancer treatment), as compared to an equivalent antibody (i.e. equivalent antigen-binding properties) without the Fc modification.

In yet another embodiment, the Fc region is modified to increase the ability of the antibody to mediate antibody dependent cellular cytotoxicity (ADCC) and/or to increase the affinity of the antibody for an Fcγ receptor by modifying one or more amino acids.

In still another embodiment, the glycosylation of an antibody is modified. For example, an aglycoslated antibody can be made (i.e., the antibody lacks glycosylation). Glycosylation can be altered to, for example, increase the affinity of the antibody for the c-Met target antigen. Such carbohydrate modifications can be accomplished by; for example, altering one or more sites of glycosylation within the antibody sequence. For example, one or more amino acid substitutions can be made that result in elimination of one or more variable region framework glycosylation sites to thereby eliminate glycosylation at that site. Such aglycosylation may increase the affinity of the antibody for antigen.

Also envisaged are variant c-Met antibodies having an altered type of glycosylation, such as a hypofucosylated antibody having reduced amounts of fucosyl residues or a non-fucosylated antibody (as described by Natsume et al., Drug Design Development and Therapy, Vol. 3, pp 7-16, 2009) or an antibody having increased bisecting GlcNac structures. Such altered glycosylation patterns have been demonstrated to increase the ADCC activity of antibodies, producing typically 10-fold enhancement of ADCC relative to an equivalent antibody comprising a "native" human Fc domain. Such carbohydrate modifications can be accomplished by, for example, expressing the antibody in a host cell with altered glycosylation enzymatic machinery (as described by Yamane-Ohnuki and Satoh, mAbs 1:3, 230-236, 2009).

Still further embodiments of the c-Met antibodies may be lacking effector function, either because the Fc portion of the antibody is of an isotype which naturally lacks effector function, or which exhibits significantly less potent effector function than human IgG1, for example human IgG2 or human IgG4, or because the Fc portion of the antibody has been engineered to reduce or substantially eliminate effector function, as described in Armour, K. L., et al., Eur. J. Immunol., 1999, 29: 2613-2624.

In still further embodiments the Fc portion of the c-Met antibody may be engineered to facilitate the preferential formation of bispecific antibodies, in which two antibody heavy chains comprising different variable domains pair to form the Fc portion of the bispecific antibody. Examples of such modifications include the "knobs-into-hole" modifications described by Ridgway J B, Presta L G, Carter P., 'Knobs-into-holes' engineering of antibody CH3 domains for heavy chain heterodimerization. Protein Eng. 1996 July; 9(7):617-21 and Merchant A M, Zhu Z, Yuan J Q, Goddard A, Adams C W, Presta L G, Carter P. An efficient route to human bispecific IgG. Nat. Biotechnol. 1998 July; 16(7): 677-81.

The invention can, in certain embodiments, encompass chimeric Camelidae/human antibodies, and in particular chimeric antibodies in which the VH and VL domains are of fully camelid sequence (e.g. Llama or alpaca) and the remainder of the antibody is of fully human sequence. C-Met antibodies can include antibodies comprising "humanised" or "germlined" variants of camelid-derived VH and VL domains, or CDRs thereof, and camelid/human chimeric antibodies, in which the VH and VL domains contain one or more amino acid substitutions in the framework regions in comparison to camelid VH and VL domains obtained by active immunisation of a camelid with a human c-Met antigen. Such "humanisation" increases the % sequence identity with human germline VH or VL domains by replacing mis-matched amino acid residues in a starting Camelidae VH or VL domain with the equivalent residue found in a human germline-encoded VH or VL domain.

c-Met antibodies may also be CDR-grafted antibodies in which CDRs (or hypervariable loops) derived from a camelid antibody, for example an camelid c-Met antibody raised by active immunisation with human c-Met protein, or otherwise encoded by a camelid gene, are grafted onto a human VH and VL framework, with the remainder of the antibody also being of fully human origin. Such CDR-grafted c-Met antibodies may contain CDRs having the amino acid sequences shown as SEQ ID NOs: 1-21, 71-73 or 83-85 (heavy chain CDRs) or CDRs having the amino acid sequences shown as SEQ ID NOs: 22-42, 74-76, 86, 87 or 137-148 (light chain CDRs).

Humanised, chimeric and CDR-grafted c-Met antibodies as described above, particularly antibodies comprising hypervariable loops or CDRs derived from active immunisation of camelids with a human c-Met antigen, can be readily produced using conventional recombinant DNA manipulation and expression techniques, making use of prokaryotic and eukaryotic host cells engineered to produce the polypeptide of interest and including but not limited to bacterial cells, yeast cells, mammalian cells, insect cells, plant cells, some of them as described herein and illustrated in the accompanying examples.

Camelid-derived c-Met antibodies include variants wherein the hypervariable loop(s) or CDR(s) of the VH domain and/or the VL domain are obtained from a conventional camelid antibody raised against human c-Met, but wherein at least one of said (camelid-derived) hypervariable loops or CDRs has been engineered to include one or more amino acid substitutions, additions or deletions relative to the camelid-encoded sequence. Such changes include "humanisation" of the hypervariable loops/CDRs. Camelid-derived HVs/CDRs which have been engineered in this manner may still exhibit an amino acid sequence which is "substantially identical" to the amino acid sequence of a camelid-encoded HV/CDR. In this context, "substantial identity" may permit no more than one, or no more than two amino acid sequence mis-matches with the camelid-encoded HV/CDR. Particular embodiments of the c-Met antibody may contain humanised variants of the CDR sequences shown as SEQ ID NOs: 1-21, 71-73 or 83-85 (heavy chain CDRs) and/or humanised variants of the CDR sequences shown as SEQ ID NOs: 22-42, 74-76, 86, 87 or 137-148 (light chain CDRs).

The camelid-derived c-Met antibodies provided herein may be of any isotype. Antibodies intended for human therapeutic use will typically be of the IgA, IgD, IgE IgG, IgM type, often of the IgG type, in which case they can belong to any of the four sub-classes IgG1, IgG2a and b, IgG3 or IgG4. Within each of these sub-classes it is permitted to make one or more amino acid substitutions, insertions or deletions within the Fc portion, or to make other structural modifications, for example to enhance or reduce Fc-dependent functionalities.

Humanisation (Germlining) of Camelid-Derived V11 and VL Domains

Camelid conventional antibodies provide an advantageous starting point for the preparation of antibodies with utility as human therapeutic agents due to the following factors, discussed in U.S. Ser. No. 12/497,239 which is incorporated herein by reference:
1) High % sequence homology between camelid VH and VL domains and their human counterparts;
2) High degree of structural homology between CDRs of camelid VH and VL domains and their human counterparts (i.e. human-like canonical fold structures and human-like combinations of canonical folds).

The camelid (e.g. llama) platform also provides a significant advantage in terms of the functional diversity of the c-Met antibodies which can be obtained.

The utility of c-Met antibodies comprising camelid VH and/or camelid VL domains for human therapy can be improved still further by "humanisation" or "germlining" of natural camelid VH and VL domains, for example to render them less immunogenic in a human host. The overall aim of humanisation is to produce a molecule in which the VH and VL domains exhibit minimal immunogenicity when introduced into a human subject, whilst retaining the specificity and affinity of the antigen binding site formed by the parental VH and VL domains.

One approach to humanisation, so-called "germlining", involves engineering changes in the amino acid sequence of a camelid VH or VL domain to bring it closer to the sequence of a human VH or VL domain.

Determination of homology between a camelid VH (or VL) domain and human VH (or VL) domains is a critical step in the humanisation process, both for selection of camelid amino acid residues to be changed (in a given VH or VL domain) and for selecting the appropriate replacement amino acid residue(s).

An approach to humanisation of camelid conventional antibodies has been developed based on alignment of a large number of novel camelid VH (and VL) domain sequences, typically somatically mutated VH (or VL) domains which are known to bind a target antigen, with human germline VH (or VL) sequences, human VH (and VL) consensus sequences, as well as germline sequence information available for llama pacos.

The following passages outline the principles which can be applied to (i) select "camelid" amino acid residues for replacement in a camelid-derived VH or VL domain or a CDR thereof, and (ii) select replacement "human" amino acid residues to substitute in, when humanising any given camelid VH (or VL) domain. This approach can be used to prepare humanised variants of camelid-derived CDRs having the amino acid sequences shown as SEQ ID NOs: 1-21, 71-73 or 83-85 (heavy chain CDRs) or having the amino acid sequences shown as SEQ ID NOs: 22-42, 74-76, 86, 87 or 137-148 (light chain CDRs), and also for humanisation of camelid-derived VH domains having the sequences shown as SEQ ID NOs: 45-51, 77 or 88 and of camelid-derived VL domains having the sequences shown as SEQ ID NOs: 52-58, 78, 89 or 149-164.

Step 1. Select human (germline) family and member of this family that shows highest homology/identity to the mature camelid sequence to be humanised. A general procedure for identifying the closest matching human germline for any given camelid VH (or VL) domain is outlined below.

Step 2. Select specific human germline family member used to germline against. Preferably this is the germline with the highest homology or another germline family member from the same family.

Step 3. Identify the preferred positions considered for germlining on the basis of the table of amino acid utilisation for the camelid germline that is closest to the selected human germline.

Step 4. Try to change amino acids in the camelid germline that deviate from the closest human germline; germlining of FR residues is preferred over CDR residues.
a. Preferred are positions that are deviating from the selected human germline used to germline against, for which the amino acid found in the camelid sequence does not match with the selected germline and is not found in other germlines of the same subclass (both for V as well as for J encoded FR amino acids).
b. Positions that are deviating from the selected human germline family member but which are used in other germlines of the same family may also be addressed in the germlining process.
c. Additional mismatches (e.g. due to additional somatic mutations) towards the selected human germline may also be addressed.

The following approach may be used to determine the closest matching human germline for a given camelid VH (or VL) domain:

Before analyzing the percentage sequence identity between Camelidae and human germline VH and VL, the canonical folds may first be determined, which allows the identification of the family of human germline segments with the identical combination of canonical folds for H1 and H2 or L1 and L2 (and L3). Subsequently the human germline family member that has the highest degree of sequence homology with the Camelidae variable region of interest may be chosen for scoring sequence homology. The determination of Chothia canonical classes of hypervariable loops L1, L2, L3, H1 and H2 can be performed with the bioinformatics tools publicly available on webpage www.bioinf.org.uk/abs/chothia.html.page. The output of the program shows the key residue requirements in a datafile. In these datafiles, the key residue positions are shown with the allowed amino acids at each position. The sequence of the variable region of the antibody is given as input and is first aligned with a consensus antibody sequence to assign the Kabat numbering scheme. The analysis of the canonical folds uses a set of key residue templates derived by an automated method developed by Martin and Thornton (Martin et al., J. Mol. Biol. 263:800-815 (1996)). The boundaries of the individual framework regions may be assigned using the IMGT numbering scheme, which is an adaptation of the numbering scheme of Chothia (Lefranc et al., NAR 27: 209-212 (1999); http://imgt.cines.fr).

With the particular human germline V segment known, which uses the same combination of canonical folds for H1 and H2 or L1 and L2 (and L3), the best matching family member in terms of sequence homology can be determined. The percentage sequence identity between Camelidae VH and VL domain framework amino acid sequences and corresponding sequences encoded by the human germline can be determined using bioinformatic tools, but manual alignment of the sequences could also be used. Human immunoglobulin sequences can be identified from several protein data bases, such as VBase (http://vbase.mrc-cpe.cam.ac.uk/) or the Pluckthun/Honegger database (http://www.bioc.unizh.ch/antibody/Sequences/Germlines. To compare the human sequences to the V regions of Camelidae VH or VL domains a sequence alignment algorithm such as available via websites like www.expasy.ch/tools/#align can be used, but also manual alignment can also be performed with a limited set of sequences. Human germline light and heavy chain sequences of the families with the same combinations of canonical folds and with the highest degree of homology with the framework regions 1, 2, and 3 of each chain may be selected and compared with the Camelidae variable region of interest; also the FR4 is checked against the human germline JH and JK or JL regions.

Note that in the calculation of overall percent sequence homology the residues of FR1, FR2 and FR3 are evaluated using the closest match sequence from the human germline family with the identical combination of canonical folds. Only residues different from the closest match or other members of the same family with the same combination of canonical folds are scored (NB—excluding any primer-encoded differences). However, for the purposes of humanization, residues in framework regions identical to members of other human germline families, which do not have the same combination of canonical folds, can be considered for humanization, despite the fact that these are scored "negative" according to the stringent conditions described above. This assumption is based on the "mix and match" approach for humanization, in which each of FR1, FR2, FR3 and FR4 is separately compared to its closest matching human germline sequence and the humanized molecule therefore contains a combination of different FRs as was done by Qu and colleagues (Qu et al., Clin. Cancer Res. 5:3095-3100 (1999)) and Ono and colleagues (Ono et al., Mol. Immunol. 36:387-395 (1999)).

By way of example only, it is contemplated that humanised variants of VH domains having the amino acid sequences shown as SEQ ID Nos: 45-51, 77 or 88 may include variants in which the amino acid residue(s) occurring at one or more of the positions listed in the following table is/are replaced with an amino acid residue which occurs at the equivalent position in a human VH domain, e.g. a human germline-encoded VH domain. Appropriate amino acid substitutions can be derived by following the general protocol for humanisation described above.

TABLE 3

List of amino acid residue positions which may be substituted during germlining (humanisation) of the listed VH domains. For each named VH domain, the listed amino acid residues are numbered according to the Kabat numbering system.

| VH | FR1 | CDR1 | FR2 | CDR2 | FR3 | CDR3 | FR4 |
|---|---|---|---|---|---|---|---|
| 38H10 SEQ ID 49 | 1, 7, 9, 11, 12, 13, 28 | | | 54*, 55* | 69, 71, 78, 80, 82a, 85 | | 108 |
| 40B8 SEQ ID 50 | 11, 12, 13 | | | | 69, 71, 78, 80, 82b | | 108 |
| 20A11 SEQ ID 47 | 30 | | | | 74, 83, 84 | | 108 |
| 12G4 SEQ ID 45 | 11, 12, 19, 30 | | 48 | | 74, 83, 84 | | 108 |
| 13E6 SEQ ID 46 | 10, 30 | | 48 | | 74, 82a, 83, 84, 85, 93 | | 108 |
| 34H7 SEQ ID 77 | 10, 23, 24, 29 | | | | 74, 83, 84, 94 | | 108 |
| 36C4 SEQ ID 51 | 2, 5, 23, 30 | | 40, 48 | 54*, 55* | 67, 68, 71, 81, 84, 85 | | 108 |
| 20F1 SEQ ID 48 | 29, 30 | | 48 | | 67, 68, 71, 81, 83, 84, 85 | | 108 |

*note substitution of residues 54 and 55 is for the purpose of removing a deamidation site, not for human germlining as such.

By way of example only, it is contemplated that humanised variants of VL domains having the amino acid sequences shown as SEQ ID Nos: 52-58, 78, 89 or 137-148 may include variants in which the amino acid residue(s) occurring at one or more of the positions listed in the following table is/are replaced with an amino acid residue which occurs at the equivalent position in a human VL domain, e.g. a human germline-encoded VL domain. Appropriate amino acid substitutions can be derived by following the general protocol for humanisation described above.

TABLE 4

List of amino acid residue positions which may be substituted during germlining (humanisation) of the listed VL domains. For each named VL domain, the listed amino acid residues are numbered according to the Kabat numbering system.

| VL | FR1 | CDR1 | FR2 | CDR2 | FR3 | CDR3 | FR4 |
|---|---|---|---|---|---|---|---|
| 38H10 SEQ ID 52 | 9, 11, 12, 13, 15, 18, 19 | | 39, 40, 43, 45, 49 | | 78, 80, 83 | | 100 |
| 40B8 SEQ ID 53 | 9, 11, 12, 13, 15, 18, 19 | | 39, 40, 43, 45 | | 78, 80, 83 | | 106 |
| 20A11 SEQ ID 58 | 14, 15, 17, 18, 19 | | | | 69, 70, 74, 76, 80 | | 100 |
| 12G4 SEQ ID 56 | 14, 15, 17, 18 | | | | 69, 70, 74, 76, 80 | | |
| 13E6 SEQ ID 57 | 14, 15, 17, 18 | | | | 69, 70, 74, 76, 80 | | |
| 34H7 SEQ ID 78 | 11, 14, 18, 22 | | 38 | | 66, 69, 74 | | 103 |
| 36C4 SEQ ID 55 | 3, 8, 17, 18 | | 39, 47, 49 | | 58, 72, 75, 80 | | 103 |
| 20F1 SEQ ID 54 | 17, 18 | | 39, 42, 47 | | 58, 80, 84, 87 | | 103, 105 |
| 48A2 SEQ ID 89 | 7, 9, 11, 12, 13, 15, 17, 18, 19 | | 39, 40, 43, 45 | | 68, 77, 78, 80, 83 | | 100, 107 |

Cross-Competing Antibodies

Monoclonal antibodies or antigen-binding fragments thereof that "cross-compete" with the molecules disclosed herein are those that bind human c-Met at site(s) that are identical to, or overlapping with, the site(s) at which the present c-Met antibodies bind. Competing monoclonal antibodies or antigen-binding fragments thereof can be identified, for example, via an antibody competition assay. For example, a sample of purified or partially purified human c-Met can be bound to a solid support. Then, an antibody compound or antigen binding fragment thereof of the present invention and a monoclonal antibody or antigen-binding fragment thereof suspected of being able to compete with such invention antibody compound are added. One of the two molecules is labelled. If the labelled compound and the unlabeled compound bind to separate and discrete sites on c-Met, the labelled compound will bind to the same level whether or not the suspected competing compound is present. However, if the sites of interaction are identical or overlapping, the unlabeled compound will compete, and the amount of labelled compound bound to the antigen will be lowered. If the unlabeled compound is present in excess, very little, if any, labelled compound will bind. For purposes of the present invention, competing monoclonal antibodies or antigen-binding fragments thereof are those that decrease the binding of the present antibody compounds to c-Met by about 50%, about 60%, about 70%, about 80%, about 85%, about 90%, about 95%, or about 99%. Details of procedures for carrying out such competition assays are well known in the art and can be found, for example, in Harlow and Lane (1988) Antibodies, A Laboratory Manual, Cold Spring Harbor Laboratory Press, Cold Spring Harbor, N.Y., pages 567-569, ISBN 0-87969-314-2. Such assays can be made quantitative by using purified antibodies. A standard curve is established by titrating one antibody against itself, i.e., the same antibody is used for both the label and the competitor. The capacity of an unlabeled competing monoclonal antibody or antigen-binding fragment thereof to inhibit the binding of the labeled molecule to the plate is titrated. The results are plotted, and the concentrations necessary to achieve the desired degree of binding inhibition are compared.

Polynucleotides Encoding c-Met Antibodies

The invention also provides a polynucleotide molecules encoding the c-Met antibodies of the invention, also expression vectors containing a nucleotide sequences which encode the c-Met antibodies of the invention operably linked to regulatory sequences which permit expression of the antigen binding polypeptide in a host cell or cell-free expression system, and a host cell or cell-free expression system containing this expression vector.

In particular embodiments, the polynucleotide encoding the c-Met antibody of the invention thereof may comprise one or more of the polynucleotide sequences shown as SEQ ID NOs: 59-70, 79-82, 90, 91, 122-135 or 165-180, which sequences encode VH or VL domains of c-Met antibodies, or a variant sequence which encodes a functional VH or VL domain of a c-Met antibody, wherein said variant sequence exhibits at least 80%, 85%, 90%, 95%, 97% or 99% sequence identity when optimally aligned to one of SEQ ID NOs: 59-70, 79-82, 90, 91, 122-135 or 165-180. In this context, % sequence identity between two polynucleotide sequences may be determined by comparing these two sequences aligned in an optimum manner and in which the polynucleotide sequence to be compared can comprise additions or deletions with respect to the reference sequence for an optimum alignment between these two sequences. The percentage of identity is calculated by determining the number of identical positions for which the nucleotide residue is identical between the two sequences, by dividing this number of identical positions by the total number of positions in the comparison window and by multiplying the result obtained by 100 in order to obtain the percentage of identity between these two sequences. For example, it is possible to use the BLAST program, "BLAST 2 sequences" (Tatusova et al, "Blast 2 sequences—a new tool for comparing protein and nucleotide sequences", FEMS Microbiol Lett. 174:247-250) available on the site http://www.ncbi.nlm.nih.gov/gorf/b12.html, the parameters used being those given by default (in particular for the parameters "open gap penalty": 5, and "extension gap penalty": 2; the matrix chosen being, for example, the matrix "BLOSUM 62" proposed by the program), the percentage of identity between the two sequences to be compared being calculated directly by the program.

Polynucleotide molecules encoding the c-Met antibodies of the invention include, for example, recombinant DNA molecules. The terms "nucleic acid", "polynucleotide" or a "polynucleotide molecule" as used herein interchangeably and refer to any DNA or RNA molecule, either single- or double-stranded and, if single-stranded, the molecule of its complementary sequence. In discussing nucleic acid molecules, a sequence or structure of a particular nucleic acid molecule may be described herein according to the normal convention of providing the sequence in the 5' to 3' direction. In some embodiments of the invention, nucleic acids or polynucleotides are "isolated." This term, when applied to a nucleic acid molecule, refers to a nucleic acid molecule that is separated from sequences with which it is immediately contiguous in the naturally occurring genome of the organism in which it originated. For example, an "isolated nucleic acid" may comprise a DNA molecule inserted into a vector, such as a plasmid or virus vector, or integrated into the genomic DNA of a prokaryotic or eukaryotic cell or non-human host organism. When applied to RNA, the term "isolated polynucleotide" refers primarily to an RNA molecule encoded by an isolated DNA molecule as defined above. Alternatively, the term may refer to an RNA molecule that has been purified/separated from other nucleic acids with which it would be associated in its natural state (i.e., in cells or tissues). An isolated polynucleotide (either DNA or RNA) may further represent a molecule produced directly by biological or synthetic means and separated from other components present during its production.

For recombinant production of a c-Met antibody according to the invention, a recombinant polynucleotide encoding it may be prepared (using standard molecular biology techniques) and inserted into a replicable vector for expression in a chosen host cell, or a cell-free expression system. Suitable host cells may be prokaryote, yeast, or higher eukaryote cells, specifically mammalian cells. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen. Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); mouse myeloma cells SP2/0-AG14 (ATCC CRL 1581; ATCC CRL 8287) or NS0 (HPA culture collections no. 85110503); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TR1 cells (Mather et al., Annals N.Y. Acad. Sci. 383:44-68 (1982)); MRC 5 cells; FS4 cells; and a human hepatoma line (Hep G2), as well as DSM's PERC-6 cell line. Expression vectors suitable for use in each of these host cells are also generally known in the art.

It should be noted that the term "host cell" generally refers to a cultured cell line. Whole human beings into which an expression vector encoding an antigen binding polypeptide according to the invention has been introduced are explicitly excluded from the definition of a "host cell".

Antibody Production

In an important aspect, the invention also provides a method of producing a c-Met antibody of the invention which comprises culturing a host cell (or cell free expression system) containing polynucleotide (e.g. an expression vector) encoding the c-Met antibody under conditions which permit expression of the c-Met antibody, and recovering the expressed c-Met antibody. This recombinant expression process can be used for large scale production of c-Met antibodies according to the invention, including monoclonal antibodies intended for human therapeutic use. Suitable vectors, cell lines and production processes for large scale manufacture of recombinant antibodies suitable for in vivo therapeutic use are generally available in the art and will be well known to the skilled person.

Therapeutic Utility of c-Met Antibodies

The c-Met antibodies provided herein can be used in the treatment of both HGF-dependent and HGF-independent cancers.

Inappropriate activation of c-Met can be induced by specific genetic lesions, transcriptional upregulation or ligand-dependent autocrine or paracrine mechanisms (Comoglio et al, Nature Reviews Drug Discovery, 7:504-516, 2008). HGF-dependent and HGF independent cancers that can be treated with the c-Met antibodies include, but are not limited to gastric carcinomas, oesophageal carcinomas, medulloblastomas, liver metastases from colon carcinoma, papillary renal carcinomas, head and neck squamous cell carcinomas, thyroid, ovarian, pancreatic, protrate, renal-cell, hepatocellular, breast and colorectal carcinomas, glioblastomas, rhabdomyosarcomas and osteosarcomas.

The term "treating" or "treatment" means slowing, interrupting, arresting, controlling, stopping, reducing severity of a symptom, disorder, condition or disease, but does not necessarily involve a total elimination of all disease-related symptoms, conditions or disorders.

For human therapeutic use the c-Met antibodies described herein may be administered to a human subject in need of treatment in an "effective amount". The term "effective amount" refers to the amount or dose of a c-Met antibody which, upon single or multiple dose administration to a human patient, provides therapeutic efficacy in the treatment of disease. Therapeutically effective amounts of the c-Met antibody can comprise an amount in the range of from about 0.1 mg/kg to about 20 mg/kg per single dose. A therapeutic effective amount for any individual patient can be determined by the healthcare professional by monitoring the effect of the c-Met antibody on a biomarker, such as cell surface c-Met in tumour tissues, or a symptom such as tumour regression, etc. The amount of antibody administered at any given time point may be varied so that optimal amounts of c-Met antibody, whether employed alone or in combination with any other therapeutic agent, are administered during the course of treatment.

It is also contemplated to administer the c-Met antibodies described herein, or pharmaceutical compositions comprising such antibodies, in combination with any other cancer treatment, as a combination therapy.

Pharmaceutical Compositions

The scope of the invention includes pharmaceutical compositions, containing one or a combination of c-Met antibodies of the invention, or antigen-binding fragments thereof, formulated with one or more a pharmaceutically acceptable carriers or excipients. Such compositions may include one or a combination of (e.g., two or more different) c-Met antibodies. For example, a pharmaceutical composition of the invention can comprise a combination of antibodies that bind to different epitopes on human c-Met, e.g. an antibody binding to the SEMA domain of human c-Met combined with an antibody which binds within the PSI-IPT domain of human c-Met.

Techniques for formulating monoclonal antibodies for human therapeutic use are well known in the art and are reviewed, for example, in Wang et al., Journal of Pharmaceutical Sciences, Vol. 96, pp 1-26, 2007.

BRIEF DESCRIPTION OF THE DRAWINGS

The invention will be further understood with reference to the following experimental examples and the accompanying Figures in which:

FIG. 15. Alignment of human and *Llama glama* c-Met amino acid sequences. X54559: SEQ ID NO:207. *Lama glama* c-Met: SEQ ID NO:208.

FIG. 25. The amino acid sequence of the extracellular portion of human c-Met, illustrating the positions of the SEMA domain and IPT domains. X54559: SEQ ID NO:209.

INCORPORATION BY REFERENCE

Various publications are cited in the foregoing description and throughout the following examples, each of which is incorporated by reference herein in its entirety.

EXAMPLES

The invention will be further understood with reference to the following non-limiting experimental examples.

Example 1: Immunization of Llamas

Immunization of llamas and harvesting of peripheral blood lymphocytes (PBLs), as well as the subsequent extraction of RNA and amplification of antibody fragments, were performed as described by De Haard and colleagues (De Haard H, et al., JBC. 274:18218-30, 1999). Eight llamas were immunized with the human gastric cell line MKN-45 over-expressing c-Met (DMSZ, ACC409)(c-Met over-expression was confirmed by Flow cytometry using PE conjugated anti-HGFR antibody (R&D systems, cat no FAB3582P)). Another two llamas were immunized with lung cancer cell line NCI-H441 cells. The llamas were immunized with intramuscular injections in the neck once per week for a period of six weeks. Approximately $10^7$ cells were injected into the neck muscles and Freund's incomplete adjuvant was injected in a second region located a few centimeters from the injection site of the cells.

Blood samples of 10 ml were collected pre- and post immunization to investigate the immune response. Three to four days after the last immunization, 400 ml blood was collected and total RNA extracted from PBLs prepared using a Ficoll-Paque gradient and the method described by Chomczynski P et al. (Anal. Biochem. 162: 156-159, 1987). The average RNA yield was 450 µg. The extracted RNA was then used for random cDNA synthesis and PCR amplification of the V-regions of the heavy and the light chains (Vλ and Vκ) in order to construct the Fab-containing phagemid libraries as described by De Haard H, et al. (Biol. Chem. 274, 1999) The resultant libraries showed good levels of diversity ($1$–$7 \times 10^8$).

Figure 1:
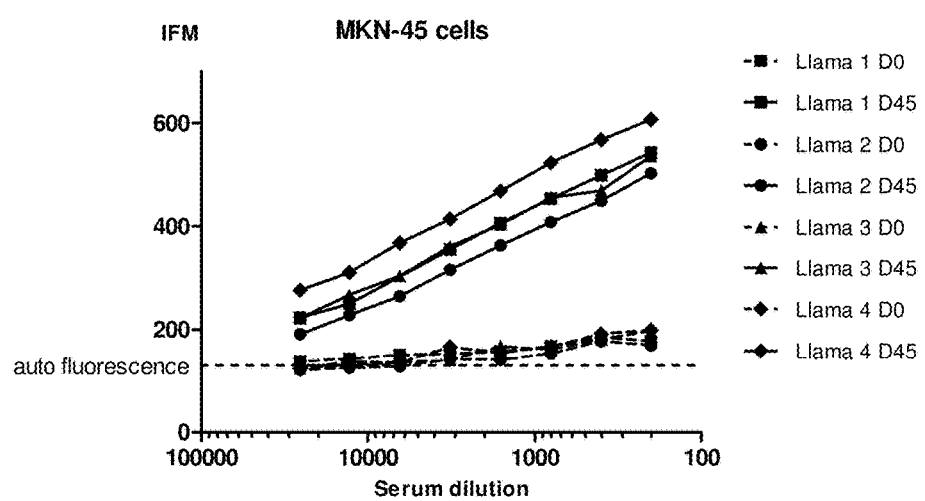
FIG. 1. The MKN-45-specific immune response in pre-immune (day 0) and post-immune (day 45) sera from llamas immunized with MKN-45 cells, as measured by Flow cytometry.

The immune response to MKN-45 cells or NCI-H441 cells was investigated using Flow cytometry. 100 µl/well of the diluted sera were added onto the cells ($2 \times 10^5$ cells/well) and incubated for 30 minutes at 4° C. After washing with PBS and 1% BSA, 0.1 µg/100 µl/well of FITC-conjugated goat anti-llama antibody (BETHYL, #A160-100F) was added and incubated for 30 minutes at 4° C. After washing with PBS and 1% BSA the results were read on a FACS Calibur and the mean fluorescence was plotted against the dilutions of the sera (FIG. 1).

Figure 2:
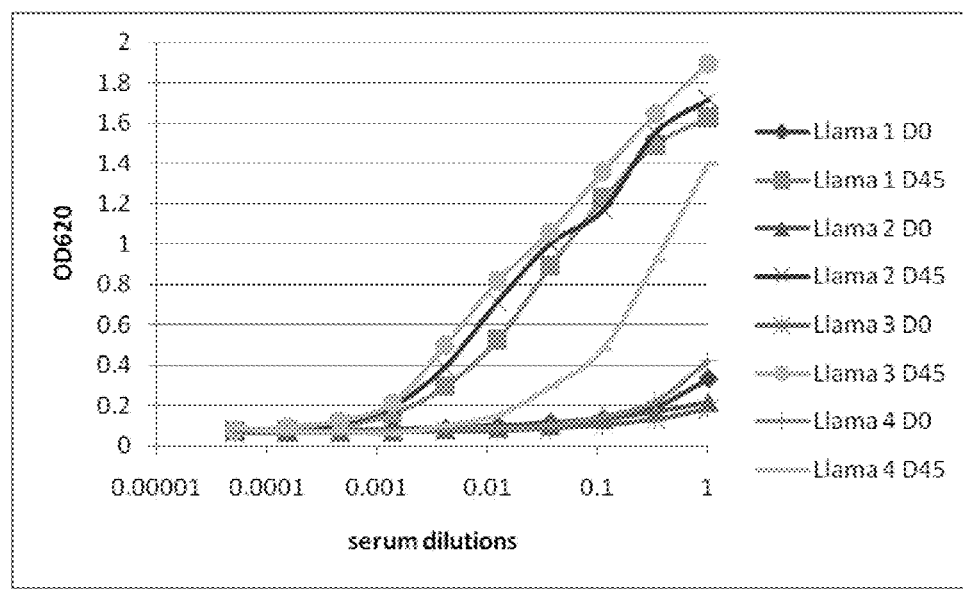
FIG. 2. The immune response to recombinant c-Met in pre-immune (day 0) and post-immune (day 45) sera from llamas immunized with MKN-45 cells, as measured by ELISA.

The specific immune response to c-Met was determined using an ELISA with immobilized recombinant c-Met (R&D systems, 358-MT/CF) using pre- and post-immune sera (Day 0 and Day 45 respectively). Llama IgG1 bound to immobilised c-Met was detected using a mouse anti-llama IgG1 (Daley L P, et al. Clin. Diagn. Lab Immunol. 12: 380-386, 2005) and a HRP-conjugated donkey anti-mouse antibody (Jackson). FIG. 2 shows the immune response of 4 of the 10 immunized llamas. A similar immune response was observed for the other 4 llamas immunized with the MKN-45 cells, but not for the NCI-H441 cell immunized llamas.

Example 2: Selections and Screenings of c-Met-Specific Fabs

Phage expressing Fabs were produced according to standard protocols and further selected on immobilized recombinant dimeric c-Met (R&D systems, 358-MT/CF) or recombinant extracellular domain of c-Met. Total elution of the c-Met binding phage with trypsin was performed according to standard phage display protocols.

Two to four rounds of selection were performed to enrich for c-Met-specific Fabs expressed by the phage. Individual colonies were isolated and periplasmic fractions (penis) were produced by IPTG induction from all the libraries according to standard protocols.

Figure 3:
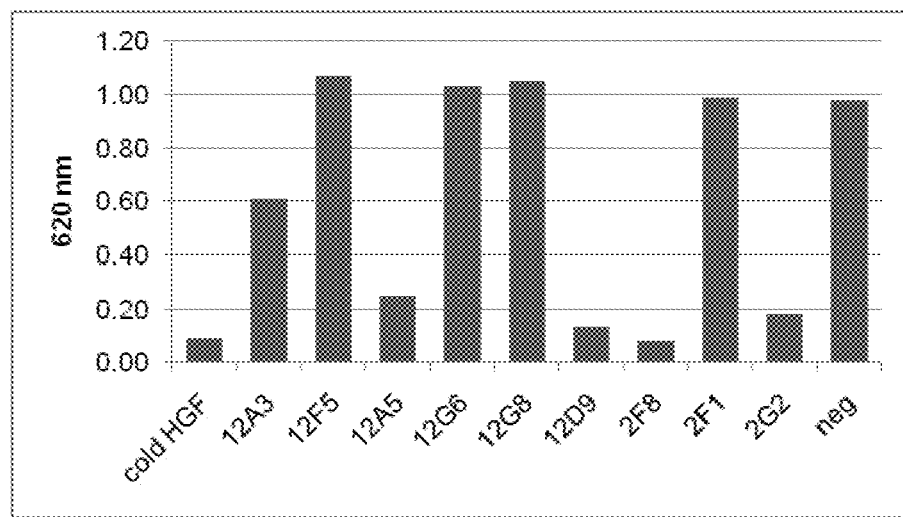
FIG. 3. Competition assay showing Fab-containing periplasmic extracts competing with N-terminally biotinylated HGF (25 ng/ml) for binding to c-Met captured via the C-terminal Fc portion.

Screening of the c-Met-specific Fabs for competition with mature HGF for binding to immobilized c-Met was performed using an ELISA-based competition assay. 2 µg/ml of goat anti-human Fcγ antibody (Jackson) was immobilized on a maxisorb plate and, after blocking with 1% casein in PBS for 2 h, 100 ng/ml recombinant dimeric c-Met was added and incubated for 1 h at room temperature. After washing, 50 µl of the Fab containing penis was added and allowed to bind to the captured c-Met, before 25 ng/ml of N-terminally biotinylated mature HGF (R&D systems, 294-HGN/CF) was added. N-terminal biotinylation was performed according to protocol provided by Thermo Scientific with a 5-fold excess of NHS-LC biotin in a 50 mM phosphate buffer (pH 6.5) at 4° C. for 24 h. Biotinylated mature HGF was incubated at room temperature for 1 h before washing and addition of horseradish-conjugated streptavidin (strep-HRP) and incubated for an additional hour. TMB was added and the plate read at 620 nm. A non-relevant periplasmic extract and a 50-fold excess of cold (non-biotinylated) HGF was included as a positive control in all the plates. An example of Fab-containing penis competing with HGF is given in FIG. 3.

HGF-competing clones were sequenced in the VH and the VL regions and divided into VH families based on the sequence of the CDR3 in the VH. These VH families were further tested with Surface Plasmon Resonance (SPR) for dissociation ($k_{off}$) and recognition of SEMA-PSI or the extracellular domain of c-Met (Decoy). Between 1000-2000 RU of dimeric c-Met, SEMA-PSI or Decoy c-Met was immobilised on a VIA chip with amine coupling in sodium acetate buffer (pH 4.5). The Fab-containing penis were added with a flow rate of 30 µl/min and Fabs were considered to be binding if an increase of the RU was observed. The $k_{off}$ was measured for 2 minutes for each sample. Table 8 summarizes the domain recognition and $k_{off}$ for different VH families.

Several VH families recognized the SEMA-PSI domain, whereas others recognized only the Decoy c-Met. The Fabs had $k_{off}$ in the range of $10^{-3}s^{-1}$-$10^{-4}s^{-1}$, with the best (12G4) having a $k_{off}$ of $1.3 \times 10^{-4}s^{-1}$.

The VH and VL domains of antagonistic clones were fused with human constant IgG1 domains and with human Cκ or Cλ domains and produced as bivalent monoclonal antibodies in the system described in patent application WO 2009/145606 with expression yields of 15-30 µg/ml after protein A purification.

TABLE 5

CDR sequences of antagonist antibodies and germlined variants
(According to Kabat numbering)

| mAb | CDR1 | SEQ ID NO | CDR2 | SEQ ID NO | CDR3 | SEQ ID NO |
|---|---|---|---|---|---|---|
| | | | VH | | | |
| 12G4 | DYAMT | 1 | TISWNDINTYYAESMKD | 2 | RRDNYYGTSGEYDY | 3 |
| 13E6 | DYVMN | 4 | AINWNGGSTYYAESMKG | 5 | DTVVSGNGY | 6 |
| 20A11 | DYAMS | 7 | AISWNGSSTYYAESMKG | 8 | DLIGSHDY | 9 |
| 20F1 | GNYYAWS | 10 | VIAYDGSTYYSPSLKS | 11 | GPGWYSGSRNDY | 12 |
| 38H10 | MNSID | 13 | RIDPEDGGTKYAQKFQG | 14 | VDDYYLGYDY | 15 |
| 40B8 | NYVID | 16 | RIDPENGGTRYAQKFQG | 17 | LEDYELAYDY | 18 |
| 36C4 | TNYYYWS | 19 | VIAYDGSTDYSPSLKS | 20 | DVRVIATGWATANALDA | 21 |
| 34H7 | SYAMS | 71 | GIYKGGGPKYANSVKG | 72 | SGYGSSLGDFGS | 73 |
| 48A2 | MNSID | 13 | RIDPEDGGTKYAQKFQG | 14 | VDDYYLGYDY | 15 |
| 55A12-54E | TNYYYWS | 19 | VIAYEGSTDYSPSLKS | 83 | DVRVIATGWATANALDA | 21 |
| 53E2-54E | TNYYYWS | 19 | VIAYEGSTDYSPSLKS | 83 | DVRVIATGWATANALDA | 21 |
| 53E3 | TNYYYWS | 19 | VIAYEGSTDYSPSLKS | 83 | DVRVIATGWATANALDA | 21 |
| 53A11 | TNYYYWS | 19 | VIAYDASTDYSPSLKS | 84 | DVRVIATGWATANALDA | 21 |
| 56F3 | MNSID | 13 | RIDPEEGGTKYAQKFQG | 85 | VDDYYLGY | 15 |
| 56D8 | MNSID | 13 | RIDPEEGGTKYAQKFQG | 85 | VDDYYLGY | 15 |
| 56B1 | MNSID | 13 | RIDPEEGGTKYAQKFQG | 85 | VDDYYLGY | 15 |
| 56E9 | MNSID | 13 | RIDPEEGGTKYAQKFQG | 85 | VDDYYLGY | 15 |
| 56E5 | MNSID | 13 | RIDPEEGGTKYAQKFQG | 85 | VDDYYLGY | 15 |
| 56E1 | MNSID | 13 | RIDPEEGGTKYAQKFQG | 85 | VDDYYLGY | 15 |
| 56G5 | MNSID | 13 | RIDPEEGGTKYAQKFQG | 85 | VDDYYLGY | 15 |
| | | | Vκ (V kappa) | | | |
| 38H10 | KSSQSVLWRSNQKNYLA | 22 | WASIRES | 23 | QQGYSFPYT | 24 |
| 40B8 | KSSQSVLLSSNQKNYLA | 25 | WASTRES | 26 | QQGVSFPLT | 27 |
| 48A2 | KSSQSVLFSSNQKNYLA | 86 | WASIRES | 23 | QQGYSFPYS | 87 |
| 56F3 | KSSQSVLFSSNQKNYLA | 86 | WASIRES | 23 | QQGYSFPYS | 87 |
| 56D8 | KSSQSVLFSSNQKNYLA | 86 | WASIRES | 23 | QQGYSFPYS | 87 |
| 56B1 | KSSQSVLFSSNQKNYLA | 86 | WASIRES | 23 | QQGYSFPYS | 87 |
| 56E9 | KSSQSVLFSSNQKNYLA | 86 | WASIRES | 23 | QQGYSFPYS | 87 |
| 56E5 | KSSQSVLFSSNQKNYLA | 86 | WASIRES | 23 | QQGYSFPYS | 87 |
| 56E1 | KSSQSVLFSSNQKNYLA | 86 | WASIRES | 23 | QQGYSFPYS | 87 |
| 56G5 | KSSQSVLFSSNQKNYLA | 86 | WASIRES | 23 | QQGYSFPYS | 87 |
| 48A1 | KSSQSVLWRSNQKNYLA | 22 | WASIRES | 23 | QQGYSFPYT | 24 |
| 48A11 | KSSQSVLYNPNQKSYLA | 137 | WASTRES | 26 | QQGYSFPYS | 87 |
| 48B8 | KSSQSVLYTSNHKNYLA | 138 | WASTRES | 26 | QQGWSFPYS | 139 |
| 48D2 | KSSQSVLYNSNQKNYLA | 140 | WASTRES | 26 | QQGWSFPYT | 141 |
| 48B6 | KSSQSVLYGSNQKNYLA | 142 | WASTRES | 26 | QQGWSFPYT | 141 |
| 48C8 | KSSQSVLYNSNQKNYLA | 140 | WASTRES | 26 | QQGWSFPYT | 141 |
| 48E5 | KSSQSVLYNSNQKNYLA | 140 | WASTRES | 26 | QQGWSFPYT | 141 |
| 48D7 | KSSQSVLFSSNQKNYLA | 86 | WASTRES | 26 | QQGYSFPYS | 87 |
| 48E2 | KSSQSVLWSSNQKNYLA | 143 | WASTRES | 26 | QQGYSFPYS | 87 |
| | | | Vλ (V lambda) | | | |
| 20F1 | TGTNSDVGYGNYVS | 28 | DVNRRAS | 29 | ASYRSANNAV | 30 |
| 36C4 | AGTSSDVGYGNYVS | 31 | AVSYRAS | 32 | ASYRSSNNAAV | 33 |
| 12G4 | AGTSSDIGNYNYVS | 34 | EVNKRPS | 35 | ASYRSSNNVV | 36 |
| 13E6 | AGTSSDIGDYNYVS | 37 | DVNKRAS | 38 | ASYRSRNDYA | 39 |
| 20A11 | AGTSSDVGYGNYVS | 40 | AVSTRAS | 41 | ASYRSSNNYA | 42 |
| 34H7 | TGSSSNIGGGYYLS | 74 | SNINRAS | 75 | SSWDDSVSGPV | 76 |
| 55A12-54E | AGTSSDVGYGNYVS | 31 | AVSYRAS | 32 | ASYRSSNNAAV | 33 |
| 53E2-54E | AGTSSDVGYGNYVS | 31 | AVSYRAS | 32 | ASYRSSNNAAV | 33 |
| 53E3 | AGTSSDVGYGNYVS | 31 | AVSYRAS | 32 | ASYRSSNNAAV | 33 |
| 53A11 | AGTSSDVGYGNYVS | 31 | AVSYRAS | 32 | ASYRSSNNAAV | 33 |
| 49A1 | AGTSSDVGYGNYVS | 31 | AVSYRAS | 32 | ASYRSSNNAAV | 33 |
| 49D2 | AGTSTDVGYGNYVS | 144 | AVSYRAS | 32 | ASYRSSNNAAV | 33 |
| 49G3 | AGTSTDVGYGNYVS | 144 | AVSYRAS | 32 | ASYRSSNNAAV | 33 |
| 49D3 | AGTSTDVGYGNYVS | 144 | AVSYRAS | 32 | ASYRSSNKNAV | 145 |
| 49A11 | AGTSSDVGYGNYVS | 31 | AVSYRAS | 32 | ASYRITNRHSV | 146 |
| 49C4 | AGTSTDVGYGNYVS | 144 | AVSYRAS | 32 | ASYRRSTNVGV | 147 |
| 49E11 | AGTSTDVGYGNYVS | 144 | AVSYRAS | 32 | ASYRTSNNVAV | 148 |

TABLE 6

Amino acid sequences of the heavy and light chain variable domains of selected antagonistic Fabs and affinity variants

Heavy chain variable domain sequences

>12G4_VH (SEQ ID NO: 45)
QLQLVESGGGMAPGGSLKLSCAASGFTFDDYAMTWVRQAPGKGLEWLSTISWNDINTYY
AESMKDRFTISRDNAKNTLYLQMNSIFSEDTAVYYCAKRRDNYYGTSGEYDYWGQGTQVT
VSS

>13E6_VH (SEQ ID NO: 46)
QVQLQESGGDLVQPGGSLRLSCAASGFTFDDYVMNWVRQAPGKGLEWISAINWNGGSTYY
AESMKGRFTISRDNAKNTLYLQMYSLQSDDTAVYYCVKDTVVSGNGYWGQGTQVTVSS

>20A11_VH (SEQ ID NO: 47)
QVQLVESGGGLVQPGGSLRLSCAASGFTFDDYAMSWVRQAPGKGLEWVSAISWNGSSTYY
AESMKGRFTISRDNAKNTLYLQMNSLKSEDTAVYYCAKDLIGSHDYWGQGTQVIVSS

>20F1_VH (SEQ ID NO: 48)
EVQVQESGPGLVKPSQTLSLTCTVSGGSMTGNYYAWSWIRQPPGKGTFWMGVIAYDGSTY
YSPSLKSRTSISRDTSKNQFSLQLSSVSPEDTAVYYCARGPGWYSGSRNDYWGQGTQVTV
SS

>38H10_VH (SEQ ID NO: 49)
EVQLVQPGVELRNPGASVKVSCKASGYIFTMNSIDWVRQAPGQGLEWMGRIDPEDGGTKY
AQKFQGRVTFTADTSTSTAYVELNSLRSEDTAVYYCARVDDYYLGYDYWGQGTQVTVSS

>40B8_VH (SEQ ID NO: 50)
EVQLVQPGAELRNPGASVKVSCKASGYTFTNYVIDWVRQAPGQGIFWMGRIDPENGGTRY
AQKFQGRVTFTADTSTSTAYVELSNLRSEDTAVYYCARIFDYELAYDYWGQGTQVIVSS

>36C4_VH (SEQ ID NO: 51)
QVQLVESGPGLVKPSQMSLTCAVSGGSITTNYYYWSWIRQSPGKGLEWMGVIAYDGSTD
YSPSLKSRTSISRDTSKNQFSLQLSSVTPEDTAVYYCARDVRVIATGWATANALDAWGQG
TLVTVSS

>48A2_VH (SEQ ID NO: 49)
EVQLVQPGVELRNPGASVKVSCKASGYIFTMNSIDWVRQAPGQGLEWMGRIDPEDGGTKY
AQKFQGRVTFTADTSTSTAYVELNSLRSEDTAVYYCARVDDYYLGYDYWGQGTQVTVSS

>36C4Q_VH (SEQ ID NO: 88)
QVQLVESGPGLVKPSQMSLTCAVSGGSITTNYYYWSWIRQSPGKGLEWMGVIAYDGSTD
YSPSLKSRTSISRDTSKNQFSLQLSSVTPEDTAVYYCARDVRVIATGWATANALDAWGQG
TQVTVSS

>34H7_VH (SEQ ID NO: 77)
ELQLVESGGALVQPGGSLRLSCVESGFTFSSYAMSWVRQAPGKGLEWVSGIYKGGGPKYA
NSVKGRFTISRDNAKNTLYLQMNSLKPEDTAVYYCAKSGYGSSLGDEGSWGQGTQVIVSS

Light chain variable domain sequences

>38H10_VK (SEQ ID NO: 52)
EIVMTQSPSSVTASAGEKVTINCKSSQSVLWRSNQKNYLAWYQQRLGQSPRLLISWASI
RESGVPDRFSGSGSTTDFTLTISSFQPEDAAVYYCQQGYSFPYEEGSGTRLEIK

>40B8_VK (SEQ ID NO: 53)
DIVMTQTPSSVTASAGEKVTINCKSSQSVLLSSNQKNYLAWYQQRLGQSPRLLIYWAST
RESGVPDRFSGSGSTTDFTLTISSFQPEDAAVYYCQQGVSFPLTEGQGTKVELK

>48A2_VK (SEQ ID NO: 89)
DIVMTQTPTSVTASAGDKVTINCKSSQSVLESSNQKNYLAWYQQRLGQSPRLLIYWASI
RESGVPDRFSGSGSATDFTLTISNFQPEDAAVYYCQQGYSFPYSFGSGTRLEIR

>20F1_VL (SEQ ID NO: 54)
QSALTQPPSVSGSPGKTVTISCTGTNSDVGYGNYVSWYQQLPGMAPKLLI
YDVNRRASGIADRFSGSKSGNTASLTISGLQSEDEGDYHCASYRSANNAV
FGGGTHLFVL

>36C4_VL (SEQ ID NO: 55)
QSVLTQPPSVSGSPGKTVTISCAGTSSDVGYGNYVSWYQQLPGTAPKLLIFAVSYRASGI
PDRFSGSKSGNTAFLTISGLQSEDEADYYCASYRSSNNAAVFGGGTHLTVL

>12G4_VL (SEQ ID NO: 56)
QSALTQPPSVSGTLGKTVTISCAGTSSDIGNYNYVSWYQQLPGTAPKWYEVNKRPSGI
PDRFSGSKSGNTASLSISGLQSEDEADYYCASYRSSNNVVFGGGTKLTVL

>13E6_VL (SEQ ID NO: 57)
QSVLIQPPSVSGTLGKTVTISCAGTSSDIGDYNYVSWYQQLPGTAPKWYDVNKRASGI
PDRFSGSKSGNTASLSISGLQSEDEADYYCASYRSRNDYAFGGGTKLTVL

TABLE 6 -continued

Amino acid sequences of the heavy and light chain variable domains
of selected antagonistic Fabs and affinity variants >20A11_VL (SEQ ID NO: 58)
QAVLTQPPSVSGTLGKTLTISCAGTSSDVGYGNYVSWYQQLPGTAPKLLIYAVSTRASGI
PDRFSGSKSGNTASLTISGLQSEDEADYYCASYRSSNNYAFGAGTKLTVL >34H7_VL (SEQ ID NO: 78)
QAGLTQLSSMSGSPGQTVTITCTGSSSNIGGGYYLSWYQHLPGTAPKWYSNINRASG
VPDRFSGSTSGISASLTITGLQAEDEADYYCSSWDDSVSGPVEGGGTSLTVL >48A1_VK (SEQ ID NO: 149)
EIVMTQSPSSVTASAGEKVTINCKSSQSVLWRSNQKNYLAWYQQRLGQSPRLLISWAS
IRESGVPDRFSGSGSTTDFTLTISSFQPEDAAVYYCQQGYSFPYPEGSGTRLEIK >48A11_VK (SEQ ID NO: 150)
DIVMTQTPSSVTAAVGEKVAINCKSSQSVLYNPNQKSYLAWYQQRPGQSPRLLIYWAS
TRESGVPDRFSGSGSTTDFALTISSFQPEDAAVYYCQQGYSFPYSEGSGTRLEIR >48B8_VK (SEQ ID NO: 151)
DVVMTQSPSSVTASVGEKVTINCKSSQSVLYTSNHKNYLAWYQQRLGQSPRLLIYWAS
TRESGVPDRFSGSGSTTDFTLTISSFQPEDAAVYYCQQGWSFPYSFGSGTRLEIK >48D2_VK (SEQ ID NO: 152)
DIVMTQTPSSVTASAGEKVTINCKSSQSVLYNSNQKNYLAWYQQRLGQSPRLLIYWAS
TRESGVPDRFSGSGSTTDFTLTISSFQPEDAAVYYCQQGWSFPYTFGSGTRLEIK >48B6_VK (SEQ ID NO: 153)
DIQLTQSPSSVTASAGEKVTINCKSSQSVLYGSNQKNYLAWYQQRLGQSPRLLIYWAS
TRESGVPDRFSGSGSTTDFTLTISSFQPEDAAVYYCQQGWSFPYTFGSGTRLEIK >48C8_VK (SEQ ID NO: 154)
DIQLTQSPSSVTVSVGEKVTINCKSSQSVLYNSNQKNYLAWYQQRLGQSPRLLIYWAS
TRESGVPDRFSGSGSTTDFTLTISSFQPEDAAVYYCQQGWSFPYTFGSGTRLEIK >48E5_VK (SEQ ID NO: 155)
DIQMTQSPSSVTASAGEKVTINCKSSQSVLYNSNQKNYLAWYQQRLGQSPRLLIYWAS
TRESGVPDRFSGSGSTTDFTLTISSFQPEDAAVYYCQQGWSFPYIPGSGTRTLEIK >48D7_VK (SEQ ID NO: 156)
DIVMTQTPASVTASAGEKVTINCKSSQSVLESSNQKNYLAWYQQRVGQSPRLLIYWAS
TRESGVPDRFSGSGSTTDFTLTISNFQPEDAAVYYCQQGYSFPYSFGSGTRLEIR >48E2_VK (SEQ ID NO: 157)
DVVMTQSPSSVTASAGEKVTINCKSSQSVLWSSNQKNYLAWYQQRVGQSPRLLIYWAS
TRESGVPDRFSGSGSTTDFTLTISNFQPEDAAVYYCQQGYSFPYSFGSGTRLEIR >49A1_VL (SEQ ID NO: 158)
QSVLTQPPSVSGSPGKTVTISCAGTSSDVGYGNYVSWYQQLPGTAPKLLIFAVSYRASGIP
DRFSGSKSGNTAFLTISGLQSEDEADYYCASYRSSNNAAVFGGGTHLTVL >49D2_VL (SEQ ID NO: 159)
QSVLTQPPSVSGTLGKTLTISCAGTSTDVGYGNYVSWYQQLPGTAPKLLIFAVSYRASGIP
DRFSGSKSGNTAFLTISGLQSEDEADYYCASYRSSNNAAVFGGGTHLTVL >49G3_VL (SEQ ID NO: 160)
QSALTQPPSVSGTLGKTLTISCAGTSTDVGYGNYVSWYQQLPGTAPKLLIFAVSYRASGIP
DRFSGSKSGNTAFLTISGLQSEDEADYYCASYRSSNNAAVFGGGTHLTVL >49D3_VL (SEQ ID NO: 161)
LPVLTQPPSVSGTLGKTLTISCAGTSSDVGYGNYVSWYQQLPGTAPKLLIYAVSYRASGIP
DRFSGSKSGNTASLSISGLQSEDEADYYCASYRSSNKNAVFGGGTHLTVL >49A11_VL (SEQ ID NO: 162)
QSALTQPPSVSGSPGKTVTISCAGTSSDVGYGNYVSWYQKLPGTAPKLLIYAVSYRASGIP
DRFSGSRSGNTASLTISGLQSEDEADYYCASYRITNRHSVEGGGTHLTVL >49C4_VL (SEQ ID NO: 163)
QSALTQPPSVSGTLGKTVTISCAGTSSDVGYGNYVSWYQKLPGTAPKLLIYAVTYRASGIP
DRFSGSKSGNTASLTISGLQSEDEADYYCASYRRSTNVGVFGGGTHLTVL >49E11_VL (SEQ ID NO: 164)
QAVLTQPPSVSGTLGKTVTISCAGTSSDVGYGNYVSWYQKLPGTAPKLLIYAVSYRASGIP
DRFSGSKSGNTASLTISGLQSEDEADYHCASYRTSNNVAVFGGGTKLTVL

TABLE 7

Nucleotide sequences encoding heavy and light chain variable
domains of selected antagonistic Fabs Heavy chain variable domain sequences >36C4_VH (SEQ ID NO: 59)
CAGGTGCAGCTCGTGGAGTCGGGCCCAGGCCTGGTGAAGCCCTCGCAGACACTCTCCCTC
ACCTGCGCTGTCTCTGGTGGCTCCATCACAACCAACTATTACTACTGGAGCTGGATTCGC
CAGTCCCCAGGGAAGGGGCTGGAGTGGATGGGAGTCATAGCTTATGATGGCAGCACTGAC
TACAGCCCATCCCTCAAGAGCCGCACTTCCATCTCCAGGGACACGTCCAAGAACCAGTTC
TCCCTGCAGCTGAGCTCTGTGACCCCTGAGGACACGGCCGTGTATTACTGTGCCAGAGAT
GTAAGGGTAATCGCTACGGGTTGGGCTACTGCCAATGCTTTGGACGCATGGGGCCAGGGG
ACCCTGGTCACTGTCTCCTCAGC >48A2_VH (SEQ ID NO: 60)
GAGGTCCAGCTGGTGCAGCCAGGGGTTGAACTGAGAAACCCTGGGGCATCAGTGAAGGTC
TCCTGCAAGGCTTCTGGATACATTTTCACCATGAACTCAATAGACTGGGTGCGACAGGCC
CCTGGACAAGGGCTTGAGTGGATGGGAAGAATTGACCCTGAAGATGGTGGCACAAAGTAT
GCACAGAAGTTCCAGGGCAGAGTCACCTTCACTGCAGACACGTCCACCAGCACAGCCTAC
GTGGAGCTGAACAGTCTGAGATCTGAGGACACGGCCGTGTATTACTGTGCGAGAGTAGAT
GACTATTACCTAGGGTATGACTACTGGGGCCAGGGGACCCAGGTCACCGTCTCCTCA >36C4Q_VH (SEQ ID NO: 90)
CAGGTGCAGCTCGTGGAGTCGGGCCCAGGCCTGGTGAAGCCCTCGCAGACACTCTCCCTC
ACCTGCGCTGTCTCTGGTGGCTCCATCACAACCAACTATTACTACTGGAGCTGGATTCGC
CAGTCCCCAGGGAAGGGGCTGGAGTGGATGGGAGTCATAGCTTATGATGGCAGCACTGAC
TACAGCCCATCCCTCAAGAGCCGCACTTCCATCTCCAGGGACACGTCCAAGAACCAGTTC
TCCCTGCAGCTGAGCTCTGTGACCCCTGAGGACACGGCCGTGTATTACTGTGCCAGAGAT
GTAAGGGTAATCGCTACGGGTTGGGCTACTGCCAATGCTTTGGACGCATGGGGCCAGGGG
ACCCAGGTCACCGTGTCCTCA >38H10_VH (SEQ ID NO: 60)
GAGGTCCAGCTGGTGCAGCCAGGGGTTGAACTGAGAAACCCTGGGGCATCAGTGAAGGTC
TCCTGCAAGGCTTCTGGATACATTTTCACCATGAACTCAATAGACTGGGTGCGACAGGCC
CCTGGACAAGGGCTTGAGTGGATGGGAAGAATTGACCCTGAAGATGGTGGCACAAAGTAT
GCACAGAAGTTCCAGGGCAGAGTCACCTTCACTGCAGACACGTCCACCAGCACAGCCTAC
GTGGAGCTGAACAGTCTGAGATCTGAGGACACGGCCGTGTATTACTGTGCGAGAGTAGAT
GACTATTACCTAGGGTATGACTACTGGGGCCAGGGGACCCAGGTCACCGTCTCCTCA >40B8_VH (SEQ ID NO: 61)
GAGGTCCAGCTGGTGCAGCCAGGGGCTGAGCTGAGAAACCCTGGGGCATCAGTGAAGGTC
TCCTGCAAGGCTTCTGGATACACCTTCACCAACTACGTCAGATGGGTACGACAGGCC
CCTGGACAAGGGCTTGAGTGGATGGGAAGAATTGACCCTGAAAACGGTGGCACGAGGTAT
GCACAGAAGTTCCAGGGCAGAGTCACCTTCACTGCAGACACGTCCACCAGCACAGCCTAC
GTGGAGTTGAGCAATCTGAGATCTGAGGACACGGCCGTGTATTACTGTCAAGACTGGAA
GACTACGAATTGGCTTATGACTACTGGGGCCAGGGGACCCAGGTCACCGTCTCTTCAG >20A11_VH (SEQ ID NO: 62)
CAGGTGCAGCTCGTGGAGTCTGGGGGAGGCTTGGTGCAGCCTGGGGGGTCTCTGAGACTC
TCCTGTGCAGCCTCTGGATTCACTTTTGATGATTATGCCATGAGCTGGGTCCGACAGGCT
CCAGGGAAGGGGCTGGAGTGGGTCTCAGCTATTAGCTGGAATGGTAGTAGCACATACTAT
GCAGAATCCATGAAGGGCCGATTCACCATCTCCAGAGACAACGCCAAGAACACGCTGTAT
CTGCAAATGAACAGTCTGAAATCTGAGGACACGGCCGTGTATTACTGTCAAAGATCTA
ATAGGATCCATGACTACTGGGGCCAGGGGACCCAGGTCACCGTGTCCTCA >34H7_VH (SEQ ID NO: 79)
GAGTTGCAGCTGGTGGAGTCTGGGGGAGCCTTGGTGCAGCCTGGGGGGTCTCTGAGACTC
TCCTGTGTAGAGTCTGGATTCACCTTCAGTAGTTATGCCATGAGCTGGTCCGCAGGCT
CCAGGAAAGGGGCTCGAGTGGGTCTCAGGTATTTATAAAGGTGGTGGTCCAAAATATGCA
AACTCCGTGAAGGGCCGATTCACCATCTCCAGAGACAACGCCAAGAACACGCTGTATCTG
CAAATGAACAGCCTGAAACCTGAGGACACGGCCGTTTATTACTGTGCAAAATCGGGGTAC
GGTAGTAGCCTTGGGGACTTTGGTTCCTGGGGCCAGGGGACCCAGGTCACCGTCTCCTCG >12G4_VH (SEQ ID NO: 63)
CAGTTGCAGCTGGTGGAGTCTGGGGGAGGCATGGCGCAGCCTGGGGGGTCTCTGAAACTC
TCCTGTGCAGCCTCTGGATTCACTTTTGATGATTATGCCATGACCTGGGTCCGACAGGCT
CCAGGGAAGGGGCTGGAGTGGCTCTCAACTATTAGCTGGAATGACATTAACACATACTAT
GCAGAATCCATGAAGGACCGATTCACCATCTCCAGAGACAACGCCAAGAACACGCTGTAT
CTGCAAATGAACAGTCTCGAATCTGAGGACACGGCCGTGTATTACTGTCAAAACGTAGG
GATAATTACTACGGGACTTCCGGGGAGTATGACTACTGGGGCCAGGGGACCCAGGTCACC
GTCTCCTCA >13E6_VH (SEQ ID NO: 64)
CAGGTGCAGCTGCAGGAGTCGGGGGGAGACTTGGTGCAGCCGGGGGGGTCTCTGAGACTC
TCCTGTGCAGCCTCTGGATTCACTTTTGATGATTATGTCATGAGCTGGGTCCGACAGGCT
CCAGGGAAGGGGCTGGAGTGGATCTCAGCTATTAACTGGAATGGTGGTAGCACATACTAT
GCAGAATCCATGAAGGGCCGATTCACCATCTCCAGAGACAACGCCAAGAACACGCTGTAT
CTGCAAATGTACAGTCTGCAATCTGACGACACGGCCGTGTATTACTGTAAAAGATACG
GTAGTGTCTGGTAATGGCTACTGGGGCCAGGGGACCCAGGTCACCGTGTCCTCA TABLE 7 -continued Nucleotide sequences encoding heavy and light chain variable
domains of selected antagonistic Fabs >20F1_VH (SEQ ID NO: 80)
GAGGTGCAGGTGCAGGAGTCGGGCCCAGGCCTGGTGAAGCCCTCGCAGACGCTCTCCCTC
ACCTGCACTGTCTCTGGTGGCTCCATGACAGGCAACTATTATGCTTGGAGCTGGATCCGC
CAGCCCCCAGGGAAGGGGCTGGAGTGGATGGGAGTCATAGCTTATGATGGCAGCACTTAC
TACAGCCCCATCCCTCAAGAGCCGCACTTCTATCTCCAGGGACACGTCCAAGAACCAGTTC
TCCCTGCAGTTGAGCTCTGTGAGCCCTGAGGACACGGCCGTGTATTACTGTGCCAGAGGC
CCAGGGTGGTATAGTGGTAGCAGGAATGACTACTGGGGCCAGGGGACCCAGGTCACCGTC
TCCTCA Light chain variable domain sequences >36C4_VL (SEQ ID NO: 65)
CAGTCTGTGTTGACGCAGCCTCCCTCCGTGTCTGGGTCTCCAGGAAAGACGGTCACCATC
TCCTGTGCAGGAACCAGCAGTGATGTTGGGTATGGAAACTATGTCTCCTGGTACCAGCAG
CTCCCAGGCACGGCCCCCAAACTCCTGATCTTTGCAGTCAGCTATCGAGCCTCAGGGATC
CCTGATCGCTTCTCTGGCTCCAAGTCAGGCAACACGGCCTTTTTGACCATCTCTGGGCTC
CAGTCCGAGGACGAGGCTGATTATTACTGTGCCTCATATAGAAGCAGCAACAATGCTGCT
GTGTTCGGCGGAGGGACCCATCTGACCGTCCTG >48A2_VK (SEQ ID NO: 91)
GATATTGTGATGACCCAGACTCCCACCTCCGTGACTGCATCTGCAGGAGACAAGGTCACC
ATCAATTGTAAGTCCAGCCAGAGTGTGTTATTCAGCTCCAACCAGAAAAACTACTTAGCT
TGGTACCAGCAGAGACTTGGACAGTCTCCTAGGCTGCTCATCTACTGGGCTTCCATCCGA
GAATCGGGGGTTCCTGATCGATTCAGCGGCAGTGGGTCCGCAACAGATTTCACGCTAACC
ATCAGCAACTTCCAGCCTGAAGACGCGGCAGTATATTACTGCCAGCAGGGTTATAGTTTT
CCATATAGTTTCGGCAGTGGGACCAGGCTGGAAATCAGA >38H10_VK (SEQ ID NO: 66)
GAAATTGTGATGACGCAGTCTCCCAGCTCCGTGACTGCGTCTGCAGGAGAGAAGGTCACC
ATCAATTGTAAGTCCAGCCAGAGTGTGTTATGGCGCTCCAACCAGAAAAACTACTTAGCT
TGGTACCAGCAGAGACTTGGACAGTCTCCTAGGCTGCTCATCAGCTGGGCATCCATCCGA
GAATCGGGGGTTCCTGATCGATTCAGCGGCAGTGGGTCCACAACAGATTTCACTCTTACC
ATCAGCAGCTTCCAGCCTGAAGACGCGGCAGTGTATTACTGCCAACAGGGTTATAGTTTT
CCATATACATTCGGCAGTGGGACCAGGCTGGAAATCAAA >34H7_VL (SEQ ID NO: 81)
GCACAGGCAGGGCTGACTCAGCTGTCCTCCATGTCTGGATCCCCGGGCCAGACGGTCACC
ATCACCTGCACAGGAAGCAGCAGCAACATCGGGGGTGGTTATTATTTGAGCTGGTACCAA
CATCTGCCAGGAACGGCCCCCAAACTCCTGATCTACAGTAACATCAATAGGGCCTCGGGG
GTCCCGGACCGCTTCTCTGGCTCCACGTCGGGCATCTCGGCCTCCCTGACTATCACTGGG
CTCCAGGCTGAGGACGAGGCTGACTATTACTGTTCATCCTGGGATGACAGCGTCAGTGGT
CCTGTGTTCGGCGGAGGGACCAGTCTGACCGTCCTC >12G4_VL (SEQ ID NO: 67)
CAGTCTGCCCTGACTCAGCCTCCCTCCGTGTCCGGAACTCTGGGAAAGACGGTCACCATC
TCTTGCGCTGGAACCAGCAGTGACATTGGGAACTATAACTATGTCTCCTGGTATCAACAG
CTCCCAGGAACAGCCCCCAAACTCCTGATATATGAGGTCAATAAACGACCCTCAGGGATC
CCTGATCGCTTCTCTGGCTCCAAGTCAGGCAACACGGCCTCCCTGAGCATCTCTGGGCTC
CAGTCTGAGGACGAGGCTGATTATTACTGTGCCTCATATAGAAGCAGCAACAATGTTGTG
TTCGGCGGAGGGACCAAGCTGACCGTCCTC >13E6_VL (SEQ ID NO: 68)
CAGTCTGTGTTGACGCAGCCTCCCTCCGTGTCCGGAACTCTGGGAAAGACGGTCACCATC
TCCTGCGCTGGAACCAGCAGTGACATTGGGGACTATAACTATGTCTCCTGGTATCAACAG
CTCCCAGGAACGGCCCCCAAACTCCTGATATATGACGTCAATAAACGAGCCTCAGGGATC
CCTGATCGCTTCTCTGGCTCCAAGTCAGGCAACACGGCCTCCCTGAGCATCTCTGGGCTC
CAGTCTGAGGACGAGGCTGATTATTACTGTGCCTCATATAGAAGCAGGAACGATTATGCC
TTCGGCGGAGGGACCAAGCTGACCGTCCTC >20A11_VL (SEQ ID NO: 69)
CAGGCTGTGCTGACTCAGCCTCCCTCCGTGTCCGGAACTCTGGGAAAGACGCTCACCATC
TCCTGCGCTGGAACCAGCAGTGATGTTGGATACGGAAACTATGTCTCCTGGTACCAACAG
CTCCCAGGCACGGCCCCCAAACTCCTGATCTATGCAGTCAGCACTCGAGCCTCAGGGATC
CCTGATCGCTTCTCTGGCTCCAAGTCAGGCAACACGGCCTCCCTGACCATCTCTGGGCTC
CAGTCTGAGGACGAGGCTGATTATTACTGTGCCTCATATAGAAGCAGCAACAATTATGCG
TTCGGCGCAGGGACCAAGCTGACCGTCCTC >40B8_VK (SEQ ID NO: 70)
GATATTGTGATGACCCAGACTCCCAGCTCCGTGACTGCGTCTGCAGGAGAGAAGGTCACC
ATCAATTGTAAGTCCAGCCAGAGTGTGTTATTGAGCTCCAACCAGAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTTACC
ATCAGCAGCTTCCAGCCTGAAGACGCGGCAGTGTATTACTGCCAGCAGGGTGTAAGTTTT
CCACTTACGTTCGGCCAGGGGACCAAGGTGGAACTCAAA TABLE 7 -continued Nucleotide sequences encoding heavy and light chain variable
domains of selected antagonistic Fabs

```
>20F1_VL (SEQ ID NO: 82)
CAGTCTGCCCTGACTCAGCCTCCCTCCGTGTCTGGGTCTCCAGGAAAGACGGTCACC
ATCTCCTGTACAGGAACCAACAGTGATGTTGGGTACGGAAACTATGTCTCCTGGTACCAG
CAGCTCCCAGGAATGGCCCCCAAACTCCTGATATATGACGTCAATAGACGGCCTCAGGG
ATCGCTGATCGCTTCTCTGGCTCCAAGTCTGGCAACACGGCCTCCCTGACCATTTCTGGG
CTCCAGTCTGAGGACGAGGGTGATTATCATTGTGCCTCATATAGAAGTGCCAACAATGCT
GTGTTCGGCGGAGGGACCCATCTGTTCGTCCTG

>48A1_VK (SEQ ID NO: 165)
GAAATTGTGATGACGCAGTCTCCCAGCTCCGTGACTGCGTCTGCAGGAGAGAAGGTCACC
ATCAATTGTAAGTCCAGCCAGAGTGTGTTATGGCGCTCCAACCAGAAAAACTACTTAGCT
TGGTACCAGCAGAGACTTGGACAGTCTCCTAGGCTGCTCATCAGCTGGGCATCCATCCGA
GAATCGGGGGTTCCTGATCGATTCAGCGGCAGTGGGTCCACAACAGATTTCACTCTTACC
ATCAGCAGCTTCCAGCCTGAAGACGCGGCAGTGTATTACTGCCAACAGGGTTATAGTTTT
CCATATACATTCGGCAGTGGGACCAGGCTGGAAATCAAA

>48A11_VK (SEQ ID NO: 166)
GATATTGTGATGACCCAGACTCCTAGCTCCGTGACTGCGGCTGTAGGAGAGAAGGTCGCT
ATCAACTGTAAGTCCAGCCAGAGCGTGTTATATAACCCCAACCAGAAAAGCTACTTAGCT
TGGTACCAACAGAGACCTGGACAATCTCCTAGGCTGCTCATCTACTGGGCATCCACCCGA
GAATCGGGGGTTCCTGATCGCTTCAGCGGCAGTGGGTCCACAACAGATTTCGCTCTTACC
ATCAGCAGCTTCCAGCCTGAAGACGCGGCAGTGTATTACTGCCAGCAGGGTTATAGTTTT
CCATATAGTTTCGGCAGTGGGACCAGGCTGGAAATCAGA

>48B8_VK (SEQ ID NO: 167)
GATGTTGTGATGACTCAGTCTCCCAGCTCCGTGACTGCATCTGTAGGAGAGAAGGTCACT
ATCAACTGTAAGTCCAGCCAGAGTGTGTTATACACCTCCAACCACAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTGACC
ATCAGCAGCTTCCAGCCTGAAGACGCGGCAGTGTATTACTGCCAGCAGGGATGGAGTTTT
CCATATAGTTTCGGCAGTGGGACCAGGCTGGAAATCAAA

>48D2_VK (SEQ ID NO: 168)
GATATTGTGATGACCCAGACTCCCAGCTCCGTGACTGCGTCTGCAGGAGAGAAGGTCACC
ATCAATTGTAAGTCCAGCCAGAGTGTATTATACAACTCCAACCAGAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTGACC
ATCAGCAGCTTCCAGCCTGAAGACGCGGCAGTGTATTACTGCCAGCAGGGATGGAGTTTT
CCATATACTTTCGGCAGTGGGACCAGGCTGGAAATCAAA

>48B6_VK (SEQ ID NO: 169)
GATATCCAGTTGACCCAGTCTCCCAGCTCCGTGACAGCGTCTGCAGGAGAGAAGGTCACC
ATCAATTGTAAGTCCAGCCAGAGTGTGTTATACGGCTCCAACCAGAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTGACC
ATCAGCAGCTTCCAGCCTGAAGACGCGGCAGTGTATTACTGCCAGCAGGGATGGAGTTTT
CCATATACTTTCGGCAGTGGGACCAGGCTGGAAATCAAA

>48C8_VK (SEQ ID NO: 170)
GACATCCAGTTGACCCAGTCTCCCAGCTCCGTGACTGTGTCTGTAGGAGAGAAGGTCACC
ATCAATTGTAAGTCCAGCCAGAGTGTATTATACAACTCCAACCAGAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTGACC
ATCAGCAGCTTCCAGCCTGAAGACGCGGCAGTGTATTACTGCCAGCAGGGATGGAGTTTT
CCATATACTTTCGGCAGTGGGACCAGGCTGGAAATCAAA

>48E5_VK (SEQ ID NO: 171)
GACATCCAGATGACCCAGTCTCCCAGCTCCGTGACTGCGTCTGCAGGAGAGAAGGTCACC
ATCAATTGTAAGTCCAGCCAGAGTGTATTATACAACTCCAACCAGAAAAACTACTTAGCT
TGGTACCAGCAGAGACTTGGACAGTCTCCTAGGCTGCTCATCTACTGGGCATCCACCCGA
GAATCGGGGGTTCCTGATCGATTCAGCGGCAGTGGGTCCACAACAGATTTCACTCTGACC
ATCAGCAGCTTCCAGCCTGAAGACGCGGCAGTGTATTACTGCCAGCAGGGATGGAGTTTT
CCATATACTTTCGGCAGTGGGACCAGGCTGGAAATCAAA

>48D7_VK (SEQ ID NO: 172)
GATATTGTGATGACCCAGACTCCCGCCTCCGTGACTGCGTCTGCAGGAGAGAAGGTCACC
ATCAATTGTAAGTCCAGCCAGAGTGTGTTATTCAGCTCCAACCAGAAAAACTACTTAGCT
TGGTACCAGCAGAGAGTTGGACAGTCTCCTAGGCTGCTCATCTACTGGGCATCCACCCGA
GAATCGGGGGTTCCTGATCGATTCAGCGGCAGTGGGTCCACAACAGATTTCACTCTTACC
ATCAGCAACTTCCAGCCTGAAGACGCGGCAGTGTATTACTGCCAGCAGGGTTATAGTTTT
CCATATAGTTTCGGCAGTGGGACTAGGCTGGAAATCAGA

>48E2_VK (SEQ ID NO: 173)
GATGTTGTGATGACTCAGTCTCCCAGCTCCGTGACTGCGTCTGCAGGAGAGAAGGTCACC
ATCAATTGTAAGTCCAGTCAGAGTGTGTTATGGAGCTCCAACCAGAAAAACTACTTAGCT
TGGTACCAGCAGAGAGTTGGACAGTCTCCTAGGCTGCTCATCTACTGGGCATCCACCCGA
```

TABLE 7 -continued

Nucleotide sequences encoding heavy and light chain variable domains of selected antagonistic Fabs

```
GAATCGGGGGTTCCTGATCGATTCAGCGGCAGTGGGTCCACAACAGATTTCACTCTTACC
ATCAGCAACTTCCAGCCTGAAGACGCGGCAGTGTATTACTGCCAGCAGGGTTATAGTTTT
CCATATAGTTTCGGCAGTGGGACCAGGCTGGAAATCAGA

>49A1_VL (SEQ ID NO: 174)
CAGTCTGTGTTGACGCAGCCTCCCTCCGTGTCTGGGTCTCCAGGAAAGACGGTCACCATC
TCCTGTGCAGGAACCAGCAGTGATGTTGGGTATGGAAACTATGTCTCCTGGTACCAGCAG
CTCCCAGGCACGGCCCCCAAACTCCTGATCTTTGCAGTCAGCTATCGAGCCTCAGGGATC
CCTGATCGCTTCTCTGGCTCCAAGTCAGGCAACACGGCCTTTTTGACCATCTCTGGGCTC
CAGTCCGAGGACGAGGCTGATTATTACTGTGCCTCATATAGAAGCAGCAACAATGCTGCT
GTGTTCGGCGGAGGGACCCATCTGACCGTCCTG

>49D2_VL (SEQ ID NO: 175)
GCACAGTCTGTGCTGACGCAGCCTCCCTCCGTGTCCGGAACTCTGGGCAAGACGCTCACC
ATCTCCTGCGCTGGAACCAGCACTGATGTTGGATACGGAAACTATGTCTCCTGGTACCAA
CAGCTCCCAGGCACGGCCCCCAAACTCCTGATCTTTGCAGTCAGCTATCGAGCCTCAGGG
ATCCCTGATCGCTTCTCTGGCTCCAAGTCAGGCAACACGGCCTTTTTGACCATCTCTGGG
CTCCAGTCCGAGGACGAGGCTGATTATTACTGTGCCTCATATAGAAGCAGCAACAATGCT
GCTGTGTTCGGCGGAGGGACCCATCTGACCGTCCTG

>49G3_VL (SEQ ID NO: 176)
CAGTCTGCCCTGACTCAGCCTCCCTCCGTGTCCGGAACTCTGGGCAAGACGCTCACCATC
TCCTGCGCTGGAACCAGCACTGATGTTGGATACGGAAACTATGTCTCCTGGTACCAACAG
CTCCCAGGCACGGCCCCCAAACTCCTGATCTTTGCAGTCAGCTATCGAGCCTCAGGGATC
CCTGATCGCTTCTCTGGCTCCAAGTCAGGCAACACGGCCTTTTTGACCATCTCTGGGCTC
CAGTCCGAGGACGAGGCTGATTATTACTGTGCCTCATATAGAAGCAGCAACAATGCTGCT
GTGTTCGGCGGAGGGACCCATCTGACCGTCCTG

>49D3_VL (SEQ ID NO: 177)
CTGCCTGTGCTGACTCAGCCTCCCTCCGTGTCCGGAACTCTGGGAAAGACGCTCACCATC
TCCTGCGCTGGAACCAGCAGTGATGTTGGATACGGAAACTATGTCTCCTGGTACCAACAG
CTCCCAGGCACGGCCCCCAAACTCCTGATCTATGCAGTCAGCTATCGAGCCTCAGGGATC
CCTGATCGCTTCTCTGGCTCCAAGTCAGGCAACACGGCCTCCCTGAGCATCTCTGGGCTC
CAGTCTGAGGACGAGGCTGATTATTACTGTGCCTCATATAGAAGCAGCAACAAAAATGCT
GTGTTCGGCGGAGGGACCCATCTGACCGTCCTG

>49A11_VL (SEQ ID NO: 178)
CAGTCTGCCCTGACTCAGCCTCCCTCCGTGTCTGGGTCTCCAGGAAAGACGGTCACCATC
TCCTGTGCAGGAACCAGCAGTGATGTTGGATACGGAAACTATGTCTCCTGGTACCAAAAG
CTCCCAGGCACAGCCCCCAAACTCCTGATCTATGCAGTCAGCTATCGAGCCTCAGGGATC
CCTGATCGCTTCTCTGGCTCCGGTCAGGCAACACGGCCTCCCTGACCATCTCTGGGCTC
CAGTCTGAGGACGAGGCTGATTATTACTGTGCCTCATATAGAATCACCAACAGGCACAGC
GTGTTCGGCGGAGGGACCCATCTGACCGTCCTG

>49C4_VL (SEQ ID NO: 179)
CAGTCTGCCCTGACTCAGCCTCCCTCCGTGTCTGGAACTCTGGGAAAGACGGTCACCATC
TCCTGCGCTGGAACCAGCAGTGATGTTGGGTATGGAAACTATGTCTCCTGGTACCAAAAG
CTCCCAGGCACAGCCCCCAAACTCCTGATCTATGCAGTCACCTATCGAGCCTCAGGGATC
CCTGATCGCTTCTCTGGCTCCAAGTCGGGCAACACGGCCTCCCTGACCATCTCTGGGCTC
CAGTCTGAGGACGAGGCTGATTATTACTGTGCCTCATATAGAAGAAGTACTAATGTGGGG
GTGTTCGGCGGAGGGACCCATCTGACCGTCCTG

>49E11_VL (SEQ ID NO: 180)
CAGGCTGTGCTGACTCAGCCTCCCTCCGTGTCCGGAACTCTGGGAAAGACGGTCACCATC
TCCTGCGCTGGAACCAGCAGTGATGTTGGATACGGAAACTATGTCTCCTGGTACCAAAAG
CTCCCAGGCACAGCCCCCAAACTCCTGATCTATGCAGTCTATCGAGCCTCAGGGATC
CCTGATCGCTTCTCTGGCTCCAAGTCAGGCAACACGGCCTCCCTGACCATCTCTGGGCTC
CAGTCTGAGGACGAGGCTGATTATCACTGTGCCTCATATAGAACCAGCAACAATGTGGCT
GTGTTCGGCGGAGGGACCAAGCTGACCGTCCTC
```

Example 3: Epitope Mapping

Different ectodomains of c-Met (Decoy, SEMA, SEMA-PSI, SEMA-PSI-IPT1-2 and IPT3-4, (C. Basilico, et al., J. Biol. Chem. 283:21267-2127, 2008) were immobilized (1 µg/ml) on a maxisorb plate in PBS over night at 4° C. The antibodies (mAbs) were added in three-fold dilutions starting with 1 µg/ml and allowed to bind for 1 h at room temperature. Binding was revealed with HRP-conjugated Protein A and TMB and read at 450 nm after stopping the reaction with $H_2SO_4$.

Figure 4:
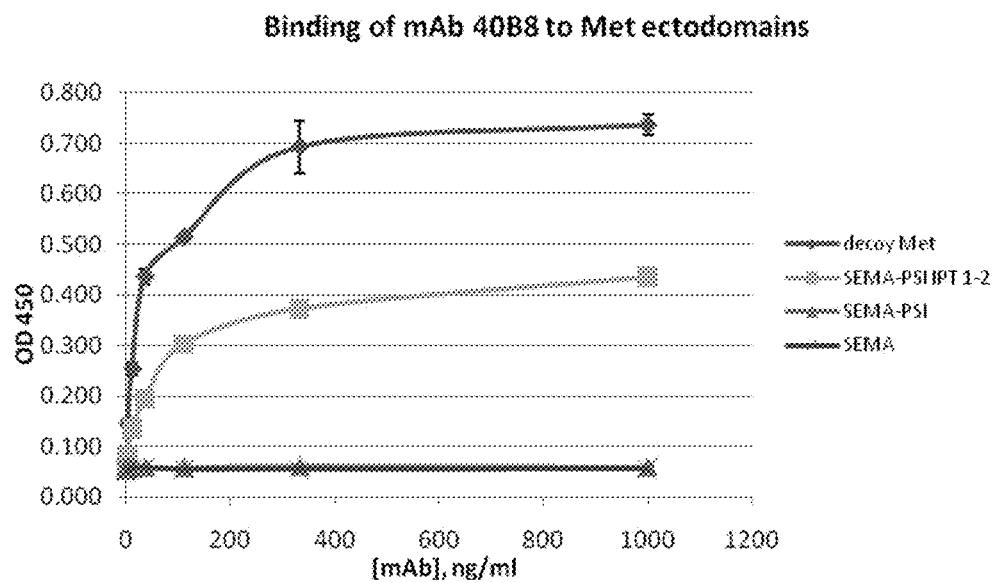
FIG. 4. ELISA illustrating antibody 40B8 binding to c-Met IPT1-2 domain (A) and 36C4 binding to c-Met SEMA domain (B).
Figure 4:
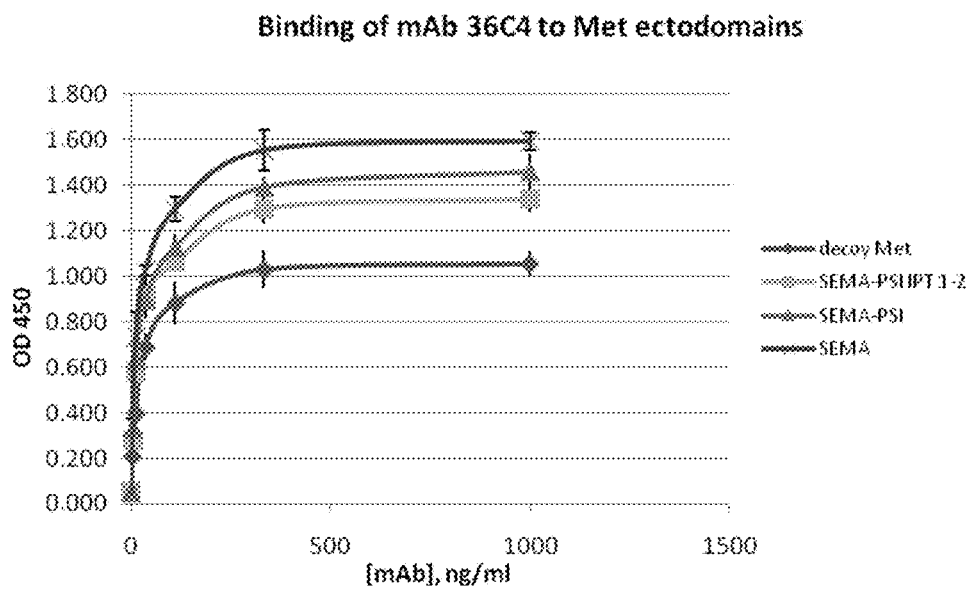

Based on the binding results, the mAbs could be mapped to different domains of c-Met, except for several mAbs that only bound to Decoy c-Met and not to any of the other domains tested (Table 8). Some antibodies binding only the Decoy c-Met may bind to the IPT 2-3 region or to a conformational epitope not seen on the recombinant c-Met protein fragments. An example of antibody 40B8 binding to the IPT1-2 domain is shown in FIG. 4A and 36C4 binding to the SEMA domain in FIG. 4B.

TABLE 8 c-Met domain recognition for antagonistic mAbs and off-rates of the corresponding Fabs

| mAb | Domain recognition | $k_{off}(10^{-4}s^{-1})$ |
|---|---|---|
| 12G4 | IPT1-2 | 1.3 |
| 13E6 | Decoy | 6.5 |
| 20F1 | SEMA | 69 |
| 20A11 | Decoy | 9 |
| 38H10 | IPT1-2 | 12 |
| 36C4 | SEMA | 6.4 |
| 40B8 | IPT1-2 | 13 |
| 34H7 | SEMA | 16 |

Example 4: Scatter Assay

Serum starved Human Pancreatic cancer cells (HPAF) cells were plated in 96-well plates, 7000 cells/well. At day 2, antibodies were added in triplicate at concentrations of 30, 10, 3 and 1 µg/ml and incubated with the cells for 30 minutes before 1.25 ng/ml HGF/well was added. The HPAF cells were also incubated with the antibodies in the absence of HGF. At day 3, the cells were fixed and stained with crystal violet. Scoring of the amount of scattering was done three times independently and by two different persons.

Figure 5:
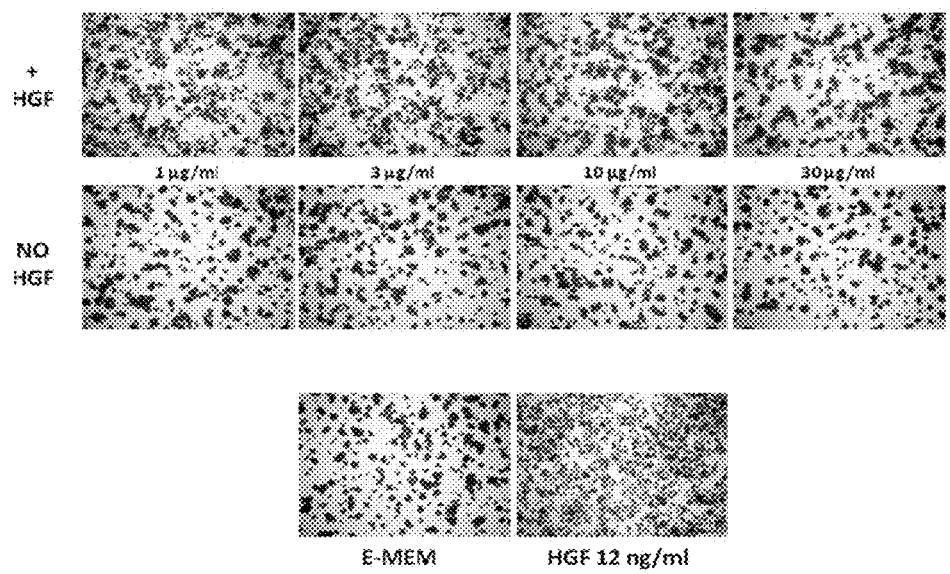
FIG. 5. The results of a scatter assay using HPAF cells demonstrating inhibition of HGF-induced scattering by antibody 38H10 in a dose-dependent manner (upper panel). No agonistic effects were observed compared to the medium only control.

The results showed a dose-dependent inhibition of HGF-induced scattering by the mAbs, with strong blocking for eight antibodies of the 13 tested, of which five (12G4, 20A11, 38H10, 36C4 and 40B8) showed complete blocking of the scattering at 30 µg/ml. All eight antagonistic mAbs (12G4, 13E6, 20F1, 20A11, 38H10, 34H7, 36C4 and 40B8) were also devoid of agonistic effects at 30 µg/ml in the absence of HGF. FIG. 5 shows an example of the scattering results of 38H10 in the presence and absence of HGF as compared to the medium control and the HGF control.

Example 5: Cross Reactivity to Rhesus and Mouse c-Met

Cross reactivity to Rhesus (*Maccaca mulatta*, US20090191580_5) c-Met ECD and mouse c-Met (R&D systems cat no: 527-ME) was performed in a binding ELISA. Rhesus ECD was immobilized in PBS (1 µg/ml) on a 96-well maxisorb plate and incubated at 4° C. over night. After blocking with 1% casein in PBS, the antibodies in dilutions starting with 10 µg/ml were added and allowed to bind for 1 h at room temperature. The plate was washed and a goat anti-human Fcγ antibody (Jackson) was added and incubated for 1 h at room temperature. After washing, TMB was added and the plate read at 620 nm.

Since the mouse c-Met also contained a Fc portion, the mAbs (2 µg/ml) were immobilized on a 96 well maxisorb plate over night at 4° C. and, after blocking, 100 ng/ml of the mouse c-Met was added and incubated for 1 h at room temperature. A HRP-conjugated mouse anti-His antibody (Serotech) was added and incubated for 1 h at room temperature. After washing, TMB was added and the plate read at 620 nm. A biotinylated goat anti-mouse c-Met antibody revealed with strep-HRP was used as a positive control for the mouse c-Met.

No significant binding (>10-fold) to mouse c-Met was observed for any of the mAbs.

All six mAbs tested showed cross-reactivity to Rhesus c-Met ECD with an almost identical binding compared to that on the human ECD c-Met (Decoy) (Table 9).

TABLE 9

EC50 (nM) of mAbs binding to Rhesus or human c-Met (Decoy)

| mAb | Rhesus | Human |
|---|---|---|
| 38H10 | 0.17 | 0.19 |
| 40B8 | 0.13 | 0.14 |
| 36C4 | 0.14 | 0.13 |
| 20A11 | 3.4 | 4.3 |
| 13E6 | 0.19 | 0.19 |
| 12G4 | 0.34 | 0.42 |

Example 6: Competition with HGF for Binding to c-Met

Figure 6:
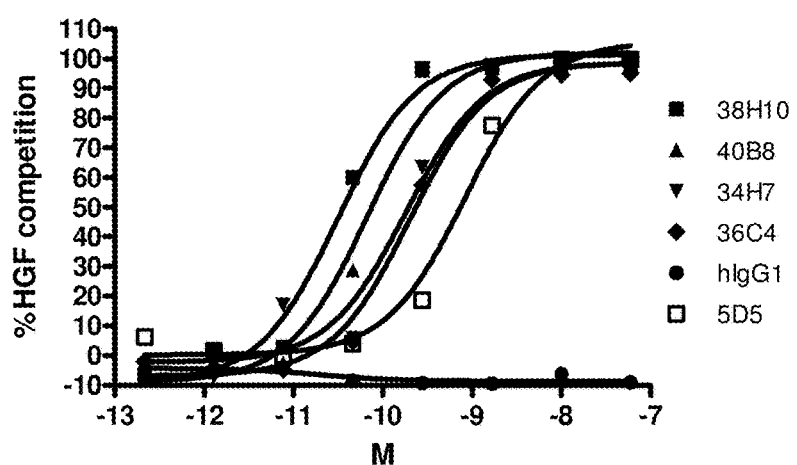
FIG. 6. An ELISA based competition assay illustrating the degree of competition between antibodies and HGF for binding c-Met at different antibody concentrations. Percentage competition was calculated compared to control antibodies.

Competition with N-terminally biotinylated HGF for binding to immobilized c-Met was performed using an ELISA-based competition assay. Five µg/ml mouse anti-His antibodies (Serotech) was immobilized on a maxisorb plate and, after blocking with 1% casein in PBS for 2 h, 100 ng/ml recombinant dimeric c-Met was added and incubated for 1 h at room temperature. After washing, dilutions of the antibodies were added and allowed to bind to the captured c-Met for 30 minutes, before 25 ng/ml N-terminally biotinylated HGF (R&D systems, 294-HGN/CF) was added. Biotinylated HGF was incubated at room temperature for 1 h before washing. Horseradish-conjugated streptavidin (strep-HRP) was added and incubated for an additional hour. TMB was added and the plate read at 620 nm. An isotype control (hIgG1λ) was included as a control as well as murine 5D5 antibody. Competition was expressed as percentage competition as compared to the controls (strep-HRP only or hIgG1λ) and plotted against the concentration of antibodies. An $IC_{50}$ was calculated using GraphPad Prism (Table 10). Antibodies 13E6 and 20A11 only displaced HGF partially (about 50%), which may be related to the epitope these two mAbs recognize on the c-Met. FIG. 6 shows an example of anti-c-Met antibodies competing with HGF for c-Met binding.

TABLE 10

$IC_{50}$ of mAbs competing with HGF for c-Met binding

| mAbs | $IC_{50}$ (nM) |
|---|---|
| 12G4 | 0.26 |
| 13E6 | partial |
| 20F1 | 0.36 |

Figure 7:
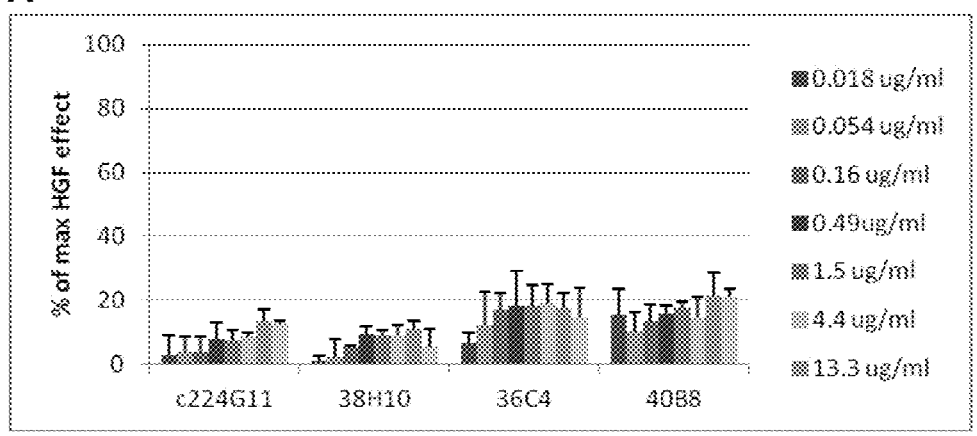
FIG. 7: Proliferation assay using BxPC3 cells. Chimeric 224G11 is c224G11. (A) Antibody-induced proliferation as a percentage of the maximum effect at 75 ng/ml of HGF. (B) The effect of antibodies on HGF-induced proliferation as compared to the maximum effect at 75 ng/ml of HGF.
Figure 7:
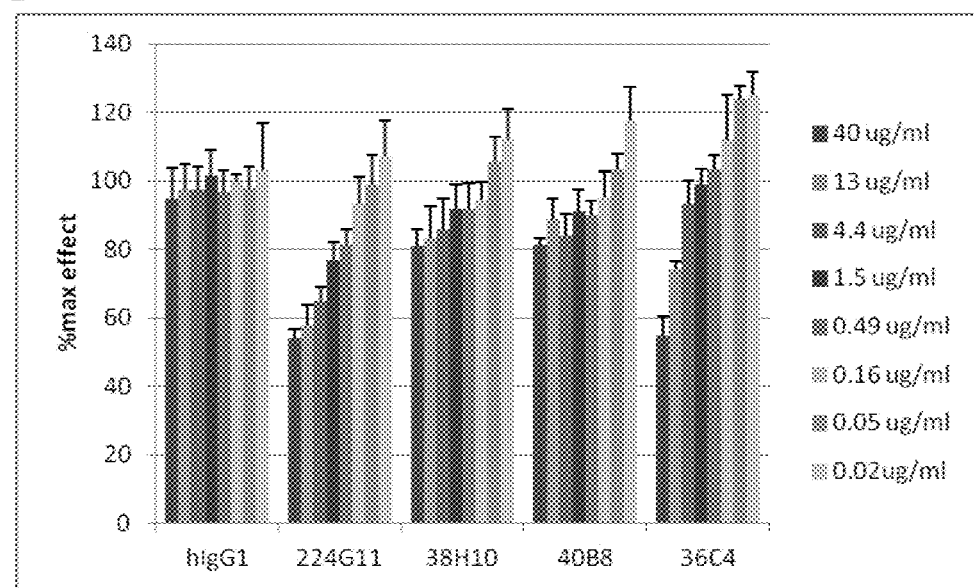

Example 7: Agonistic and Antagonistic Properties of mAbs Measured in the Proliferation Assay Using HGF-Dependent Pancreatic BxPC3 Cells Human pancreatic BxPC3 cells (ATCC cat no.CRL-1687) respond to HGF and were used for the proliferation assay to investigate the eight candidate mAbs further. In brief, 15,000 cells were seeded in the presence of serum and then serum starved over night following attachment (4-6 hours after seeding). The mAbs were added in doses from 20 ng/ml to 40 µg/ml in the presence or absence of 75 ng/ml HGF in order to test antagonism and agonism respectively. After three days incubation, Alamar blue was added to the cells and incubated at 37° C. for 4 hours before reading fluorescence at excitation 550 nm and emission 590 nm, thereby yielding a read-out on cell proliferation. The assay was repeated three times. An example of one independently performed experiment for agonism (FIG. 7A) and one for antagonism (FIG. 7B) is shown for the candidate mAbs and benchmark mAbs, including chimeric 224G11 (c224G11, Pierre Fabre). Proliferation is expressed as a percentage of the proliferation obtained with 75 ng/ml HGF. Three of the mAbs (38H10, 40B8 and 36C4) show less than 20% induced proliferation, with 38H10 in the same range as the benchmark c224G11.

Example 8: VL Shuffling for Improved Affinity

VL chain shuffling was used to improve the affinity of the two mAbs, 38H10 and 48A2. In this method, the heavy chain of the parental clone (VHCH1 of 36C4 or 38H10) was reintroduced in the phagemid-light chain library (see Example 1). The heavy chain was extracted from an expression vector, which lacks the bacteriophage-derived gene 3 necessary for display, to further avoid contamination of the parental light chain in the selection procedure. The heavy chain was cloned into the phagemid-light chain library and the ligated DNA was electroporated into E. coli TG1 cells to create the light chain shuffled library. The size of libraries was above $10^8$ clones.

Affinity selections, combined with off-rate washes, were performed to select for chain shuffled Fabs with an improved affinity for c-Met. A set-up was chosen where different amounts of Fab-expressing phages were incubated with different concentrations of Fc-Met in solution (see Table 11). By adding the c-Met in excess over the phage, but in a concentration lower than the desired affinity constant, the binding of the higher affinity phage was favored. The Fc-Met:phage complexes were then captured on a microtiterplate coated with an anti-Fc mAb. The plate was washed with decoy cMein solution at 37° C. to prevent the rebinding of dissociated phages to the captured Fc-Met. Each round the time of washing was increased (see Table 11) to select for phages with a better off-rate by washing away the lower affinity variants. Phages were eluted with trypsin and used for infection of E. coli TG1 cells. In total, 5 rounds of selection were done. In addition the amount of input phage was decreased in subsequent rounds to reduce background on the one hand and on the other hand to lower the mAb concentration thereby increasing the stringency of the selection.

Screenings of at least 30 clones from selection rounds III, IV and V were performed. The clones were grown in deep well plates (1 ml expressions) and periplasmic fractions were prepared. These periplasmic extracts were first tested for competition with HGF in an ELISA (see Example 2). For 38H10 the frequency of competing clones that gave low ELISA signals increased in subsequent selection rounds, with clear enrichment of the competitors in the different rounds.

The clones were then tested for their dissociation constants by Surface Plasmon Resonance. Around 3000 RU of Fc-Met was immobilized directly onto a CM5 chip to obtain a clear binding profile from the periplasmic extracts. Clones with an improved off-rate were sent for sequencing.

Originally paired light chains (both Vkappa for 38H10 and Vlambda for 36C4) were obtained after light chain shuffling, but an improved off-rate over the parental Fab was only found for 38H10 variant 48A2 (10-fold by Surface Plasmon Resonance). For 36C4 no improvement in affinity was obtained so the parental mAb was retained for further work.

TABLE 11

Parameter variation for each round of selection for VL shuffling.

|  | RI | RII | RIII | RIV | RV |
|---|---|---|---|---|---|
| Concentrations Fc-Met | 24 nM 2.4 nM 0.24 nM | 2.4 nM 0.24 nM 0.024 nM | 240 pM 24 pM 2.4 pM | 24 pM 2.4 pM 0.24 pM | 24 pM 2.4 pM 0.24 pM |
| Vol. Phage | 10 µl | 1 µl | 0.1 µl | 0.1 µl/0.01 µl | 0.1 µl/0.01 µl |
| Time of washing | 0 h | 2 h | O/N | O/3N | O/6N |
| Conditions | — | 37° C., 12 nM Decoy Met in 1% casein | 37° C., 1.2 nM Decoy Met in 1% casein | 37° C., 0.12 nM Decoy Met in 1% casein | 37° C., 0.12 nM Decoy Met in 1% casein |

A number of VL shuffled Fabs sharing the 38H10 heavy chain variable domain (SEQ ID NO: 49). The shuffled light chains are listed below (amino acid and nucleotide sequences are listed in Tables 6 and 7) together with the off-rates for the corresponding Fabs (each Fab includes 38H10 as the heavy chain) (Table 19).

TABLE 19

| VL shuffled Fab | $k_{off}(10^{-4}s^{-1})$ |
|---|---|
| 48A1 | 8.1 |
| 48A11 | 2.5 |
| 48B8 | 3.3 |
| 48D2 | 1.3 |
| 48B6 | 1.2 |
| 48A2 | 2.3 |
| 48C8 | 3.3 |
| 48E2 | 2.9 |
| 48E5 | 1.9 |
| 48D7 | 2.5 |
| 38H10 | 5.0 |

A number of VL shuffled Fabs sharing the 36C4Q heavy chain variable domain (SEQ ID NO: 88). The shuffled light chains are listed below (amino acid and nucleotide sequences are listed in Tables 6 and 7) together with the off-rates for the corresponding Fabs (each Fab includes 36C4Q as the heavy chain) (Table 20).

TABLE 20

| VL shuffled Fab | $k_{off}(10^{-4}s^{-1})$ |
|---|---|
| 49A1 | 1.7 |
| 49D2 | 1.7 |
| 49G3 | 1.9 |
| 49D3 | 8.2 |
| 49A11 | 4.8 |

TABLE 20-continued

| VL shuffled Fab | $k_{off}(10^{-4}s^{-1})$ |
|---|---|
| 49C4 | 1.8 |
| 49E11 | 6.3 |
| 36C4Q | 1.7 |

Example 9: Agonistic and Antagonistic Properties of mAbs Measured in the Phosphorylation Assay Using HGF-Dependent NSCLC A549 Cells In order to further investigate the mAbs a phosphorylation assay was set up using HGF-dependent NSCLC A549 cells (ATCC no. CCL-185). The cells were incubated both in the absence of HGF in order to assess agonistic activity of each antibody as well as in the presence of HGF in order to assess antagonistic potency of each antibody. In brief, 40,000 cells were plated and serum starved overnight after attachment to the plate (4-6 h after seeding). The cells were then treated for 15 minutes at 37° C. with mAbs. For the antagonism assay 100 ng/ml HGF was added and incubated for another 15 minutes at 37° C. HGF alone (100 ng/ml) was also tested to provide reference values for the experiment. The cells were washed with cold PBS and lysed with mild lysis buffer containing PMSF (Cell signalling #9803 including 1 mM PMSF, Sigma Aldrich) for 15 minutes on ice. 50 µl of the lysate was added per well in a 96-well plate pre-coated with goat anti-c-Met antibody and blocked with 1% casein-PBS. The c-Met in the lysate was then allowed to bind overnight at 4° C. Phospho-c-Met was revealed with a rabbit anti-pY1234/1235 antibody (Cell signaling) and a HRP-conjugated goat anti-rabbit antibody (Jackson Laboratories). TMB was added and the reaction stopped with 1M $H_2SO_4$ and read at 450 nm.

Figure 8:
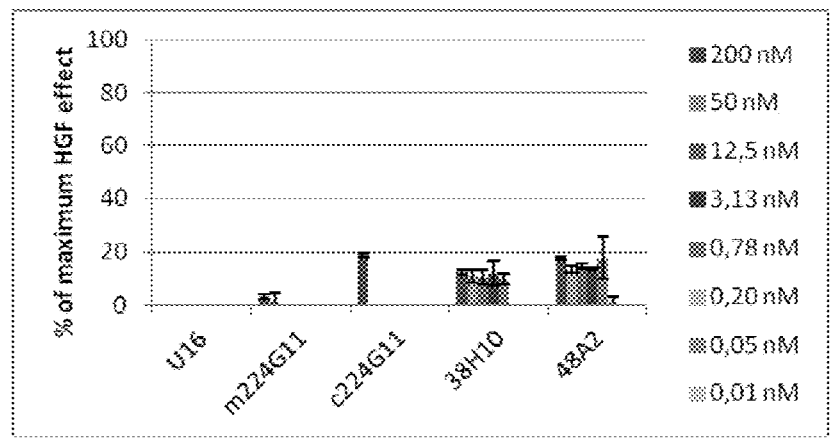
FIG. 8: Agonism as measured in a phosphorylation assay using NSCLC A549 cells. The percentage of c-Met phosphorylation induced by antibodies 38H10 and 48A2 (A) and 36C4 (B) is expressed as a percentage of phosphorylation induced by 100 ng/ml HGF. Murine 224G11 (m224G11) and chimeric 224G11 (c224G11) were included as positive controls and antibody U16 was included as a negative control.
Figure 8:
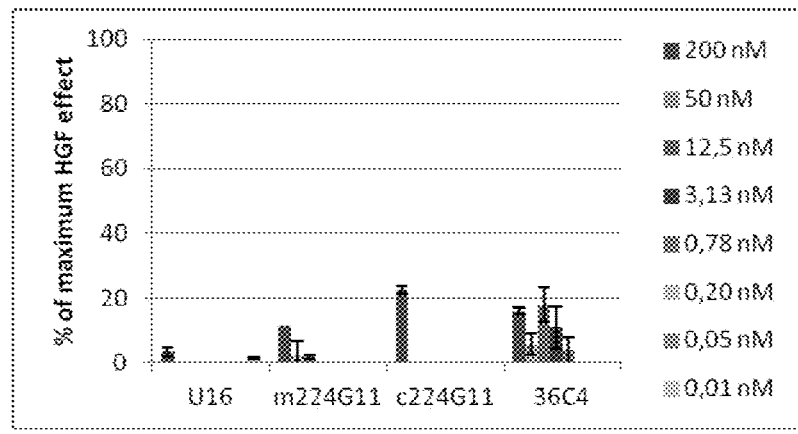
Figure 9:
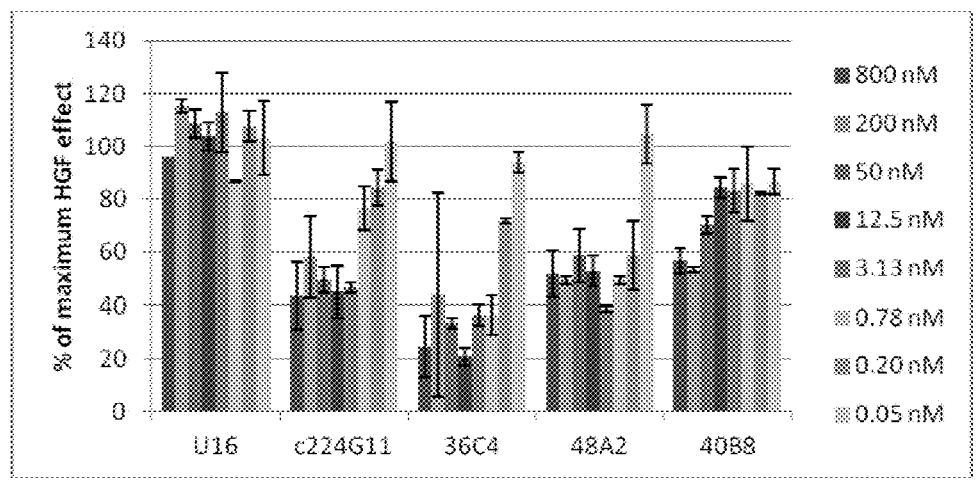
FIG. 9: Antagonism as measured in a phosphorylation assay using A549 cells. Inhibition of HGF-induced c-Met phosphorylation by antibodies is indicated as a percentage compared to the maximum effect of 100 ng/ml HGF alone in A549 cells. Chimeric 224G11 (c224G11) was included as positive control and antibody U16 as a negative control.

The antibodies were tested in duplicate at different concentrations, and the control mAbs U16 (irrelevant mAb, negative control), chimeric 224G11 (c224G11, Pierre Fabre) and murine 224G11 (mPF, Pierre Fabre) were included in each run alongside HGF only and cells only as positive and negative controls. FIG. 8A-B shows the low agonistic effects of three mAbs as compared to the controls. Compared to the benchmark c224G11, the antibodies 38H10, 48A2 and 36C4 (not shown) all give lower levels of phosphorylated c-Met. FIG. 9 shows the potency of mAbs 48A2, 36C4 and 40B8 in blocking HGF-induced phosphorylation compared to the benchmark c224G11, with 36C4 having the best blocking potency. The percentage phosphorylation is expressed as the percentage of maximum phosphorylation induced by 100 ng/ml HGF.

Phosphorylation assays using BxPC3 cells were done in the same way as for A549 cells and the results correlated very well to those obtained with the A549 cells (data not shown).

Example 10: Inhibitory Effect of Anti-cMet Antibodies on cMet Autophosphorylation MKN-45 Cells To examine the capability of the mAbs to inhibit phosphorylation in constitutively activated cells we used gastric MKN-45 cells (DMSZ cat no. ACC 409). These cells have a c-Met gene amplification resulting in over-expression of c-Met and thereby constitutive phosphorylation, i.e. independent of HGF.

Briefly, 5,000 cells were seeded in the presence of serum and incubated for 24 h with different concentrations of the mAbs at 37° C. An ELISA was performed for quantification of phosphorylated c-Met as described in Example 8.

Figure 10:
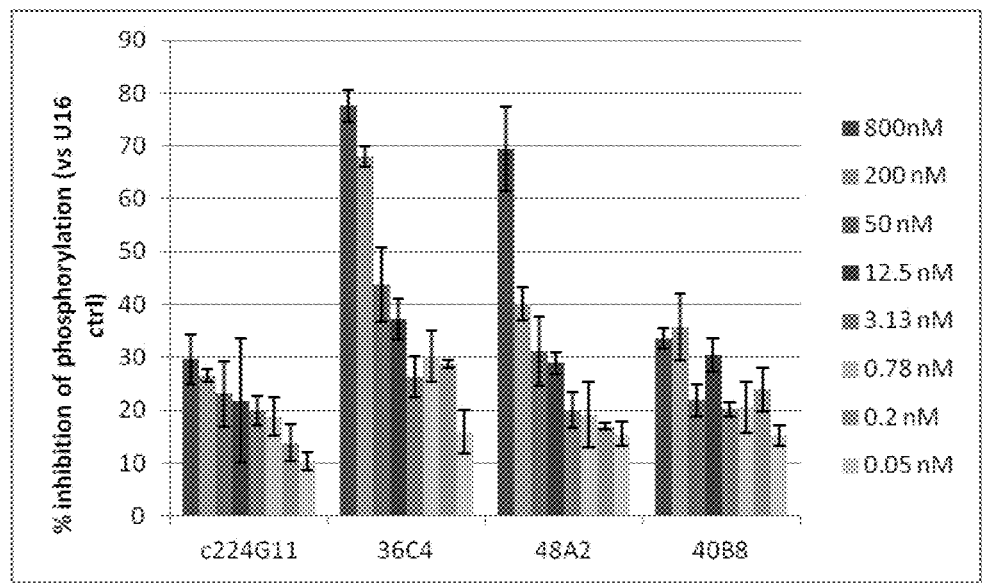
FIG. 10: Blocking of HGF-independent activation measured in a phosphorylation assay using MKN-45 cells Inhibition of autophosphorylation in MKN-45 cells by antibodies was compared to the negative control U16.1, where inhibition by U16.1 was set as 0%.

In FIG. 10 the blocking effect of the mAbs on cMet phosphorylation in MKN-45 cells can be seen (% inhibition). The response was normalized against the negative control mAb U16.1 (0% inhibition). It can be concluded that SIMPLE™ antibody 36C4 is the most potent inhibitor of HGF-independent phosphorylation in MKN-45 cells. c224G11 was not as potent as 36C4 and 48A2. 40B8 only blocks around 40% at the highest concentration and levels off rapidly.

Example 11: Antibody Induced ADCC in MKN-45 Cells 200,000 MKN-45 cells were seeded the day before addition of the antibody. Dilutions of antibodies were added to the cells and pre-incubated 60 minutes before effector cells (whole blood-derived PBMCs from one donor, incubated over night before addition to the target cells) were added at an E:T ratio (natural killer cells (NK):target cell line) of 5:1. The NK cell subpopulation in PBMCs was determined by flow cytometry for every donor as the ratio of anti-CD16 to anti-CD56. After 4 hrs incubation the plates were read using the Dead-Cell Protease Kit (CytoTox-Glo™ Cytotoxicity Assay from Promega (CAT# G9291)) to give the percentage of lysed cells.

Figure 11:
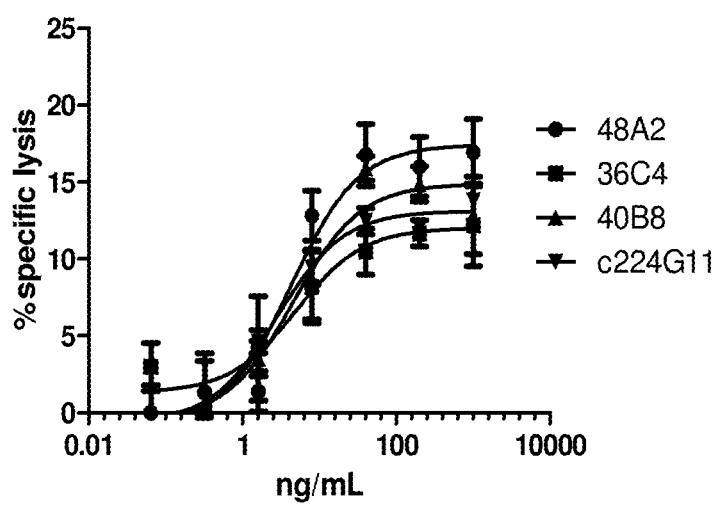
FIG. 11: Antibody-induced ADCC in MKN-45 cells using Dead-Cell Protease Kit (CytoTox-Glo™ Cytotoxicity Assay). The percentage lysis is expressed as specific lysis compared to the negative isotype control.

FIG. 11 shows the specific lysis induced by three mAbs, 48A2, 40B8 and 36C4, tested in a dose response compared with c224G11. The EC50 of the three tested mAbs is in the same in the same range as c224G11 (4.3, 4.6, 5.0, for 48A2, 40B8 and 36C4 and 2.8 ng/ml for c224G11).

Example 12: Potelligent™ 36C4 Induced ADCC in NCI-H441 Cells

Defucosylated 36C4 was produced in the Potelligent™ CHO cells (Biowa) and purified with Protein A. Human peripheral blood mononuclear cells (PBMC) from 3 donors were separately purified from heparinized whole blood by standard ficoll separation and were used as effector cells. The cells were suspended at $2 \times 10^6$/ml in media containing 200 U/ml of human IL-2 and incubated over night at 37° C. The following day, adherent and non-adherent cells were collected and washed once in culture media.

Target to effector ratios of 1:50 were used. The cells were suspended at $5 \times 10^6$ cells/ml and 100 µl added per well.

$10^6$ target cells NCI-H441, were incubated with 100 µCi $^{51}$Cr in 0.5 ml FCS for 60 minutes in a water bath at 37° C. The cells were washed, resuspended in 1 ml FCS and incubated for 30 minutes in a water bath at 37° C. Then the cells were washed twice with medium and brought to a final volume of $2 \times 10^5$ cells/ml and 50 µl was added per well.

The assay was carried out in triplicate. 50 µl of the labelled cells were incubated with 100 µl of effector cells and 50 µl of antibody. One row of a 96-well plate contained only target cells in order to control for spontaneous release of $^{51}$Cr. On another 96-well plate, one row of wells contained only target cells treated with 1% Triton-X (in order to completely lyse the cells) giving a read-out for maximum release of $^{51}$Cr. After 4 hours incubation at 37° C., 50 µl of supernatant was collected, transferred to a Lumaplate-96, dried and counted in a beta counter.

Figure 12:
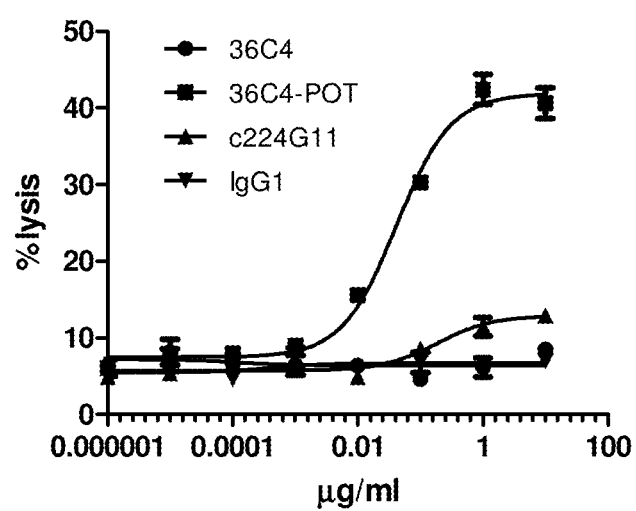
FIG. 12: Potelligent™ 36C4-induced ADCC in NCI-H441 cells expressed as percentage lysis of the cells as measured using a $^{51}Cr$ release assay.

The percent lysis was determined by the equation: % Lysis=(sample CPM−spontaneous release CPM)/(maximum release CPM−spontaneous release CPM)×100. FIG. 12 shows the percentage lysis of the NCI-H441 cells by Potelligent 36C4 (ADCC-enhanced by defucosylation) versus normal fucosylated 36C4. Defucosylated 36C4 (Potelligent 36C4) induces excellent lysis of NCI-H441 cells with an IC50 of 0.13 ng/ml, whereas normal fucosylated 36C4 does not induce any lysis of the NCI-H441 cells. The percentage lysis induced by c224G11 was very low. Clearly defucosylation of 36C4 dramatically enhances its capacity to induce ADCC of NCI-H441 cells.

Example 13: In Vitro Effect of ADCC-Enhanced 36C4 on NCI-H441 Cells

Non-fucosylated mAbs by the Potelligent™ technology has no significant effect in vivo in mice. However, Fc mutations (S239D, I332E) have been shown to have an effect in vivo, enhancing the ADCC effect of mAbs by increasing the affinity to the mouse FcγRIII, CD16 (Lazar G A et al, PNAS, 103. 2006).

The S239D, I332E mutations were inserted into the IgG1 of 36C4 using site-directed mutagenesis with specific primers, generating 36C4E. 36C4E was produced in the same way as the parental 36C4 using HEK293E cells and purified using Protein A. There was no difference in production levels or the level of HGF displacement in an ELISA based competition assay after the mutations as compared to the parental 36C4. The ADCC effect was investigated in the $^{51}$CR release assay on NCI-H441 cells (as described in Example 12). There was no effect of the 36C4 and the Potelligent 36C4 showed a slightly lower percentage lysis than the ADCC-enhanced Fc mutant 36C4E. The $EC_{50}$ for 36C4-POT vs 36C4E was 0.04 µg/ml versus 0.26 µg/ml.

Example 14: In Vivo Effect of ADCC-Enhanced 36C4 on MKN-45 Xenografts 6-8 week old CD-1 nude mice were injected subcutaneously with 3 million MKN-45 cells. The tumors were measurable after 8 days post injections and the treatment was started on day 9 with intraperitoneal injections twice per week with different amounts of test antibody. Groups of six mice were injected with 36C4E (30, 10, 3 and 1 mg/kg) and the volume of the tumors were measured (at the time injections were performed). An IgG1 isotype control (Synagis®) was included as a control as well as c224G11, both at the highest concentration 30 mg/kg.

Figure 13:
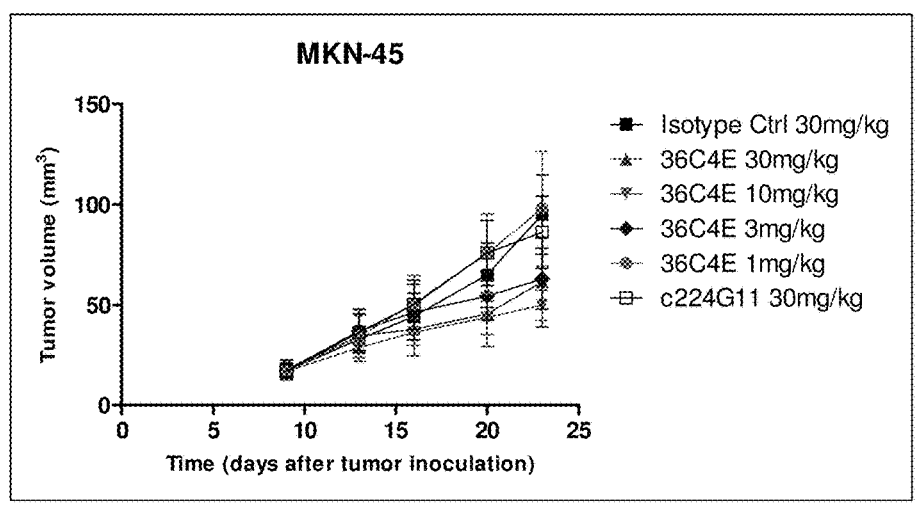
FIG. 13. In vivo effect of ADCC-enhanced 36C4 on MKN-45 xenografts with twice weekly injections of mAb.
Figure 14:
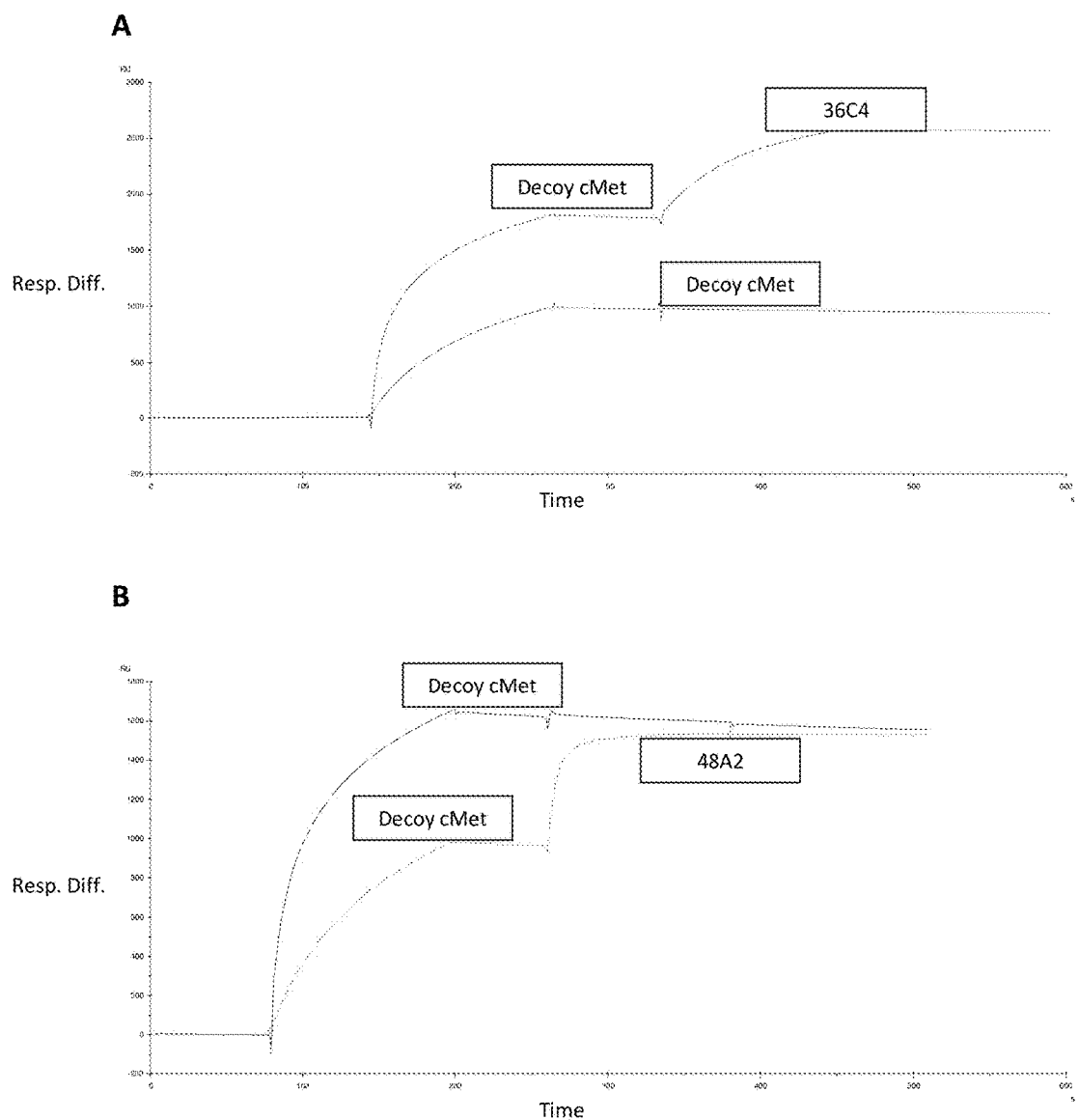
FIG. 14A-B. Surface Plasmon Resonance of 36C4 and 48A2 for binding to non-overlapping epitopes. Binding is observed to the Met:48A2 complex only (A) and to the Met:36C4 complex only (B).

At day 23 after the injection of the cells (15 days after the start of the treatment) a dose-dependent effect on the tumor volume could be observed in the mice treated with the 36C4-E. c224G11 had no effect on the tumor growth as compared to the isotype control (FIG. 13).

Example 15: Human-*Llama glama* Chimeric c-Met Fusion Proteins

Human-*Llama glama* chimeric c-Met ECD fusion proteins were constructed by exchanging the IPT domain of human and *Llama glama* c-Met in order to map the domain recognition of the mAbs. The construction was done using standard recombinant DNA and PCR methodologies. The *Llama glama* and human c-Met were amplified from RNA converted to cDNA from peripheral blood lymphocytes (PBLs) from two donors of each species. The llama and human c-Met ECD (aa 25-932) were cloned into a eukaryote expression vector with a His tag for expression as soluble proteins by HEK293 cells. The IPT1-4 (aa 568-932) from llama was exchanged with the human IPT1-4 in the human c-Met and conversely the human IPT1-4 was exchanged with the llama IPT1-4 in the llama c-Met using splicing and overlap extension PCR. All four constructs, llama c-Met, llama/human-IPT, human c-Met, human/llama-IPT were expressed in HEK293 cells and purified using IMAC columns FIG. 15 shows the alignment (88% identity) of human c-Met (Genbank X54559) with the *Llama glama* c-Met amplified from PBLs from two donors.

Example 16: Domain Mapping of mAbs Using Chimeric c-Met ECD 200 ng of the different chimeric recombinant cMet proteins were immobilized on maxisorb plates overnight at 4° C. After washing with PBS, the plates were blocked with 0.1% casein for 2 h at RT, before the mAbs were added and allowed to bind to the c-Met for 1 h at RT. After washing, HRP-conjugated goat anti-human antibody (diluted 1/5000, Jackson Labs) was added and incubated for 1 h at RT before additional washing and addition of TMB. The optical density at 620 nm was read and the values were represented in a graph against the concentration of mAbs.

Figure 16:
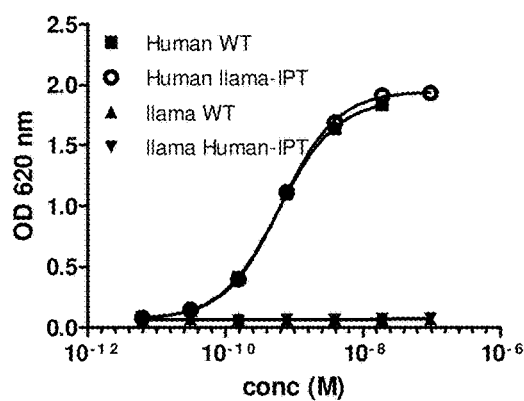
FIG. 16A-B. Domain mapping of mAbs using chimeric c-Met ECD. 36C4 binding to the human c-Met (WT) and the human/llama IPT1-4 indicating binding to the SEMA-PSI region (A). Binding of mAb 13E6 to the human c-Met and to the llama/human IPT1-4 (B).
Figure 16:
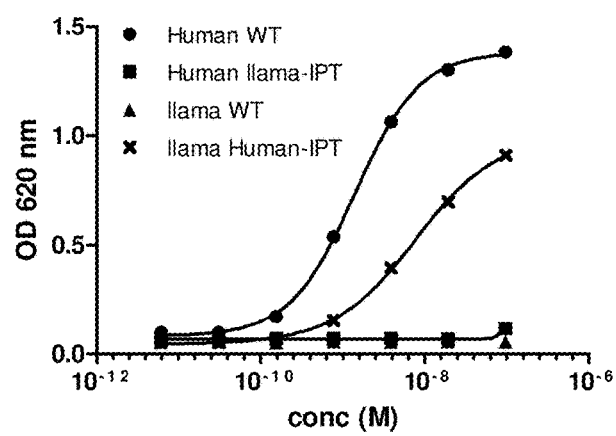

FIG. 16A shows binding of the 36C4 to the human c-Met (WT) and the human/llama IPT1-4 thus indicating binding to the SEMA-PSI region. FIG. 16B shows binding of mAb 13E6 to the human c-Met and to the llama/human IPT1-4. No binding was observed to the llama c-Met for any of the mAbs. 48A2 was also tested but mainly showed binding to the construct with the human SEMA-PSI and some binding to the construct with the human IPT, indicating that there was binding to an overlapping region in the PSI-IPT domains.

Example 17: Binding of 36C4 and 48A2 to Non-Overlapping Epitopes on c-Met Using Surface Plasmon Resonance To investigate if the two mAbs 36C4 and 48A2 bound to non-overlapping epitopes, 3000 RU of 36C4 or 48A2 were coupled to a CM5 chip. 60 µl of 40 µg/ml monomeric Decoy Met was injected to form a complex on the chip. 60 µl of 10 µg/ml 36C4 was injected (FIG. 16A). As shown in FIG. 16A, binding is observed to the Met:48A2 complex only. Similarly binding of 48A2 mAb to the Met:36C4 complex and Met:48A2 complex was performed using 3000 RU of 36C4 or 48A2 coupled to a CM5 chip. 60 µl 40 µg/ml Decoy Met was injected to perform a complex on the chip. Then 60 µl 10 µg/ml 48A2 was injected. Binding was observed to the Met:36C4 complex only as shown in FIG. 16B. These results indicate recognition of non-overlapping epitopes of mAbs 36C4 and 48A2.

Figure 17:
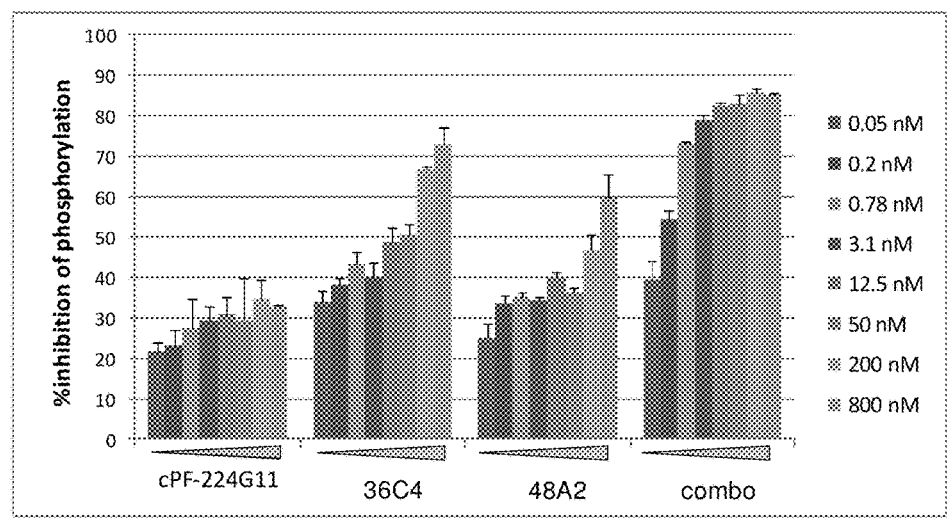
FIG. 17. Inhibition of autophosphorylation using combinations of c-Met mAbs in MKN-45 cells.

Example 18: Increased Inhibitory Effect on c-Met Autophosphorylation Using a Combination of Anti-cMet Antibodies The two mAbs 36C4 and 48A2, recognizing non-overlapping epitopes on c-Met as shown by Biacore (FIG. 16), were combined at ratio 1:1 in a phopshorylation assay using the HGF-independent MKN-45 cells as described in Example 10. The antibody mix was compared with 36C4 and 48A2 over a range of concentrations for the ability to block c-Met autophosphorylation (note that total antibody concentrations of the mix are equal to total antibody concentration for the individual antibodies: i.e. for the 0.2 nM dose the mix is 0.1 nM of each of 36C4 and 48A2, whilst for the pure mAb this would contain 0.2 nM 36C4 or 48A2). The combination showed significantly better inhibition of cMet autophosphorylation compared with the individual mAbs. At 0.78 nM mAb, the mix shows 75% inhibition of phosphorylation compared to 42% and 32% for 36C4 and 48A2 alone (FIG. 17). The combination of 36C4 and 48A2 was also more potent than the individual antibodies at blocking autophosphorylation of the NSCLC EBC-1 cells (data not shown).

Figure 18:
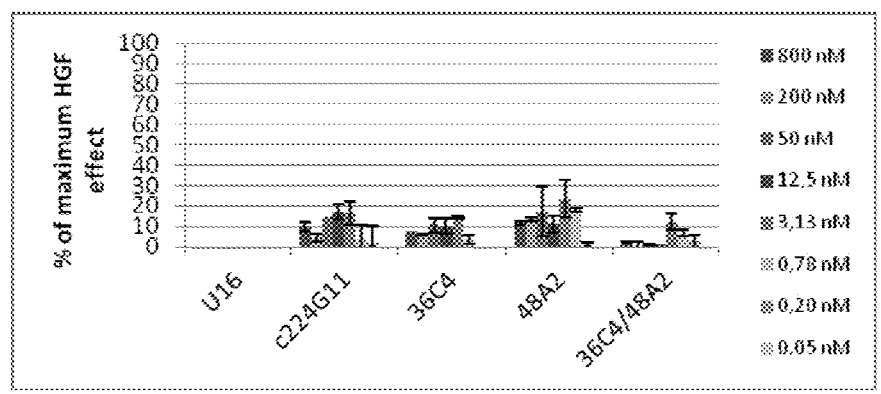
FIG. 18. The results of a phosphorylation assay using combinations of c-Met mAbs in NSCLC A549 cells showing agonistic effects (A) and antagonistic effects (B). U16 is the isotype control and c224G11 the positive control.
Figure 18:
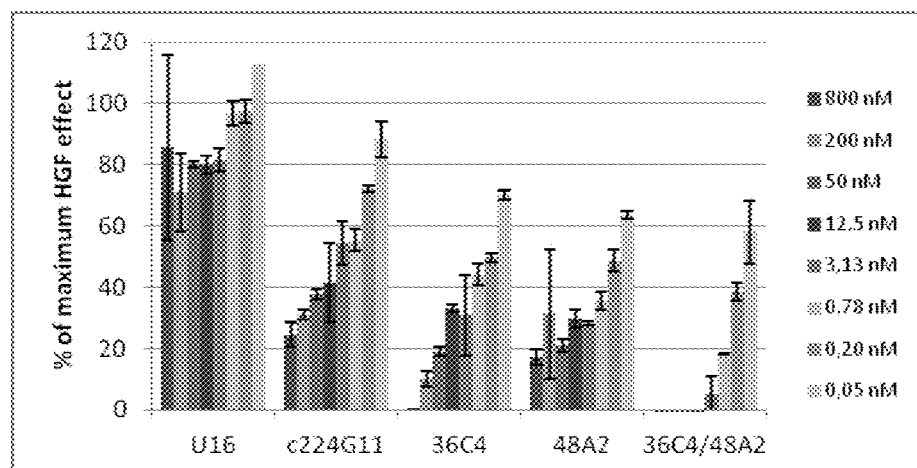

Example 19: Combination of Non-Overlapping mAbs Show Lower Levels of Agonism and Better Blocking Potency in a Phosphorylation Assay Using NSCLC A549 Cells A phosphorylation assay using NSCLC A549 cells was run as in Example 9 to investigate the mAbs 36C4 and 48A2 either in combination (ratio 1:1) or individually for their agonistic activity and antagonistic activity (in the absence or presence of HGF respectively). The level of agonism was lower for the combination (36C4 and 48A2) than for either of the mAbs alone (FIG. 18A) and the effect of blocking HGF-induced phosphorylation was significantly increased for the combination (36C4 and 48A2) compared to either mAb alone (FIG. 18B).

Example 20: Inhibition of Tumor Growth in a U87-MG Xenograft Model

Figure 19:
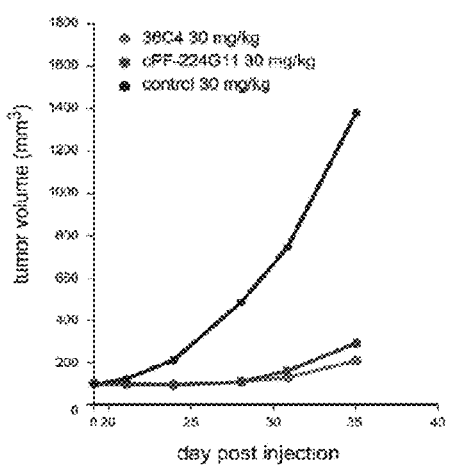
FIG. 19. In vivo U87 MG xenograft experiment testing the effects of administering 30 mg/kg 36C4 on tumour growth versus the effect of administering 30 mg/kg of c224G11.

To investigate the inhibitory effect of 36C4 mAb on tumor growth in vivo, 3×10$^6$ U87-MG cells with autocrine HGF (ATCC HTB-14) were injected subcutaneously in the right hind flank of Nude CD1 nu/nu mice. When the tumor reached 70-120 mm$^3$ (day 19), the mice were stratified and began treatment with 30 mg/kg intraperitoneal (i.p.) 36C4, c224G11 or isotype control antibody twice per week. The treatment continued until day 35 post-injection of the tumour cells, when the experiment was terminated. The tumor size was measured periodically during the experiment when mAbs were administered and the results are presented in FIG. 19. 30 mg/kg of 36C4 inhibits U87-MG tumor growth as well as the comparator mAb c224G11.

Example 21: Germlining of 36C4 and 48A2

The VH and VL sequences of 36C4 and 48A2 were blasted against human germline VH and VL sequences and 36C4 was closest related to the germline sequences of the IGHV4-30-4*01 (66/76 framework identity) and IGLV2-18*02 (61/69 framework identity). 48A2 was closest related to the germline sequences of IGHV1-46*01 (66/76 framework identity) and IGKV4-1*01 (53/70 framework identity).

The germlining process was performed as described in WO 2010/001251 and by Baca et al. (J. Biol. Chem. (1997) 272: 10678-10684) and Tsurushita et al. (J. Immunol. Methods (2004) 295: 9-19). It was a library/phage display approach, in which the deviating FR residues for both the human and the llama residues were incorporated. The germlined library of VH36C4 or 48A2 and VL36C4 and 48A2 were created by PCR-based gene assembly using overlapping oligonucleotides with specific mutations on certain positions (identified in Tables 3 and 4). The mutations were degenerate in order to encode the human as well as the llama amino acid, this being to prevent complete loss of binding in case the wild type residue is critical for high affinity binding. The assembled genes were cloned into a phagemid vector with the human CH and CL and TG1 *E. coli* were transformed generating libraries of a total size of 10$^9$ clones.

Phage display, applying stringent selection conditions (3-5 rounds of selections with decreasing the amount of antigen and phage and increasing length of competitive washes with access of c-Met), was used to select for functional Fabs (as described in Example 8). Individual clones were screened for off-rate and the best hits were sequenced to determine the human sequence identity. Clones with >94% human identity were produced by transient expression upon transfection of HEK293E cells and if productions were >15 µg/ml, they were further characterized.

TABLE 12

Amino acid sequences of the heavy and light chain variable domains of germlined variants of 36C4

>55A12-54E_VH (SEQ ID NO: 92)
QVQLVESGPGLVKPSQTLSLTCTVSGGSISTNYYYWSWIRQSPGKGLEWIGVIAYEGSTDYSPSLKSRV
TISRDTSKNQFSLKLSSVTAEDTAVYYCARDVRVIATGWATANALDAWGQGTLVTVSS

>55A12-54E_VL (SEQ ID NO: 93)
QSALTQPPSVSGSPGQSVTISCAGTSSDVGYGNYVSWYQQPPGTAPKLLIFAVSYRASGVPDRFSGSKS
GNTASLTISGLQAEDEADYYCASYRSSNNAAVFGGGTKLTVL

>53E2-54E_VH (SEQ ID NO: 94)
QVQLQESGPGLVKPSQTLSLTCAVSGGSISTNYYYWSWIRQHPGKGLEWIGVIAYEGSTDYSPSLKSRV
TISVDTSKNQFSLQLSSVTPEDTAVYYCARDVRVIATGWATANALDAWGQGTLVTVSS

>53E2-54E_VL (SEQ ID NO: 95)
QSALTQPRSVSGSPGQSVTISCAGTSSDVGYGNYVSWYQQHPGTAPKLMIFAVSYRASGIPDRFSGSKS
GNTAFLTISGLQAEDEADYYCASYRSSNNAAVFGGGTKLTVL

>53E3_VH (SEQ ID NO: 96)
QVQLQESGPGLVKPSQTLSLTCTVSGGSITTNYYYWSWIRQSPGKGLEWIGVIAYEGSTDYSPSLKSRV
TISRDTSKNQFSLQLSSVTAEDTAVYYCARDVRVIATGWATANALDAWGQGTLVTVSS

>53E3_VL (SEQ ID NO: 97)
QSVLTQPPSVSGSPGQTVTISCAGTSSDVGYGNYVSWYQQLPGTAPKLMIFAVSYRASGIPDRFSGSKS
GNTASLTISGLQSEDEADYYCASYRSSNNAAVFGGGTKLTVL

>53A11_VH (SEQ ID NO: 98)
QVQLQESGPGLVKPSQTLSLTCTVSGGSITTNYYYWSWIRQSPGKGLEWIGVIAYDASTDYSPSLKSRV
TISRDTSKNQFSLQLSSVTAEDTAVYYCARDVRVIATGWATANALDAWGQGTLVTVSS

TABLE 12 -continued

Amino acid sequences of the heavy and light chain variable domains of germlined variants of 36C4

>53A11_VL (SEQ ID NO: 99)
QSVLTQPPSVSGSPGQTVTISCAGTSSDVGYGNYVSWYQQPPGTAPKLMIFAVSYRASGIPDRFSGSKS
GNTAFLTISGLQSEDEADYYCASYRSSNNAAVFGGGTKLTVL

TABLE 13

Nucleotide sequences encoding heavy and light chain variable domains of germlined variants of 36C4

>55A12-54E_VH (SEQ ID NO: 100)
CAGGTGCAGCTCGTGGAGTCGGGCCCAGGCCTGGTGAAGCCCTCGCAGACACTCTCCCTCACCTG
CACAGTCTCTGGTGGCTCCATCAGCACCAACTATTACTACTGGAGCTGGATTCGCCAGTCGCCAGG
GAAGGGGCTGGAGTGGATTGGAGTCATAGCTTATGAAGGCAGCACTGACTACAGCCCATCCCTCA
AGAGCCGCGTGACCATCTCCAGGGACACGTCCAAAAACCAGTTCTCCCTGAAACTGAGCTCTGTG
ACCGCGGAGGACACGGCCGTGTATTACTGTGCCAGAGATGTAAGGGTAATCGCTACGGGTTGGGC
TACTGCCAATGCTTTGGACGCATGGGGCCAGGGGACCCTGGTCACCGTGTCCTCA

>55A12-54E_VL (SEQ ID NO: 101)
CAGTCTGCGTTGACGCAGCCTCCTTCCGTGTCTGGGTCTCCAGGACAAAGCGTCACCATCTCCTGT
GCAGGAACCAGCAGTGATGTTGGGTATGGAAACTATGTCTCCTGGTACCAGCAGCCGCCAGGCAC
GGCCCCCAAACTCCTGATCTTTGCAGTCAGCTATCGAGCCTCAGGGGTTCCTGATCGCTTCTCTGG
CTCCAAGTCAGGCAACACGGCCTCTTTGACCATCTCTGGGCTCCAGGCTGAGGACGAGGCTGATTA
TTACTGTGCCTCATATAGAAGCAGCAACAATGCTGCTGTGTTCGGCGGAGGGACCAAACTGACCG
TCCTA

>53E2-54E_VH (SEQ ID NO: 102)
CAGGTGCAGCTCCAGGAGTCGGGCCCAGGCCTGGTGAAGCCCTCGCAGACACTCTCCCTCACCTG
CGCAGTCTCTGGTGGCTCCATCAGCACCAACTATTACTACTGGAGCTGGATTCGCCAGCATCCAGG
GAAGGGGCTGGAGTGGATTGGAGTCATAGCTTATGAAGGCAGCACTGACTACAGCCCATCCCTCA
AGAGCCGCGTGACCATCTCCGTGGACACGTCCAAGAACCAGTTCTCCCTGCAACTGAGCTCTGTGA
CCCCGGAGGACACGGCCGTGTATTACTGTGCCAGAGATGTAAGGGTAATCGCTACGGGTTGGGCT
ACTGCCAATGCTTTGGACGCATGGGGCCAGGGGACCCTGGTCACCGTGTCCTCA

>53E2-54E_VL (SEQ ID NO: 103)
CAGTCTGCGTTGACGCAGCCTCGTTCCGTGTCTGGGTCTCCAGGACAAAGCGTCACCATCTCCTGT
GCAGGAACCAGCAGTGATGTTGGGTATGGAAACTATGTCTCCTGGTACCAGCAGCATCCAGGCAC
GGCCCCCAAACTCATGATCTTTGCAGTCAGCTATCGAGCCTCAGGGATTCCTGATCGCTTCTCTGG
CTCCAAGTCAGGCAACACGGCCTTTTTGACCATCTCTGGGCTCCAGGCTGAGGACGAGGCTGATTA
TTACTGTGCCTCATATAGAAGCAGCAACAATGCTGCTGTGTTCGGCGGAGGGACCAAACTGACCG
TCCTA

>53E3_VH (SEQ ID NO: 104)
CAGGTGCAGCTCCAGGAGTCGGGCCCAGGCCTGGTGAAGCCCTCGCAGACACTCTCCCTCACCTG
CACAGTCTCTGGTGGCTCCATCACCACCAACTATTACTACTGGAGCTGGATTCGCCAGTCTCCAGG
GAAGGGGCTGGAGTGGATTGGAGTCATAGCTTATGAAGGCAGCACTGACTACAGCCCATCCCTCA
AGAGCCGCGTGACCATCTCCAGGGACACGTCCAAGAACCAGTTCTCCCTGCAACTGAGCTCTGTG
ACCGCGGAGGACACGGCCGTGTATTACTGTGCCAGAGATGTAAGGGTAATCGCTACGGGTTGGGC
TACTGCCAATGCTTTGGACGCATGGGGCCAGGGGACCCTGGTCACCGTGTCCTCA

>53E3_VL (SEQ ID NO: 105)
CAGTCTGTGTTGACGCAGCCTCCTTCCGTGTCTGGGTCTCCAGGACAAACCGTCACCATCTCCTGT
GCAGGAACCAGCAGTGATGTTGGGTATGGAAACTATGTCTCCTGGTACCAGCAGCTGCCAGGCAC
GGCCCCCAAACTCATGATCTTTGCAGTCAGCTATCGAGCCTCAGGGATTCCTGATCGCTTCTCTGG
CTCCAAGTCAGGCAACACGGCCTCTTTGACCATCTCTGGGCTCCAGTCTGAGGACGAGGCTGATTA
TTACTGTGCCTCATATAGAAGCAGCAACAATGCTGCTGTGTTCGGCGGAGGGACCAAACTGACCG
TCCTA

>53A11_VH (SEQ ID NO: 106)
CAGGTGCAGCTCCAGGAGTCGGGCCCAGGCCTGGTGAAGCCCTCGCAGACACTCTCCCTCACCTG
CACAGTCTCTGGTGGCTCCATCACCACCAACTATTACTACTGGAGCTGGATTCGCCAGTCGCCAGG
GAAGGGGCTGGAGTGGATTGGAGTCATAGCTTATGATGCGAGCACTGATTACAGCCCATCCCTCA
AGAGCCGCGTGACCATCTCCAGGGACACGTCCAAGAACCAGTTCTCCCTGCAACTGAGCTCTGTG
ACCGCGGAGGACACGGCCGTGTATTACTGTGCCAGAGATGTAAGGGTAATCGCTACGGGTTGGGC
TACTGCCAATGCTTTGGACGCATGGGGCCAGGGGACCCTGGTCACCGTGTCCTCA

>53A11_VL (SEQ ID NO: 107)
CAGTCTGTGTTGACGCAGCCTCCTTCCGTGTCTGGGTCTCCAGGACAAACCGTCACCATCTCCTGT
GCAGGAACCAGCAGTGATGTTGGGTATGGAAACTATGTCTCCTGGTACCAGCAGCCGCCAGGCAC
GGCCCCCAAACTCATGATCTTTGCAGTCAGCTATCGAGCCTCAGGGATTCCTGATCGCTTCTCTGG
CTCCAAGTCAGGCAACACGGCCTTTTTGACCATCTCTGGGCTCCAGTCTGAGGACGAGGCTGATTA
TTACTGTGCCTCATATAGAAGCAGCAACAATGCTGCTGTGTTCGGCGGAGGGACCAAACTGACCG
TCCTA

TABLE 14

Amino acid sequences of the heavy and light chain variable domains of germlined variants of 48A2

>56F3_VH (SEQ ID NO: 108)
EVQLVQPGAEVKKPGASVKVSCKASGYIFTMNSIDWVRQAPGQGLEWMGRIDPEEGGTKYAQKF
QGRVTMTADTSTSTAYMELSSERSDDTAVYYCARVDDYYLGYDYWGQGTQVIVSS

>56F3_VK (SEQ ID NO: 109)
DIVMTQSPDSLAASEGERVTINCKSSQSVLFSSNQKNYLAWYQQRPGQSPKLLIYWASIRESGVPDR
FSGSGSGTDFTLTISSLQAEDVAVYYCQQGYSFPYSFGSGTRLEIK

>56D8_VH (SEQ ID NO: 110)
QVQLVQSGAEVKKPGASVKVSCKASGYIFTMNSIDWVRQAPGQGLEWMGRIDPEEGGTKYAQKF
QGRVTFTRDTSTSTAYMELSSERSDDTAVYYCARVDDYYLGYDYWGQGTQVIVSS

>56D8_VK (SEQ ID NO: 111)
DIVMTQSPDSETASEGERVTINCKSSQSVLFSSNQKNYLAWYQQKPGQSPKLLIYWASIRESGVPDR
FSGSGSGTDFTLTISSLQPEDVAVYYCQQGYSFPYSFGQGTRLEIR

>56B1_VH (SEQ ID NO: 112)
EVQLVQPGAEVKKPGASVKVSCKASGYTFTMNSIDWVRQAPGQGLEWMGRIDPEEGGTKYAQKF
QGRVTFTRDTSTSTAYVELSSLRSDDTAVYYCARVDDYYLGYDYWGQGTLVTVSS

>56B1_VK (SEQ ID NO: 113)
DIVMTQSPDSLAVSEGERVTINCKSSQSVLFSSNQKNYLAWYQQKPGQSPRLLIYWASIRESGVPDR
FSGSGSATDFTLTISSLQAEDVAVYYCQQGYSFPYSFGQGTRIFIR

>56E9_VH (SEQ ID NO: 114)
QVQLVQPGVEVKKPGASVKVSCKASGYIFTMNSIDWVRQAPGQGLEWMGRIDPEEGGTKY
AQKFQGRVTFTADTSTSTAYMELSSIRSDDTAVYYCARVDDYYLGYDYWGQGTQVIVSS

>56E9_VK (SEQ ID NO: 115)
DIVMTQSPTSVAVSEGERATINCKSSQSVLFSSNQKNYLAWYQQKPGQPPRELIYWASIR
ESGVPDRFSGSGSGTDFTLTISSLQPEDVAVYYCQQGYSFPYSFGQGTRIFIR

>56E5_VH (SEQ ID NO: 116)
QVQLVQPGAEVKKPGASVKVSCKASGYIFTMNSIDWVRQAPGQGLEWMGRIDPEEGGIKY
AQKFQGRVTFTADTSTSTAYVELNSERSEDTAVYYCARVDDYYLGYDYWGQGTQVIVSS

>56E5_VK (SEQ ID NO: 117)
DIVMTQSPDSLAVSLGEKVTINCKSSQSVLFSSNQKNYLAWYQQRPGQPPKLLIYWASIR
ESGVPDRFSGSGSATDFTLTISSLQPEDVAVYYCQQGYSFPYSFGQGTRIFIK

>56E1_VH (SEQ ID NO: 118)
QVQLVQPGAELRNPGASVKVSCKASGYTFTMNSIDWVRQAPGQGLEWMGRIDPEEGGTKYAQKF
QGRVTMTRDTSTSTAYMELSSERSEDTAVYYCARVDDYYLGYDYWGQGTQVIVSS

>56E1_VK (SEQ ID NO: 119)
DIVMTQTPDSLAVSAGERVTINCKSSQSVLFSSNQKNYLAWYQQKPGQSPKLLIYWASIRESGVPDR
FSGSGSGTDFTETISSLQPEDVTVYYCQQGYSFPYSFGQGTRLEIK

>56G5_VH (SEQ ID NO: 120)
QVQLVQPGAEVKKPGASVKVSCKASGYIFTMNSIDWVRQAPGQGLEWMGRIDPEEGGTKYAQKF
QGRVTMTADTSTSTAYMELNSERSEDTAVYYCARVDDYYLGYDYWGQGTLVTVSS

>56G5_VK (SEQ ID NO: 121)
DIVMTQTPTSLAPSAGERATINCKSSQSVLFSSNQKNYLAWYQQKPGQPPKLLIYWASIRESGVPDR
FSGSGSATDFTLTISSLQPEDVAVYYCQQGYSFPYSFGSGTRLEIK

TABLE 15

Nucleotide sequences encoding heavy and light chain variable domains of germlined variants of 48A2

>56F3_VH (SEQ ID NO: 122)
GAGGTCCAGCTGGTGCAGCCAGGGGCGGAAGTGAAAAAACCTGGGGCATCAGTGAAGGTC
TCCTGCAAGGCTTCTGGATACATCTTCACCATGAACTCAATAGACTGGGTGCGACAGGCC
CCTGGACAAGGGCTTGAGTGGATGGGAAGAATTGACCCTGAAGAGGGTGGCACAAAGTAT
GCACAGAAGTTCCAGGGCAGAGTCACCATGACTGCAGACACGTCCACCAGCACAGCCTAC
ATGGAGCTGAGCAGTCTGAGATCTGACGACACGGCCGTGTATTACTGTGCGAGAGTAGAT
GACTATTACCTTGGGTATGACTACTGGGGCCAGGGGACCCAGGTCACCGTCTCCTCA

>56F3_VK (SEQ ID NO: 123)
GATATTGTGATGACCCAGAGCCCCGATTCCTTGGCAGCGTCTTTAGGAGAACGTGTGACC
ATCAATTGTAAGTCCAGCCAGAGTGTGTTATTCAGCTCCAACCAGAAAAACTACTTAGCT
TGGTACCAGCAGAGACCGGGACAGTCTCCTAAGCTGCTCATCTACTGGGCTTCCATCCGA
GAATCGGGGGTTCCTGATCGATTCAGCGGCAGTGGGTCCGGCACAGATTTCACGCTAACC

TABLE 15 -continued

Nucleotide sequences encoding heavy and light chain variable
domains of germlined variants of 48A2

ATCAGCTCTCTTCAGGCTGAAGACGTGGCAGTATATTACTGCCAGCAGGGTTATAGTTTT
CCATATAGTTTCGGCAGTGGGACCAGGCTCGAGATCAAA

>56D8_VH (SEQ ID NO: 124)
CAGGTCCAGCTGGTGCAGTCTGGGGCGGAAGTGAAAAAACCTGGGGCATCAGTGAAGGTC
TCCTGCAAGGCTTCTGGATACACCTTCACCATGAACTCAATAGACTGGGTGCGAGAGGCC
CCTGGACAAGGGCTTGAGTGGATGGGAAGAATTGACCCTGAAGAGGGTGGCACAAAGTAT
GCACAGAAGTTCCAGGGCAGAGTCACCTTCACTCGAGACACGTCCACCAGCACAGCCTAC
ATGGAGCTGAGCAGTCTGAGATCTGACGACACGGCCGTGTATTACTGTGCGAGAGTAGAT
GACTATTACCTTGGGTATGACTACTGGGGCCAGGGGACCCAGGTCACCGTCTCCTCA

>56D8_VK (SEQ ID NO: 125)
GATATTGTGATGACCCAGAGCCCCGATTCCTTGACAGCGTCTTTAGGAGAACGTGTGACC
ATCAATTGTAAGTCCAGCCAGAGTGTGTTATTCAGCTCCAACCAGAAAAACTACTTAGCT
TGGTACCAGCAGAAACCGGGACAGTCTCCTAAGCTGCTCATCTACTGGGCTTCCATCCGA
GAATCGGGGGTTCCTGATCGATTCAGCGGCAGTGGGTCCGGCACAGATTTCACGCTAACC
ATCAGCTCTCTTCAGCCTGAAGACGTGGCAGTATATTACTGCCAGCAGGGTTATAGTTTT
CCATATAGTTTCGGCCAGGGCACCAGGCTCGAGATCAGA

>56B1_VH (SEQ ID NO: 126)
GAGGTCCAGCTGGTGCAGCCAGGGGCGGAAGTGAAAAAACCTGGGGCATCAGTGAAGGTC
TCCTGCAAGGCTTCTGGATACACCTTCACCATGAACTCAATAGACTGGGTGCGAGAGGCC
CCTGGACAAGGGCTTGAGTGGATGGGAAGAATTGACCCTGAAGAGGGTGGCACAAAGTAT
GCACAGAAGTTCCAGGGCAGAGTCACCTTCACTCGAGACACGTCCACCAGCACAGCCTAC
GTGGAGCTGAGCAGTCTGAGATCTGACGACACGGCCGTGTATTACTGTGCGAGAGTAGAT
GACTATTACCTTGGGTATGACTACTGGGGCCAGGGGACCCTGGTCACCGTCTCCTCA

>56B1_VK (SEQ ID NO: 127)
GATATTGTGATGACCCAGAGCCCCGATTCCTTGGCAGTGTCTGAAGGAGAACGTGTGACC
ATCAATTGTAAGTCCAGCCAGAGTGTGTTATTCAGCTCCAACCAGAAAAACTACTTAGCT
TGGTACCAGCAGAAACCGGGACAGTCTCCTAGGCTGCTCATCTACTGGGCTTCCATCCGA
GAATCGGGGGTTCCTGATCGATTCAGCGGCAGTGGGTCCGCCACAGATTTCACGCTAACC
ATCAGCTCTCTTCAGGCTGAAGACGTGGCAGTATATTACTGCCAGCAGGGTTATAGTTTT
CCATATAGTTTCGGCCAGGGGACCAGGCTCGAGATCAGA

>56E9_VH (SEQ ID NO: 128)
CAGGTCCAGCTGGTGCAGCCAGGGGTGGAAGTGAAAAAACCTGGGGCATCAGTGAAGGTC
TCCTGCAAGGCTTCTGGATACACCTTCACCATGAACTCAATAGACTGGGTGCGACAGGCC
CCTGGACAAGGGCTTGAGTGGATGGGAAGAATTGACCCTGAAGAGGGTGGCACAAAGTAT
GCACAGAAGTTCCAGGGCAGAGTCACCTTCACTGCAGACACGTCCACCAGCACAGCCTAC
ATGGAGCTGAGCAGTCTGAGATCTGACGACACGGCCGTGTATTACTGTGCGAGAGTAGAT
GACTATTACCTTGGGTATGACTACTGGGGCCAGGGGACCCAGGTCACCGTCTCCTCA

>56E9_VK (SEQ ID NO: 129)
GATATTGTGATGACCCAGAGCCCCACCTCCGTGGCAGTGTCTTTAGGAGAACGTGCGACCAT
CAATTGTAAGTCCAGCCAGAGTGTGTTATTCAGCTCCAACCAGAAAAACTACTTAGCTTGGT
ACCAGCAGAAACCGGGACAGCCTCCTAGGCTGCTCATCTACTGGGCTTCCATCCGAGAATCG
GGGGTTCCTGATCGATTCAGCGGCAGTGGGTCCGGCACAGATTTCACGCTAACCATCAGCTCT
CTTCAGCCTGAAGACGTGGCAGTATATTACTGCCAGCAGGGTTATAGTTTTCCATATAGTTTCG
GCCAGGGGACCAGGCTCGAGATCAGA

>56E5_VH (SEQ ID NO: 130)
CAGGTCCAGCTGGTGCAGCCAGGGGCGGAAGTGAAAAAACCTGGGGCATCAGTGAAGGTC
TCCTGCAAGGCTTCTGGATACACCTTCACCATGAACTCAATAGACTGGGTGCGACAGGCC
CCTGGACAAGGGCTTGAGTGGATGGGAAGAATTGACCCTGAAGAGGGTGGCACAAAGTAT
GCACAGAAGTTCCAGGGCAGAGTCACCTTCACTGCAGACACGTCCACCAGCACAGCCTAC
GTGGAGCTGAACAGTCTGAGATCTGAGGACACGGCCGTGTATTACTGTGCGAGAGTAGAT
GACTATTACCTTGGGTATGACTACTGGGGCCAGGGGACCCAGGTCACCGTCTCCTCA

>56E5_VK (SEQ ID NO: 131)
GATATTGTGATGACCCAGAGCCCCGATTCCTTGGCAGTGTCTTTAGGAGAAAAGGTGACCAT
CAATTGTAAGTCCAGCCAGAGTGTGTTATTCAGCTCCAACCAGAAAAACTACTTAGCTTGGT
ACCAGCAGAGACCGGGACAGCCTCCTAAGCTGCTCATCTACTGGGCTTCCATCCGAGAATCG
GGGGTTCCTGATCGATTCAGCGGCAGTGGGTCCGCCACAGATTTCACGCTAACCATCAGCTCT
CTTCAGCCTGAAGACGTGGCAGTATATTACTGCCAGCAGGGTTATAGTTTTCCATATAGTTTCG
GCCAGGGGACCAGGCTCGAGATCAAA

>56E1_VH (SEQ ID NO: 132)
GAGGTCCAGCTGGTGCAGCCAGGGGCGGAACTGAGAAACCCTGGGGCATCAGTGAAGGTC
TCCTGCAAGGCTTCTGGATACACCTTCACCATGAACTCAATAGACTGGGTGCGACAGGCC
CCTGGACAAGGGCTTGAGTGGATGGGAAGAATTGACCCTGAAGAGGGTGGCACAAAGTAT
GCACAGAAGTTCCAGGGCAGAGTCACCATGACTCGAGACACGTCCACCAGCACAGCCTAC
ATGGAGCTGAGCAGTCTGAGATCTGAGGACACGGCCGTGTATTACTGTGCGAGAGTAGAT
GACTATTACCTTGGGTATGACTACTGGGGCCAGGGGACCCAGGTCACCGTCTCCTCA

TABLE 15 -continued

Nucleotide sequences encoding heavy and light chain variable
domains of germlined variants of 48A2

>56E1_VK (SEQ ID NO: 133)
GATATTGTGATGACCCAGACCCCCGATTCCTTGGCAGTGTCTGCAGGAGAACGTGTGACC
ATCAATTGTAAGTCCAGCCAGAGTGTGTTATTCAGCTCCAACCAGAAAAACTACTTAGCT
TGGTACCAGCAGAAACCGGGACAGTCTCCTAAGCTGCTCATCTACTGGGCTTCCATCCGA
GAATCGGGGGTTCCTGATCGATTCAGCGGCAGTGGGTCCGGCACAGATTTTACGCTAACC
ATCAGCTCTCTTCAGCCTGAAGACGTGACAGTATATTACTGCCAGCAGGGTTATAGTTTT
CCATATAGTTTCGGCCAGGGGACCAGGCTCGAGATCAAA

>56G5_VH (SEQ ID NO: 134)
CAGGTCCAGCTGGTGCAGCCAGGGGCGGAAGTGAAAAAACCTGGGGCATCAGTGAAGGTC
TCCTGCAAGGCTTCTGGATACATCTTCACCATGAACTCAATAGACTGGGTGCGACAGGCC
CCTGGACAAGGGCTTGAGTGGATGGGAAGAATTGACCCTGAAGAGGGTGGCACAAAGTAT
GCACAGAAGTTCCAGGGCAGAGTCACCATGACTGCAGACACGTCCACCAGCACAGCCTAC
ATGGAGCTGAACAGTCTGAGATCTGAGGACACGGCCGTGTATTACTGTGCGAGAGTAGAT
GACTATTACCTTGGGTATGACTACTGGGGCCAGGGGACCCTGGTCACCGTCTCCTCA

>56G5_VK (SEQ ID NO: 135)
GATATTGTGATGACCCAGACCCCCACCTCCTTGGCACCGTCTGCAGGAGAACGTGCGACC
ATCAATTGTAAGTCCAGCCAGAGTGTGTTATTCAGCTCCAACCAGAAAAACTACTTAGCT
TGGTACCAGCAGAAACCGGGACAGCCTCCTAAGCTGCTCATCTACTGGGCTTCCATCCGA
GAATCGGGGGTTCCTGATCGATTCAGCGGCAGTGGGTCCGCCACAGATTTCACGCTAACC
ATCAGCTCTCTTCAGCCTGAAGACGTGGCAGTATATTACTGCCAGCAGGGTTATAGTTTT
CCATATAGTTTCGGCAGTGGGACCAGGCTCGAGATCAAA

Example 22: Germlining of 36C4 does not Lead to Loss in Potency

Figure 20:
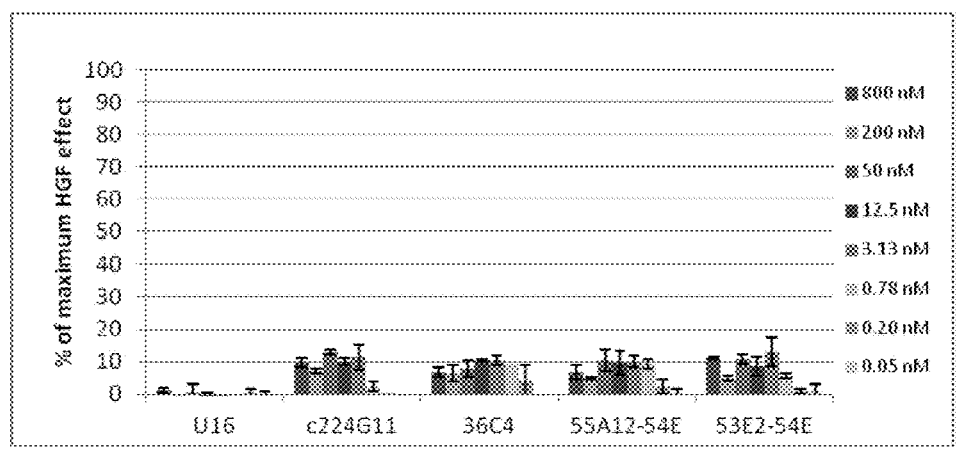
FIG. 20. Phosphorylation assay using germlined 36C4 mAbs on A549 cells showing agonism (A) and antagonism (B). U16 is the isotype control and c224G11 the positive control.
Figure 20:
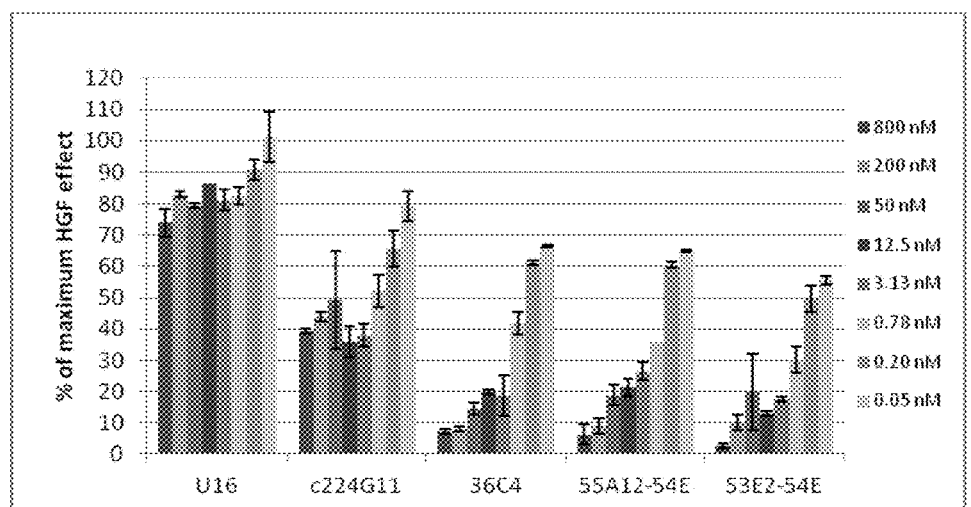

For 36C4, four germlined clones (55A12-54E, 53E2-54E, 53E3, 53A11) were further characterized for agonistic and antagonistic properties in the A549 phosphorylation assay as described in Example 9. As shown in FIG. 20A, there were no increased agonistic properties of the germlined mAbs 55A12-54E and 53E2-54E as compared to the parental 36C4. The germlined variants 53E3 and 53A11 showed the same results. The antagonistic effect of the germlined mAbs were not significantly altered either as shown in FIG. 20B, exemplified by 55A12-54E and 53E2-54E.

Example 23: PBS Stability of Germlined 36C4 mAbs

Figure 21:
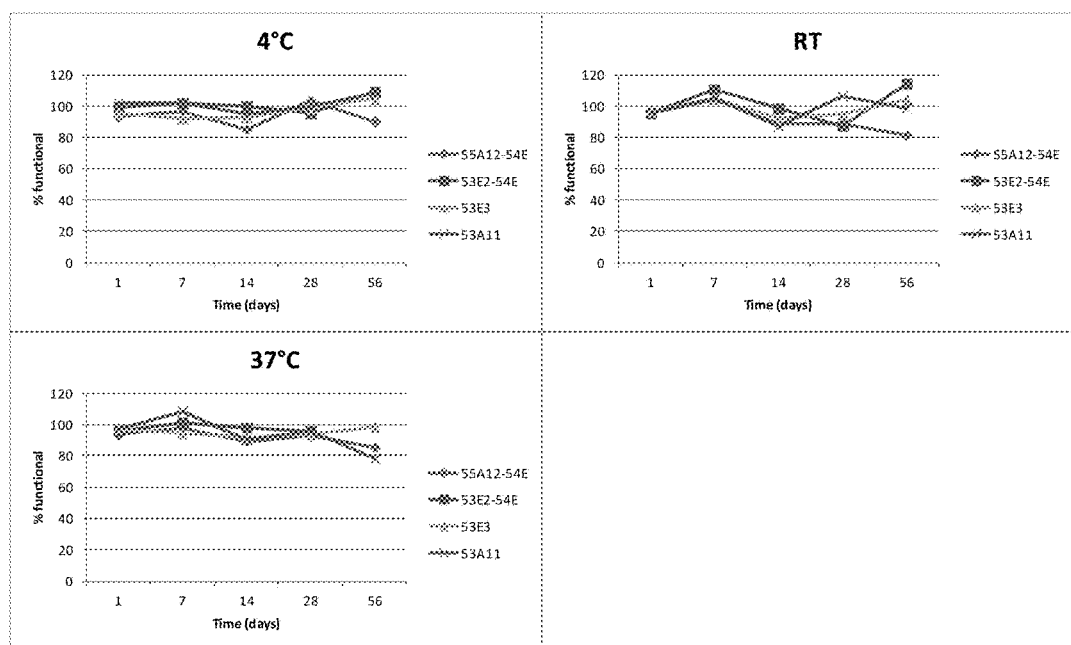
FIG. 21. PBS stability of germlined 36C4 variants at various temperatures. Functionality tests were performed using Surface Plasmon Resonance on germlined 36C4 mAbs after incubation in PBS at 4° C., RT and 37° C. for up to 56 days.

Stability of 3 mg/ml IgG in PBS+0.02% Tween-80 was investigated at days 0-1-7-14-28-56 after storage at 4° C., RT and 37° C. All samples were tested for their potency by Surface Plasmon Resonance investigating binding to coupled c-Met (15,000-17,000 RU) and determining the slope between 100-130 seconds at a flow rate of 30 µl/min. The percentage of functional mAbs was calculated based on the reference (germlined mAbs stored at −20° C.). FIG. 21 shows that there was not significant loss of functionality after 56 days incubation at the different temperatures and there did not seem to be a significant difference between the four germlined mAbs.

Example 24: Thermotolerance of Germlined 36C4 and 48A2 mAbs

Figure 22:
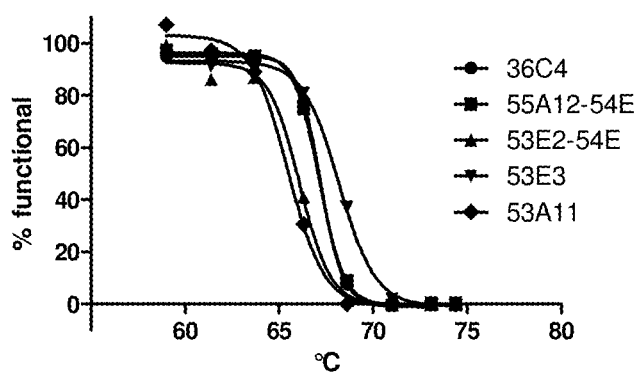
FIG. 22. Thermotolerance of germlined 36C4 (A) and 48A2 (B). Functionality investigated using Surface Plasmon Resonance after incubation at different temperatures for 1 h.
Figure 22:
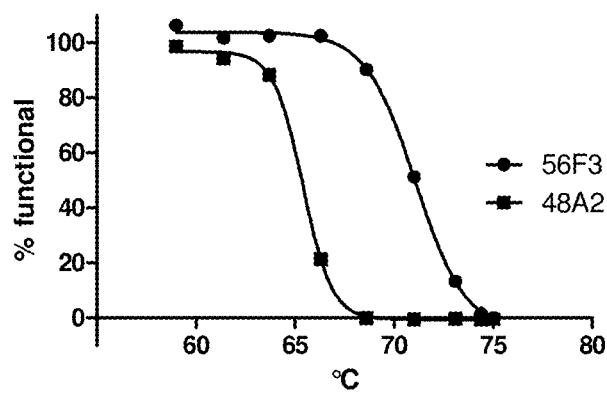

The thermotolerance of germlined 36C4 and 48A2 mAbs was investigated by incubation at different temperatures for 1 h before the samples (0.5 µg/ml) were run on CM-5 chip coupled with 15,000-17,000 RU Decoy c-Met and the slope determining the slope between 100-130 seconds at a flow rate of 30 µl/min. The percentage of functional mAbs was calculated based on the reference (incubated at 4° C.) set to 100%. As shown in FIG. 22A, the melting temperatures (EC50) of the germlined mAbs was 67.2° C. for 36C4, 67.1° C. for 55A12-54E, 66.1° C. for 53E2-54E, 68.2° C. for 53E3 and 65.5° C. for 53A11. For 48A2, germlined mAb 56F3, there was a significant improvement in melting temperature from 65.4 to 71.1° C. (FIG. 22B).

Figure 23:
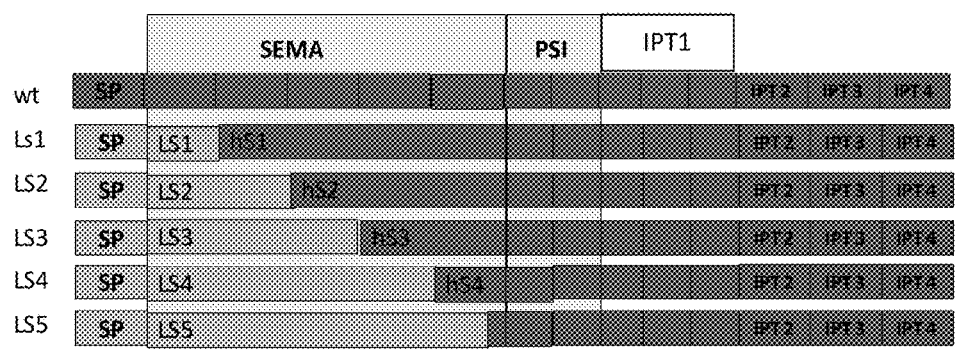
FIG. 23. Schematic illustration of the structure of chimeric llama-human c-Met constructs prepared for: (A) peptide mapping of mAb (e.g. 36C4) binding to the SEMA domain of c-Met. Light grey shading indicates llama c-Met sequence (LS); dark grey shading indicates human c-Met sequence (hS). The relative positions of the signal sequence, SEMA domain, PSI domain and IPT domains 1, 2, 3 and 4 are indicated; (B) peptide mapping of mAb (e.g. 48A2) binding to the PSI-IPT1 domain of c-Met. Light grey shading indicates llama c-Met sequence; dark grey shading indicates human c-Met sequence. The relative positions of the signal sequence, SEMA domain, PSI domain and IPT domains 1, 2, 3 and 4 are indicated.
Figure 23:
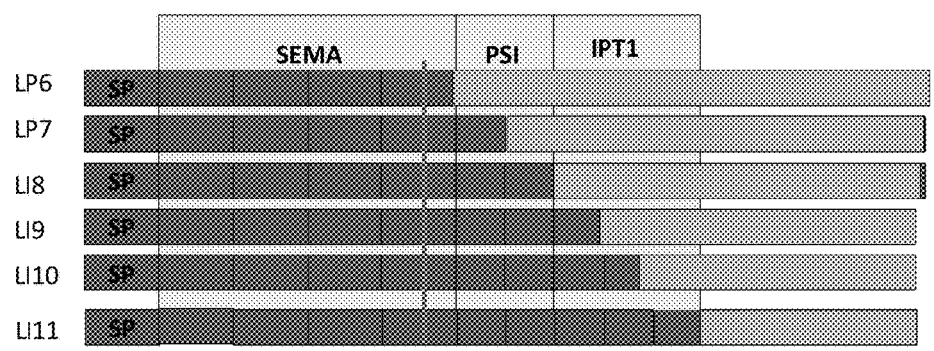

Example 25: Determination of c-Met Peptide Binding Sites of mAbs 36C4 and 48A2 Using Human-Llama Chimeric c-Met To further define the amino acid (aa) stretches of c-Met to which the mAbs 36C4 and 48A2 were binding, chimeric c-Met constructs containing approximately 20-300 aa exchanges from human to llama c-Met were prepared using PCR amplifications and ligations into the human c-Met containing vector with a Flag and a strep tag. FIG. 23A shows the chimeric c-Met constructs used for peptide mapping of 36C4 binding to the SEMA domain, whereas FIG. 23B show the chimeric c-Met constructs for the peptide mapping of 48A2 binding to the PSI-IPT1 domain.

The llama-human c-Met chimeras were produced in HEK293E cells and purified using strep-tactin sepharose HP (2-3 h at 11° C.) before washing of unbound proteins. The bound proteins were eluted with 2.5 mM desthiobiotin pH 8.2 and fractions of 1.5 ml were collected. Protein concentration was determined by Nanodrop. Protein was quality controlled by SDS-PAGE.

An ELISA was run to investigate the binding of the mAbs to the different chimeras. 2 µg/ml 36C4 or 48A2 were immobilized and, after blocking, the c-Met chimeras were added and revealed with 1/10,000 streptavidin-HRP (ELISA in Table 16).

Surface Plasmon Resonance (SPR) was also used to investigate the binding of the mAbs to the different llama-human c-Met chimeras. 3000 RU of 36C4, 48A2 and HGF were coupled on a CM-5 chip in 10 mM NaAc (pH4.5). 60 µl of a 10 µg/ml solution of the different c-Met chimeras was run over the chip at a flow rate of 30 µl/min and the association for 2 min was evaluated. The chip was regenerated with 20 mM NaOH and 1 M NaCl.

Table 16 show the chimeras with the human c-Met and the amino acids (starting with aa E in the mature protein of the human c-Met) that were exchanged with the llama c-Met peptides and the binding results using Plasmon resonance and ELISA. The results were consistent and showed that 36C4 binding stops at aa 199, indicating a recognition site within aa 98-199 of human c-Met. This is the part of the SEMA domain that contains the HGF β-chain binding site, as shown in the crystal structure published by Stamos et al, (EMBO J, 2004).

The 48A2 mAb bound to aa 523-633 of human c-Met, which covers both part of the PSI and the IPT1 domains indicating recognition of a conformational epitope in both domains.

Western Blot with c-Met run under reducing conditions was used to investigate if 36C4 and 48A2 bound linear or conformational epitopes. No binding was observed for 36C4 or 48A2 indicating recognition of a conformational epitope (data not shown), which was confirmed with the chimeric c-Met proteins.

TABLE 16

Llama-human c-Met chimeras and binding results of 36C4 and 48A2 measured by SPR and ELISA

| | SPR | | | ELISA (EC$_{50}$ ng/ml) | |
|---|---|---|---|---|---|
| Chimera | HGF | 36C4 | 48A2 | 36C4 | 48A2 |
| LS1 (aa1-98) | + | + | + | 68 | 31 |
| LS2 (aa1-199) | + | − | + | − | 34 |
| LS3 (aa1-287) | + | − | + | − | 50 |
| LS4 (aa1-348) | + | − | + | − | 70 |
| LS5 (aa1-448) | + | − | + | − | 50 |
| LP6 (aa497-909) | + | − | + | 50 | − |
| LP7* (aa523-909) | + | − | + | 55 | − |
| Ll8 (aa540-909) | + | + | +/− | 47 | >40 |
| Ll9 (aa572-909) | + | + | +/− | 47 | >40 |
| Ll10 (aa608-909) | + | + | +/− | 47 | >40 |
| Ll11 (aa634-909) | + | + | + | 45 | 42 |
| LMet | − | − | − | − | − |
| HMet | + | + | + | 60 | 45 |

*T737I
Sequence of the human c-Met peptide recognized by mAb 36C4 (aa98-199) SEQ ID NO: 181
VDTYYDDQLISCGSVNRGTCQRHVFPHNHTADIQSEVHCIFSPQIEEPSQCPDCVVSAL-
GAKVLSSVKDRFINFFVGNTINSSYFPDHPLHSISVRRLKETK
Sequence of the human c-Met peptide recognized by mAb 48A2 (aa523-633) SEQ ID NO: 136
RSEECLSGTWTQQICLPAIYKVFPNSAPLEGGTRLTICGWDFGFRRNNKFDLKKTRVLL-
GNESCTLTLSESTMNTLKCTVGPAMNKHFNMSIIISNGHGTTQYSTFSYVD P Example 26: Down-Regulation of Total c-Met by the mAbs on MKN-45 Cells The amount of total cMet present on the surface of MKN-45 cells after incubation with the mAbs was measured using Flow cytometry.

25,000 MKN-45 cells/well in a 96-well plate were seeded and incubated for 24 h at 37° C., 5% CO$_2$. The cells were serum starved for 8 h before addition of the mAbs and HGF at 10 or 1 µg/ml diluted in serum-free medium and in triplicates. Murine 5D5 antibody and HGF were included as controls for down-regulation of the total c-Met. The negative control is an irrelevant IgG1 mAb produced in the same way as the 36C4 and 48A2.

The cells were washed with PBS and 50 µl/well of enzyme-free cell dissociation solution was added and incubated for 15 min at 37° C. The cells were collected in a FACS plate and 100 µl binding buffer (PBS+1% BSA) was added before centrifugation at 2000 rpm for 3 min. The cells were kept at 4° C. from this point on. The cells were washed twice with binding buffer and then 2.5 µg/ml mouse anti-c-Met antibody (R&D Systems) added. The cells were then incubated for 1 h with shaking at 4° C., followed by washing twice with the binding buffer. APC-conjugated goat anti-mouse antibody (Jackson Lab) was added at a concentration of 1/500 and the cells incubated for 1 h with shaking. The cells were then washed with binding buffer and read on a FACS Calibur. 2000 events were collected and the down-regulation was expressed as a percentage of the down-regulation in the medium control.

Figure 24:
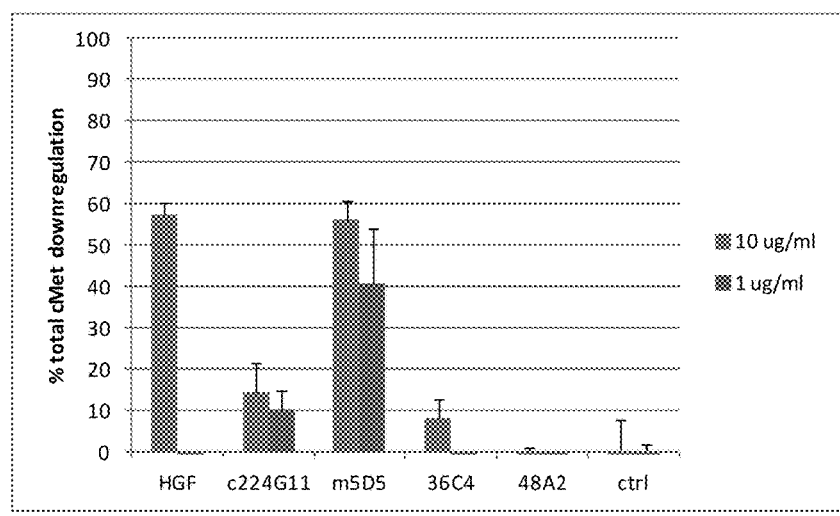
FIG. 24. An assay for down-regulation of total c-Met protein on the surface of MKN-45 cells following treatment with various c-Met mAbs at concentrations of 1 µg/ml or 10 µg/ml. Results are expressed as a percentage total of c-Met down-regulation.

The mAbs 36C4 and 48A2 do not induce significant down-regulation of c-Met on the surface of MKN-45 cells compared to either 5D5 or HGF (see FIG. 24), both of which induce 50-60% down-regulation of cMet after incubation over night.

The invention claimed is:

1. An isolated antibody or antigen-binding fragment thereof which specifically binds human c-Met protein, the antibody or antigen-binding fragment comprising a heavy chain variable domain comprising CDRH3, CDRH2, and CDRH1 regions, and a light chain variable domain comprising CDRL3, CDRL2, and CDRL1 regions, wherein the CDRH3, CDRH2, CDRH1, CDRL3, CDRL2, and CDRL1 regions comprise the amino acid sequences set forth in SEQ ID NOs: 21, 83, 19, 33, 32, and 31, respectively, wherein the antibody or antigen-binding fragment comprises the CH1 domain, hinge, CH2 domain, and CH3 domain of a human IgG.

2. The isolated antibody or antigen-binding fragment of claim 1 wherein the CH1 domain, hinge, CH2 domain, and CH3 domain are from human IgG1.

3. An isolated antibody or antigen-binding fragment thereof which specifically binds human c-Met protein, the antibody or antigen-binding fragment comprising a heavy chain variable domain comprising CDRH3, CDRH2, and CDRH1 regions, and a light chain variable domain comprising CDRL3, CDRL2, and CDRL1 regions, wherein the CDRH3, CDRH2, CDRH1, CDRL3, CDRL2, and CDRL1 regions comprise the amino acid sequences set forth in SEQ ID NOs: 21, 83, 19, 33, 32, and 31, respectively, wherein the antibody or antigen-binding fragment is a non-fucosylated IgG.

4. A pharmaceutical composition comprising the antibody or antigen-binding fragment according to any one of claims 1-3 and a pharmaceutically acceptable carrier or excipient.

5. An immunoconjugate comprising the antibody or antigen-binding fragment according to any one of claims 1-3, wherein the antibody or antigen-binding fragment is conjugated to a cytotoxic agent, cytostatic agent, toxin, or radionuclide.

6. The isolated antibody or antigen-binding fragment of any one of claims 1-3, wherein the heavy chain variable domain comprises an amino acid sequence selected from the group consisting of SEQ ID NOs: 92, 94, and 96.

7. The isolated antibody or antigen-binding fragment of any one of claims 1-3, wherein the light chain variable domain comprises an amino acid sequence selected from the group consisting of SEQ ID NOs: 93, 95, and 97.

8. The isolated antibody or antigen-binding fragment of any one of claims 1-3, wherein the heavy chain variable domain and the light chain variable domain comprise the amino acid sequences set forth in SEQ ID NOs: 92 and 93; 94 and 95; or 96 and 97, respectively.

9. A pharmaceutical composition comprising the antibody or antigen-binding fragment of claim 8 and a pharmaceutically acceptable carrier or excipient.

* * * * *